United States Patent
Narine et al.

(10) Patent No.: US 10,106,558 B2
(45) Date of Patent: Oct. 23, 2018

(54) AZOLOBENZAZINE COMPOUNDS, COMPOSITIONS COMPRISING THESE COMPOUNDS AND THEIR USE FOR CONTROLLING INVERTEBRATE PESTS

(71) Applicant: BASF SE, Ludwigshafen am Rhein (DE)

(72) Inventors: Arun Narine, Mannheim (DE); Sunderraman Sambasivan, Chennai (IN); Ramakrishnan Vallinayagam, Navi Mumbai (IN); Harish Shinde, Pune (IN); Ashokkumar Adisechan, Navi Mumbai (IN)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/543,759

(22) PCT Filed: Jan. 13, 2016

(86) PCT No.: PCT/EP2016/050497
§ 371 (c)(1),
(2) Date: Jul. 14, 2017

(87) PCT Pub. No.: WO2016/113272
PCT Pub. Date: Jul. 21, 2016

(65) Prior Publication Data
US 2018/0002346 A1 Jan. 4, 2018

(30) Foreign Application Priority Data
Jan. 14, 2015 (IN) .............. 115/DEL/2015

(51) Int. Cl.
*C07D 498/14* (2006.01)
*A01N 43/90* (2006.01)
*C07D 495/14* (2006.01)
*C07D 491/14* (2006.01)
*C07D 471/14* (2006.01)

(52) U.S. Cl.
CPC .......... *C07D 498/14* (2013.01); *A01N 43/90* (2013.01); *C07D 471/14* (2013.01); *C07D 491/14* (2013.01); *C07D 495/14* (2013.01)

(58) Field of Classification Search
CPC .............................. C07D 498/14; A01N 43/90
See application file for complete search history.

(56) References Cited

U.S. PATENT DOCUMENTS

2012/0202687 A1  8/2012  Crouse et al.

FOREIGN PATENT DOCUMENTS

| EP | 2070923 A1 | 6/2009 |
| EP | 2738171 A1 | 6/2014 |
| WO | 2015007682 A1 | 1/2015 |

OTHER PUBLICATIONS

International Preliminary Report on Patentability for PCT Patent Application No. PCT/EP2016/050497, dated Jul. 18, 2017, 6 pages.
International Search Report and Written Opinion issued for PCT/EP2016/050497 dated Mar. 9, 2016 (8 pages).

*Primary Examiner* — Golam M Shameem
(74) *Attorney, Agent, or Firm* — Armstrong Teasdale LLP

(57) ABSTRACT

Azolobenzazine compounds of the formula I and N-oxides, stereoisomers, tautomers and agriculturally or veterinarily acceptable salts thereof are disclosed, as well as are methods for controlling invertebrate pests using the disclosed compounds. Further disclosed are plant propagation materials, agricultural compositions, and veterinary compositions that include the disclosed compounds.

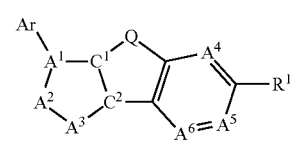

(I)

13 Claims, No Drawings

AZOLOBENZAZINE COMPOUNDS, COMPOSITIONS COMPRISING THESE COMPOUNDS AND THEIR USE FOR CONTROLLING INVERTEBRATE PESTS

CROSS-REFERENCE TO RELATED APPLICATIONS

This application is a U.S. National Phase Application of PCT Application No. PCT/EP2016/050497, filed Jan. 13, 2016, which claims the benefit of priority to Indian Application No. 115/DEL/2015, filed Jan. 14, 2015, the entire contents of which are hereby incorporated by reference herein.

BACKGROUND

The present invention relates to novel azolobenzazine compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an on-going need for new agents for combating invertebrate pests, in particular insects, arachnids and nematodes.

WO 2009/102736 describes linear triaryls having a rhamnose type radical which is bound to a terminal aryl group via a bivalent linker such as (thio)carbamate or iminoxy linker. Similar compounds are known from WO 2012/027521.

WO 2011/017504 describes linear triaryls having a methyliden(thio)carbazone motive that carries a (het)aryl or (het)arylalkyl radical.

WO 2011/017513 describe linear triaryls having a carbamate or thiocarbamate motive that carries a (het)arylalkyl radical.

US 2012/0202687 describes linear triaryls having a methylideniminoisothiourea motive that carries a (het)aryl or (het)arylalkyl radical.

Earlier filed patent application PCT/EP2014/065034 describes insecticide compounds having a fused tricyclic core comprising a heterocyclic ring and a benzene ring which both are fused to a central ring, where the fused heterocyclic ring carries an aromatic or heteroaromatic radical and where the fused benzene ring carries a side chain, which may, inter alia, be a carbamate or thiocarbamate motiv, a methyliden(thio)carbazone motive, a methylideniminoisothiourea motive or an iminoxy motive.

DETAILED DESCRIPTION

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by compounds of the formula I below, by their stereoisomers, their tautomers, their N-oxides and by their salts, in particular their agriculturally or veterinarily acceptable salts.

Therefore, in a first aspect, the invention relates to compounds of formula I

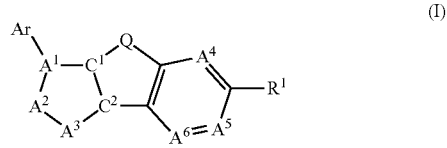

wherein
$C^1$ is C or CH
$C^2$ is C or CH
$A^1$ is N or C
$A^2$ is N, $C(R^2)$, $N(R^3)$, O, S or $C(R^4,R^5)$; and
$A^3$ is N, O, S, $N(R^6)$, $C(R^7)$ or $C(R^8,R^9)$;
$A^4$ is N or C(R);
$A^5$ is N or C(R);
$A^6$ is N or C(R);
where one or two non-adjacent bonds in the 5-membered ring formed by $C^1$, $C^2$, $A^1$, $A^2$ and $A^3$ are double bonds, while the others are single bonds, provided that the bond between $A^1$ and $A^2$ or the bond between $A^1$ and $C^1$ or the bond between $A^2$ and $A^3$ or the bond between $C^1$ and $C^2$ or the bond between $A^3$ and $C^2$ is a double bond further provided that at least one of $A^1$, $A^2$ and $A^3$ is N, $N(R^3)$ or $N(R^6)$,
provided that 1 or 2 of $A^4$, $A^5$ and $A^6$ is N;
and where
$R^2$, $R^7$ independently of each other, are selected from the group consisting of hydrogen, halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$ and S(=O)$_m R^e$;
$R^3$, $R^6$ independently of each other, are selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$, S(=O)$_m R^e$, phenyl and benzyl, where the phenyl ring in the last 2 radicals is unsubstituted or carry 1, 2, 3, 4 or 5 radicals $R^f$;
$R^4$, $R^5$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or $C(R^4,R^5)$ may be a carbonyl group or thiocarbonyl group;

R$^8$, R$^9$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio or C(R$^8$,R$^9$) may be a carbonyl group or thiocarbonyl group;

Ar is phenyl or 5- or 6-membered hetaryl, which are unsubstituted or carry 1, 2, 3 or 4 radicals R$^{Ar}$, which are identical or different, where R$^{Ar}$ independently of each other, are selected from the group consisting of halogen, N$_3$, OH, CN, NO$_2$, —SCN, —SF$_5$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, where the phenyl ring in the last 5 radicals is unsubstituted or carry 1, 2, 3, 4 or 5 radicals R$^f$;

Q is —O—, —S—, —S(=O)—, —S(=O)$_2$—, —C(R$^{Q2a}$R$^{Q2b}$)—, —N(R$^{Q1}$)—, —N(R$^{Q2}$)—C(=O)—, —N(R$^{Q2}$)—C(=S)—, —O—C(=O)—, —C(R$^{Q3}$)=C(R$^{Q4}$)—, —C(R$^{Q3a}$R$^{Q3b}$)—C(R$^{Q4a}$R$^{Q4b}$)—, —C(R$^{Q3a}$R$^{Q3b}$)—C(=O)—, —O—C(R$^{Q4a}$R$^{Q4b}$)—, —S(=O)$_n$—C(R$^{Q4a}$R$^{Q4b}$)—, —N=C(R$^{Q3c}$), —S(=O)$_2$—N(R$^{Q2}$)— or —N(R$^{Q2}$)—C(R$^{Q4a}$R$^{Q4b}$)—, where n is 0, 1 or 2;

R$^{Q1a}$, R$^{Q2}$ independently of each other are selected from the group consisting of hydrogen, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, where the phenyl ring in the last 2 radicals is unsubstituted or carry 1, 2, 3, 4 or 5 radicals R$^f$;

R$^{Q3}$, R$^{Q4}$ independently of each other are selected from the group consisting of hydrogen, halogen, OH, CN, C$_1$-C$_4$-alkyl, C$_1$-C$_4$-haloalkyl, C$_1$-C$_4$-alkoxy, C$_1$-C$_4$-haloalkoxy, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$;

R$^{Q2a}$, R$^{Q2b}$ independently of each other are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio or —C(R$^{Q2a}$R$^{Q2b}$)— is C=O or C=S;

R$^{Q3a}$, R$^{Q3b}$ independently of each other are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^{Q3c}$ is selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^{Q4a}$, R$^{Q4b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^1$ is a moiety of the formula -T-X$^1$—Y—Z$^1$—R$^{11}$ or a moiety -T-X$^2$—Y—Z$^2$—R$^{12}$, where R$^{11}$ is selected from the group consisting of C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, where the alkyl, cycloalkyl, cycloalkoxy and alkoxy parts of the last four mentioned radicals are unsubstituted or partially or completely halogenated, C$_1$-C$_6$-alkylen-NR$^b$R$^c$, C$_1$-C$_6$-alkylen-CN, C(O)—NR$^b$R$^c$, C(O)—R$^d$, aryl, arylcarbonyl, aryl-C$_1$-C$_4$-alkyl, aryloxy-C$_1$-C$_4$-alkyl, hetaryl, hetarylcarbonyl, hetaryl-C$_1$-C$_4$-alkyl and hetaryloxy-C$_1$-C$_4$-alkyl, where the aryl and hetaryl rings in the last 8 radicals are unsubstituted or carry 1, 2, 3, 4 or 5 radicals R$^g$ and where hetaryl is a 5- or 6-membered monocyclic hetaryl or a 8-, 9- or 10-membered bicyclic hetaryl;

R$^{12}$ is a radical of the formula A;

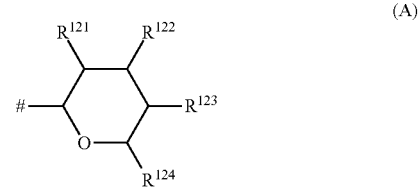

(A)

wherein # indicates the point of attachment to Z$^2$;

R$^{121}$, R$^{122}$, R$^{123}$ independently of each other are selected from the group consisting of hydrogen, halogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_1$-C$_6$-alkoxy, C$_1$-C$_6$-haloalkoxy, C$_2$-C$_6$-alkenyloxy, C$_2$-C$_6$-alkynyloxy, C$_1$-C$_6$-alkoxy-C$_1$-C$_4$-alkoxy, C$_1$-C$_6$-alkylcarbonlyoxy, C$_1$-C$_6$-haloalkylcarbonlyoxy, C$_1$-C$_6$-alkenylcarbonlyoxy, C$_3$-C$_6$-cycloalkylcarbonlyoxy and NR$^b$R$^c$, or one of R$^{121}$, R$^{122}$, R$^{123}$ may also be oxo;

R$^{124}$ is selected from the group consisting of hydrogen, C$_1$-C$_6$-alkyl, C$_1$-C$_6$-haloalkyl, C$_1$-C$_6$-alkoxy-C$_1$-C$_4$-alkyl, C$_1$-C$_6$-alkoxy, C$_1$-C$_6$-haloalkoxy and C$_2$-C$_6$-alkenyloxy;

T is selected from a single bond, (CHR$^{xa}$)$_s$ with s being 1, 2, 3 or 4, cyclopropane-1,1-diyl or cyclopropane-1,2-diyl, X$^1$, X$^2$ independently of each other, are selected from NR$^{x1}$, a bivalent group —N(R$^{x2}$)—C(=O)—, where C=O is bound to Y, a bivalent group —N(R$^{x2}$)—C(=S)—, where C=S is bound to Y, and a bivalent group —C(R$^{x3}$)=N—, where the nitrogen is bound to Y, Y is a single bond, or one of the bivalent groups —N(R$^{y1}$)—C(=O)—, —N(R$^{y2}$)—C(=S)—, —N=C((O)$_p$R$^{y3}$)— or —N=C((S)$_p$—R$^{y3}$)—, where the left hand nitrogen atom in the four groups is bound to X$^1$ or X$^2$, respectively, and where p is 0 or 1, provided that Y is not a single bond, if X$^1$ or X$^2$ are a single bond;

Z$^1$ is O, S, N—R$^{z1}$, C(R$^{z3}$)=C((S)$_q$—R$^{z4}$)—N(R$^{z5}$), wherein R$^{11}$ is bound to the nitrogen atom and q is 0 or 1, or C(S—R$^{z6}$)=N, wherein R$^{11}$ is bound to the nitrogen atom; or Y—Z$^1$ is selected from the following bivalent radicals N(R$^{y4}$)—C(S—R$^{z6}$)=N, O—N(R$^{y4}$)—C(S—R$^{z6}$)=N and N(R$^{y44}$)—N(R$^{y4}$)—C(S—R$^{z6}$)=N, where in these bivalent radicals R$^{11}$ is bound to the nitrogen atom, $Z^2$ is O, S or N—$R^{z2}$;

and where $R^{x1}$, $R^{x2}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, S(=O)$_m R^e$, phenyl and benzyl, where the phenyl ring in the last 2 radicals is unsubstituted or carry 1, 2, 3, 4 or 5 radicals $R^f$;

$R^{x3}$ is selected from the group consisting of hydrogen, halogen, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl, cycloalkoxy and alkoxy parts of the last 6 mentioned radicals are unsubstituted or partially or completely halogenated, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, phenyl, phenoxy, phenylcarbonyl, phenylthio and benzyl, where the phenyl ring in the last 5 radicals is unsubstituted or carry 1, 2, 3, 4 or 5 radicals $R^f$;

$R^{xa}$ is selected from the group consisting of hydrogen, halogen and $C_1$-$C_6$-alkyl, it being possible for s=2, 3 or 4 that $R^{xa}$ is identical or different;

p is 0 or 1;

$R^{y1}$, $R^{y2}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, S(=O)$_m R^e$, phenyl and benzyl, where the phenyl ring in the last 2 radicals is unsubstituted or carry 1, 2, 3, 4 or 5 radicals $R^f$;

$R^{y3}$ is selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl and alkoxy parts of the last four mentioned radicals are unsubstituted or partially or completely halogenated, $C_1$-$C_6$-alkylen-$NR^bR^c$, $C_1$-$C_6$-alkylen-CN, C(O)—$NR^bR^c$, C(O)—$R^d$, phenyl, phenylcarbonyl and benzyl, where the phenyl ring in the last 3 radicals is unsubstituted or carry 1, 2, 3, 4 or 5 radicals $R^f$;

$R^{y4}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, S(=O)$_m R^e$, phenyl and benzyl, where the phenyl ring in the last 2 radicals is unsubstituted or carry 1, 2, 3, 4 or 5 radicals $R^f$;

$R^{y44}$ is selected from the group consisting of hydrogen, $C_1$-$C_6$-alkyl, $C_1$-$C_6$-haloalkyl, C(O)$NR^bR^c$, C(O)—$R^d$, phenyl, phenylcarbonyl and benzyl, where the phenyl ring in the last 3 radicals is unsubstituted or carries 1, 2, 3, 4 or 5 radicals $R^f$;

$R^{z1}$, $R^{z2}$ independently of each other are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, S(=O)$_m R^e$, phenyl and benzyl, where the phenyl ring in the last 2 radicals is unsubstituted or carry 1, 2, 3, 4 or 5 radicals $R^f$, or $R^{z1}$ together with $R^{y3}$, if present, may also form a linear $C_1$-$C_6$-alkylene group or a linear $C_2$-$C_6$-alkenylene group, where in the linear $C_1$-$C_6$-alkylene group and the linear $C_2$-$C_6$-alkenylene group a $CH_2$ moiety may be replaced by a carbonyl group or a group C=N—R' and/or wherein 1 or 2 $CH_2$ moieties may be replaced by O or S and/or wherein the linear $C_1$-$C_6$-alkylene group and the linear $C_2$-$C_6$-alkenylene group may be unsubstituted or substituted by 1, 2, 3, 4, 5 or 6 radicals $R^{hh}$;

$R^{z3}$, $R^{z6}$ independently of each other, are selected from the group consisting of hydrogen, CN, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carries 1, 2, 3, 4 or 5 radicals $R^f$;

$R^{z4}$, $R^{z5}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carries 1, 2, 3, 4 or 5 radicals $R^f$;

or $R^{z4}$ together with $R^{z5}$, if present, may also form a linear $C_1$-$C_6$-alkylene group or a linear $C_2$-$C_6$-alkenylene group, where in the linear $C_1$-$C_6$-alkylene group and the linear $C_2$-$C_6$-alkenylene group a $CH_2$ moiety may be replaced by a carbonyl group or a group C=N—R' and/or wherein 1 or 2 $CH_2$ moieties may be replaced by O or S and/or wherein the linear $C_1$-$C_6$-alkylene group and the linear $C_2$-$C_6$-alkenylene group may be unsubstituted or substituted by 1, 2, 3, 4, 5 or 6 radicals $R^{hh}$;

$R^{y4}$ together with $R^{z6}$ may also form a linear $C_1$-$C_6$-alkylene group or a linear $C_2$-$C_6$-alkenylene group, where in the linear $C_1$-$C_6$-alkylene group and the linear $C_2$-$C_6$-alkenylene group a $CH_2$ moiety may be replaced by a carbonyl group or a group C=N—R' and/or wherein 1 or 2 $CH_2$ moieties may be replaced by O or S and/or wherein the linear $C_1$-$C_6$-alkylene group and the linear $C_1$-$C_6$- alkenylene group may be unsubstituted or substituted by 1, 2, 3, 4, 5 or 6 radicals $R^{hh}$;

R is selected from the group consisting of hydrogen, halogen, $N_3$, OH, CN, $NO_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, where the phenyl ring in the last 5 radicals is unsubstituted or carry 1, 2, 3, 4 or 5 radicals R$^f$;

R' is selected from the group consisting of hydrogen, halogen, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl, cycloalkoxy and alkoxy parts of the last 6 mentioned radicals are unsubstituted or partially or completely halogenated, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, phenyl, phenoxy, phenylcarbonyl, phenylthio and benzyl, where the phenyl ring in the last 5 radicals is unsubstituted or carry 1, 2, 3, 4 or 5 radicals R$^f$;

and where each m is independently 0, 1 or 2;

each R$^a$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, $C_1$-$C_6$-alkylen-NR$^b$R$^c$, $C_1$-$C_6$-alkylen-CN, phenyl and benzyl, where the phenyl ring in the last 2 radicals is unsubstituted or carry 1, 2, 3, 4 or 5 radicals R$^f$;

each R$^b$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, $C_1$-$C_6$-alkylen-CN, phenyl and benzyl, where the phenyl ring in the last 2 radicals is unsubstituted or carry 1, 2, 3, 4 or 5 radicals R$^f$;

each R$^c$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, $C_1$-$C_6$-alkylen-CN, phenyl and benzyl, where the phenyl ring in the last 2 radicals is unsubstituted or carry 1, 2, 3, 4 or 5 radicals R$^f$;

each moiety NR$^b$R$^c$ may also form an N-bound, saturated 5- to 8-membered heterocycle, which in addition to the nitrogen atom may have 1 or 2 further heteroatoms or heteroatom moieties selected from O, S(=O)$_m$ and N—R', where R' is hydrogen or $C_1$-$C_6$-alkyl and where the N-bound heterocycle is unsubstituted or carries 1, 2, 3, 4, 5 or 6 radicals selected from halogen, $C_1$-$C_4$-alkyl, $C_1$-$C_4$-haloalkyl, $C_1$-$C_4$-alkoxy and $C_1$-$C_4$-haloalkoxy;

each R$^d$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 4 mentioned radicals are unsubstituted or partially or completely halogenated, phenyl and benzyl, where the phenyl ring in the last 2 radicals is unsubstituted or carry 1, 2, 3, 4 or 5 radicals R$^f$;

each R$^e$ is selected from the group consisting of $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, where the alkyl and cycloalkyl parts of the last 2 mentioned radicals are unsubstituted or partially or completely halogenated, phenyl and benzyl, where the phenyl ring in the last 2 radicals is unsubstituted or carry 1, 2, 3, 4 or 5 radicals R$^f$;

each R$^f$ is selected from the group consisting of halogen, $N_3$, OH, CN, $NO_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$;

each R$^g$ is selected from the group consisting of halogen, $N_3$, OH, CN, $NO_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$;

each R$^{hh}$ is selected from halogen, OH, $C_1$-$C_6$-alkyl, $C_3$-$C_6$-cycloalkyl, and CN;

and the N-oxides, stereoisomers, tautomers and agriculturally or veterinarily acceptable salts thereof.

The present invention also relates to a compound of the formula INT and to the tautomers and salts thereof

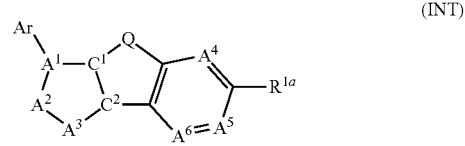

(INT)

where R$^{1a}$ is -T-NCO, -T-C(=O)R$^{x3a}$, -T-C(=O)—N$_3$, T-CN, -T-N(R$^{y1a}$)H or halogen and where T is selected from a single bond, $(CHR^{xa})_s$ with s being 1, 2, 3 or 4, cyclopropane-1,1-diyl or cyclopropane-1,2-diyl, $R^{y1a}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, $C_1$-$C_6$-alkylen-$NR^bR^c$, $C_1$-$C_6$-alkylen-CN, phenyl and benzyl, where the phenyl ring in the last 2 radicals is unsubstituted or carry 1, 2, 3, 4 or 5 radicals $R^f$;

$R^{x3a}$ is selected from the group consisting of hydrogen, OH, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, where the alkyl, cycloalkyl, cycloalkoxy and alkoxy parts of the last 6 mentioned radicals are unsubstituted or partially or completely halogenated, $C_1$-$C_6$-alkylen-$NR^bR^c$, O—$C_1$-$C_6$-alkylen-$NR^bR^c$, $C_1$-$C_6$-alkylen-CN, phenyl, phenoxy, phenylcarbonyl, phenylthio and benzyl, where the phenyl ring in the last 5 radicals is unsubstituted or carry 1, 2, 3, 4 or 5 radicals $R^f$;

and where Ar, $R^{xa}$, $A^1$, $A^2$, $A^3$, $A^4$, $A^5$, $A^6$, $C^1$, $C^2$ and Q are as defined in any of the preceding claims and the salts thereof.

The compounds of formula INT and their tautomers and salts are valuable intermediates in the preparation of the compounds of formula I.

Moreover, the present invention also relates to and includes the following aspects:

an agricultural composition comprising at least one compound of formula (I) or a stereoisomer, a tautomer, a N-oxide or an agriculturally acceptable salt thereof, and at least one liquid and/or solid carrier.

a veterinary composition comprising at least one compound of formula (I) or a stereoisomer, a tautomer, a N-oxide or a verterinarily acceptable salt thereof, and at least one liquid and/or solid carrier.

a method for combating or controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound selected from compounds of formula I, the N-oxides, stereoisomers, tautomers or salts thereof as defined herein.

a method for protecting growing plants from attack or infestation by invertebrate pests, which method comprises contacting a plant, or soil or water in which the plant is growing, with a pesticidally effective amount of at least one compound of formula (I) or a stereoisomer, a tautomer, a N-oxide or an agriculturally or veterinarily acceptable salt thereof, or a composition as defined herein.

a method for the protection of plant propagation material, especially seeds, from soil insects and of the seedlings' roots and shoots from soil and foliar insects comprising contacting the plant propagation material respectively seeds before sowing and/or after pre-germination with at least one compound of formula (I) or a stereoisomer, a tautomer, a N-oxide or an agriculturally or veterinarily acceptable salt thereof, or a composition as defined herein.

plant propagation material, in particular seed, comprising at least one compound of formula I, an N-oxide, a stereoisomer, a tautomer and/or an agriculturally acceptable salt thereof as defined herein.

use of a compound of formula (I) or a stereoisomer, a tautomer, a N-oxide or an agriculturally or veterinarily acceptable salt thereof, or a composition as defined herein for combating or controlling invertebrate pests of the group of insects, arachnids or nematodes.

use of a compound of formula (I) or a stereoisomer, a tautomer, a N-oxide or an agriculturally or veterinarily acceptable salt thereof, or a composition as defined herein for protecting growing plants from attack or infestation by invertebrate pests.

use of a compound of formula (I) or a stereoisomer, a tautomer, a N-oxide or a veterinarily acceptable salt thereof or a composition as defined herein for combating or controlling invertebrate parasites in and on animals.

a method for treating a non-human animal infested or infected by parasites or for preventing a non-human animal from getting infested or infected by parasites or for protecting a non-human animal against infestation or infection by parasites which comprises orally, topically or parenteraly administering or applying to the non-human animal a parasiticidally effective amount of a compound compound of formula (I) or a stereoisomer, a tautomer, a N-oxide or a veterinarily acceptable salt thereof or a composition as defined in claim herein.

a compound compound of formula (I) or a stereoisomer, a tautomer, a N-oxide or a veterinarily acceptable salt thereof for use as a medicament.

a compound compound of formula (I) or a stereoisomer, a tautomer, a N-oxide or a veterinarily acceptable salt thereof for use in the treatment, control, prevention or protection of animals against infestation or infection by parasites.

The term "tautomers" encompasses isomers, which are derived from the compounds of formula I by the shift of an H-atom involving at least one H-atom located at a nitrogen, oxygen or sulphur atom. Examples of tautomeric forms are keto-enol forms, imine-enamine forms, urea-isourea forms, thiourea-isothiourea forms, (thio)amide-(thio)imidate forms etc.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of an N-heterocycle, e.g. a pyridine or pyrimidine ring present in Ar or $R^{11}$, or an imino-nitrogen present in central tricyclic core, with a suitable oxidizing agent, such as peroxo carboxylic acids or other peroxides. The person skilled in the art knows if and in which positions compounds of the present invention may form N-oxides.

The compounds of the present invention may be amorphous or may exist in one or more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethyl ammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDPglycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora* infestans derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case F, Br, Cl or I, in particular F, Cl or Br.

The term "partially or fully halogenated" will be taken to mean that 1 or more, e.g. 1, 2, 3, 4 or 5 or all of the hydrogen atoms of a given radical have been replaced by a halogen atom, in particular by F or Cl. A partially or fully halogenated radical is termed below also "halo-radical".

For example, partially or fully halogenated alkyl is also termed haloalkyl, partially or fully halogenated cycloalkyl is also termed halocycloalkyl, partially or fully halogenated alkylenyl is also termed haloalkenyl, partially or fully halogenated alkylynyl is also termed haloalkynyl, partially or fully halogenated cycloalkylalkyl is also termed halocycloalkylalkyl.

The term "alkyl" as used herein and in the alkyl moieties of alkoxy, alkylthio, and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is $CH_3$ or $C_2H_5$, $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethyl propyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" is $CH_3$ in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkylene" (or alkanediyl) as used herein in each case denotes an alkyl radical as defined above, wherein one hydrogen atom at any position of the carbon backbone is replaced by one further binding site, thus forming a bivalent moiety. Alkylene has preferably 1 to 6 carbon atoms ($C_1$-$C_6$-alkylene), 2 to 6 carbon atoms ($C_2$-$C_6$-alkylene), in particular 1 to 4 carbon atoms ($C_1$-$C_4$-alkylene) or 2 to 4 carbon atoms ($C_2$-$C_4$-alkylene). Examples of alkylene are methylene (CH2), 1,1-ethandiyl, 1,2-ethandiyl, 1,3-propandiyl, 1,2-propandiyl, 2,2-propandiyl, 1,4-butandiyl, 1,2-butandiyl, 1,3-butandiyl, 2,3-butandiyl, 2,2-butandiyl, 1,5-pentandiyl, 2,2-dimethylpropan-1,3-diyl, 1,3-dimethyl-1,3-propandiyl, 1,6-hexandiyl etc.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$- alkenyl) carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular F, Cl and Br, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl"), 3 to 4 ("$C_3$-$C_4$-haloalkynyl") or 2 to 6 ("$C_2$-$C_6$-haloalkynyl") carbon atoms and one or two triple bonds in any position (as mentioned above), where some or all of the hydrogen atoms in these groups are replaced by halogen atoms as mentioned above, in particular F, Cl and Br;

The term "cycloalkyl" as used herein refers to mono- or bi- or polycyclic saturated hydrocarbon radicals having in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1] octyl. Preferably, the term cycloalkyl denotes a monocyclic saturated hydrocarbon radical.

The term "cycloalkoxy" as used herein refers to a cycloalkyl radical, in particular a monocyclic cycloalkyl radical, as defined above having in particular 3 to 6 ("$C_3$-$C_6$-cycloalkoxy") or 3 to 5 ("$C_3$-$C_5$-cycloalkoxy") or 3 to 4 ("$C_3$-$C_4$-cycloalksoxy") carbon atoms, which is bound via an oxygen atom to the remainder of the molecule.

The term "halocycloalkyl" as used herein, which is also expressed as "cycloalkyl which is partially or fully halogenated", refers to mono- or bi- or polycyclic saturated hydrocarbon groups having preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular F, Cl and Br.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl.

The term "$C_3$-$C_6$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_3$-$C_6$-cycloalkxoy-$C_1$-$C_4$-alkyl" refers to a $C_3$-$C_6$-cycloalkoxy group ("$C_3$-$C_8$-cycloalkoxy-$C_1$-$C_4$-alkyl"), as defined above (preferably a monocyclic cycloalkoxy group) which is bound to the remainder of the molecule via a $C_1$-$C_4$-alkyl group, as defined above. Examples for $C_3$-$C_4$-cycloalkoxy-$C_1$-$C_4$-alkyl are cyclopropyloxymethyl, cyclopropyloxyethyl, cyclopropyloxypropyl, cyclobutyloxymethyl, 1-cyclobutyloxyethyl and 2-cyclobutyloxypropyl, Examples for $C_3$-$C_6$-cycloalkoxy-$C_1$-$C_4$-alkyl, apart those mentioned for $C_3$-$C_4$-cycloalkoxy-$C_1$-$C_4$-alkyl, are cyclopentyloxymethyl, cyclopentyloxyethyl, cyclopentyloxypropyl, cyclohexyloxymethyl, cyclohexyloxyethyl and cyclohexyloxypropyl.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethyl butoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_4$-alkoxy-methyl" as used herein, refers to $CH_3$ in which one hydrogen atom is replaced by a $C_1$-$C_4$-alkoxy group, as defined above. The term "$C_1$-$C_6$-alkoxymethyl" as used herein, refers to $CH_3$ in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

The term "alkoxyalkoxy" as used herein refers to an alkoxyalkyl radical, in particular a $C_1$-$C_6$-alkoxy-$C_1$-$C_4$-alkyl radical, as defined above, which is bound via an oxygen atom to the remainder of the molecule. Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

$C_1$-$C_6$-Haloalkoxy-$C_1$-$C_6$-alkyl is a straight-chain or branched alkyl group having from 1 to 6, especially 1 to 4 carbon atoms (=$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The substituent "oxo" replaces a $CH_2$ group by a $C(=O)$ group.

The term "aryl" relates to phenyl and bi- or polycyclic carbocycles having at least one fused phenylene ring, which is bound to the remainder of the molecule. Examples of bi- or polycyclic carbocycles having at least one phenylene ring include naphthyl, tetrahydronaphthyl, indanyl, indenyl, anthracenyl, fluorenyl etc.

The term "aryl-$C_1$-$C_4$-alkyl" relates to $C_1$-$C_4$-alkyl, as defined above, wherein one hydrogen atom has been replaced by an aryl radical, in particular a phenyl radical. Particular examples of aryl-$C_1$-$C_4$-alkyl include benzyl, 1-phenethyl, 2-phenetyl, 1-phenylpropyl, 2-phenylpropyl, 3-phenyl-1-propyl and 2-phenyl-2-propyl.

The term "aryloxy-$C_1$-$C_4$-alkyl" relates to $C_1$-$C_4$-alkyl, as defined above, wherein one hydrogen atom has been replaced by an aryloxy radical, in particular a phenoxy radical. Particular examples of aryloxy-$C_1$-$C_4$-alkyl include phenoxymethyl, 1-phenoxyethyl, 2-phenoxyetyl, 1-phenoxypropyl, 2-phenoxypropyl, 3-phenoxy-1-propyl and 2-phenoxy-2-propyl.

The term "aryl-$C_1$-$C_4$-carbonyl" relates to aryl as defined above, in particular a phenyl radical, which is bound by a carbonyl group to the remainder of the molecule. Particular examples of arylcarbonyl include benzoyl, 1-naphthoyl and 2-naphthoyl.

The term hetaryl relates to aromatic heterocycles having either 5 or 6 ring atoms (5- or 6-membered hetaryl) and being monocyclic or 8, 9 or 10 ring atoms and bing bicyclic. Hetaryl will generally have at least one ring atom selected from O, S and N, which in case of N may be an imino-nitrogen or an amino-nitrogen, which carries hydrogen or a radical different from hydrogen. Hetaryl may have 1, 2, 3 or 4 further nitrogen atoms as ring members, which are imino nitrogens. Examples of 5- or 6-membered hetaryl include 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,3,4-oxadiazolyl-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl and 1,3,5-triazin-2-yl. Examples of 8-, 9- or 10-membered hetaryl include, for example, quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Examples of N-bound 5-, 6-, 7 or 8-membered saturated heterocycles include: pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 1-oxothiomorpholin-4-yl, 1,1-dioxothiomorpholin-4-yl, azepan-1-yl and the like.

The term "hetaryl-$C_1$-$C_4$-alkyl" relates to $C_1$-$C_4$-alkyl, as defined above, wherein one hydrogen atom has been replaced by a hetaryl radical, in particular a pyridyl radical. Particular examples of hetaryl-$C_1$-$C_4$-alkyl include 2-pyridylmethyl, 3-pyridylmethyl, 4-pyridylmethyl, 1-(2-pyridyl)ethyl, 2-(2-pyridyl)ethyl, 1-(3-pyridyl)ethyl, 2-(3-pyridyl)ethyl, 1-(4-pyridyl)ethyl, 2-(4-pyridyl)ethyl etc.

The term "hetaryloxy-$C_1$-$C_4$-alkyl" relates to $C_1$-$C_4$-alkyl, as defined above, wherein one hydrogen atom has been replaced by an hetaryloxy radical, in particular a pyridyloxy radical. Particular examples of hetaryloxy-$C_1$-$C_4$-alkyl include 2-pyridyloxymethyl, 3-pyridyloxymethyl, 4-pyridyloxymethyl, 1-(2-pyridyloxy)ethyl, 2-(2-pyridyloxy)ethyl, 1-(3-pyridyloxy)ethyl, 2-(3-pyridyloxy)ethyl, 1-(4-pyridyloxy)ethyl, 2-(4-pyridyloxy)ethyl etc.

The term "hetaryl-$C_1$-$C_4$-carbonyl" relates to hetaryl as defined above, in particular a C-bound hetaryl radical, e.g. 2-, 3- or 4-pyridyl, 2- or 3-thienyl, 2- or 3-furyl, 1-, 2- or 3-pyrrolyl, 2- or 4-pyrimidinyl, pyridazinyl, 1-, 3- or 4-pyrazolyl, 1-, 2- or 4-imidazolyl radical, which is bound by a carbonyl group to the remainder of the molecule.

A first particular group of embodiments of the present invention relates to compounds of the formula Ia, including their N-oxides, stereoisomers, tautomers and their agriculturally or veterinarily acceptable salts:

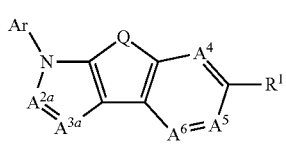

(Ia)

wherein:
$A^{2a}$ is N or $C(R^2)$; and
$A^{3a}$ is N or $C(R^7)$;
and wherein Q, $A^4$, $A^5$, $A^6$, $R^1$, $R^2$ and $R^7$ are as defined herein.

In a particular group of embodiments of the compounds of formula Ia, $A^{2a}$ is N and $A^{3a}$ is $C(R^7)$ (compounds of formula (I-aa).

In another particular group of embodiments of the compounds of formula Ia, $A^{2a}$ is $C(R^2)$ and $A^{3a}$ is N (compounds of formula (I-ab).

In a further particular group of embodiments of the compounds of formula Ia, $A^{2a}$ and $A^{3a}$ are both N (compounds of formula (I-ac).

A second particular group of embodiments of the present invention relates to compounds of the formula Ib, including their N-oxides, stereoisomers, tautomers and their agriculturally or veterinarily acceptable salts:

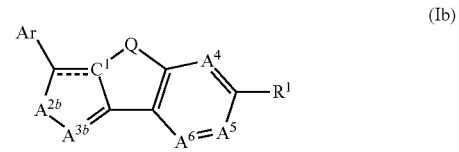

(Ib)

wherein:
$C^1$ is CH or C, provided that ---- indicates a single bond, if $C^1$ is CH or a double bond, if $C^1$ is C,
$A^{2b}$ is $N(R^3)$, O or S; and
A3b is N or $C(R^7)$;
provided that one or both of $A^{2b}$ and $A^{3b}$ are N or $N(R^3)$, respectively;
and wherein Q, $A^4$, $A^5$, $A^6$, $R^1$, $R^3$ and $R^7$ are as defined herein.

In a particular group of embodiments of the compounds of formula Ib, $C^1$ is C, $A^{2b}$ is O and $A^{3b}$ is $C(R^7)$ (compounds of formula I-ba).

In another particular group of embodiments of the compounds of formula Ib, $C^1$ is C, $A^{2b}$ is S and $A^{3b}$ is $C(R^7)$ (compounds of formula I-bb).

In a further particular group of embodiments of the compounds of formula Ib, $C^1$ is C, $A^{2b}$ is $N(R^3)$ and $A^{3b}$ is $C(R^7)$ (compounds of formula I-bc).

In yet a further particular group of embodiments of the compounds of formula Ib, $C^1$ is C, $A^{2b}$ is O and $A^{3b}$ is N (compounds of formula I-bd).

In yet a further particular group of embodiments of the compounds of formula Ib, $C^1$ is CH, $A^{2b}$ is O and $A^{3b}$ is N (compounds of formula I-be).

In yet a further particular group of embodiments of the compounds of formula Ib, $C^1$ is C, $A^{2b}$ is $N(R^3)$ and $A^{3b}$ is N (compounds of formula I-bf).

In yet a further particular group of embodiments of the compounds of formula Ib, $C^1$ is CH, $A^{2b}$ is $N(R^3)$ and $A^{3b}$ is N (compounds of formula I-bg).

In yet a further particular group of embodiments of the compounds of formula Ib, $C^1$ is C, $A^{2b}$ is S and $A^{3b}$ is N (compounds of formula I-bh).

In yet a further particular group of embodiments of the compounds of formula Ib, $C^1$ is CH, $A^{2b}$ is S and $A^{3b}$ is N (compounds of formula I-bi).

A third particular group of embodiments of the present invention relates to compounds of the formula Ic, including their N-oxides, stereoisomers, tautomers and their agriculturally or veterinarily acceptable salts:

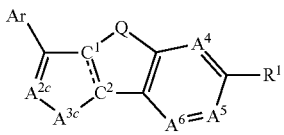

(Ic)

wherein
$C^1$ and $C^2$ are both CH or both C provided that ---- indicates a single bond, if $C^1$ and $C^2$ are CH, or a double bond, if C and $C^2$ are C,
$A^{2c}$ is N or $C(R^2)$; and
$A^{3c}$ is O, S, $N(R^6)$ or $C(R^8,R^9)$;
and wherein Ar, Q, $A^4$, $A^5$, $A^6$, $R^1$, $R^2$, $R^6$, $R^8$ and $R^9$ are as defined herein.

In a particular group of embodiments of the compounds of formula Ic, $C^1$ and $C^2$ are CH, $A^{2c}$ is N and $A^{3c}$ is $C(R^8,R^9)$ (compounds of formula I-ca).

In another particular group of embodiments of the compounds of formula Ic, $C^1$ and $C^2$ are CH, $A^{2c}$ is N and $A^{3c}$ is O (compounds of formula I-cb).

In a further particular group of embodiments of the compounds of formula Ic, $C^1$ and $C^2$ are CH, $A^{2c}$ is N and $A^{3c}$ is S (compounds of formula I-cc).

In yet a further particular group of embodiments of the compounds of formula Ic, C and $C^2$ are CH, $A^{2c}$ is N and $A^{3c}$ is $N(R^6)$ (compounds of formula I-cd).

In yet a further particular group of embodiments of the compounds of formula Ic, C and $C^2$ are C, $A^{2c}$ is N and $A^{3c}$ is O (compounds of formula I-ce).

In yet a further particular group of embodiments of the compounds of formula Ic, C and $C^2$ are C, $A^{2c}$ is N and $A^{3c}$ is S (compounds of formula I-cf).

In yet a further particular group of embodiments of the compounds of formula Ic, C and $C^2$ are C, $A^{2c}$ is N and $A^{3c}$ is $N(R^6)$ (compounds of formula I-cg).

A fourth particular group of embodiments of the present invention relates to compounds of the formula Id, including their N-oxides, stereoisomers, tautomers and their agriculturally or veterinarily acceptable salts:

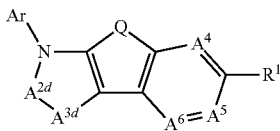

(Id)

where in formula Id
$A^{2d}$ is $N(R^3)$, O, S or $C(R^4,R^5)$; and
$A^{3d}$ is O, S, $N(R^6)$ or $C(R^8,R^9)$;
provided that at least one of $A^{2d}$ and $A^{3d}$ is different from O and S and that the bond between $A^{2d}$ and $A^{3d}$ is a single bond;
and wherein k, Ar, Q, $A^4$, $A^5$, $A^6$, $R^1$, $R^3$, $R^4$, $R^5$, $R^6$, $R^8$ and $R^9$ are as defined herein.

In a particular group of embodiments of the compounds of formula Id, $A^{2d}$ is $C(R^4,R^5)$, in particular $CH_2$, C=O or C=S and $A^{3d}$ is O (compounds of formula I-da).

In another particular group of embodiments of the compounds of formula Id, $A^{2d}$ is $C(R^4,R^5)$, in particular $CH_2$, C=O or C=S and $A^{3d}$ is S (compounds of formula I-db).

In a further particular group of embodiments of the compounds of formula Id, $A^{2d}$ is $C(R^4,R^5)$, in particular $CH_2$, C=O or C=S and $A^{3d}$ is $N(R^6)$ (compounds of formula I-dc).

Particular preference is given to the compounds of the formula Ia, where either $A^{2a}$ is N and $A^{3a}$ is $C(R^7)$ or $A^{2a}$ is $C(R^2)$ and $A^{3a}$ is N, or an N-oxide, stereoisomer or agriculturally or veterinarily acceptable salt thereof.

Particular preference is given to the compounds of the formula Ib, where either $C^1$ is C, $A^{2b}$ is $N(R^3)$, and A3b is N, or an N-oxide, stereoisomer or agriculturally or veterinarily acceptable salt thereof.

Irrespectively of their occurrence, in particular in context with formulae Ia, Ib, Ic and Id but also in context with formula INT the variables $R^2$, $R^3$, $R^4$, $R^5$, $R^6$, $R^7$, $R^8$ and $R^9$ have in particular the following meanings:

$R^2$ is in particular hydrogen, halogen, such as F or Cl, $C_1$-$C_4$-alkyl, such as $CH_3$, $C_2H_5$, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, especially hydrogen.

$R^3$ is in particular $C_1$-$C_4$-alkyl, such as $CH_3$, $C_2H_5$, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, and especially $C_1$-$C_4$-alkyl.

$R^4$, $R^5$ independently of each other are in particular hydrogen, halogen, such as F or Cl, $C_1$-$C_4$-alkyl, such as $CH_3$, $C_2H_5$, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, or $C(R^4,R^5)$ forms a carbonyl (C=O) or thiocarbonyl (C=S), especially $R^4$, $R^5$ are hydrogen or $C(R^4,R^5)$ forms a carbonyl (C=O) or thiocarbonyl (C=S).

$R^6$ is in particular $C_1$-$C_4$-alkyl, such as $CH_3$, $C_2H_5$, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, and especially $C_1$-$C_4$-alkyl.

$R^7$ is in particular hydrogen, halogen, such as F or Cl, $C_1$-$C_4$-alkyl, such as $CH_3$, $C_2H_5$, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, especially hydrogen.

$R^8$, $R^9$ independently of each other are in particular hydrogen, halogen, such as F or Cl, $C_1$-$C_4$-alkyl, such as $CH_3$, $C_2H_5$, n-propyl or isopropyl, $C_1$-$C_4$-haloalkyl, such as fluoromethyl, difluoromethyl or trifluoromethyl, $C_1$-$C_4$-alkoxy, such as methoxy or ethoxy, or $C_1$-$C_4$-haloalkoxy, such as fluoromethoxy, difluoromethoxy or trifluoromethoxy, or $C(R^8,R^9)$ forms a carbonyl (C=O) or thiocarbonyl (C=S), especially $R^8$, $R^9$ are hydrogen or $C(R^8,R^9)$ forms a carbonyl (C=O) or thiocarbonyl (C=S).

Irrespectively of their occurrence, in particular in context with formulae I, Ia, Ib, Ic and Id, and also in context with formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, but also in context with formula INT the variable R is preferably selected from the group consisting of hydrogen, halogen such as F, Cl or Br, CN, $NO_2$, SCN, $C_1$-$C_6$-alkyl, in particular $C_1$-$C_3$-alkyl such as $CH_3$, $C_2H_5$, n-propyl or isopropyl, $C_1$-$C_6$-haloalkyl, in particular fluorinated $C_1$-$C_3$- alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl. R is in particular hydrogen, F, Cl, $C_1$-$C_3$-alkyl such as $CH_3$, $C_2H_5$, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$. Especially, R is hydrogen. If two radicals R are present, they may be identical or different.

A particular group of embodiments relates to compounds of the formula I and also to compounds of the formulae Ia, Ib, Ic and Id, and also to compounds formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, wherein $A^4$ is N, while $A^5$ is CH and $A^6$ is CH.

Another particular group of embodiments relates to compounds of the formula I and also to compounds of the formulae Ia, Ib, Ic and Id, and also to compounds formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, wherein $A^5$ is N, while $A^4$ is CH and $A^6$ is CH.

A further particular group of embodiments relates to compounds of the formula I and also to compounds of the formulae Ia, Ib, Ic and Id, and also to compounds formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, wherein $A^6$ is N, while $A^4$ is CH and $A^5$ is CH.

A further particular group of embodiments relates to compounds of the formula I and also to compounds of the formulae Ia, Ib, Ic and Id, and also to compounds formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, wherein $A^4$ is N, $A^5$ is N and $A^6$ is CH A further particular group of embodiments relates to compounds of the formula I and also to compounds of the formulae Ia, Ib, Ic and Id, and also to compounds formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, wherein $A^4$ is N, $A^6$ is N and $A^5$ is CH.

A further particular group of embodiments relates to compounds of the formula I and also to compounds of the formulae Ia, Ib, Ic and Id, and also to compounds formulae I-aa, I-ab, I-ac, I-ba, I-bb, I-bc, I-bd, I-be, Ibf, I-bg, I-bi, I-bk, I-ca, I-cb, I-cc, I-cd, I-ce, I-cf, I-cg, I-da, I-db and I-dc, wherein $A^5$ is N, $A^6$ is N and $A^4$ is CH.

Particular groups of embodiments relate to compounds of the formulae I, Ia, Ib, Ic and Id, including their N-oxides, stereoisomers, tautomers and their agriculturally or veterinarily acceptable salts, wherein Q is —O—, —S—, N($R^{Q1}$), —C($R^{Q2a}R^{Q2b}$)—, —N($R^{Q2}$)—C(=O)—, —N($R^{Q2}$)—C(=S)—, —C($R^{Q3}$)=C($R^{Q4}$)—, —C($R^{Q3a}R^{Q3b}$)—C($R^{Q4a}R^{Q4b}$)—, —N=C($R^{Q3c}$)—, —S(=O)$_2$—N($R^{Q2}$)—, —O—C($R^{Q4a}R^{Q4b}$)—, —S(=O)$_n$—C($R^{Q4a}R^{Q4b}$)— or —N($R^{Q2}$)—C($R^{Q4a}R^{Q4b}$)—, where $R^{Q2}$, $R^{Q3}$, $R^{Q3a}$, $R^{Q3b}$, $R^{Q3c}$, $R^{Q4}$, $R^{Q4a}$ and $R^{Q4b}$ are as defined herein and where, $R^{Q2}$ is in particular hydrogen, $C_1$-$C_4$-alkyl, such as $CH_3$, $C_2H_5$, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, and especially hydrogen or $CH_3$;

$R^{Q3}$ is in particular hydrogen, Cl, F, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q4}$ is in particular hydrogen, Cl, F, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q2a}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q2b}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q3a}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q3b}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q3c}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q4a}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q4b}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen.

Particular groups of embodiments relate to compounds of the formulae I, INT, Ia, Ib, Ic and Id, including their N-oxides, stereoisomers, tautomers and their agriculturally or veterinarily acceptable salts, wherein Q is —O—, —S—, —C($R^{Q2a}R^{Q2b}$)—, —C($R^{Q3}$)=C($R^{Q4}$)—, —C($R^{Q3a}R^{Q3b}$)—C($R^{Q4a}R^{Q4b}$)—, —O—C($R^{Q4a}R^{Q4b}$)—, —S(=O)$_n$—C($R^{Q4a}R^{Q4b}$)—, —N($R^{Q2}$)—C(=O)—, —N($R^{Q2}$)—C($R^{Q4a}R^{Q4b}$)—, —N($R^{Q2}$)—C(=S)— or —N($R^{Q2}$)—S(=O)$_2$—, where $R^{Q2}$, $R^{Q3}$, $R^{Q2a}$, $R^{Q2b}$, $R^{Q3a}$, $R^{Q3b}$, $R^{Q4}$, $R^{Q4a}$ and $R^{Q4b}$ are as defined herein and where, $R^{Q3}$ is in particular hydrogen, Cl, F, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q4}$ is in particular hydrogen, Cl, F, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q2a}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q2b}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q3a}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q3b}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q4a}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen;

$R^{Q4b}$ is in particular hydrogen, $C_1$-$C_4$-alkyl, such as $CH_3$ or $C_2H_5$, or $C_1$-$C_4$-haloalkyl, such as fluoromethyl, difluoromethyl or trifluoromethyl, and especially hydrogen.

Particular preferred groups of embodiments relate to compounds of the formulae I, INT, Ia, Ib, Ic and Id, including their N-oxides, stereoisomers, tautomers and their agriculturally or veterinarily acceptable salts, wherein Q is selected from the group consisting of O, S, —CH$_2$—, —N(R$^{Q1}$)—, —CH=CH—, —CH$_2$CH$_2$—, —N=CH—, O—CH$_2$, —S—CH$_2$, —S(=O)—CH$_2$—, —S(=O)$_2$—CH$_2$—, —N(R$^{Q2}$)—C(=O)—, —N(R$^{Q2}$)—C(=S)—, —N(R$^{Q2}$)—S(=O)$_2$— and —N(R$^{Q2}$)—CH$_2$—, where R$^{Q2}$ is as defined herein.

Especially preferred groups of embodiments relate to compounds of the formulae I, Ia, Ib, Ic and Id, including their N-oxides, stereoisomers, tautomers and their agriculturally or veterinarily acceptable salts, wherein Q is selected from the group consisting of O, S, —CH$_2$—, —CH=CH—, —CH$_2$CH$_2$—, —O—CH$_2$—, —S—CH$_2$—, —S(=O)—CH$_2$—, —S(=O)$_2$—CH$_2$—, —N(R')—C(=O)—, —N(R')—S(=O)$_2$— and —N(R')—CH$_2$—, wherein R' is hydrogen or methyl.

A particular group of embodiments relates to the compounds of formulae Ia.1 to Ia.96 as described below, to their N-oxides, their stereoisomers, their tautomers and to the agriculturally or veterinarily acceptable salt thereof. In formulae Ia.1 to Ia.96 Ar, R$^1$ and R$^{Q2}$ are as defined above and hereinafter and R$^{Q2}$ is in particular hydrogen, C$_1$-C$_4$-alkyl, such as CH$_3$, C$_2$H$_5$, n-propyl or isopropyl, C$_3$-C$_6$-cycloalkyl such as cyclopropyl, cyclobutyl, or cyclohexyl, C$_3$-C$_6$-cycloalkymethyl, such as cyclopropylmethyl, cyclobutylmethyl or cyclopentylmethyl, or benzyl, especially hydrogen or methyl.

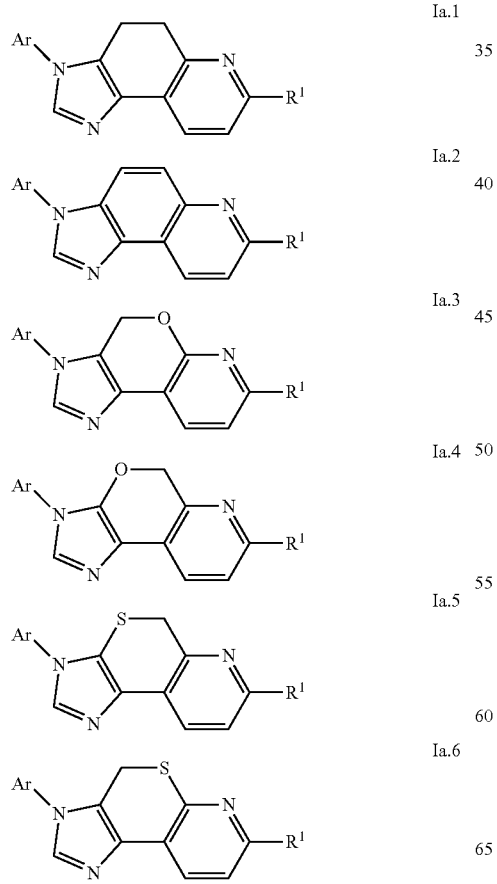

Ia.1
Ia.2
Ia.3
Ia.4
Ia.5
Ia.6

-continued

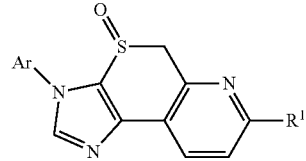

Ia.7

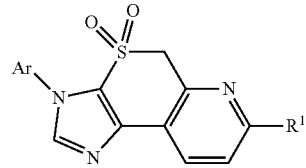

Ia.8

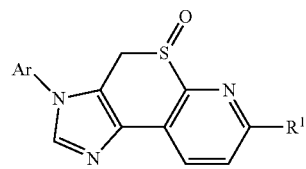

Ia.9

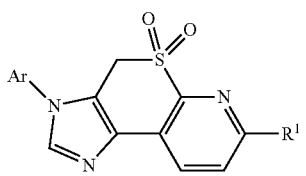

Ia.10

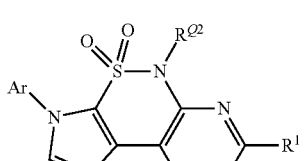

Ia.11

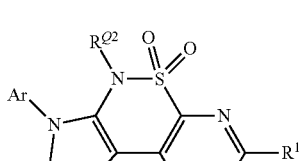

Ia.12

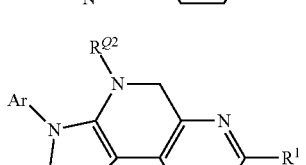

Ia.13

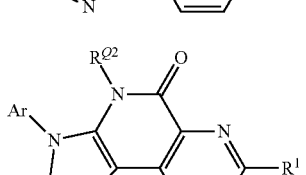

Ia.14

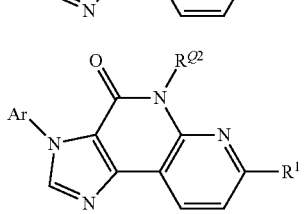

Ia.15

-continued

Ia.16

Ia.17

Ia.18

Ia.19

Ia.20

Ia.21

Ia.22

Ia.23

Ia.24

Ia.25

-continued

Ia.26

Ia.27

Ia.28

Ia.29

Ia.30

Ia.31

Ia.32

Ia.33

Ia.34

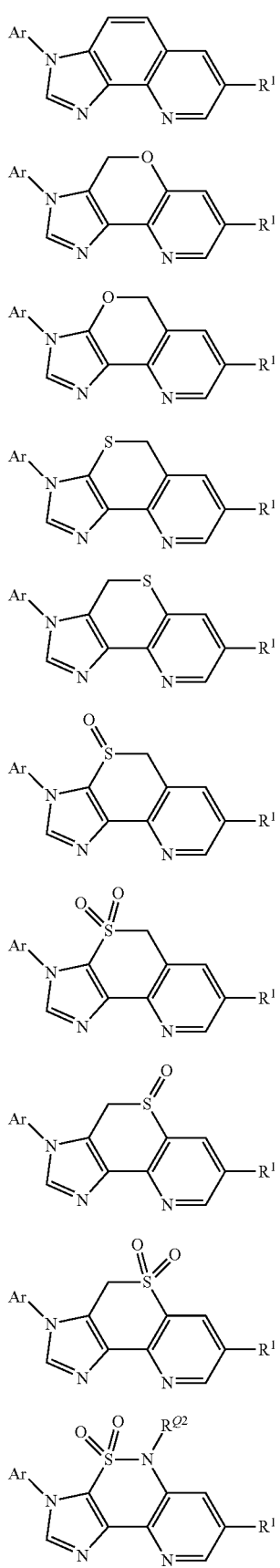
Ia.35
Ia.36
Ia.37
Ia.38
Ia.39
Ia.40
Ia.41
Ia.42
Ia.43
Ia.44
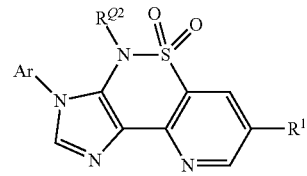
Ia.45
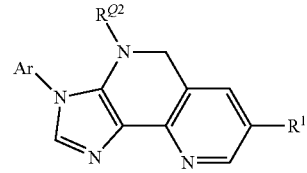
Ia.46
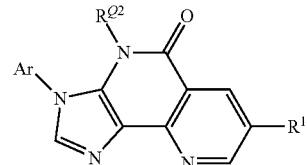
Ia.47
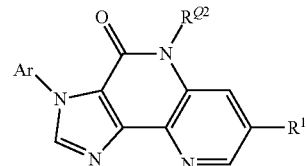
Ia.48
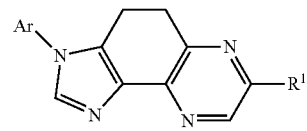
Ia.49
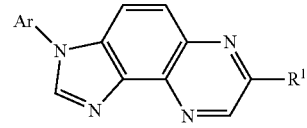
Ia.50
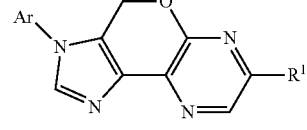
Ia.51
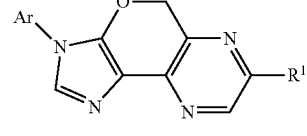
Ia.52
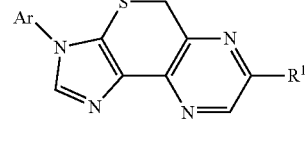
Ia.53
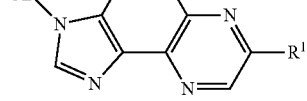
Ia.54

-continued

-continued

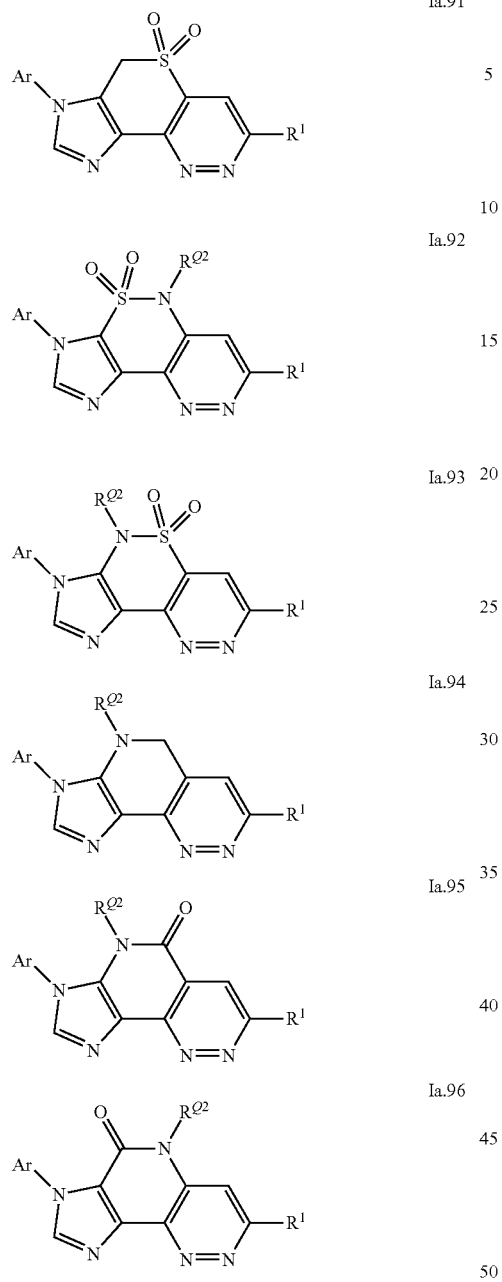

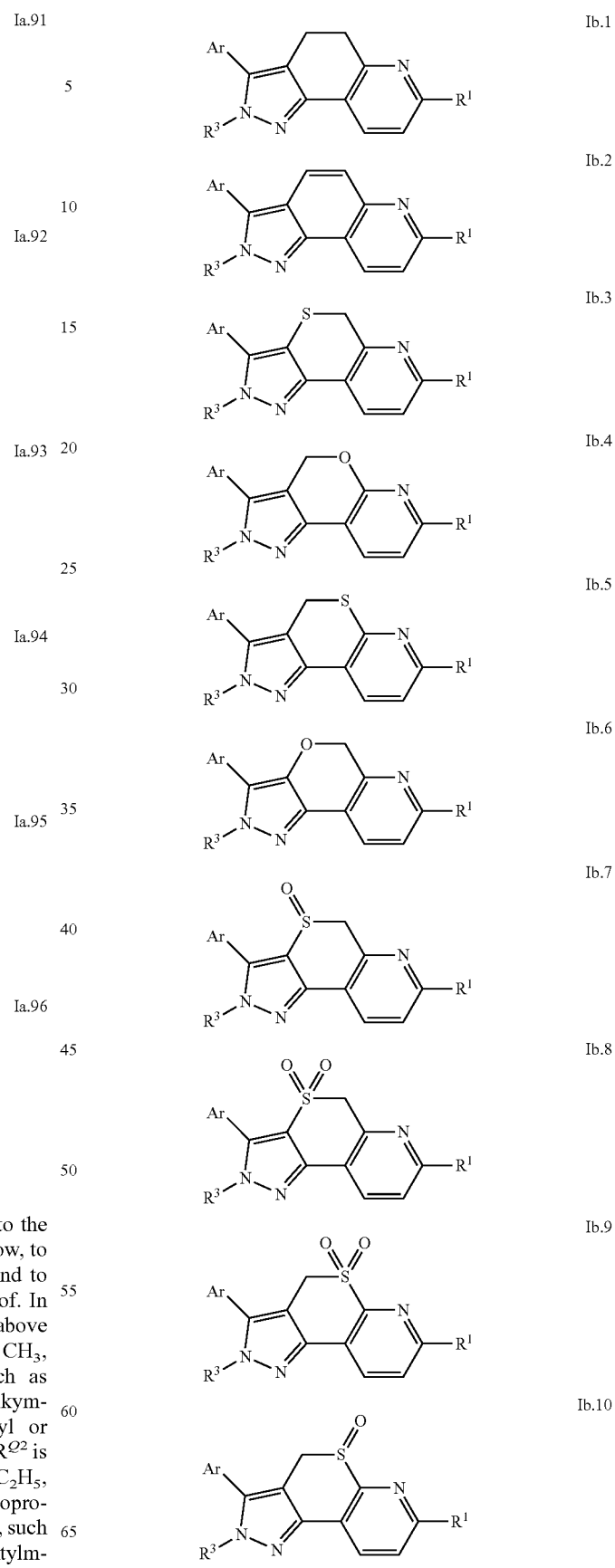

A further particular group of embodiments relates to the compounds of formulae Ib.1 to Ib.96 as described below, to their N-oxides, their stereoisomers, their tautomers and to the agriculturally or veterinarily acceptable salt thereof. In formulae Ib.1 to Ib.96 Ar, $Q^2$, $R^1$ and $R^3$ are as defined above and hereinafter. $R^3$ is in particular $C_1$-$C_4$-alkyl, such as $CH_3$, $C_2H_5$, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially $C_1$-$C_4$-alkyl. $R^{Q2}$ is in particular hydrogen, $C_1$-$C_4$-alkyl, such as $CH_3$, $C_2H_5$, n-propyl or isopropyl, $C_3$-$C_6$-cycloalkyl such as cyclopropyl, cyclobutyl, or cyclohexyl, $C_3$-$C_6$-cycloalkymethyl, such as cyclopropylmethyl, cyclobutylmethyl or cyclopentylmethyl, or benzyl, especially hydrogen or methyl.

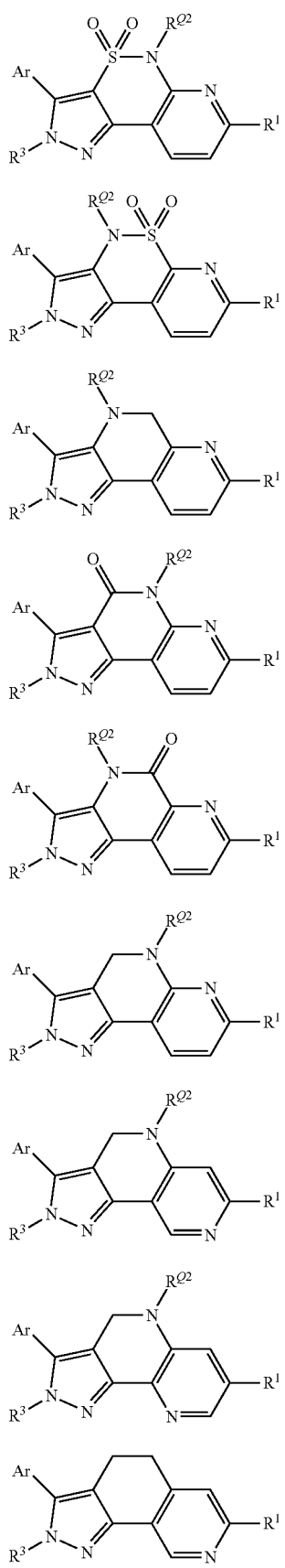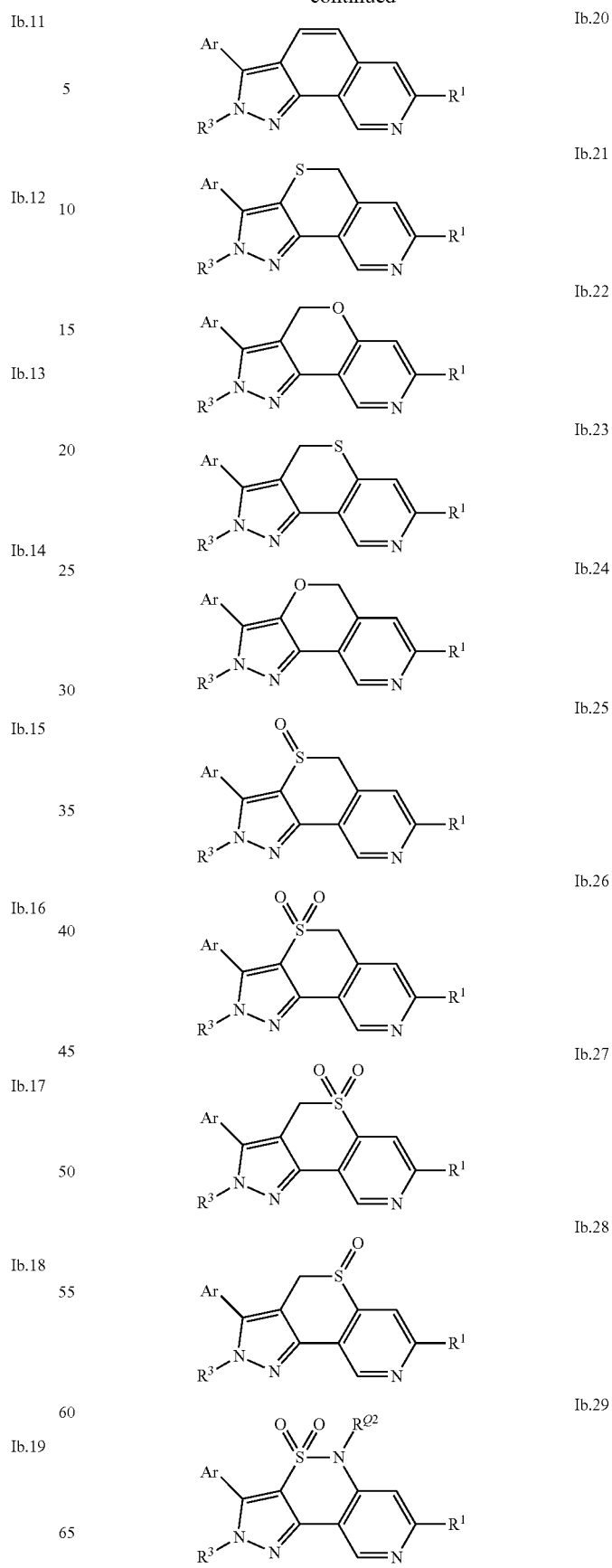

-continued
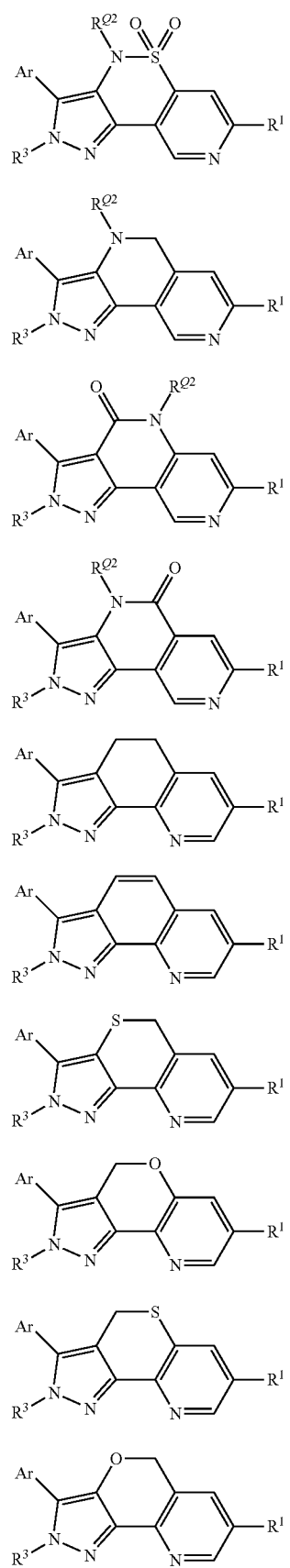
Ib.30
Ib.31
Ib.32
Ib.33
Ib.34
Ib.35
Ib.36
Ib.37
Ib.38
Ib.39
-continued
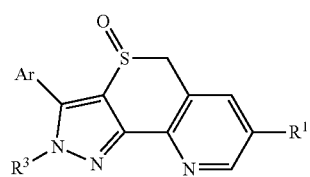
Ib.40
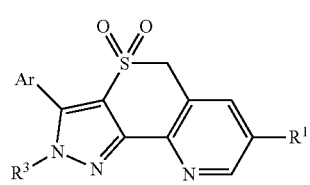
Ib.41
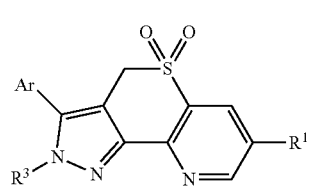
Ib.42
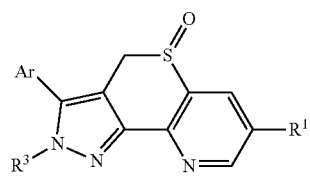
Ib.43
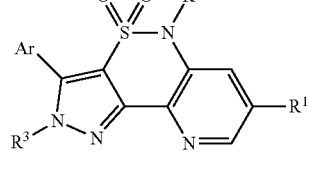
Ib.44
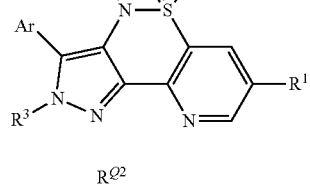
Ib.45
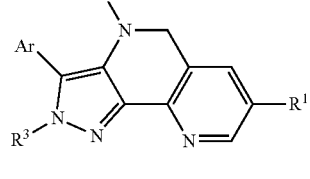
Ib.46
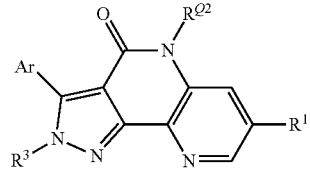
Ib.47

-continued

-continued
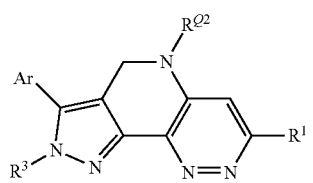
Ib.66
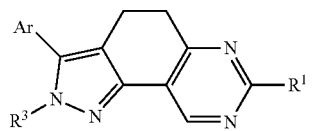
Ib.67
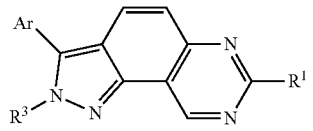
Ib.68
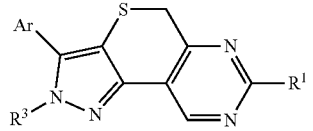
Ib.69
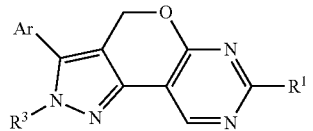
Ib.67
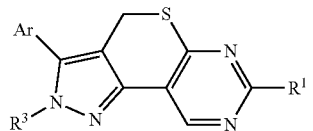
Ib.68
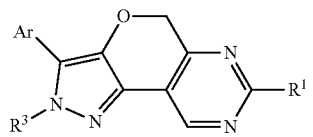
Ib.69
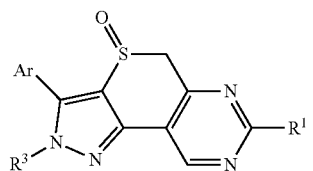
Ib.73
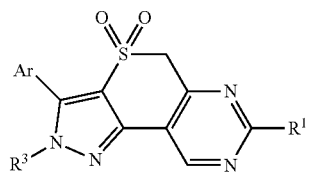
Ib.74
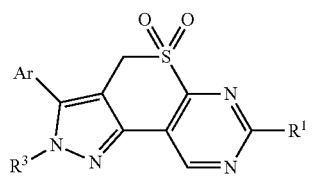
Ib.75
-continued
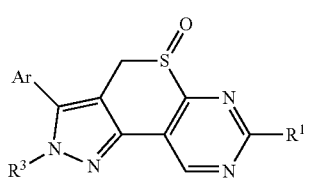
Ib.76
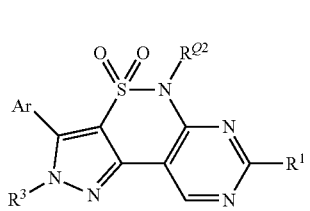
Ib.77
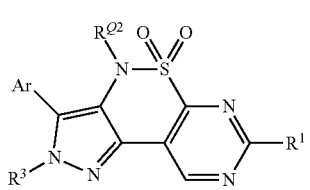
Ib.78
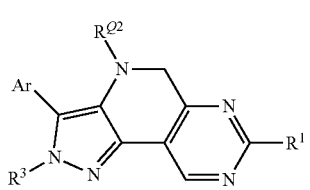
Ib.79
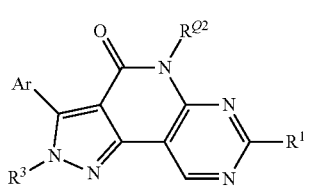
Ib.80
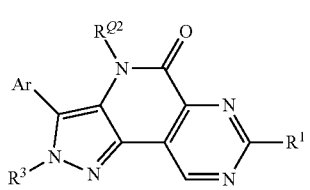
Ib.81
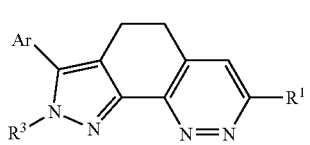
Ib.82
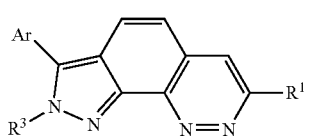
Ib.83
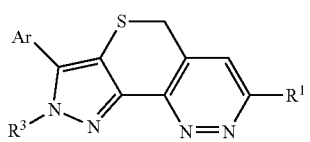
Ib.84

Ib.85 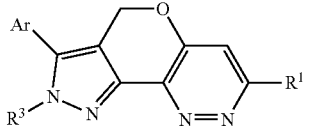

Ib.86 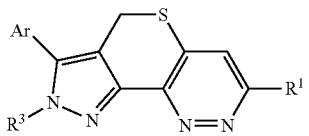

Ib.87 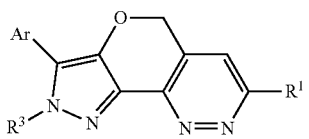

Ib.88 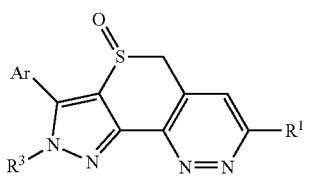

Ib.89 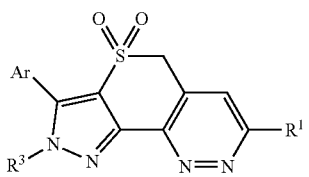

Ib.90 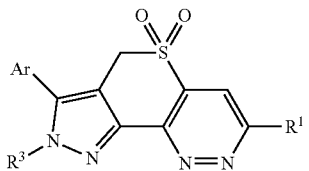

Ib.91 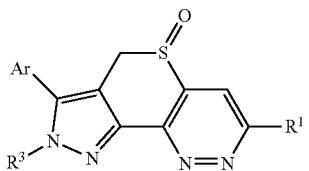

Ib.92 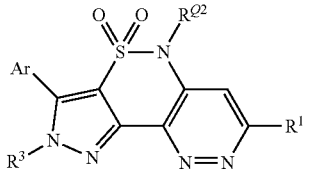

Ib.93 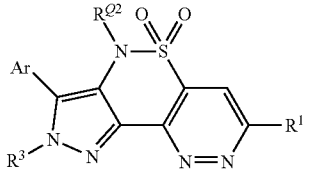

Ib.94 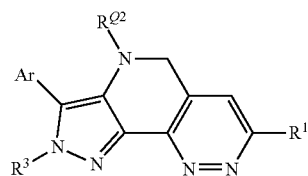

Ib.95 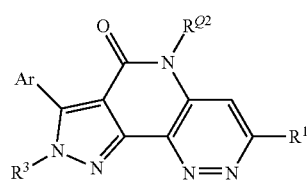

Ib.96 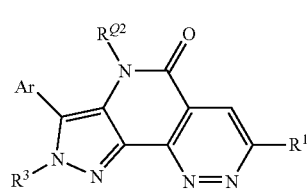

Amongst formulae Ia.1 to Ia.96 particular preference is given to the following formulae Ia.1, Ia.2, Ia.19, Ia.20, Ia.34, Ia.35, Ia.49, Ia.50, Ia.67, Ia.68, Ia.82 and Ia.83.

Amongst formulae Ib.1 to Ib.96 particular preference is given to the following formulae: Ib.1, Ib.2, Ib.19, Ib.20, Ib.34, Ib.35, Ib.49, Ib.50, Ib.67, Ib.68, Ib.82 and Ib.83.

In formula I as well as in formulae Ia, I-aa to I-ad, Ia.1 to Ia.96, Ib, I-ba to I-bi, Ib.1 to Ib.96, Ic, I-ca to I-cg, I.d and I-da to I-dc, the radical Ar is in particular selected from the group consisting of phenyl, pyrimidinyl, pyridazinyl and pyridyl, which are unsubstituted or carry 1, 2 or 3 radicals $R^{Ar}$. $R^{Ar}$ is in particular selected from the group consisting of halogen, such as F, Cl or Br, OH, CN, $NO_2$, SCN, $C_1$-$C_6$-alkyl, in particular $C_1$-$C_3$-alkyl such as $CH_3$, $C_2H_5$, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as $CH_3$, $C_2H_5$, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$.

In formula I as well as in formulae Ia, I-aa to I-ad, Ia.1 to Ia.96, Ib, I-ba to I-bi, Ib.1 to Ib.96, Ic, I-ca to I-cg, I.d and I-da to I-dc, Ar is especially selected from the group consisting of phenyl, which carries one radical $R^{Ar}$ in the 4-position, 3-pyridyl and 3-pyridazinyl, which carry one radical $R^{Ar}$ in the 6-position and where phenyl, 3-pyridyl and 3-pyridazinyl may carry 1 or 2 further radicals $R^{Ar}$. In this context, $R^{Ar}$ is in particular selected from the group consisting of halogen, such as F, Cl or Br, $C_1$-$C_6$-alkyl, in particular $C_1$-$C_3$-alkyl such as $CH_3$, $C_2H_5$, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as $CH_3$, $C_2H_5$, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF_2CF_3$. In this context, the radical $R^{Ar}$ in the 4-position of phenyl is preferably selected from the group consisting of $C_1$-$C_4$-haloalkyl, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$; $C_1$-$C_4$-haloalkoxy, especially fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_4$-haloalkyl, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$. In this context, the radical $R^{Ar}$ in the 6-position of 3-pyridyl or 3-pyridazinyl is preferably selected from the group consisting of $C_1$-$C_4$-haloalkyl, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$; $C_1$-$C_4$-haloalkoxy, especially fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_4$-haloalky, especially fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$.

The further 1 or 2 radicals $R^{Ar}$, if present, are preferably selected from the group consisting of halogen, such as F, Cl or Br, $C_1$-$C_3$-alkyl such as $CH_3$, $C_2H_5$, n-propyl or isopropyl, fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_3$-alkoxy such as methoxy, ethoxy, n-propyloxy or isopropyloxy, and fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, Examples of particularly preferred radicals Ar are the radicals Ar-1 to Ar-9 summarized in Table A below.

TABLE A

| Examples of radicals Ar | |
| --- | --- |
| Ar-1 | 4-trifluoromethylphenyl |
| Ar-2 | 4-trifluoromethoxyphenyl |
| Ar-3 | 4-(pentafluoroethoxy)phenyl |
| Ar-4 | 4-(trifluoromethylthio)phenyl |
| Ar-5 | 6-trifluoro-3-pyridyl |
| Ar-6 | 6-trifluoromethoxy-3-pyridyl |
| Ar-7 | 6-(pentafluoroethoxy)-3-pyridyl |
| Ar-8 | 6-(trifluoromethylthio)-3-pyridyl |
| Ar-9 | 6-(trifluoromethylthio)-3-pyridazinyl |
| Ar-10 | 6-trifluoromethyl-3-pyridazinyl |
| Ar-11 | 4-difluoromethoxyphenyl |

In a first particular group (1) of embodiments, the radical $R^1$ in formula I as well as in formulae Ia, I-aa to I-ad, Ia.1 to Ia.96, Ib, I-ba to I-bi, Ib.1 to Ib.96, Ic, I-ca to I-cg, I.d and I-da to I-dc, is a moiety of the formula -T-$X^2$—Y—$Z^2$—$R^{12}$.

In this group (1) of embodiments, T is preferably selected from the group consisting of $CHR^{xa}$, $CH(R^{xa})CH(R^{xa})$ and cyclopropane-1,2-diyl. In this context $R^{xa}$, independently of each other, preferably are selected from the group consisting of hydrogen and $C_1$-$C_4$-alkyl, in particular from the group consisting of hydrogen and methyl. In this context, $R^{xa}$ is especially hydrogen. In this group (1) of embodiments, T is in particular selected from the group consisting of a single bond, $CH_2$, $CH_2CH_2$ and 1,2-cycloprandiyl. In this group (1) of embodiments, T is especially a single bond.

In this group (1) of embodiments, $X^2$ is preferably selected from the group consisting of —N($R^{x2}$)—C(=O)—, —N($R^{x2}$)—C(=S)— and —C($R^{x3}$)=N—.

In the context of group (1) of embodiments $R^{x2}$ is preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{x2}$ is in particular hydrogen or $C_1$-$C_4$-alkyl, especially hydrogen.

In the context of group (1) of embodiments $R^{x3}$ is preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, where the alkyl, cycloalkyl and alkoxy parts of the last 3 mentioned radicals are unsubstituted or partially or completely halogenated, and phenyl, where the phenyl ring is unsubstituted or carries 1, 2 or 3 radicals $R^f$. In this context $R^{x3}$ is in particular hydrogen or $C_1$-$C_4$-alkyl, especially hydrogen.

Especially, $X^2$ is —NH—C(=O)— or —CH=N—.

In this group (1) of embodiments, Y is preferably a single bond.

In this group (1) of embodiments, $Z^2$ is preferably O.

In this group (1) of embodiments the moiety of the formula -T-$X^2$—Y—$Z^2$— is preferably a group of the formulae XYZ-1 or XYZ-2:

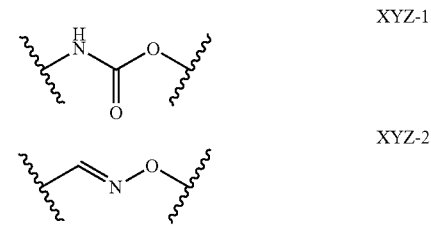

XYZ-1

XYZ-2

In this group (1) of embodiments, $R^{12}$ is a radical of the formula (A),

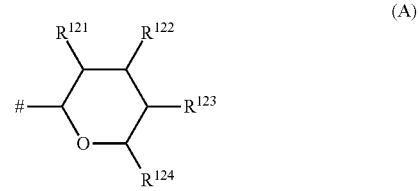

(A)

wherein # indicates the point of attachment to $Z^2$ and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular methoxy or ethoxy;

$R^{122}$ is $C_1$-$C_4$-alkoxy, such as methoxy or ethoxy, or $C_3$-$C_4$-alkenyloxy, such as allyloxy, with $R^{122}$ in particular being methoxy or ethoxy;

$R^{123}$ is OH, $C_1$-$C_4$-alkoxy, such as methoxy or ethoxy, or $C_3$-$C_4$-alkenyloxy, such as allyloxy, with $R^{123}$ in particular being methoxy or ethoxy;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

In this group (1) of embodiments, $R^{12}$ is in particular a radical of the formula (A'), e.g. (A'-a) or (A'-b)

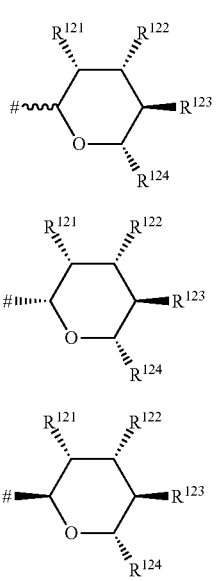

wherein # indicates the point of attachment to $Z^2$ and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular methoxy or ethoxy;

$R^{122}$ is $C_1$-$C_4$-alkoxy, such as methoxy, ethoxy, n-propoxyx or isopropoxy, or $C_3$-$C_4$-alkenyloxy, such as allyloxy, with $R^{122}$ in particular being methoxy, ethoxy or n-propoxy;

$R^{123}$ is OH, $C_1$-$C_4$-alkoxy, such as methoxy or ethoxy, or $C_3$-$C_4$-alkenyloxy, such as allyloxy, with $R^{123}$ in particular being methoxy or ethoxy;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

Particular examples of radicals $R^{12}$ are the following radicals A'-1, A'-1a, A'-1b, A'-2, A'-2a, A'-2b, A'-3, A'-3a and A'-3b:

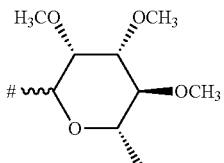

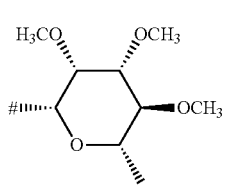

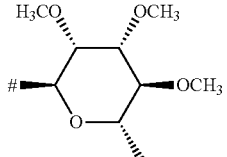

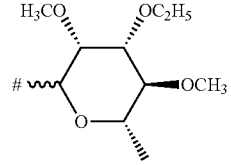

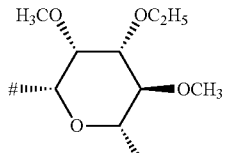

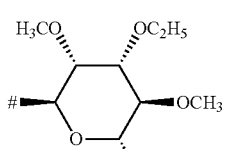

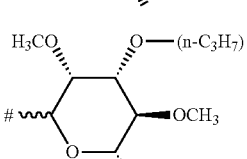

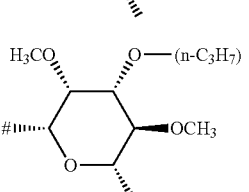

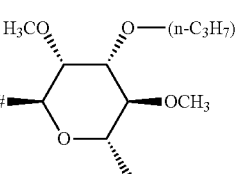

In a second particular group (2) of embodiments, the radical $R^1$ in formula I as well as in formulae Ia, I-aa to I-ad, Ia.1 to Ia.96, Ib, I-ba to I-bi, Ib.1 to Ib.96, Ic, I-ca to I-cg, I.d and I-da to I-dc, is a moiety of the formula -T-$X^1$—Y—$Z^1$—$R^{11}$.

In this group (2) of embodiments, T is preferably selected from the group consisting of $CHR^{xa}$, $CH(R^{xa})CH(R^{xa})$ and cyclopropane-1,2-diyl. In this context $R^{xa}$, independently of each other, preferably are selected from the group consisting of hydrogen and $C_1$-$C_4$-alkyl, in particular from the group consisting of hydrogen and methyl. In this context, $R^{xa}$ is especially hydrogen. In this group (2) of embodiments, T is in particular selected from the group consisting of a single bond, $CH_2$, $CH_2CH_2$ and 1,2-cycloprandiyl.

In this group (2) of embodiments, $X^1$ is is preferably selected from the group consisting of —N($R^{x2}$)—C(=O)—, —N($R^{x2}$)—C(=S)— and —C($R^{x3}$)=N—.

In the context of group (2) of embodiments $R^{x2}$ is preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{x2}$ is in particular hydrogen or $C_1$-$C_4$-alkyl, especially hydrogen.

In the context of group (2) of embodiments $R^{x3}$ is preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, where the alkyl, cycloalkyl and alkoxy parts of the last 3 mentioned radicals are unsubstituted or partially or completely halogenated, and phenyl, where the phenyl ring is unsubstituted or carries 1, 2 or 3 radicals $R^f$. In this context $R^{x3}$ is in particular hydrogen or $C_1$-$C_4$-alkyl, especially hydrogen.

In this group (2) of embodiments, $X^1$ is especially —NH—C(=O)—, —NH—C(=S)— or —CH=N—.

In this group (2) of embodiments, Y is preferably selected from the group consisting of a single bond, —N($R^{y1}$)—C(=O)—, —N($R^{y2}$)—C(=S)—, —N=C(O—$R^{y3}$)— and —N=C(S—$R^{y3}$)—.

In the context of group (2) of embodiments $R^{y1}$, $R^{y2}$, independently of each other, are preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{y1}$, $R^{y2}$ are in particular hydrogen or $C_1$-$C_4$-alkyl, especially hydrogen.

In the context of group (2) of embodiments $R^{y3}$ is preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{y3}$ is in particular hydrogen or $C_1$-$C_4$-alkyl, especially hydrogen.

In this group (2) of embodiments, Y is especially selected from the group consisting of a single bond, —NH—C(=O)—, —NH—C(=S)—, —N=C(O—$R^{y3}$)— and —N=C(S—$R^{y3}$)—.

In this group (2) of embodiments, $Z^1$ is preferably selected from the group consisting of O and —N—$R^{z1}$.

In the context of group (2) of embodiments $R^{z1}$ is preferably selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{z1}$ is in particular hydrogen or $C_1$-$C_4$-alkyl, especially hydrogen.

In the context of group (2) of embodiments, $R^{z1}$ together with $R^{y3}$, if present, may also form a linear $C_1$-$C_4$-alkylene group, such as $CH_2$, $CH_2CH_2$ or $CH_2CH_2CH_2$ or a linear $C_2$-$C_4$-alkenylene group, such as CH=CH or $CH_2$—CH=CH, where in the alkylene and alkenylene groups a $CH_2$ moiety may be replaced by a carbonyl group or a group =N—R' and/or wherein the alkylene group and the alkenylene group may be substituted by 1, 2, 3 or 4 radicals $R^{hh}$ which are preferably OH or $C_1$-$C_3$-alkyl such as $CH_3$, $C_2H_5$, or n-propyl. In this context R' is preferably selected from hydrogen, CN and $C_1$-$C_4$-alkyl.

In a particular subgroup (2a) of group (2) of embodiments, $Z^1$ may in particular also form a bivalent moiety of the formula C($R^{z3}$)=C(S—$R^{z4}$)—N($R^{z5}$). In the context of this subgroup (2a) of embodiments $R^{z3}$, $R^{z4}$ and $R^{z5}$ are as defined above and have in particular the following meanings:

$R^{z3}$ is selected from the group consisting of hydrogen, halogen, such as F or Cl, CN, $C_1$-$C_6$-alkyl and $C_1$-$C_6$-haloalkyl, more preferably from the group consisting of hydrogen, F, Cl, CN and $CH_3$ and especially hydrogen or CN;

$R^{z4}$ is selected from the group consisting of hydrogen, $C_1$-$C_6$-alkyl and $C_1$-$C_6$-haloalkyl, more preferably from the group consisting of $C_1$-$C_4$-alkyl and $C_1$-$C_4$-haloalkyl, especially $CH_3$, $C_2H_5$, or trifluoromethyl;

$R^{z5}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{z5}$ is in particular hydrogen or $C_1$-$C_4$-alkyl, especially hydrogen.

In the context of subgroup (2a) of embodiments, $R^{z4}$ together with $R^{z5}$ may also form a linear $C_1$-$C_4$-alkylene group, such as $CH_2$, $CH_2CH_2$ or $CH_2CH_2CH_2$ or a linear $C_2$-$C_4$-alkenylene group, such as CH=CH or $CH_2$—CH=CH, where in the alkylene and alkenylene groups a $CH_2$ moiety may be replaced by a carbonyl group or a group =N—R' and/or wherein the alkylene group and the alkenylene group may be substituted by 1, 2, 3 or 4 radicals $R^{hh}$ which are preferably OH, halogen or $C_1$-$C_3$-alkyl such as $CH_3$, $C_2H_5$, or n-propyl. In this context R' is preferably selected from hydrogen, CN and $C_1$-$C_4$-alkyl.

In another particular subgroup (2b) of group (2) of embodiments, Y—$Z^1$ may in particular also form a bivalent moiety of the formula N($R^{y4}$)—C(S—$R^{z6}$)=N, O—N($R^{y4}$)—C(S—$R^{z6}$)=N and N($R^{y44}$)—N($R^{y4}$)—C(S—$R^{z6}$)=N, where in these bivalent radicals $R^{11}$ is bound to the imino nitrogen atom. In the context of this subgroup (2b) of embodiments $R^{y4}$, $R^{y44}$, and $R^{z6}$ are as defined above and have in particular the following meanings:

$R^{y4}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{y4}$ is in particular hydrogen or $C_1$-$C_4$-alkyl, especially hydrogen.

$R^{y44}$ is selected from the group consisting of hydrogen, $C_1$-$C_6$-alkyl, $C_1$-$C_6$-haloalkyl and benzyl, where the phenyl ring in benzyl is unsubstituted or carry 1, 2 or 3 radicals $R^f$. In this context $R^{y44}$ is in particular hydrogen or $C_1$-$C_4$-alkyl, especially hydrogen.

$R^{z6}$ is selected from the group consisting of $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, where the alkyl, cycloalkyl parts of the last two mentioned radicals are unsubstituted or partially or completely halogenated, phenyl and benzyl, where the phenyl ring in the last 2 radicals is unsubstituted or carry 1, 2 or 3 radicals $R^f$. In this context $R^{z6}$ is in particular $C_1$-$C_4$-alkyl or $C_1$-$C_4$-haloalkyl, especially $CH_3$, $C_2H_5$, or trifluoromethyl.

In the context of subgroup (2b) of embodiments, $R^{y4}$ together with $R^{z6}$ may also form a linear $C_1$-$C_4$-alkylene group, such as $CH_2$, $CH_2CH_2$ or $CH_2CH_2CH_2$ or a linear $C_2$-$C_4$-alkenylene group, such as $CH=CH$ or $CH_2—CH=CH$, where in the alkylene and alkenylene groups a $CH_2$ moiety may be replaced by a carbonyl group or a group $=N—R'$ and/or wherein the alkylene group and the alkenylene group may be substituted by 1, 2, 3 or 4 radicals $R^{hh}$ which are preferably OH, halogen or $C_1$-$C_3$-alkyl such as $CH_3$, $C_2H_5$, or n-propyl. In this context $R'$ is preferably selected from hydrogen, CN and $C_1$-$C_4$-alkyl.

Irrespectively of their occurrence, i.e. either in the variables $X^1$, $X^2$, Y, $Z^1$ and $Z^2$ as well as in context with formulae $R^1$-1 to $R^1$-60 the variables $R'$, $R^h$, $R^{hh}$, $R^{x1}$, $R^{x2}$, $R^{x3}$, $R^{y1}$, $R^{y2}$, $R^{y3}$, $R^{y4}R^{y44}$, $R^{z1}$, $R^{z3}$, $R^{z4}$, $R^{z5}$ and $R^{z6}$ preferably have one of the following meanings:

$R^{x1}$, $R^{x2}$ independently of each other, are selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$;

$R^{x3}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, where the alkyl, cycloalkyl and alkoxy parts of the last 3 mentioned radicals are unsubstituted or partially or completely halogenated, and phenyl, where the phenyl ring is unsubstituted or carries 1, 2 or 3 radicals $R^f$;

$R^{y1}$, $R^{y2}$ independently of each other, are selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$;

$R^{y3}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$;

$R^{z1}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$; or $R^{z3}$ is selected from the group consisting of hydrogen, halogen, such as F or Cl, CN, $C_1$-$C_6$-alkyl and $C_1$-$C_6$-haloalkyl, more preferably from the group consisting of hydrogen, F, Cl, CN and $CH_3$ and especially hydrogen or CN;

$R^{z4}$ is selected from the group consisting of hydrogen, $C_1$-$C_6$-alkyl and $C_1$-$C_6$-haloalkyl, more preferably from the group consisting of $C_1$-$C_4$-alkyl and $C_1$-$C_4$-haloalkyl, especially $CH_3$, $C_2H_5$, or trifluoromethyl;

$R^{z5}$ is selected from the group consisting of hydrogen, $C_1$-$C_6$-alkyl, $C_1$-$C_6$-haloalkyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, where the alkyl, cycloalkyl, cycloalkoxy and alkoxy parts of the last four mentioned radicals are unsubstituted or partially or completely halogenated, phenyl and benzyl, where the phenyl ring in the last 2 radicals is unsubstituted or carry 1, 2 or 3 radicals $R^f$. In this context $R^{z5}$ is in particular hydrogen or $C_1$-$C_4$-alkyl, especially hydrogen;

$R^{z6}$ is selected from the group consisting of $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, where the alkyl, cycloalkyl parts of the last two mentioned radicals are unsubstituted or partially or completely halogenated, phenyl and benzyl, where the phenyl ring in the last 2 radicals is unsubstituted or carry 1, 2 or 3 radicals $R^f$. In this context $R^{z6}$ is in particular $C_1$-$C_4$-alkyl or $C_1$-$C_4$-haloalkyl, especially $CH_3$, $C_2H_5$, or trifluoromethyl;

$R^{y4}$ together with $R^{z6}$ may also form a linear $C_1$-$C_4$-alkylene group, such as $CH_2$, $CH_2CH_2$ or $CH_2CH_2CH_2$ or a linear $C_2$-$C_4$-alkenylene group, such as $CH=CH$ or $CH_2—CH=CH$, where in the alkylene and alkenylene groups a $CH_2$ moiety may be replaced by a carbonyl group or a group $=N—R'$ and/or wherein the alkylene group and the alkenylene group may be substituted by 1, 2, 3 or 4 radicals $R^{hh}$;

$R^{z1}$ together with $R^{y3}$ may also form a linear $C_1$-$C_4$-alkylene group, such as $CH_2$, $CH_2CH_2$ or $CH_2CH_2CH_2$ or a linear $C_2$-$C_4$-alkenylene group, such as $CH=CH$ or $CH_2—CH=CH$, where in the alkylene and alkenylene groups a $CH_2$ moiety may be replaced by a carbonyl group or a group $=N—R'$ and/or wherein the alkylene group and the alkenylene group may be substituted by 1, 2, 3 or 4 radicals $R^{hh}$;

$R^{z4}$ together with $R^{z5}$ may also form a linear $C_1$-$C_4$-alkylene group, such as $CH_2$, $CH_2CH_2$ or $CH_2CH_2CH_2$ or a linear $C_2$-$C_4$-alkenylene group, such as $CH=CH$ or $CH_2—CH=CH$, where in the alkylene and alkenylene groups a $CH_2$ moiety may be replaced by a carbonyl group or a group $=N—R'$ and/or wherein the alkylene group and the alkenylene group may be substituted by 1, 2, 3 or 4 radicals $R^{hh}$;

$R^{hh}$ is selected from the group consisting of OH, halogen, such as Cl or F, $C_1$-$C_4$-alkyl such as $CH_3$, $C_2H_5$, n-propyl or isopropyl, and fluorinated $C_1$-$C_4$-alkyl such as trifluoromethyl;

$R^h$ is selected from the group consisting of hydrogen, OH, halogen, such as Cl or F $C_1$-$C_4$-alkyl such as $CH_3$, $C_2H_5$, n-propyl or isopropyl, and fluorinated $C_1$-$C_4$-alkyl such as trifluoromethyl with particular preference given to $R^h$=hydrogen;

R' is selected from hydrogen, CN and $C_1$-$C_4$-alkyl.

Irrespectively of their occurrence, i.e. either in the variables X, Y and Z as well as in context with formulae $R^{1a}$ to $R^{1v}$ the variables R', $R^h$, $R^{hh}$, $R^{x1}$, $R^{x2}$, $R^{x3}$, $R^{y1}$, $R^{y2}$, $R^{y3}$, $R^{y4}$, $R^{y44}$, $R^{z1}$, $R^{z3}$, $R^{z4}$, $R^{z5}$ and $R^{z6}$ especially have one of the following meanings:

$R^{x1}$, $R^{x2}$ independently of each other, are selected from the group consisting of hydrogen and $C_1$-$C_4$-alkyl such as $CH_3$, $C_2H_5$, n-propyl or isopropyl;

$R^{x3}$ is selected from the group consisting of hydrogen and $C_1$-$C_4$-alkyl such as $CH_3$, $C_2H_5$, n-propyl or isopropyl;

$R^{y1}$, $R^{y2}$ independently of each other, are selected from the group consisting of hydrogen and $C_1$-$C_4$-alkyl such as $CH_3$, $C_2H_5$, n-propyl or isopropyl;

$R^{y3}$ is selected from the group consisting of hydrogen and $C_1$-$C_4$-alkyl such as $CH_3$, $C_2H_5$, n-propyl or isopropyl;

$R^{y4}$ is selected from the group consisting of hydrogen and $C_1$-$C_4$-alkyl such as $CH_3$, $C_2H_5$, n-propyl or isopropyl;

$R^{y44}$ is selected from the group consisting of hydrogen and $C_1$-$C_4$-alkyl such as $CH_3$, $C_2H_5$, n-propyl or isopropyl;

$R^{z1}$ is selected from the group consisting of hydrogen and $C_1$-$C_4$-alkyl such as $CH_3$, $C_2H_5$, n-propyl or isopropyl; or $R^{z1}$ together with $R^{y3}$, if present, may also form —$CH_2$—, —$CH_2CH_2$—, —$CH_2CH_2CH_2$—, —CH=CH—, —CH=C($CH_3$)—, —CH=C—$CH_2$—, —$CH_2$—CH(OH)—, —$CH_2$—C(OH)($CH_3$)—, —$CH_2$—C(O)—, —$CH_2CH_2$C(O)—, —$CH_2$—C(NH)—, —$CH_2CH_2$C(NH)—, —$CH_2$—C(N($CH_3$))—, —$CH_2CH_2$C(N($CH_3$))—, —$CH_2$—C(N—CN)—, —$CH_2CH_2$C(N—CN)—, —$CH_2$—C(S)—, or —$CH_2CH_2$C(S)—;

$R^{z4}$ together with $R^{z5}$, if present, may also form —$CH_2$—, —$CH_2CH_2$—, —$CH_2CH_2CH_2$—, —CH=CH—, —CH=C($CH_3$)—, —CH=C—$CH_2$—, —$CH_2$—CH(OH)—, —$CH_2$—C(OH)($CH_3$)—, —$CH_2$—C(O)—, —$CH_2CH_2$C(O)—, —$CH_2$—C(NH)—, —$CH_2CH_2$C(NH)—, —$CH_2$—C(N($CH_3$))—, —$CH_2CH_2$C(N($CH_3$))—, —$CH_2$—C(N—CN)—, —$CH_2CH_2$C(N—CN)—, —$CH_2$—C(S)—, or —$CH_2CH_2$C(S)—;

$R^{z6}$ together with $R^{y4}$, if present, may also form —$CH_2$—, —$CH_2CH_2$—, —$CH_2CH_2CH_2$—, —CH=CH—, —CH=C($CH_3$)—, —CH=C—$CH_2$—, —$CH_2$—CH(OH)—, —$CH_2$—C(OH)($CH_3$)—, —$CH_2$—C(O)—, —$CH_2CH_2$C(O)—, —$CH_2$—C(NH)—, —$CH_2CH_2$C(NH)—, —$CH_2$—C(N($CH_3$))—, —$CH_2CH_2$C(N($CH_3$))—, —$CH_2$—C(N—CN)—, —$CH_2CH_2$C(N—CN)—, —$CH_2$—C(S)—, or —$CH_2CH_2$C(S)—;

$R^h$ is selected from the group consisting of hydrogen, $CH_3$, CN and trifluoromethyl;

$R^{hh}$ is selected from the group consisting of $CH_3$, CN and trifluoromethyl;

R' is selected from the group consisting of H, $CH_3$ and CN.

In this group (2) of embodiments the radical $R^1$ is preferably selected from the moieties of the formulae $R^1$-1 to $R^1$-60:

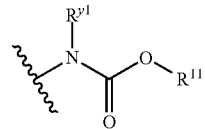
$R^1$-1

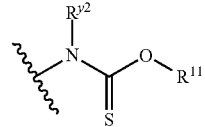
$R^1$-2

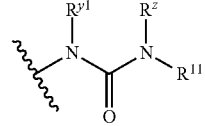
$R^1$-3

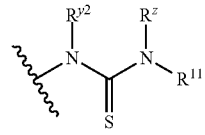
$R^1$-4

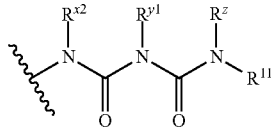
$R^1$-6

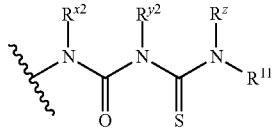
$R^1$-7

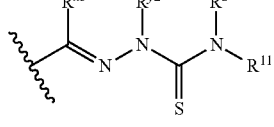
$R^1$-8

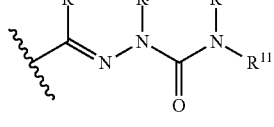
$R^1$-9

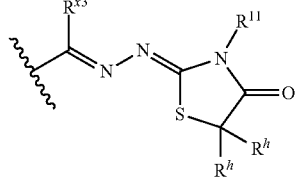
$R^1$-10

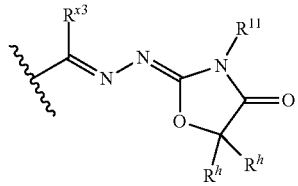
$R^1$-11

R¹-12 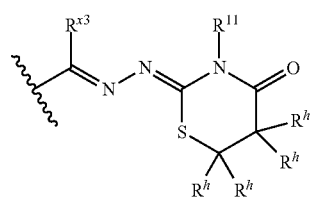
R¹-13 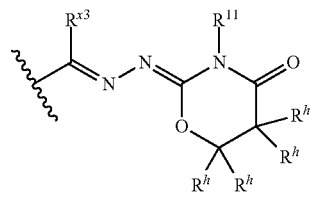
R¹-14 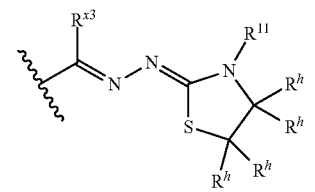
R¹-15 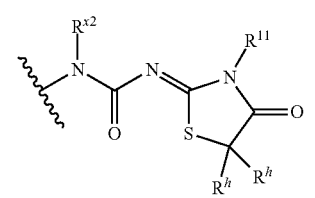
R¹-16 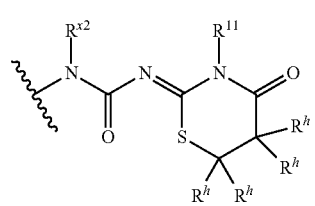
R¹-17 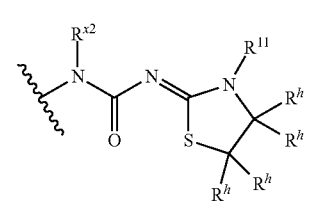
R¹-18 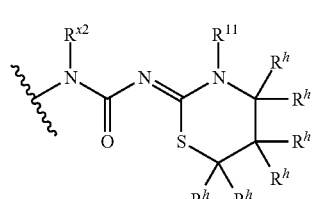
R¹-19 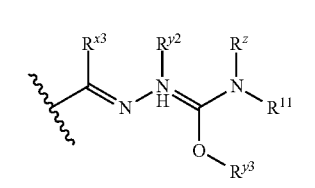
R¹-20 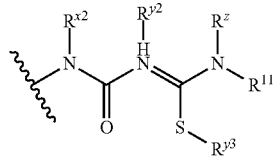
R¹-21 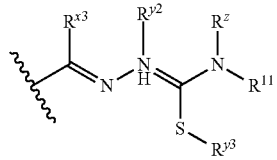
R¹-22 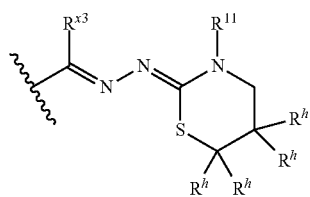
R¹-23 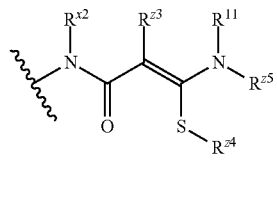
R¹-24 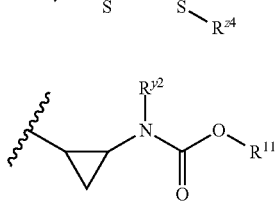
R¹-25 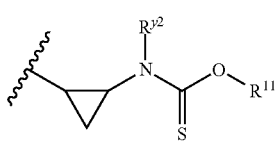
R¹-26 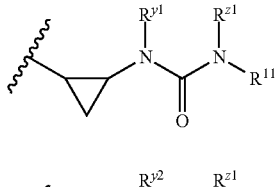
R¹-27
R¹-28

-continued
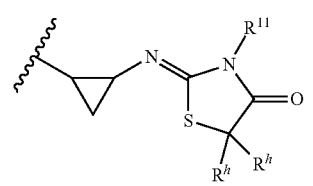 R¹-29
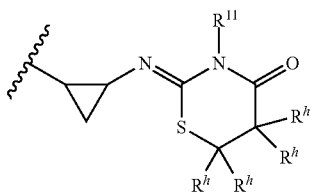 R¹-30
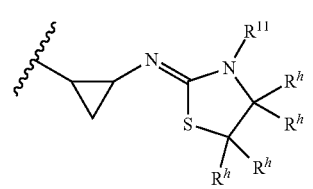 R¹-31
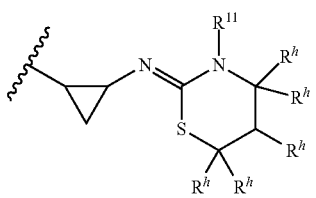 R¹-32
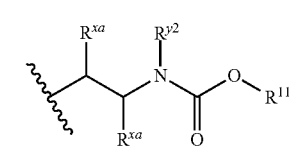 R¹-33
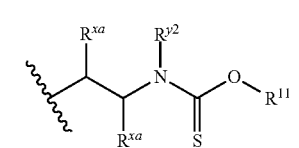 R¹-34
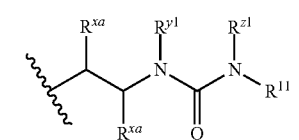 R¹-35
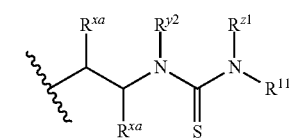 R¹-36
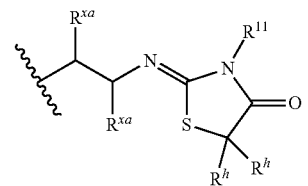 R¹-37
-continued
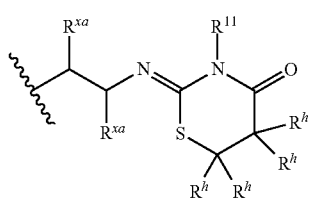 R¹-38
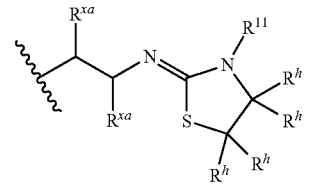 R¹-39
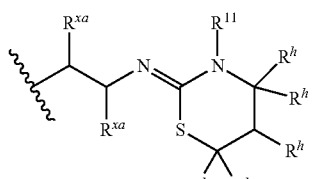 R¹-40
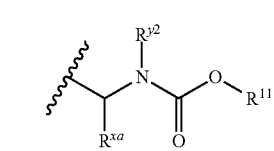 R¹-41
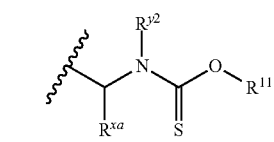 R¹-42
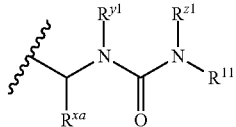 R¹-43
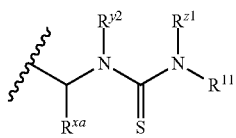 R¹-44
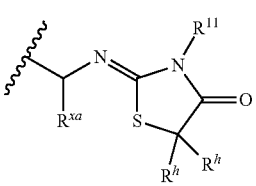 R¹-45
R¹-46

-continued

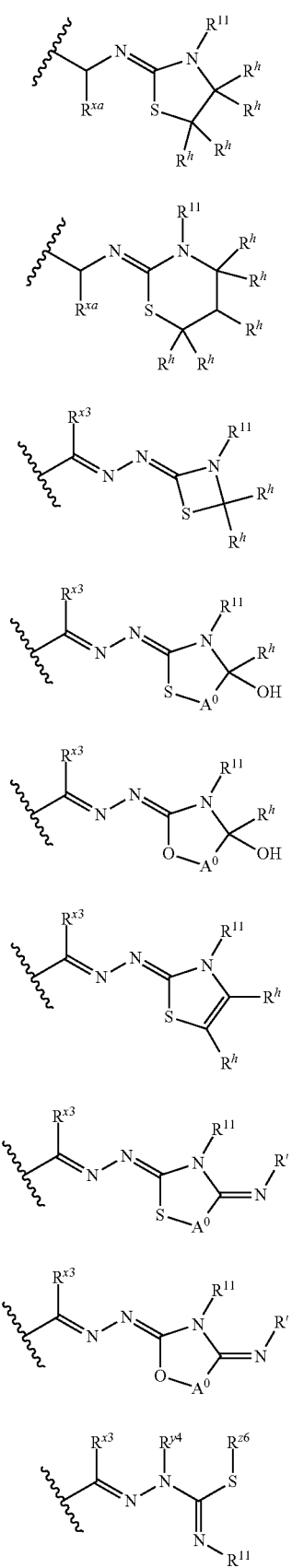

R¹-47
R¹-48
R¹-49
R¹-50
R¹-51
R¹-52
R¹-53
R¹-54
R¹-55

-continued

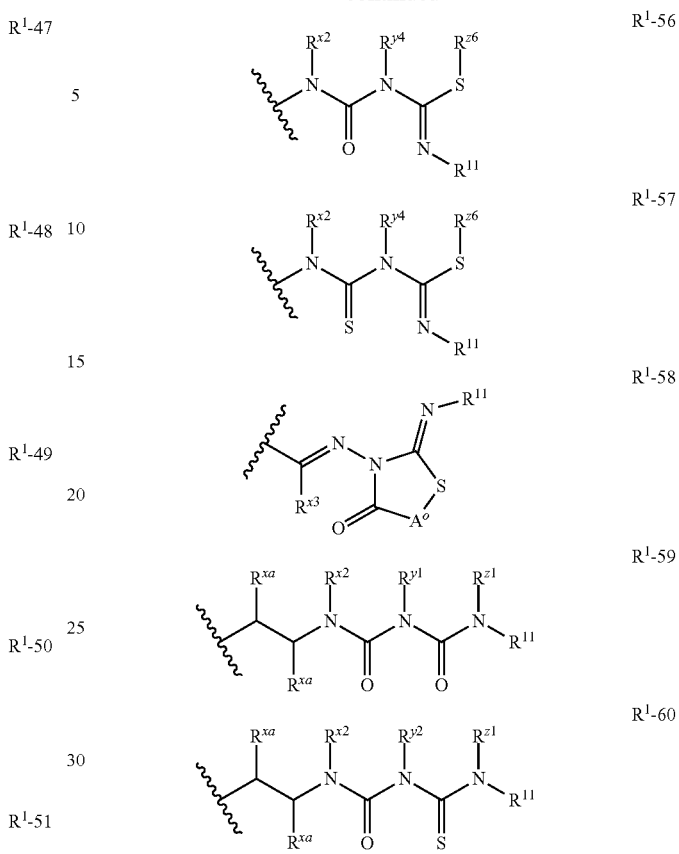

R¹-56
R¹-57
R¹-58
R¹-59
R¹-60 where R¹, R¹¹, $R^{x2}$, $R^{x3}$, $R^{y1}$, $R^{y2}$, $R^{y3}$, $R^{y4}$, $R^{z1}$, $R^{z3}$, $R^{z4}$, $R^{z5}$ and $R^{z6}$ are as defined in claim 1, $A^o$ is $C(R^h)_2$ or $C(R^h)_2C(R^h)_2$ and $R^h$, irrespectively of its occurrence, is selected from hydrogen or has one of the meanings given for $R^{hh}$, and where $R^h$ is in particular selected from the group consisting of hydrogen, $CH_3$, CN and trifluoromethyl.

In this group (2) of embodiments the radical $R^{11}$ is in particular aryl, aryl-$C_1$-$C_4$-alkyl, hetaryl, or hetaryl-$C_1$-$C_4$-alkyl, where the aryl and hetaryl rings in the last 4 radicals are unsubstituted or carry 1, 2, 3, 4 or 5 radicals $R^g$ and where hetaryl in hetaryl or hetaryl-$C_1$-$C_4$-alkyl, is preferably a 5- or 6-membered monocyclic hetaryl such as pyridyl, pyrimidinyl, pyridazinyl, pyrrolyl, pyrazolyl, imidazolyl, oxazolyl, thiazolyl, isoxazolyl or isothiazolyl which 5- or 6-membered hetaryl is unsubstituted or carries 1, 2 or 3 radicals $R^g$.

In this group (2) of embodiments the radical $R^{11}$ is especially phenyl, benzyl, 1-phenylethyl, pyridyl, pyridylmethyl and 1-(pyridyl)ethyl, where phenyl and pyridyl in the last 6 radicals may be unsubstituted or preferably carry 1, 2 or 3 radicals $R^g$.

In context of $R^{11}$, the radicals $R^g$ are independently of each other selected from the group consisting of halogen, such as F, Cl or Br, $C_1$-$C_6$-alkyl, in particular $C_1$-$C_3$-alkyl such as $CH_3$, $C_2H_5$, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or OCH$_2$CF$_2$CF$_3$, and S—R$^e$, where R$^e$ is C$_1$-C$_6$-alkyl, in particular C$_1$-C$_3$-alkyl such as CH$_3$, C$_2$H$_5$, n-propyl or isopropyl, or C$_1$-C$_6$-haloalkyl, in particular fluorinated C$_1$-C$_3$-alkyl such as CH$_2$F, CHF$_2$, CF$_3$, CH$_2$CF$_3$, CF$_2$CHF$_2$, C$_2$F$_5$, CH$_2$CH$_2$CF$_3$, CH$_2$CF$_2$CHF$_2$ or CH$_2$CF$_2$CF$_3$. If two or more radicals R$^g$ are present on R$^{11}$, it is possible that the radicals R$^g$ are identical or different.

Examples of particularly preferred radicals R$^{11}$ are the radicals R$^{11}$-1 to R$^{11}$-29 summarized in Table B below.

TABLE B

Examples of radicals R$^{11}$

| | |
|---|---|
| R$^{11}$-1 | 2-isopropylphenyl |
| R$^{11}$-2 | 2-trifluoromethyphenyl |
| R$^{11}$-3 | 2-ethylphenyl |
| R$^{11}$-4 | 2-methoxyphenyl |
| R$^{11}$-5 | 2,4-dichlorophenyl |
| R$^{11}$-6 | 2,5-dimethylphenyl |
| R$^{11}$-7 | 2,5-dichlorophenyl |
| R$^{11}$-8 | 2,6-dichlorophenyl |
| R$^{11}$-9 | 2,6-difluorophenyl |
| R$^{11}$-10 | 2,6-dimethylphenyl |
| R$^{11}$-11 | 2,4,6-trifluorophenyl |
| R$^{11}$-12 | 2,4,6-trichlorophenyl |
| R$^{11}$-13 | 2,4,6-trimethylphenyl |
| R$^{11}$-14 | 2-methyl-4-chlorophenyl |
| R$^{11}$-15 | 2-methyl-5-chlorophenyl |
| R$^{11}$-16 | 2-chloro-5-trifluoromethylphenyl |
| R$^{11}$-17 | 2,6-dimethyl-4-bromophenyl |
| R$^{11}$-18 | 1-(5-chloro-2-pyridyl)ethyl |
| R$^{11}$-19 | 1-(5-fluoro-2-pyridyl)ethyl |
| R$^{11}$-20 | 1-(5-methoxy-2-pyridyl)ethyl |
| R$^{11}$-21 | 1-(6-chloro-2-pyridyl)ethyl |
| R$^{11}$-22 | 1-naphthyl |
| R$^{11}$-23 | 2-chlorophenyl |
| R$^{11}$-24 | 2-fluorophenyl |
| R$^{11}$-25 | 2-methylphenyl |
| R$^{11}$-26 | 2,4-difluorophenyl |
| R$^{11}$-27 | 2,4-dimethylphenyl |
| R$^{11}$-28 | 2-methyl-5-methoxyphenyl |
| R$^{11}$-29 | 2-isopropyl-5-methyl-phenyl |

Special examples of the moieties of the formulae -T-X$^1$—Y—Z$^1$— and T-X$^2$—Y—Z$^2$ are the bivalent moieties of the formulae XYZ-3 to XYZ-90

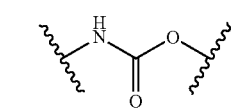

XYZ-3

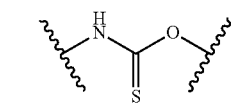

XYZ-4

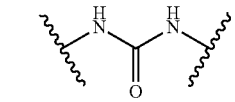

XYZ-5

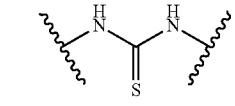

XYZ-6

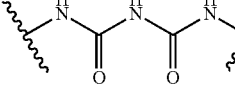

XYZ-7

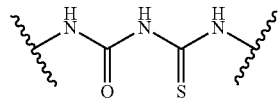

XYZ-8

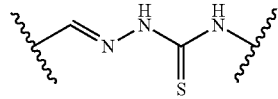

XYZ-9

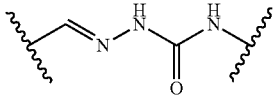

XYZ-10

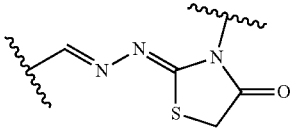

XYZ-11

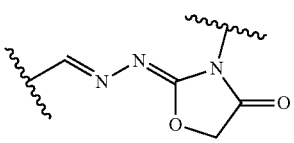

XYZ-12

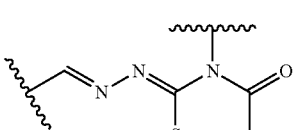

XYZ-13

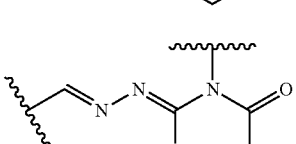

XYZ-14

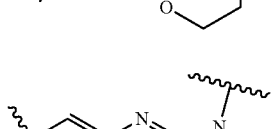

XYZ-15

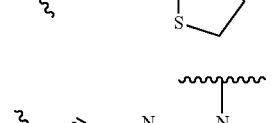

XYZ-16

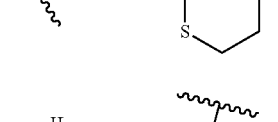

XYZ-17

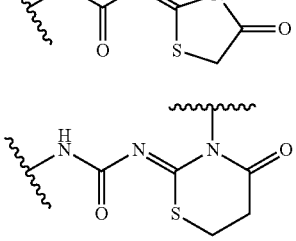

XYZ-18

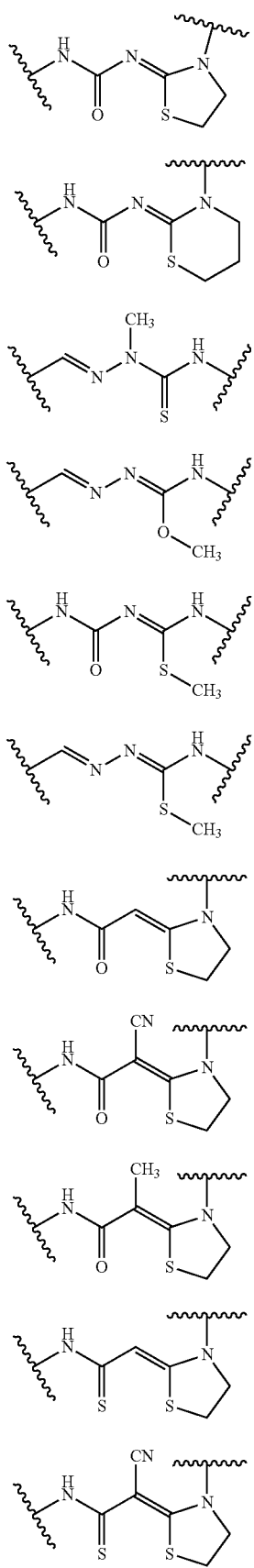
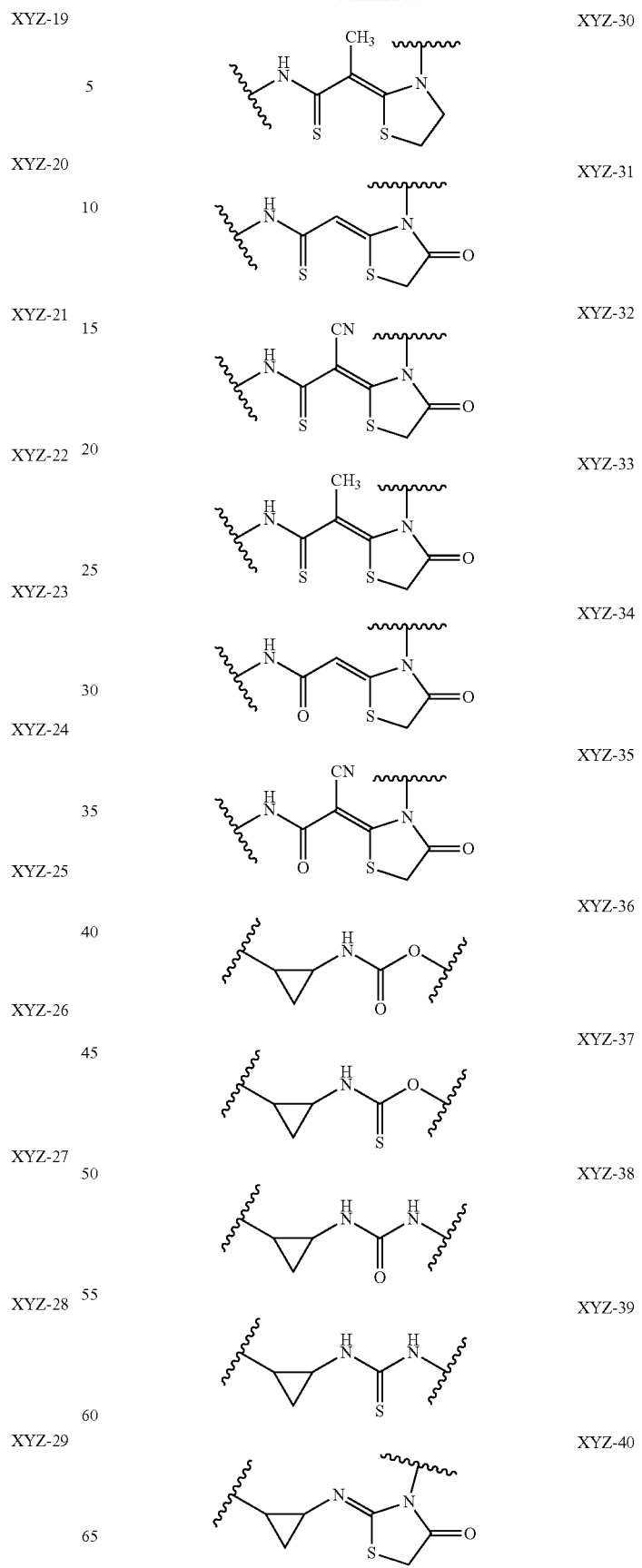

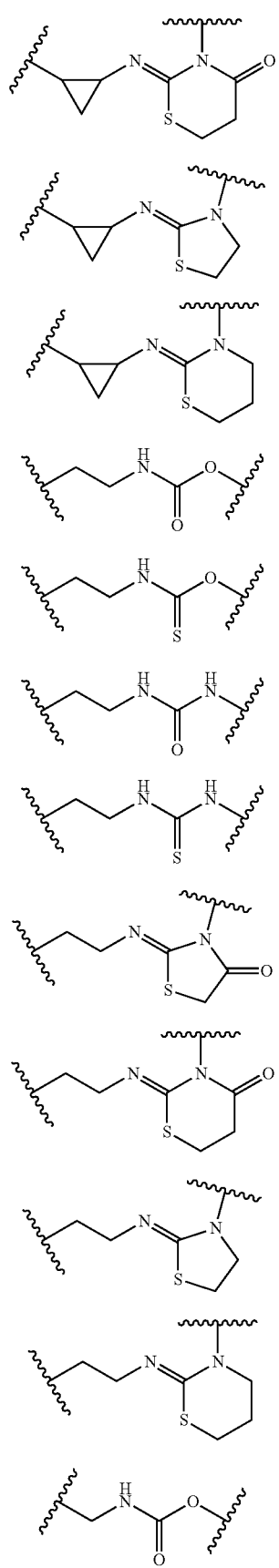
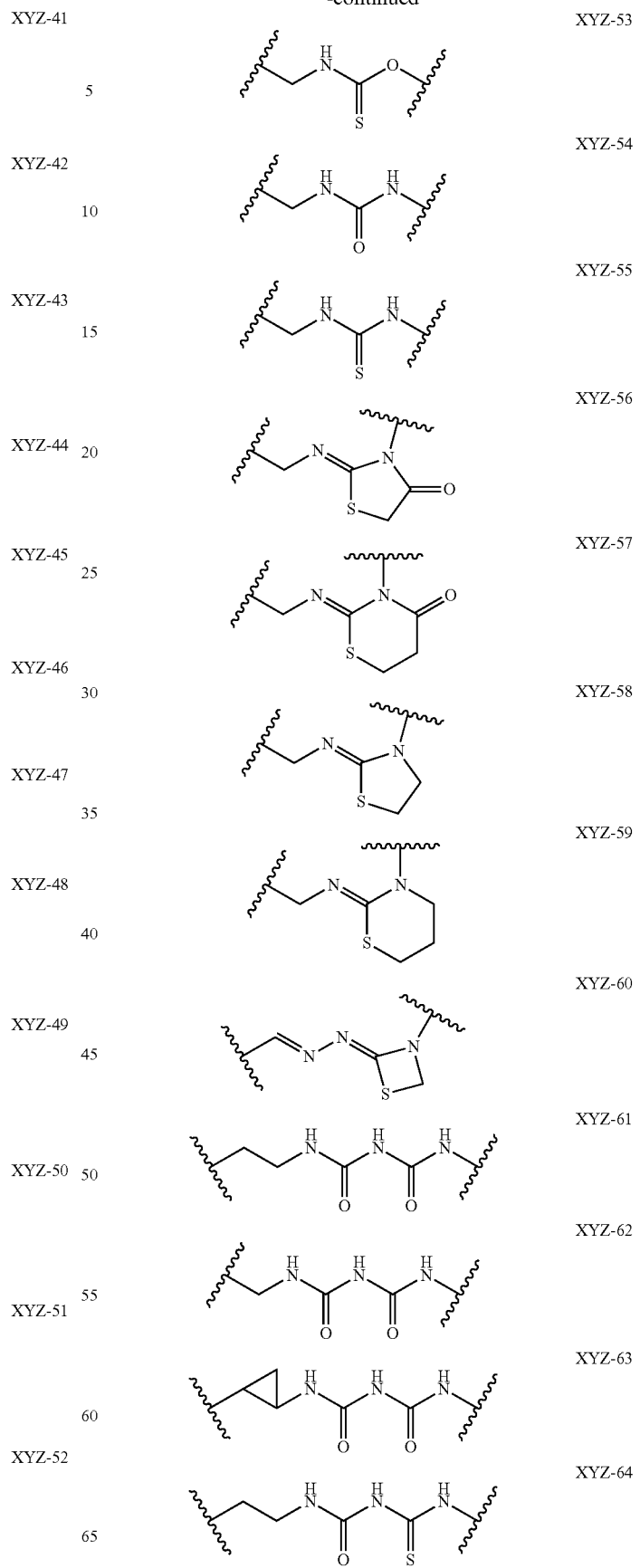

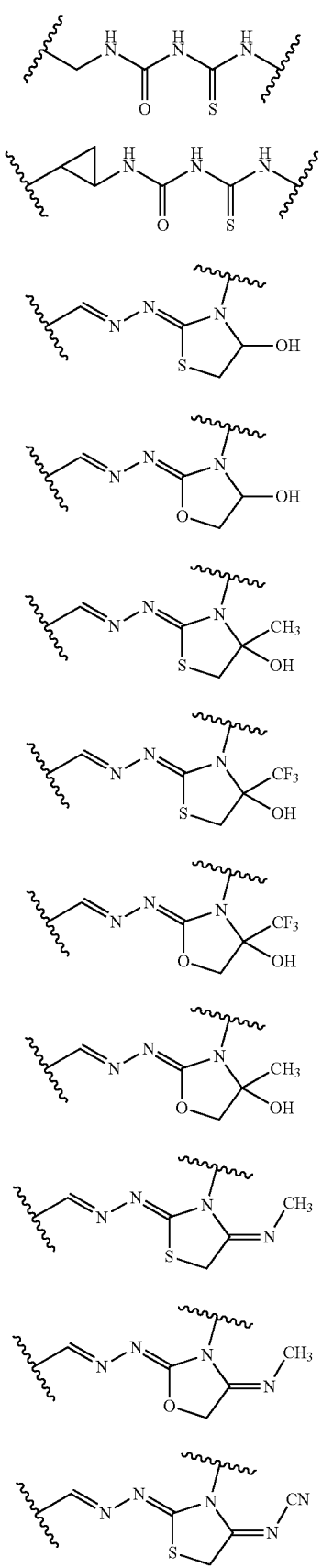
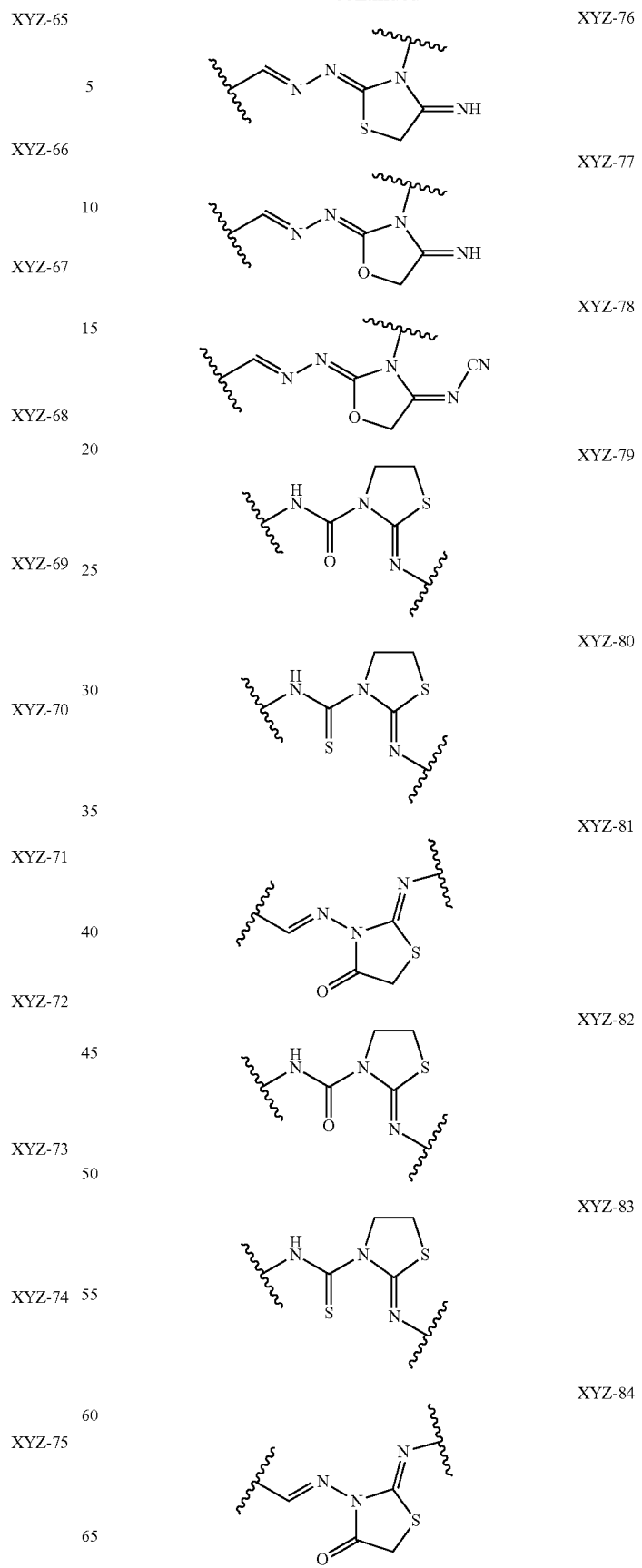

-continued

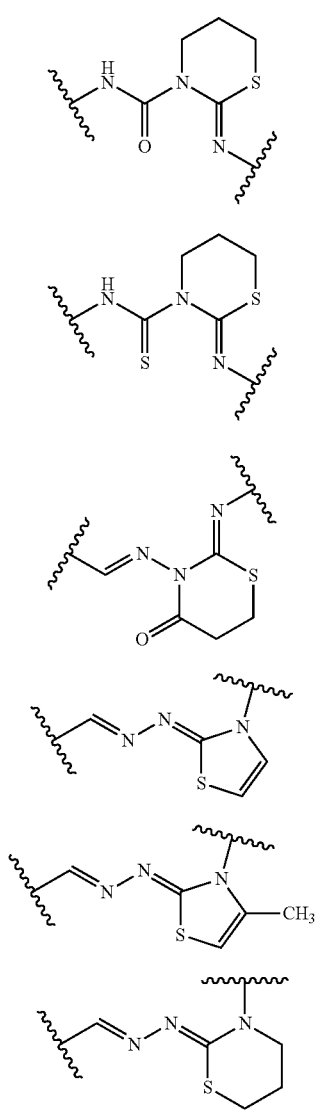

XYZ-85

XYZ-86

XYZ-87

XYZ-88

XYZ-89

XYZ-90

Apart from that, the variables $R^{x1}$, $R^a$, $R^b$, $R^c$, $R^d$, $R^e$, $R^f$ and $R^g$ independently of each other, preferably have one of the following meanings:

Preferably, each $R^a$ is independently selected from the group consisting of $C_1$-$C_6$-alkyl, $C_1$-$C_6$-haloalkyl, $C_3$-$C_5$-cycloalkyl, $C_3$-$C_5$-halocycloalkyl, benzyl and phenyl, where the phenyl ring in the last two radicals is unsubstituted or may be substituted by 1, 2 or 3 radicals $R^f$.

Preferably, $R^c$ and $R^d$ are, independently of each other and independently of their occurrence, selected from the group consisting of hydrogen, $C_1$-$C_4$-alkyl, $C_1$-$C_4$-haloalkyl, $C_3$-$C_6$-cycloalkyl-$CH_2$, $C_3$-$C_6$-cycloalkyl, benzyl and phenyl, where the phenyl ring in the last two radicals is unsubstituted or may be substituted by 1, 2 or 3 radicals $R^f$; or $R^b$ and $R^c$ together with the nitrogen atom to which they are bound may form a saturated 5-, 6- or 7-membered saturated N-bound heterocycle, which may contain 1 or 2 further heteroatoms selected from N, O and S as ring members, where the heterocyclic ring may carry 1, 2, 3 or 4 substituents selected from $C_1$-$C_4$-alkyl, examples including 1-pyrrolidinyl, 1-piperidinyl, 1-piperazinyl, 4-methyl-1-piperazinyl, 4-morpholinyl and 4-thiomorpholinyl.

Preferably, each $R^d$ is independently selected from the group consisting of $C_1$-$C_4$-alkyl, $C_1$-$C_4$-haloalkyl, $C_3$-$C_8$-cycloalkyl, benzyl and phenyl, where the phenyl ring in the last two radicals is unsubstituted or may be substituted by 1, 2 or 3 radicals $R^f$.

Preferably, each $R^e$ is independently selected from the group consisting of $C_1$-$C_4$-alkyl, $C_1$-$C_4$-haloalkyl, $C_3$-$C_8$-cycloalkyl, benzyl and phenyl, where the phenyl ring in the last two radicals is unsubstituted or may be substituted by 1, 2 or 3 radicals $R^f$.

Preferably each $R^f$ is independently selected from the group consisting of halogen, in particular F, Cl or Br, $C_1$-$C_4$-alkyl, $C_1$-$C_4$-haloalkyl, $C_1$-$C_4$-alkoxycarbonyl, cyano, $C_1$-$C_4$-alkoxy and $C_1$-$C_4$-haloalkoxy, especially from the group consisting of halogen, in particular F, Cl or Br, $CH_3$, halomethyl, e.g. trifluoromethyl, difluoromethyl or bromodifluoromethyl, cyano, methoxy and halomethoxy, e.g. trifluoromethoxy, difluoromethoxy or fluoromethoxy. If two or more radicals $R^f$ are present, it is possible that the radicals $R^f$ are identical or different.

$R^g$ are independently of each other selected from the group consisting of halogen, such as F, Cl or Br, $C_1$-$C_6$-alkyl, in particular $C_1$-$C_3$-alkyl such as $CH_3$, $C_2H_5$, n-propyl or isopropyl, $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$, or $CH_2CF_2CF_3$, $C_1$-$C_6$-alkoxy, in particular $C_1$-$C_3$-alkoxy such as methoxy, ethoxy, n-propyloxy or isopropyloxy, $C_1$-$C_6$-haloalkoxy, in particular fluorinated $C_1$-$C_3$-alkoxy such as $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, or $OCH_2CF_2CF_3$, and S—$R^e$, where $R^e$ is $C_1$-$C_6$-alkyl, in particular $C_1$-$C_3$-alkyl such as $CH_3$, $C_2H_5$, n-propyl or isopropyl, or $C_1$-$C_6$-haloalkyl, in particular fluorinated $C_1$-$C_3$-alkyl such as $CH_2F$, $CHF_2$, $CF_3$, $CH_2CF_3$, $CF_2CHF_2$, $C_2F_5$, $CH_2CH_2CF_3$, $CH_2CF_2CHF_2$ or $CH_2CF2CF_3$. If two or more radicals $R^g$ are present, it is possible that the radicals $R^g$ are identical or different.

Examples of compounds of the present invention are given in the tables 1 to 274 below:

Table 1: Compounds of the formula Ia.1, their stereoisomers, their tautomers and the agriculturally or veterinarily acceptable salts, wherein $R^1$ is a radical —XYZ—$R^{11}$ or XYZ—$R^{12}$, respectively, where Ar, —XYZ— and $R^{11}$/$R^{12}$ are as defined in the rows of table C.

Table 2: Compounds of the formula Ia.2, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 3: Compounds of the formula Ia.3, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 4: Compounds of the formula Ia.4, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 5: Compounds of the formula Ia.5, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 6: Compounds of the formula Ia.6, their stereoisomers, their tautomers and the agriculturally or veterinarily acceptable salts, wherein $R^1$ is a radical XYZ—$R^{11}$ or Table 7: Compounds of the formula Ia.7, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 8: Compounds of the formula Ia.8, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 9: Compounds of the formula Ia.9, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 10: Compounds of the formula Ia.10, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 11: Compounds of the formula Ia.11, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 12: Compounds of the formula Ia.12, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 13: Compounds of the formula Ia.13, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 14: Compounds of the formula Ia.14, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 15: Compounds of the formula Ia.15, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 16: Compounds of the formula Ia.16, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 17: Compounds of the formula Ia.17, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 18: Compounds of the formula Ia.18, their stereoisomers, their tautomers and the agriculturally or veterinarily acceptable salts, wherein $R^{Q2}$ is hydrogen, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 19: Compounds of the formula Ia.11, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 20: Compounds of the formula Ia.12, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 21: Compounds of the formula Ia.13, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 22: Compounds of the formula Ia.14, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 23: Compounds of the formula Ia.15, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 24: Compounds of the formula Ia.16, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 25: Compounds of the formula Ia.17, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 27: Compounds of the formula Ia.18, their stereoisomers, their tautomers and the agriculturally or veterinarily acceptable salts, wherein $R^{Q2}$ is $CH_3$, $R^1$ is a radical $XYZ$—$R^{11}$ or $XYZ$—$R^{12}$, respectively, where Ar, —$XYZ$— and $R^{11}/R^{12}$ are as defined in the rows of table C.

Table 28: Compounds of the formula Ia.19, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 29: Compounds of the formula Ia.20, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 30: Compounds of the formula Ia.21, their stereoisomers, their tautomers and the agriculturally or veterinarily acceptable salts, wherein $R^1$ is a radical $XYZ$—$R^{11}$ or $XYZ$—$R^{12}$, respectively, where Ar, —$XYZ$— and $R^{11}/R^{12}$ are as defined in the rows of table C.

Table 31: Compounds of the formula Ia.22, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 32: Compounds of the formula Ia.23, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 33: Compounds of the formula Ia.24, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 34: Compounds of the formula Ia.25, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 35: Compounds of the formula Ia.26, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 36: Compounds of the formula Ia.27, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 37: Compounds of the formula Ia.28, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 38: Compounds of the formula Ia.29, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 39: Compounds of the formula Ia.30, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 40: Compounds of the formula Ia.31, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 41: Compounds of the formula Ia.32, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 42: Compounds of the formula Ia.33, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 43: Compounds of the formula Ia.29, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 44: Compounds of the formula Ia.30, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 45: Compounds of the formula Ia.31, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 46: Compounds of the formula Ia.32, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 47: Compounds of the formula Ia.33, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 48: Compounds of the formula Ia.34, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 49: Compounds of the formula Ia.35, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 50: Compounds of the formula Ia.36, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 51: Compounds of the formula Ia.37, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 52: Compounds of the formula Ia.38, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 53: Compounds of the formula Ia.39, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 54: Compounds of the formula Ia.40, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 55: Compounds of the formula Ia.41, their stereoisomers, their tautomers and the agriculturally or veterinarily acceptable salts, wherein $R^1$ is a radical XYZ—$R^{11}$ or Table 56: Compounds of the formula Ia.42, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 57: Compounds of the formula Ia.43, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 58: Compounds of the formula Ia.44, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 59: Compounds of the formula Ia.44, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 60: Compounds of the formula Ia.45, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 61: Compounds of the formula Ia.45, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 62: Compounds of the formula Ia.45, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 63: Compounds of the formula Ia.45, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 64: Compounds of the formula Ia.46, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 65: Compounds of the formula Ia.46, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 66: Compounds of the formula Ia.47, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 67: Compounds of the formula Ia.47, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 68: Compounds of the formula Ia.48, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}$/$R^{12}$ are as defined in the rows of table C.

Table 69: Compounds of the formula Ia.48, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}$/$R^{12}$ are as defined in the rows of table C.

Table 70: Compounds of the formula Ia.49, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 71: Compounds of the formula Ia.50, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 72: Compounds of the formula Ia.51, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 73: Compounds of the formula Ia.52, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 74: Compounds of the formula Ia.52, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 75: Compounds of the formula Ia.53, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 76: Compounds of the formula Ia.54, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 77: Compounds of the formula Ia.55, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 78: Compounds of the formula Ia.56, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}$/$R^{12}$ are as defined in the rows of table C.

Table 79: Compounds of the formula Ia.57, their stereoisomers, their tautomers and the agriculturally or veterinarily acceptable salts, wherein $R^1$ is a radical XYZ—$R^{11}$ or Table 80: Compounds of the formula Ia.58, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 81: Compounds of the formula Ia.59, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 82: Compounds of the formula Ia.59, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 83: Compounds of the formula Ia.60, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 84: Compounds of the formula Ia.60, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 85: Compounds of the formula Ia.61, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 86: Compounds of the formula Ia.61, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 87: Compounds of the formula Ia.62, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 88: Compounds of the formula Ia.62, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 89: Compounds of the formula Ia.63, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 90: Compounds of the formula Ia.63, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 91: Compounds of the formula Ia.64, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 92: Compounds of the formula Ia.64, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 93: Compounds of the formula Ia.65, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 94: Compounds of the formula Ia.65, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 95: Compounds of the formula Ia.66, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 96: Compounds of the formula Ia.66, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 97: Compounds of the formula Ia.67, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 98: Compounds of the formula Ia.68, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 99: Compounds of the formula Ia.69, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 100: Compounds of the formula Ia.70, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 101: Compounds of the formula Ia.71, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 102: Compounds of the formula Ia.72, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 103: Compounds of the formula Ia.73, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 104: Compounds of the formula Ia.74, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 105: Compounds of the formula Ia.75, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 106: Compounds of the formula Ia.76, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 108: Compounds of the formula Ia.77, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 109: Compounds of the formula Ia.77, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 110: Compounds of the formula Ia.78, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 111: Compounds of the formula Ia.78, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 112: Compounds of the formula Ia.79, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 113: Compounds of the formula Ia.79, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 114: Compounds of the formula Ia.80, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 115: Compounds of the formula Ia.80, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 116: Compounds of the formula Ia.81, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 117: Compounds of the formula Ia.81, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 118: Compounds of the formula Ia.82, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 119: Compounds of the formula Ia.83, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 120: Compounds of the formula Ia.84, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 121: Compounds of the formula Ia.85, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 122: Compounds of the formula Ia.86, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 123: Compounds of the formula Ia.87, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 124: Compounds of the formula Ia.88, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 125: Compounds of the formula Ia.89, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 126: Compounds of the formula Ia.90, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 127: Compounds of the formula Ia.91, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 128: Compounds of the formula Ia.91, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 129: Compounds of the formula Ia.92, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 130: Compounds of the formula Ia.92, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 131: Compounds of the formula Ia.93, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 132: Compounds of the formula Ia.93, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 133: Compounds of the formula Ia.94, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 134: Compounds of the formula Ia.94, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 135: Compounds of the formula Ia.95, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 136: Compounds of the formula Ia.95, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 137: Compounds of the formula Ia.96, their stereoisomers, their tautomers and the agriculturally or veterinarily acceptable salts, wherein $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 138: Compounds of the formula Ia.96, their stereoisomers, their tautomers and the agriculturally or veterinarily acceptable salts, wherein $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 139: Compounds of the formula Ib.1, their stereoisomers, their tautomers and the agriculturally or veterinarily acceptable salts, wherein $R^3$ is $CH_3$, $R^1$ is a radical —XYZ—$R^{11}$ or XYZ—$R^{12}$, respectively, where Ar, —XYZ— and $R^{11}/R^{12}$ are as defined in the rows of table C.

Table 140: Compounds of the formula Ib.2, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 141: Compounds of the formula Ib.3, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 142: Compounds of the formula Ib.4, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 143: Compounds of the formula Ib.5, their stereoisomers, their tautomers and the agriculturally or veterinarily acceptable salts, wherein $R^3$ is $CH_3$, $R^1$ is a radical XYZ—$R^{11}$ or XYZ—$R^{12}$ respectively, where Ar, —XYZ— and $R^{11}/R^{12}$ are as defined in the rows of table C.

Table 144: Compounds of the formula Ib.6, their stereoisomers, their tautomers and the agriculturally or veterinarily acceptable salts, wherein $R^3$ is $CH_3$, $R^1$ is a radical XYZ—$R^{11}$ or XYZ—$R^{12}$ respectively, where Ar, —XYZ— and $R^{11}/R^{12}$ are as defined in the rows of table C.

Table 145: Compounds of the formula Ib.7, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 146: Compounds of the formula Ib.8, their stereoisomers, their tautomers and the agriculturally or veterinarily acceptable salts, wherein $R^1$ is a radical XYZ—$R^{11}$ or XYZ—$R^{12}$, respectively, where Ar, —XYZ— and $R^{11}/R^{12}$ are as defined in the rows of table C.

Table 147: Compounds of the formula Ib.9, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 148: Compounds of the formula Ib.10, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 149: Compounds of the formula Ib.11, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 150: Compounds of the formula Ib.12, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 151: Compounds of the formula Ib.13, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 152: Compounds of the formula Ib.14, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 153: Compounds of the formula Ib.15, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 154: Compounds of the formula Ib.16, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 155: Compounds of the formula Ib.17, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 156: Compounds of the formula Ib.18, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.

Table 157: Compounds of the formula Ib.11, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 158: Compounds of the formula Ib.12, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 159: Compounds of the formula Ib.13, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 160: Compounds of the formula Ib.14, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 161: Compounds of the formula Ib.15, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 162: Compounds of the formula Ib.16, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 163: Compounds of the formula Ib.17, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 164: Compounds of the formula Ib.18, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 165: Compounds of the formula Ib.19, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 166: Compounds of the formula Ib.20, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 167: Compounds of the formula Ib.21, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 168: Compounds of the formula Ib.22, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 169: Compounds of the formula Ib.23, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 170: Compounds of the formula Ib.24, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 171: Compounds of the formula Ib.25, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.

Table 172: Compounds of the formula Ib.26, their stereoisomers, their tautomers and the agriculturally or veterinarily acceptable salts, wherein $R^3$ is $CH_3$, $R^1$ is a radical XYZ—R$^{11}$ or XYZ—R$^{12}$, respectively, where Ar, —XYZ— and R$^{11}$/R$^{12}$ are as defined in the rows of table C.

- Table 173: Compounds of the formula Ib.27, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 174: Compounds of the formula Ib.28, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 175: Compounds of the formula Ib.29, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 176: Compounds of the formula Ib.30, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 177: Compounds of the formula Ib.31, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 178: Compounds of the formula Ib.32, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 179: Compounds of the formula Ib.33, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 180: Compounds of the formula Ib.29, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 181: Compounds of the formula Ib.30, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 182: Compounds of the formula Ib.31, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 183: Compounds of the formula Ib.32, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 184: Compounds of the formula Ib.33, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 185: Compounds of the formula Ib.34, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 186: Compounds of the formula Ib.35, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 187: Compounds of the formula Ib.36, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 188: Compounds of the formula Ib.37, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 189: Compounds of the formula Ib.38, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 190: Compounds of the formula Ib.39, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 191: Compounds of the formula Ib.40, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 192: Compounds of the formula Ib.41, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 193: Compounds of the formula Ib.42, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 194: Compounds of the formula Ib.43, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 195: Compounds of the formula Ib.44, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 196: Compounds of the formula Ib.44, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 197: Compounds of the formula Ib.45, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 198: Compounds of the formula Ib.45, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 199: Compounds of the formula Ib.45, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 200: Compounds of the formula Ib.45, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 201: Compounds of the formula Ib.46, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 202: Compounds of the formula Ib.46, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 203: Compounds of the formula Ib.47, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 204: Compounds of the formula Ib.47, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 205: Compounds of the formula Ib.48, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 206: Compounds of the formula Ib.48, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 207: Compounds of the formula Ib.49, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 208: Compounds of the formula Ib.50, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 209: Compounds of the formula Ib.51, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 210: Compounds of the formula Ib.52, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 211: Compounds of the formula Ib.52, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 212: Compounds of the formula Ib.53, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 213: Compounds of the formula Ib.54, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 214: Compounds of the formula Ib.55, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 215: Compounds of the formula Ib.56, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 216: Compounds of the formula Ib.57, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 217: Compounds of the formula Ib.58, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 218: Compounds of the formula Ib.59, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 219: Compounds of the formula Ib.59, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 220: Compounds of the formula Ib.60, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 221: Compounds of the formula Ib.60, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 222: Compounds of the formula Ib.61, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 223: Compounds of the formula Ib.61, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 224: Compounds of the formula Ib.62, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 225: Compounds of the formula Ib.62, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 226: Compounds of the formula Ib.63, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 227: Compounds of the formula Ib.63, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 228: Compounds of the formula Ib.64, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 229: Compounds of the formula Ib.64, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 230: Compounds of the formula Ib.65, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 231: Compounds of the formula Ib.65, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 232: Compounds of the formula Ib.66, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.
- Table 233: Compounds of the formula Ib.66, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 234: Compounds of the formula Ib.67, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 235: Compounds of the formula Ib.68, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 236: Compounds of the formula Ib.69, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 237: Compounds of the formula Ib.70, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.
- Table 238: Compounds of the formula Ib.71, their stereoisomers, their tautomers and the agriculturally or veterinarily acceptable salts, wherein R$^3$ is CH$_3$, R$^1$ is a radical

- Table 239: Compounds of the formula Ib.72, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 240: Compounds of the formula Ib.73, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 241: Compounds of the formula Ib.74, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 242: Compounds of the formula Ib.75, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 243: Compounds of the formula Ib.76, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 244: Compounds of the formula Ib.77, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.
- Table 245: Compounds of the formula Ib.77, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 246: Compounds of the formula Ib.78, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.
- Table 247: Compounds of the formula Ib.78, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 248: Compounds of the formula Ib.79, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.
- Table 249: Compounds of the formula Ib.79, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 250: Compounds of the formula Ib.80, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.
- Table 251: Compounds of the formula Ib.80, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 252: Compounds of the formula Ib.81, their stereoisomers, their tautomers and the agriculturally or veterinarily acceptable salts, wherein $R^3$ is $CH_3$, $R^{Q2}$ is hydrogen, $R^1$ is a radical XYZ—$R^{11}$ or XYZ—$R^{12}$, respectively, where Ar, —XYZ— and $R^{11}/R^{12}$ are as defined in the rows of table C.
- Table 253: Compounds of the formula Ib.81, their stereoisomers, their tautomers and the agriculturally or veterinarily acceptable salts, wherein $R^3$ is $CH_3$, $R^{Q2}$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 254: Compounds of the formula Ib.82, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 255: Compounds of the formula Ib.83, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 256: Compounds of the formula Ib.84, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 257: Compounds of the formula Ib.85, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 258: Compounds of the formula Ib.86, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 259: Compounds of the formula Ib.87, their stereoisomers, their tautomers and the agriculturally or veterinarily acceptable salts, wherein $R^3$ is $CH_3$, $R^1$ is a radical XYZ—$R^{11}$ or XYZ—$R^{12}$, respectively, where Ar, —XYZ— and $R^{11}/R^{12}$ are as defined in the rows of table C.
- Table 260: Compounds of the formula Ib.88, their stereoisomers, their tautomers and the agriculturally or veterinarily acceptable salts, wherein $R^3$ is $CH_3$, $R^1$ is a radical XYZ—R$^{11}$ or XYZ—R$^{12}$, respectively, where Ar, —XYZ— and R$^{11}$/R$^{12}$ are as defined in the rows of table C.

Table 261: Compounds of the formula Ib.89, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 262: Compounds of the formula Ib.90, their stereoisomers, their tautomers and the agriculturally or veterinarily acceptable salts, wherein R$^3$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 263: Compounds of the formula Ib.91, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 264: Compounds of the formula Ib.91, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 265: Compounds of the formula Ib.92, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 266: Compounds of the formula Ib.92, their stereoisomers, their tautomers and the agriculturally or veterinarily acceptable salts, wherein R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 267: Compounds of the formula Ib.93, their stereoisomers, their tautomers and the agriculturally or veterinarily acceptable salts, wherein R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 268: Compounds of the formula Ib.93, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 269: Compounds of the formula Ib.94, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 270: Compounds of the formula Ib.94, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 271: Compounds of the formula Ib.95, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 272: Compounds of the formula Ib.95, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Table 273: Compounds of the formula Ib.96, their stereoisomers, their tautomers and the agriculturally or veterinarily acceptable salts, wherein R$^3$ is CH$_3$, R$^{Q2}$ is hydrogen, R$^1$ is a radical XYZ—R$^{11}$ or XYZ—R$^{12}$, respectively, where Ar, —XYZ— and R$^{11}$/R$^{12}$ are as defined in the rows of table C.

Table 274: Compounds of the formula Ib.96, their stereoisomers, their tautomers and the agriculturally or veterinarily acceptable salts, wherein R$^3$ is CH$_3$, R$^{Q2}$ is CH$_3$, R$^1$ is a radical XYZ—R$^{11}$ or XYZ—R$^{12}$, respectively, where Ar, —XYZ— and R$^{11}$/R$^{12}$ are as defined in the rows of table C.

Further examples of compounds of the present invention are given in the tables 275 to 2466 below:

Tables 165 to 548: Compounds of the formulae Ia.1 to Ib.96, which correspond to the compounds of the formulae Ia.1 to Ib.96 summarized in tables 1 to 274, wherein Ar is Ar-2 instead of Ar-1.

Tables 549 to 822: Compounds of the formulae Ia.1 to Ib.96, which correspond to the compounds of the formulae Ia.1 to Ib.96 summarized in tables 1 to 274, wherein Ar is Ar-3 instead of Ar-1.

Tables 823 to 1096: Compounds of the formulae Ia.1 to Ib.96, which correspond to the compounds of the formulae Ia.1 to Ib.96 summarized in tables 1 to 274, wherein Ar is Ar-4 instead of Ar-1.

Tables 1097 to 1370: Compounds of the formulae Ia.1 to Ib.96, which correspond to the compounds of the formulae Ia.1 to Ib.96 summarized in tables 1 to 274, wherein Ar is Ar-5 instead of Ar-1.

Tables 1371 to 1644: Compounds of the formulae Ia.1 to Ib.96, which correspond to the compounds of the formulae Ia.1 to Ib.96 summarized in tables 1 to 274, wherein Ar is Ar-6 instead of Ar-1.

Tables 1645 to 1918: Compounds of the formulae Ia.1 to Ib.96, which correspond to the compounds of the formulae Ia.1 to Ib.96 summarized in tables 1 to 274, wherein Ar is Ar-7 instead of Ar-1.

Tables 1919 to 2192: Compounds of the formulae Ia.1 to Id.4, which correspond to the compounds of the formulae Ia.1 to Ib.96 summarized in tables 1 to 274, wherein Ar is Ar-8 instead of Ar-1.

Tables 2193 to 2466: Compounds of the formulae Ia.1 to Ib.96, which correspond to the compounds of the formulae Ia.1 to Ib.96 summarized in tables 1 to 274, wherein Ar is Ar-9 instead of Ar-1.

TABLE C

| | Ar | -X-Y-Z- | R$^{11}$/R$^{12}$ |
|---|---|---|---|
| 1. | Ar-1 | XYZ-1 | A'-1 |
| 2. | Ar-1 | XYZ-1 | A'-1a |
| 3. | Ar-1 | XYZ-1 | A'-1b |
| 4. | Ar-1 | XYZ-1 | A'-2 |
| 5. | Ar-1 | XYZ-1 | A'-2a |
| 6. | Ar-1 | XYZ-1 | A'-2b |
| 7. | Ar-1 | XYZ-1 | A'-3 |
| 8. | Ar-1 | XYZ-1 | A'-3a |
| 9. | Ar-1 | XYZ-1 | A'-3b |

TABLE C-continued

|  | Ar | -X-Y-Z- | $R^{11}/R^{12}$ |
|---|---|---|---|
| 10. | Ar-1 | XYZ-2 | A'-1 |
| 11. | Ar-1 | XYZ-2 | A'-1a |
| 12. | Ar-1 | XYZ-2 | A'-1b |
| 13. | Ar-1 | XYZ-2 | A'-2 |
| 14. | Ar-1 | XYZ-2 | A'-2a |
| 15. | Ar-1 | XYZ-2 | A'-2b |
| 16. | Ar-1 | XYZ-2 | A'-3 |
| 17. | Ar-1 | XYZ-2 | A'-3a |
| 18. | Ar-1 | XYZ-2 | A'-3b |
| 19. | Ar-1 | XYZ-3 | $R^{11}$-1 |
| 20. | Ar-1 | XYZ-3 | $R^{11}$-2 |
| 21. | Ar-1 | XYZ-3 | $R^{11}$-3 |
| 22. | Ar-1 | XYZ-3 | $R^{11}$-4 |
| 23. | Ar-1 | XYZ-3 | $R^{11}$-5 |
| 24. | Ar-1 | XYZ-3 | $R^{11}$-6 |
| 25. | Ar-1 | XYZ-3 | $R^{11}$-7 |
| 26. | Ar-1 | XYZ-3 | $R^{11}$-8 |
| 27. | Ar-1 | XYZ-3 | $R^{11}$-9 |
| 28. | Ar-1 | XYZ-3 | $R^{11}$-10 |
| 29. | Ar-1 | XYZ-3 | $R^{11}$-11 |
| 30. | Ar-1 | XYZ-3 | $R^{11}$-12 |
| 31. | Ar-1 | XYZ-3 | $R^{11}$-13 |
| 32. | Ar-1 | XYZ-3 | $R^{11}$-14 |
| 33. | Ar-1 | XYZ-3 | $R^{11}$-15 |
| 34. | Ar-1 | XYZ-3 | $R^{11}$-16 |
| 35. | Ar-1 | XYZ-3 | $R^{11}$-17 |
| 36. | Ar-1 | XYZ-3 | $R^{11}$-18 |
| 37. | Ar-1 | XYZ-3 | $R^{11}$-19 |
| 38. | Ar-1 | XYZ-3 | $R^{11}$-20 |
| 39. | Ar-1 | XYZ-3 | $R^{11}$-21 |
| 40. | Ar-1 | XYZ-3 | $R^{11}$-22 |
| 41. | Ar-1 | XYZ-3 | $R^{11}$-23 |
| 42. | Ar-1 | XYZ-3 | $R^{11}$-24 |
| 43. | Ar-1 | XYZ-3 | $R^{11}$-25 |
| 44. | Ar-1 | XYZ-3 | $R^{11}$-26 |
| 45. | Ar-1 | XYZ-3 | $R^{11}$-27 |
| 46. | Ar-1 | XYZ-3 | $R^{11}$-28 |
| 47. | Ar-1 | XYZ-3 | $R^{11}$-29 |
| 48. | Ar-1 | XYZ-4 | $R^{11}$-1 |
| 49. | Ar-1 | XYZ-4 | $R^{11}$-2 |
| 50. | Ar-1 | XYZ-4 | $R^{11}$-3 |
| 51. | Ar-1 | XYZ-4 | $R^{11}$-4 |
| 52. | Ar-1 | XYZ-4 | $R^{11}$-5 |
| 53. | Ar-1 | XYZ-4 | $R^{11}$-6 |
| 54. | Ar-1 | XYZ-4 | $R^{11}$-7 |
| 55. | Ar-1 | XYZ-4 | $R^{11}$-8 |
| 56. | Ar-1 | XYZ-4 | $R^{11}$-9 |
| 57. | Ar-1 | XYZ-4 | $R^{11}$-10 |
| 58. | Ar-1 | XYZ-4 | $R^{11}$-11 |
| 59. | Ar-1 | XYZ-4 | $R^{11}$-12 |
| 60. | Ar-1 | XYZ-4 | $R^{11}$-13 |
| 61. | Ar-1 | XYZ-4 | $R^{11}$-14 |
| 62. | Ar-1 | XYZ-4 | $R^{11}$-15 |
| 63. | Ar-1 | XYZ-4 | $R^{11}$-16 |
| 64. | Ar-1 | XYZ-4 | $R^{11}$-17 |
| 65. | Ar-1 | XYZ-4 | $R^{11}$-18 |
| 66. | Ar-1 | XYZ-4 | $R^{11}$-19 |
| 67. | Ar-1 | XYZ-4 | $R^{11}$-20 |
| 68. | Ar-1 | XYZ-4 | $R^{11}$-21 |
| 69. | Ar-1 | XYZ-4 | $R^{11}$-22 |
| 70. | Ar-1 | XYZ-4 | $R^{11}$-23 |
| 71. | Ar-1 | XYZ-4 | $R^{11}$-24 |
| 72. | Ar-1 | XYZ-4 | $R^{11}$-25 |
| 73. | Ar-1 | XYZ-4 | $R^{11}$-26 |
| 74. | Ar-1 | XYZ-4 | $R^{11}$-27 |
| 75. | Ar-1 | XYZ-4 | $R^{11}$-28 |
| 76. | Ar-1 | XYZ-4 | $R^{11}$-29 |
| 77. | Ar-1 | XYZ-5 | $R^{11}$-1 |
| 78. | Ar-1 | XYZ-5 | $R^{11}$-2 |
| 79. | Ar-1 | XYZ-5 | $R^{11}$-3 |
| 80. | Ar-1 | XYZ-5 | $R^{11}$-4 |
| 81. | Ar-1 | XYZ-5 | $R^{11}$-5 |
| 82. | Ar-1 | XYZ-5 | $R^{11}$-6 |
| 83. | Ar-1 | XYZ-5 | $R^{11}$-7 |
| 84. | Ar-1 | XYZ-5 | $R^{11}$-8 |
| 85. | Ar-1 | XYZ-5 | $R^{11}$-9 |
| 86. | Ar-1 | XYZ-5 | $R^{11}$-10 |
| 87. | Ar-1 | XYZ-5 | $R^{11}$-11 |
| 88. | Ar-1 | XYZ-5 | $R^{11}$-12 |
| 89. | Ar-1 | XYZ-5 | $R^{11}$-13 |
| 90. | Ar-1 | XYZ-5 | $R^{11}$-14 |
| 91. | Ar-1 | XYZ-5 | $R^{11}$-15 |
| 92. | Ar-1 | XYZ-5 | $R^{11}$-16 |
| 93. | Ar-1 | XYZ-5 | $R^{11}$-17 |
| 94. | Ar-1 | XYZ-5 | $R^{11}$-18 |
| 95. | Ar-1 | XYZ-5 | $R^{11}$-19 |
| 96. | Ar-1 | XYZ-5 | $R^{11}$-20 |
| 97. | Ar-1 | XYZ-5 | $R^{11}$-21 |
| 98. | Ar-1 | XYZ-5 | $R^{11}$-22 |
| 99. | Ar-1 | XYZ-5 | $R^{11}$-23 |
| 100. | Ar-1 | XYZ-5 | $R^{11}$-24 |
| 101. | Ar-1 | XYZ-5 | $R^{11}$-25 |
| 102. | Ar-1 | XYZ-5 | $R^{11}$-26 |
| 103. | Ar-1 | XYZ-5 | $R^{11}$-27 |
| 104. | Ar-1 | XYZ-5 | $R^{11}$-28 |
| 105. | Ar-1 | XYZ-5 | $R^{11}$-29 |
| 106. | Ar-1 | XYZ-6 | $R^{11}$-1 |
| 107. | Ar-1 | XYZ-6 | $R^{11}$-2 |
| 108. | Ar-1 | XYZ-6 | $R^{11}$-3 |
| 109. | Ar-1 | XYZ-6 | $R^{11}$-4 |
| 110. | Ar-1 | XYZ-6 | $R^{11}$-5 |
| 111. | Ar-1 | XYZ-6 | $R^{11}$-6 |
| 112. | Ar-1 | XYZ-6 | $R^{11}$-7 |
| 113. | Ar-1 | XYZ-6 | $R^{11}$-8 |
| 114. | Ar-1 | XYZ-6 | $R^{11}$-9 |
| 115. | Ar-1 | XYZ-6 | $R^{11}$-10 |
| 116. | Ar-1 | XYZ-6 | $R^{11}$-11 |
| 117. | Ar-1 | XYZ-6 | $R^{11}$-12 |
| 118. | Ar-1 | XYZ-6 | $R^{11}$-13 |
| 119. | Ar-1 | XYZ-6 | $R^{11}$-14 |
| 120. | Ar-1 | XYZ-6 | $R^{11}$-15 |
| 121. | Ar-1 | XYZ-6 | $R^{11}$-16 |
| 122. | Ar-1 | XYZ-6 | $R^{11}$-17 |
| 123. | Ar-1 | XYZ-6 | $R^{11}$-18 |
| 124. | Ar-1 | XYZ-6 | $R^{11}$-19 |
| 125. | Ar-1 | XYZ-6 | $R^{11}$-20 |
| 126. | Ar-1 | XYZ-6 | $R^{11}$-21 |
| 127. | Ar-1 | XYZ-6 | $R^{11}$-22 |
| 128. | Ar-1 | XYZ-6 | $R^{11}$-23 |
| 129. | Ar-1 | XYZ-6 | $R^{11}$-24 |
| 130. | Ar-1 | XYZ-6 | $R^{11}$-25 |
| 131. | Ar-1 | XYZ-6 | $R^{11}$-26 |
| 132. | Ar-1 | XYZ-6 | $R^{11}$-27 |
| 133. | Ar-1 | XYZ-6 | $R^{11}$-28 |
| 134. | Ar-1 | XYZ-6 | $R^{11}$-29 |
| 135. | Ar-1 | XYZ-7 | $R^{11}$-1 |
| 136. | Ar-1 | XYZ-7 | $R^{11}$-2 |
| 137. | Ar-1 | XYZ-7 | $R^{11}$-3 |
| 138. | Ar-1 | XYZ-7 | $R^{11}$-4 |
| 139. | Ar-1 | XYZ-7 | $R^{11}$-5 |
| 140. | Ar-1 | XYZ-7 | $R^{11}$-6 |
| 141. | Ar-1 | XYZ-7 | $R^{11}$-7 |
| 142. | Ar-1 | XYZ-7 | $R^{11}$-8 |
| 143. | Ar-1 | XYZ-7 | $R^{11}$-9 |
| 144. | Ar-1 | XYZ-7 | $R^{11}$-10 |
| 145. | Ar-1 | XYZ-7 | $R^{11}$-11 |
| 146. | Ar-1 | XYZ-7 | $R^{11}$-12 |
| 147. | Ar-1 | XYZ-7 | $R^{11}$-13 |
| 148. | Ar-1 | XYZ-7 | $R^{11}$-14 |
| 149. | Ar-1 | XYZ-7 | $R^{11}$-15 |
| 150. | Ar-1 | XYZ-7 | $R^{11}$-16 |
| 151. | Ar-1 | XYZ-7 | $R^{11}$-17 |
| 152. | Ar-1 | XYZ-7 | $R^{11}$-18 |
| 153. | Ar-1 | XYZ-7 | $R^{11}$-19 |
| 154. | Ar-1 | XYZ-7 | $R^{11}$-20 |
| 155. | Ar-1 | XYZ-7 | $R^{11}$-21 |
| 156. | Ar-1 | XYZ-7 | $R^{11}$-22 |
| 157. | Ar-1 | XYZ-7 | $R^{11}$-23 |
| 158. | Ar-1 | XYZ-7 | $R^{11}$-24 |
| 159. | Ar-1 | XYZ-7 | $R^{11}$-25 |
| 160. | Ar-1 | XYZ-7 | $R^{11}$-26 |
| 161. | Ar-1 | XYZ-7 | $R^{11}$-27 |
| 162. | Ar-1 | XYZ-7 | $R^{11}$-28 |
| 163. | Ar-1 | XYZ-7 | $R^{11}$-29 |
| 164. | Ar-1 | XYZ-8 | $R^{11}$-1 |
| 165. | Ar-1 | XYZ-8 | $R^{11}$-2 |

TABLE C-continued

|  | Ar | -X-Y-Z- | $R^{11}/R^{12}$ |
|---|---|---|---|
| 166. | Ar-1 | XYZ-8 | $R^{11}$-3 |
| 167. | Ar-1 | XYZ-8 | $R^{11}$-4 |
| 168. | Ar-1 | XYZ-8 | $R^{11}$-5 |
| 169. | Ar-1 | XYZ-8 | $R^{11}$-6 |
| 170. | Ar-1 | XYZ-8 | $R^{11}$-7 |
| 171. | Ar-1 | XYZ-8 | $R^{11}$-8 |
| 172. | Ar-1 | XYZ-8 | $R^{11}$-9 |
| 173. | Ar-1 | XYZ-8 | $R^{11}$-10 |
| 174. | Ar-1 | XYZ-8 | $R^{11}$-11 |
| 175. | Ar-1 | XYZ-8 | $R^{11}$-12 |
| 176. | Ar-1 | XYZ-8 | $R^{11}$-13 |
| 177. | Ar-1 | XYZ-8 | $R^{11}$-14 |
| 178. | Ar-1 | XYZ-8 | $R^{11}$-15 |
| 179. | Ar-1 | XYZ-8 | $R^{11}$-16 |
| 180. | Ar-1 | XYZ-8 | $R^{11}$-17 |
| 181. | Ar-1 | XYZ-8 | $R^{11}$-18 |
| 182. | Ar-1 | XYZ-8 | $R^{11}$-19 |
| 183. | Ar-1 | XYZ-8 | $R^{11}$-20 |
| 184. | Ar-1 | XYZ-8 | $R^{11}$-21 |
| 185. | Ar-1 | XYZ-8 | $R^{11}$-22 |
| 186. | Ar-1 | XYZ-8 | $R^{11}$-23 |
| 187. | Ar-1 | XYZ-8 | $R^{11}$-24 |
| 188. | Ar-1 | XYZ-8 | $R^{11}$-25 |
| 189. | Ar-1 | XYZ-8 | $R^{11}$-26 |
| 190. | Ar-1 | XYZ-8 | $R^{11}$-27 |
| 191. | Ar-1 | XYZ-8 | $R^{11}$-28 |
| 192. | Ar-1 | XYZ-8 | $R^{11}$-29 |
| 193. | Ar-1 | XYZ-9 | $R^{11}$-1 |
| 194. | Ar-1 | XYZ-9 | $R^{11}$-2 |
| 195. | Ar-1 | XYZ-9 | $R^{11}$-3 |
| 196. | Ar-1 | XYZ-9 | $R^{11}$-4 |
| 197. | Ar-1 | XYZ-9 | $R^{11}$-5 |
| 198. | Ar-1 | XYZ-9 | $R^{11}$-6 |
| 199. | Ar-1 | XYZ-9 | $R^{11}$-7 |
| 200. | Ar-1 | XYZ-9 | $R^{11}$-8 |
| 201. | Ar-1 | XYZ-9 | $R^{11}$-9 |
| 202. | Ar-1 | XYZ-9 | $R^{11}$-10 |
| 203. | Ar-1 | XYZ-9 | $R^{11}$-11 |
| 204. | Ar-1 | XYZ-9 | $R^{11}$-12 |
| 205. | Ar-1 | XYZ-9 | $R^{11}$-13 |
| 206. | Ar-1 | XYZ-9 | $R^{11}$-14 |
| 207. | Ar-1 | XYZ-9 | $R^{11}$-15 |
| 208. | Ar-1 | XYZ-9 | $R^{11}$-16 |
| 209. | Ar-1 | XYZ-9 | $R^{11}$-17 |
| 210. | Ar-1 | XYZ-9 | $R^{11}$-18 |
| 211. | Ar-1 | XYZ-9 | $R^{11}$-19 |
| 212. | Ar-1 | XYZ-9 | $R^{11}$-20 |
| 213. | Ar-1 | XYZ-9 | $R^{11}$-21 |
| 214. | Ar-1 | XYZ-9 | $R^{11}$-22 |
| 215. | Ar-1 | XYZ-9 | $R^{11}$-23 |
| 216. | Ar-1 | XYZ-9 | $R^{11}$-24 |
| 217. | Ar-1 | XYZ-9 | $R^{11}$-25 |
| 218. | Ar-1 | XYZ-9 | $R^{11}$-26 |
| 219. | Ar-1 | XYZ-9 | $R^{11}$-27 |
| 220. | Ar-1 | XYZ-9 | $R^{11}$-28 |
| 221. | Ar-1 | XYZ-9 | $R^{11}$-29 |
| 222. | Ar-1 | XYZ-10 | $R^{11}$-1 |
| 223. | Ar-1 | XYZ-10 | $R^{11}$-2 |
| 224. | Ar-1 | XYZ-10 | $R^{11}$-3 |
| 225. | Ar-1 | XYZ-10 | $R^{11}$-4 |
| 226. | Ar-1 | XYZ-10 | $R^{11}$-5 |
| 227. | Ar-1 | XYZ-10 | $R^{11}$-6 |
| 228. | Ar-1 | XYZ-10 | $R^{11}$-7 |
| 229. | Ar-1 | XYZ-10 | $R^{11}$-8 |
| 230. | Ar-1 | XYZ-10 | $R^{11}$-9 |
| 231. | Ar-1 | XYZ-10 | $R^{11}$-10 |
| 232. | Ar-1 | XYZ-10 | $R^{11}$-11 |
| 233. | Ar-1 | XYZ-10 | $R^{11}$-12 |
| 234. | Ar-1 | XYZ-10 | $R^{11}$-13 |
| 235. | Ar-1 | XYZ-10 | $R^{11}$-14 |
| 236. | Ar-1 | XYZ-10 | $R^{11}$-15 |
| 237. | Ar-1 | XYZ-10 | $R^{11}$-16 |
| 238. | Ar-1 | XYZ-10 | $R^{11}$-17 |
| 239. | Ar-1 | XYZ-10 | $R^{11}$-18 |
| 240. | Ar-1 | XYZ-10 | $R^{11}$-19 |
| 241. | Ar-1 | XYZ-10 | $R^{11}$-20 |
| 242. | Ar-1 | XYZ-10 | $R^{11}$-21 |
| 243. | Ar-1 | XYZ-10 | $R^{11}$-22 |
| 244. | Ar-1 | XYZ-10 | $R^{11}$-23 |
| 245. | Ar-1 | XYZ-10 | $R^{11}$-24 |
| 246. | Ar-1 | XYZ-10 | $R^{11}$-25 |
| 247. | Ar-1 | XYZ-10 | $R^{11}$-26 |
| 248. | Ar-1 | XYZ-10 | $R^{11}$-27 |
| 249. | Ar-1 | XYZ-10 | $R^{11}$-28 |
| 250. | Ar-1 | XYZ-10 | $R^{11}$-29 |
| 251. | Ar-1 | XYZ-11 | $R^{11}$-1 |
| 252. | Ar-1 | XYZ-11 | $R^{11}$-2 |
| 253. | Ar-1 | XYZ-11 | $R^{11}$-3 |
| 254. | Ar-1 | XYZ-11 | $R^{11}$-4 |
| 255. | Ar-1 | XYZ-11 | $R^{11}$-5 |
| 256. | Ar-1 | XYZ-11 | $R^{11}$-6 |
| 257. | Ar-1 | XYZ-11 | $R^{11}$-7 |
| 258. | Ar-1 | XYZ-11 | $R^{11}$-8 |
| 259. | Ar-1 | XYZ-11 | $R^{11}$-9 |
| 260. | Ar-1 | XYZ-11 | $R^{11}$-10 |
| 261. | Ar-1 | XYZ-11 | $R^{11}$-11 |
| 262. | Ar-1 | XYZ-11 | $R^{11}$-12 |
| 263. | Ar-1 | XYZ-11 | $R^{11}$-13 |
| 264. | Ar-1 | XYZ-11 | $R^{11}$-14 |
| 265. | Ar-1 | XYZ-11 | $R^{11}$-15 |
| 266. | Ar-1 | XYZ-11 | $R^{11}$-16 |
| 267. | Ar-1 | XYZ-11 | $R^{11}$-17 |
| 268. | Ar-1 | XYZ-11 | $R^{11}$-18 |
| 269. | Ar-1 | XYZ-11 | $R^{11}$-19 |
| 270. | Ar-1 | XYZ-11 | $R^{11}$-20 |
| 271. | Ar-1 | XYZ-11 | $R^{11}$-21 |
| 272. | Ar-1 | XYZ-11 | $R^{11}$-22 |
| 273. | Ar-1 | XYZ-11 | $R^{11}$-23 |
| 274. | Ar-1 | XYZ-11 | $R^{11}$-24 |
| 275. | Ar-1 | XYZ-11 | $R^{11}$-25 |
| 276. | Ar-1 | XYZ-11 | $R^{11}$-26 |
| 277. | Ar-1 | XYZ-11 | $R^{11}$-27 |
| 278. | Ar-1 | XYZ-11 | $R^{11}$-28 |
| 279. | Ar-1 | XYZ-11 | $R^{11}$-29 |
| 280. | Ar-1 | XYZ-12 | $R^{11}$-1 |
| 281. | Ar-1 | XYZ-12 | $R^{11}$-2 |
| 282. | Ar-1 | XYZ-12 | $R^{11}$-3 |
| 283. | Ar-1 | XYZ-12 | $R^{11}$-4 |
| 284. | Ar-1 | XYZ-12 | $R^{11}$-5 |
| 285. | Ar-1 | XYZ-12 | $R^{11}$-6 |
| 286. | Ar-1 | XYZ-12 | $R^{11}$-7 |
| 287. | Ar-1 | XYZ-12 | $R^{11}$-8 |
| 288. | Ar-1 | XYZ-12 | $R^{11}$-9 |
| 289. | Ar-1 | XYZ-12 | $R^{11}$-10 |
| 290. | Ar-1 | XYZ-12 | $R^{11}$-11 |
| 291. | Ar-1 | XYZ-12 | $R^{11}$-12 |
| 292. | Ar-1 | XYZ-12 | $R^{11}$-13 |
| 293. | Ar-1 | XYZ-12 | $R^{11}$-14 |
| 294. | Ar-1 | XYZ-12 | $R^{11}$-15 |
| 295. | Ar-1 | XYZ-12 | $R^{11}$-16 |
| 296. | Ar-1 | XYZ-12 | $R^{11}$-17 |
| 297. | Ar-1 | XYZ-12 | $R^{11}$-18 |
| 298. | Ar-1 | XYZ-12 | $R^{11}$-19 |
| 299. | Ar-1 | XYZ-12 | $R^{11}$-20 |
| 300. | Ar-1 | XYZ-12 | $R^{11}$-21 |
| 301. | Ar-1 | XYZ-12 | $R^{11}$-22 |
| 302. | Ar-1 | XYZ-12 | $R^{11}$-23 |
| 303. | Ar-1 | XYZ-12 | $R^{11}$-24 |
| 304. | Ar-1 | XYZ-12 | $R^{11}$-25 |
| 305. | Ar-1 | XYZ-12 | $R^{11}$-26 |
| 306. | Ar-1 | XYZ-12 | $R^{11}$-27 |
| 307. | Ar-1 | XYZ-12 | $R^{11}$-28 |
| 308. | Ar-1 | XYZ-12 | $R^{11}$-29 |
| 309. | Ar-1 | XYZ-13 | $R^{11}$-1 |
| 310. | Ar-1 | XYZ-13 | $R^{11}$-2 |
| 311. | Ar-1 | XYZ-13 | $R^{11}$-3 |
| 312. | Ar-1 | XYZ-13 | $R^{11}$-4 |
| 313. | Ar-1 | XYZ-13 | $R^{11}$-5 |
| 314. | Ar-1 | XYZ-13 | $R^{11}$-6 |
| 315. | Ar-1 | XYZ-13 | $R^{11}$-7 |
| 316. | Ar-1 | XYZ-13 | $R^{11}$-8 |
| 317. | Ar-1 | XYZ-13 | $R^{11}$-9 |
| 318. | Ar-1 | XYZ-13 | $R^{11}$-10 |
| 319. | Ar-1 | XYZ-13 | $R^{11}$-11 |
| 320. | Ar-1 | XYZ-13 | $R^{11}$-12 |
| 321. | Ar-1 | XYZ-13 | $R^{11}$-13 |

TABLE C-continued

|  | Ar | -X-Y-Z- | $R^{11}/R^{12}$ |
|---|---|---|---|
| 322. | Ar-1 | XYZ-13 | $R^{11}$-14 |
| 323. | Ar-1 | XYZ-13 | $R^{11}$-15 |
| 324. | Ar-1 | XYZ-13 | $R^{11}$-16 |
| 325. | Ar-1 | XYZ-13 | $R^{11}$-17 |
| 326. | Ar-1 | XYZ-13 | $R^{11}$-18 |
| 327. | Ar-1 | XYZ-13 | $R^{11}$-19 |
| 328. | Ar-1 | XYZ-13 | $R^{11}$-20 |
| 329. | Ar-1 | XYZ-13 | $R^{11}$-21 |
| 330. | Ar-1 | XYZ-13 | $R^{11}$-22 |
| 331. | Ar-1 | XYZ-13 | $R^{11}$-23 |
| 332. | Ar-1 | XYZ-13 | $R^{11}$-24 |
| 333. | Ar-1 | XYZ-13 | $R^{11}$-25 |
| 334. | Ar-1 | XYZ-13 | $R^{11}$-26 |
| 335. | Ar-1 | XYZ-13 | $R^{11}$-27 |
| 336. | Ar-1 | XYZ-13 | $R^{11}$-28 |
| 337. | Ar-1 | XYZ-13 | $R^{11}$-29 |
| 338. | Ar-1 | XYZ-14 | $R^{11}$-1 |
| 339. | Ar-1 | XYZ-14 | $R^{11}$-2 |
| 340. | Ar-1 | XYZ-14 | $R^{11}$-3 |
| 341. | Ar-1 | XYZ-14 | $R^{11}$-4 |
| 342. | Ar-1 | XYZ-14 | $R^{11}$-5 |
| 343. | Ar-1 | XYZ-14 | $R^{11}$-6 |
| 344. | Ar-1 | XYZ-14 | $R^{11}$-7 |
| 345. | Ar-1 | XYZ-14 | $R^{11}$-8 |
| 346. | Ar-1 | XYZ-14 | $R^{11}$-9 |
| 347. | Ar-1 | XYZ-14 | $R^{11}$-10 |
| 348. | Ar-1 | XYZ-14 | $R^{11}$-11 |
| 349. | Ar-1 | XYZ-14 | $R^{11}$-12 |
| 350. | Ar-1 | XYZ-14 | $R^{11}$-13 |
| 351. | Ar-1 | XYZ-14 | $R^{11}$-14 |
| 352. | Ar-1 | XYZ-14 | $R^{11}$-15 |
| 353. | Ar-1 | XYZ-14 | $R^{11}$-16 |
| 354. | Ar-1 | XYZ-14 | $R^{11}$-17 |
| 355. | Ar-1 | XYZ-14 | $R^{11}$-18 |
| 356. | Ar-1 | XYZ-14 | $R^{11}$-19 |
| 357. | Ar-1 | XYZ-14 | $R^{11}$-20 |
| 358. | Ar-1 | XYZ-14 | $R^{11}$-21 |
| 359. | Ar-1 | XYZ-14 | $R^{11}$-22 |
| 360. | Ar-1 | XYZ-14 | $R^{11}$-23 |
| 361. | Ar-1 | XYZ-14 | $R^{11}$-24 |
| 362. | Ar-1 | XYZ-14 | $R^{11}$-25 |
| 363. | Ar-1 | XYZ-14 | $R^{11}$-26 |
| 364. | Ar-1 | XYZ-14 | $R^{11}$-27 |
| 365. | Ar-1 | XYZ-14 | $R^{11}$-28 |
| 366. | Ar-1 | XYZ-14 | $R^{11}$-29 |
| 367. | Ar-1 | XYZ-15 | $R^{11}$-1 |
| 368. | Ar-1 | XYZ-15 | $R^{11}$-2 |
| 369. | Ar-1 | XYZ-15 | $R^{11}$-3 |
| 370. | Ar-1 | XYZ-15 | $R^{11}$-4 |
| 371. | Ar-1 | XYZ-15 | $R^{11}$-5 |
| 372. | Ar-1 | XYZ-15 | $R^{11}$-6 |
| 373. | Ar-1 | XYZ-15 | $R^{11}$-7 |
| 374. | Ar-1 | XYZ-15 | $R^{11}$-8 |
| 375. | Ar-1 | XYZ-15 | $R^{11}$-9 |
| 376. | Ar-1 | XYZ-15 | $R^{11}$-10 |
| 377. | Ar-1 | XYZ-15 | $R^{11}$-11 |
| 378. | Ar-1 | XYZ-15 | $R^{11}$-12 |
| 379. | Ar-1 | XYZ-15 | $R^{11}$-13 |
| 380. | Ar-1 | XYZ-15 | $R^{11}$-14 |
| 381. | Ar-1 | XYZ-15 | $R^{11}$-15 |
| 382. | Ar-1 | XYZ-15 | $R^{11}$-16 |
| 383. | Ar-1 | XYZ-15 | $R^{11}$-17 |
| 384. | Ar-1 | XYZ-15 | $R^{11}$-18 |
| 385. | Ar-1 | XYZ-15 | $R^{11}$-19 |
| 386. | Ar-1 | XYZ-15 | $R^{11}$-20 |
| 387. | Ar-1 | XYZ-15 | $R^{11}$-21 |
| 388. | Ar-1 | XYZ-15 | $R^{11}$-22 |
| 389. | Ar-1 | XYZ-15 | $R^{11}$-23 |
| 390. | Ar-1 | XYZ-15 | $R^{11}$-24 |
| 391. | Ar-1 | XYZ-15 | $R^{11}$-25 |
| 392. | Ar-1 | XYZ-15 | $R^{11}$-26 |
| 393. | Ar-1 | XYZ-15 | $R^{11}$-27 |
| 394. | Ar-1 | XYZ-15 | $R^{11}$-28 |
| 395. | Ar-1 | XYZ-15 | $R^{11}$-29 |
| 396. | Ar-1 | XYZ-16 | $R^{11}$-1 |
| 397. | Ar-1 | XYZ-16 | $R^{11}$-2 |
| 398. | Ar-1 | XYZ-16 | $R^{11}$-3 |
| 399. | Ar-1 | XYZ-16 | $R^{11}$-4 |
| 400. | Ar-1 | XYZ-16 | $R^{11}$-5 |
| 401. | Ar-1 | XYZ-16 | $R^{11}$-6 |
| 402. | Ar-1 | XYZ-16 | $R^{11}$-7 |
| 403. | Ar-1 | XYZ-16 | $R^{11}$-8 |
| 404. | Ar-1 | XYZ-16 | $R^{11}$-9 |
| 405. | Ar-1 | XYZ-16 | $R^{11}$-10 |
| 406. | Ar-1 | XYZ-16 | $R^{11}$-11 |
| 407. | Ar-1 | XYZ-16 | $R^{11}$-12 |
| 408. | Ar-1 | XYZ-16 | $R^{11}$-13 |
| 409. | Ar-1 | XYZ-16 | $R^{11}$-14 |
| 410. | Ar-1 | XYZ-16 | $R^{11}$-15 |
| 411. | Ar-1 | XYZ-16 | $R^{11}$-16 |
| 412. | Ar-1 | XYZ-16 | $R^{11}$-17 |
| 413. | Ar-1 | XYZ-16 | $R^{11}$-18 |
| 414. | Ar-1 | XYZ-16 | $R^{11}$-19 |
| 415. | Ar-1 | XYZ-16 | $R^{11}$-20 |
| 416. | Ar-1 | XYZ-16 | $R^{11}$-21 |
| 417. | Ar-1 | XYZ-16 | $R^{11}$-22 |
| 418. | Ar-1 | XYZ-16 | $R^{11}$-23 |
| 419. | Ar-1 | XYZ-16 | $R^{11}$-24 |
| 420. | Ar-1 | XYZ-16 | $R^{11}$-25 |
| 421. | Ar-1 | XYZ-16 | $R^{11}$-26 |
| 422. | Ar-1 | XYZ-16 | $R^{11}$-27 |
| 423. | Ar-1 | XYZ-16 | $R^{11}$-28 |
| 424. | Ar-1 | XYZ-16 | $R^{11}$-29 |
| 425. | Ar-1 | XYZ-17 | $R^{11}$-1 |
| 426. | Ar-1 | XYZ-17 | $R^{11}$-2 |
| 427. | Ar-1 | XYZ-17 | $R^{11}$-3 |
| 428. | Ar-1 | XYZ-17 | $R^{11}$-4 |
| 429. | Ar-1 | XYZ-17 | $R^{11}$-5 |
| 430. | Ar-1 | XYZ-17 | $R^{11}$-6 |
| 431. | Ar-1 | XYZ-17 | $R^{11}$-7 |
| 432. | Ar-1 | XYZ-17 | $R^{11}$-8 |
| 433. | Ar-1 | XYZ-17 | $R^{11}$-9 |
| 434. | Ar-1 | XYZ-17 | $R^{11}$-10 |
| 435. | Ar-1 | XYZ-17 | $R^{11}$-11 |
| 436. | Ar-1 | XYZ-17 | $R^{11}$-12 |
| 437. | Ar-1 | XYZ-17 | $R^{11}$-13 |
| 438. | Ar-1 | XYZ-17 | $R^{11}$-14 |
| 439. | Ar-1 | XYZ-17 | $R^{11}$-15 |
| 440. | Ar-1 | XYZ-17 | $R^{11}$-16 |
| 441. | Ar-1 | XYZ-17 | $R^{11}$-17 |
| 442. | Ar-1 | XYZ-17 | $R^{11}$-18 |
| 443. | Ar-1 | XYZ-17 | $R^{11}$-19 |
| 444. | Ar-1 | XYZ-17 | $R^{11}$-20 |
| 445. | Ar-1 | XYZ-17 | $R^{11}$-21 |
| 446. | Ar-1 | XYZ-17 | $R^{11}$-22 |
| 447. | Ar-1 | XYZ-17 | $R^{11}$-23 |
| 448. | Ar-1 | XYZ-17 | $R^{11}$-24 |
| 449. | Ar-1 | XYZ-17 | $R^{11}$-25 |
| 450. | Ar-1 | XYZ-17 | $R^{11}$-26 |
| 451. | Ar-1 | XYZ-17 | $R^{11}$-27 |
| 452. | Ar-1 | XYZ-17 | $R^{11}$-28 |
| 453. | Ar-1 | XYZ-17 | $R^{11}$-29 |
| 454. | Ar-1 | XYZ-18 | $R^{11}$-1 |
| 455. | Ar-1 | XYZ-18 | $R^{11}$-2 |
| 456. | Ar-1 | XYZ-18 | $R^{11}$-3 |
| 457. | Ar-1 | XYZ-18 | $R^{11}$-4 |
| 458. | Ar-1 | XYZ-18 | $R^{11}$-5 |
| 459. | Ar-1 | XYZ-18 | $R^{11}$-6 |
| 460. | Ar-1 | XYZ-18 | $R^{11}$-7 |
| 461. | Ar-1 | XYZ-18 | $R^{11}$-8 |
| 462. | Ar-1 | XYZ-18 | $R^{11}$-9 |
| 463. | Ar-1 | XYZ-18 | $R^{11}$-10 |
| 464. | Ar-1 | XYZ-18 | $R^{11}$-11 |
| 465. | Ar-1 | XYZ-18 | $R^{11}$-12 |
| 466. | Ar-1 | XYZ-18 | $R^{11}$-13 |
| 467. | Ar-1 | XYZ-18 | $R^{11}$-14 |
| 468. | Ar-1 | XYZ-18 | $R^{11}$-15 |
| 469. | Ar-1 | XYZ-18 | $R^{11}$-16 |
| 470. | Ar-1 | XYZ-18 | $R^{11}$-17 |
| 471. | Ar-1 | XYZ-18 | $R^{11}$-18 |
| 472. | Ar-1 | XYZ-18 | $R^{11}$-19 |
| 473. | Ar-1 | XYZ-18 | $R^{11}$-20 |
| 474. | Ar-1 | XYZ-18 | $R^{11}$-21 |
| 475. | Ar-1 | XYZ-18 | $R^{11}$-22 |
| 476. | Ar-1 | XYZ-18 | $R^{11}$-23 |
| 477. | Ar-1 | XYZ-18 | $R^{11}$-24 |

TABLE C-continued

|  | Ar | -X-Y-Z- | $R^{11}/R^{12}$ |
|---|---|---|---|
| 478. | Ar-1 | XYZ-18 | $R^{11}$-25 |
| 479. | Ar-1 | XYZ-18 | $R^{11}$-26 |
| 480. | Ar-1 | XYZ-18 | $R^{11}$-27 |
| 481. | Ar-1 | XYZ-18 | $R^{11}$-28 |
| 482. | Ar-1 | XYZ-18 | $R^{11}$-29 |
| 483. | Ar-1 | XYZ-19 | $R^{11}$-1 |
| 484. | Ar-1 | XYZ-19 | $R^{11}$-2 |
| 485. | Ar-1 | XYZ-19 | $R^{11}$-3 |
| 486. | Ar-1 | XYZ-19 | $R^{11}$-4 |
| 487. | Ar-1 | XYZ-19 | $R^{11}$-5 |
| 488. | Ar-1 | XYZ-19 | $R^{11}$-6 |
| 489. | Ar-1 | XYZ-19 | $R^{11}$-7 |
| 490. | Ar-1 | XYZ-19 | $R^{11}$-8 |
| 491. | Ar-1 | XYZ-19 | $R^{11}$-9 |
| 492. | Ar-1 | XYZ-19 | $R^{11}$-10 |
| 493. | Ar-1 | XYZ-19 | $R^{11}$-11 |
| 494. | Ar-1 | XYZ-19 | $R^{11}$-12 |
| 495. | Ar-1 | XYZ-19 | $R^{11}$-13 |
| 496. | Ar-1 | XYZ-19 | $R^{11}$-14 |
| 497. | Ar-1 | XYZ-19 | $R^{11}$-15 |
| 498. | Ar-1 | XYZ-19 | $R^{11}$-16 |
| 499. | Ar-1 | XYZ-19 | $R^{11}$-17 |
| 500. | Ar-1 | XYZ-19 | $R^{11}$-18 |
| 501. | Ar-1 | XYZ-19 | $R^{11}$-19 |
| 502. | Ar-1 | XYZ-19 | $R^{11}$-20 |
| 503. | Ar-1 | XYZ-19 | $R^{11}$-21 |
| 504. | Ar-1 | XYZ-19 | $R^{11}$-22 |
| 505. | Ar-1 | XYZ-19 | $R^{11}$-23 |
| 506. | Ar-1 | XYZ-19 | $R^{11}$-24 |
| 507. | Ar-1 | XYZ-19 | $R^{11}$-25 |
| 508. | Ar-1 | XYZ-19 | $R^{11}$-26 |
| 509. | Ar-1 | XYZ-19 | $R^{11}$-27 |
| 510. | Ar-1 | XYZ-19 | $R^{11}$-28 |
| 511. | Ar-1 | XYZ-19 | $R^{11}$-29 |
| 512. | Ar-1 | XYZ-20 | $R^{11}$-1 |
| 513. | Ar-1 | XYZ-20 | $R^{11}$-2 |
| 514. | Ar-1 | XYZ-20 | $R^{11}$-3 |
| 515. | Ar-1 | XYZ-20 | $R^{11}$-4 |
| 516. | Ar-1 | XYZ-20 | $R^{11}$-5 |
| 517. | Ar-1 | XYZ-20 | $R^{11}$-6 |
| 518. | Ar-1 | XYZ-20 | $R^{11}$-7 |
| 519. | Ar-1 | XYZ-20 | $R^{11}$-8 |
| 520. | Ar-1 | XYZ-20 | $R^{11}$-9 |
| 521. | Ar-1 | XYZ-20 | $R^{11}$-10 |
| 522. | Ar-1 | XYZ-20 | $R^{11}$-11 |
| 523. | Ar-1 | XYZ-20 | $R^{11}$-12 |
| 524. | Ar-1 | XYZ-20 | $R^{11}$-13 |
| 525. | Ar-1 | XYZ-20 | $R^{11}$-14 |
| 526. | Ar-1 | XYZ-20 | $R^{11}$-15 |
| 527. | Ar-1 | XYZ-20 | $R^{11}$-16 |
| 528. | Ar-1 | XYZ-20 | $R^{11}$-17 |
| 529. | Ar-1 | XYZ-20 | $R^{11}$-18 |
| 530. | Ar-1 | XYZ-20 | $R^{11}$-19 |
| 531. | Ar-1 | XYZ-20 | $R^{11}$-20 |
| 532. | Ar-1 | XYZ-20 | $R^{11}$-21 |
| 533. | Ar-1 | XYZ-20 | $R^{11}$-22 |
| 534. | Ar-1 | XYZ-20 | $R^{11}$-23 |
| 535. | Ar-1 | XYZ-20 | $R^{11}$-24 |
| 536. | Ar-1 | XYZ-20 | $R^{11}$-25 |
| 537. | Ar-1 | XYZ-20 | $R^{11}$-26 |
| 538. | Ar-1 | XYZ-20 | $R^{11}$-27 |
| 539. | Ar-1 | XYZ-20 | $R^{11}$-28 |
| 540. | Ar-1 | XYZ-20 | $R^{11}$-29 |
| 541. | Ar-1 | XYZ-21 | $R^{11}$-1 |
| 542. | Ar-1 | XYZ-21 | $R^{11}$-2 |
| 543. | Ar-1 | XYZ-21 | $R^{11}$-3 |
| 544. | Ar-1 | XYZ-21 | $R^{11}$-4 |
| 545. | Ar-1 | XYZ-21 | $R^{11}$-5 |
| 546. | Ar-1 | XYZ-21 | $R^{11}$-6 |
| 547. | Ar-1 | XYZ-21 | $R^{11}$-7 |
| 548. | Ar-1 | XYZ-21 | $R^{11}$-8 |
| 549. | Ar-1 | XYZ-21 | $R^{11}$-9 |
| 550. | Ar-1 | XYZ-21 | $R^{11}$-10 |
| 551. | Ar-1 | XYZ-21 | $R^{11}$-11 |
| 552. | Ar-1 | XYZ-21 | $R^{11}$-12 |
| 553. | Ar-1 | XYZ-21 | $R^{11}$-13 |
| 554. | Ar-1 | XYZ-21 | $R^{11}$-14 |
| 555. | Ar-1 | XYZ-21 | $R^{11}$-15 |
| 556. | Ar-1 | XYZ-21 | $R^{11}$-16 |
| 557. | Ar-1 | XYZ-21 | $R^{11}$-17 |
| 558. | Ar-1 | XYZ-21 | $R^{11}$-18 |
| 559. | Ar-1 | XYZ-21 | $R^{11}$-19 |
| 560. | Ar-1 | XYZ-21 | $R^{11}$-20 |
| 561. | Ar-1 | XYZ-21 | $R^{11}$-21 |
| 562. | Ar-1 | XYZ-21 | $R^{11}$-22 |
| 563. | Ar-1 | XYZ-21 | $R^{11}$-23 |
| 564. | Ar-1 | XYZ-21 | $R^{11}$-24 |
| 565. | Ar-1 | XYZ-21 | $R^{11}$-25 |
| 566. | Ar-1 | XYZ-21 | $R^{11}$-26 |
| 567. | Ar-1 | XYZ-21 | $R^{11}$-27 |
| 568. | Ar-1 | XYZ-21 | $R^{11}$-28 |
| 569. | Ar-1 | XYZ-21 | $R^{11}$-29 |
| 570. | Ar-1 | XYZ-22 | $R^{11}$-1 |
| 571. | Ar-1 | XYZ-22 | $R^{11}$-2 |
| 572. | Ar-1 | XYZ-22 | $R^{11}$-3 |
| 573. | Ar-1 | XYZ-22 | $R^{11}$-4 |
| 574. | Ar-1 | XYZ-22 | $R^{11}$-5 |
| 575. | Ar-1 | XYZ-22 | $R^{11}$-6 |
| 576. | Ar-1 | XYZ-22 | $R^{11}$-7 |
| 577. | Ar-1 | XYZ-22 | $R^{11}$-8 |
| 578. | Ar-1 | XYZ-22 | $R^{11}$-9 |
| 579. | Ar-1 | XYZ-22 | $R^{11}$-10 |
| 580. | Ar-1 | XYZ-22 | $R^{11}$-11 |
| 581. | Ar-1 | XYZ-22 | $R^{11}$-12 |
| 582. | Ar-1 | XYZ-22 | $R^{11}$-13 |
| 583. | Ar-1 | XYZ-22 | $R^{11}$-14 |
| 584. | Ar-1 | XYZ-22 | $R^{11}$-15 |
| 585. | Ar-1 | XYZ-22 | $R^{11}$-16 |
| 586. | Ar-1 | XYZ-22 | $R^{11}$-17 |
| 587. | Ar-1 | XYZ-22 | $R^{11}$-18 |
| 588. | Ar-1 | XYZ-22 | $R^{11}$-19 |
| 589. | Ar-1 | XYZ-22 | $R^{11}$-20 |
| 590. | Ar-1 | XYZ-22 | $R^{11}$-21 |
| 591. | Ar-1 | XYZ-22 | $R^{11}$-22 |
| 592. | Ar-1 | XYZ-22 | $R^{11}$-23 |
| 593. | Ar-1 | XYZ-22 | $R^{11}$-24 |
| 594. | Ar-1 | XYZ-22 | $R^{11}$-25 |
| 595. | Ar-1 | XYZ-22 | $R^{11}$-26 |
| 596. | Ar-1 | XYZ-22 | $R^{11}$-27 |
| 597. | Ar-1 | XYZ-22 | $R^{11}$-28 |
| 598. | Ar-1 | XYZ-22 | $R^{11}$-29 |
| 599. | Ar-1 | XYZ-23 | $R^{11}$-1 |
| 600. | Ar-1 | XYZ-23 | $R^{11}$-2 |
| 601. | Ar-1 | XYZ-23 | $R^{11}$-3 |
| 602. | Ar-1 | XYZ-23 | $R^{11}$-4 |
| 603. | Ar-1 | XYZ-23 | $R^{11}$-5 |
| 604. | Ar-1 | XYZ-23 | $R^{11}$-6 |
| 605. | Ar-1 | XYZ-23 | $R^{11}$-7 |
| 606. | Ar-1 | XYZ-23 | $R^{11}$-8 |
| 607. | Ar-1 | XYZ-23 | $R^{11}$-9 |
| 608. | Ar-1 | XYZ-23 | $R^{11}$-10 |
| 609. | Ar-1 | XYZ-23 | $R^{11}$-11 |
| 610. | Ar-1 | XYZ-23 | $R^{11}$-12 |
| 611. | Ar-1 | XYZ-23 | $R^{11}$-13 |
| 612. | Ar-1 | XYZ-23 | $R^{11}$-14 |
| 613. | Ar-1 | XYZ-23 | $R^{11}$-15 |
| 614. | Ar-1 | XYZ-23 | $R^{11}$-16 |
| 615. | Ar-1 | XYZ-23 | $R^{11}$-17 |
| 616. | Ar-1 | XYZ-23 | $R^{11}$-18 |
| 617. | Ar-1 | XYZ-23 | $R^{11}$-19 |
| 618. | Ar-1 | XYZ-23 | $R^{11}$-20 |
| 619. | Ar-1 | XYZ-23 | $R^{11}$-21 |
| 620. | Ar-1 | XYZ-23 | $R^{11}$-22 |
| 621. | Ar-1 | XYZ-23 | $R^{11}$-23 |
| 622. | Ar-1 | XYZ-23 | $R^{11}$-24 |
| 623. | Ar-1 | XYZ-23 | $R^{11}$-25 |
| 624. | Ar-1 | XYZ-23 | $R^{11}$-26 |
| 625. | Ar-1 | XYZ-23 | $R^{11}$-27 |
| 626. | Ar-1 | XYZ-23 | $R^{11}$-28 |
| 627. | Ar-1 | XYZ-23 | $R^{11}$-29 |
| 628. | Ar-1 | XYZ-24 | $R^{11}$-1 |
| 629. | Ar-1 | XYZ-24 | $R^{11}$-2 |
| 630. | Ar-1 | XYZ-24 | $R^{11}$-3 |
| 631. | Ar-1 | XYZ-24 | $R^{11}$-4 |
| 632. | Ar-1 | XYZ-24 | $R^{11}$-5 |
| 633. | Ar-1 | XYZ-24 | $R^{11}$-6 |

TABLE C-continued

| | Ar | -X-Y-Z- | $R^{11}/R^{12}$ |
|---|---|---|---|
| 634. | Ar-1 | XYZ-24 | $R^{11}$-7 |
| 635. | Ar-1 | XYZ-24 | $R^{11}$-8 |
| 636. | Ar-1 | XYZ-24 | $R^{11}$-9 |
| 637. | Ar-1 | XYZ-24 | $R^{11}$-10 |
| 638. | Ar-1 | XYZ-24 | $R^{11}$-11 |
| 639. | Ar-1 | XYZ-24 | $R^{11}$-12 |
| 640. | Ar-1 | XYZ-24 | $R^{11}$-13 |
| 641. | Ar-1 | XYZ-24 | $R^{11}$-14 |
| 642. | Ar-1 | XYZ-24 | $R^{11}$-15 |
| 643. | Ar-1 | XYZ-24 | $R^{11}$-16 |
| 644. | Ar-1 | XYZ-24 | $R^{11}$-17 |
| 645. | Ar-1 | XYZ-24 | $R^{11}$-18 |
| 646. | Ar-1 | XYZ-24 | $R^{11}$-19 |
| 647. | Ar-1 | XYZ-24 | $R^{11}$-20 |
| 648. | Ar-1 | XYZ-24 | $R^{11}$-21 |
| 649. | Ar-1 | XYZ-24 | $R^{11}$-22 |
| 650. | Ar-1 | XYZ-24 | $R^{11}$-23 |
| 651. | Ar-1 | XYZ-24 | $R^{11}$-24 |
| 652. | Ar-1 | XYZ-24 | $R^{11}$-25 |
| 653. | Ar-1 | XYZ-24 | $R^{11}$-26 |
| 654. | Ar-1 | XYZ-24 | $R^{11}$-27 |
| 655. | Ar-1 | XYZ-24 | $R^{11}$-28 |
| 656. | Ar-1 | XYZ-24 | $R^{11}$-29 |
| 657. | Ar-1 | XYZ-25 | $R^{11}$-1 |
| 658. | Ar-1 | XYZ-25 | $R^{11}$-2 |
| 659. | Ar-1 | XYZ-25 | $R^{11}$-3 |
| 660. | Ar-1 | XYZ-25 | $R^{11}$-4 |
| 661. | Ar-1 | XYZ-25 | $R^{11}$-5 |
| 662. | Ar-1 | XYZ-25 | $R^{11}$-6 |
| 663. | Ar-1 | XYZ-25 | $R^{11}$-7 |
| 664. | Ar-1 | XYZ-25 | $R^{11}$-8 |
| 665. | Ar-1 | XYZ-25 | $R^{11}$-9 |
| 666. | Ar-1 | XYZ-25 | $R^{11}$-10 |
| 667. | Ar-1 | XYZ-25 | $R^{11}$-11 |
| 668. | Ar-1 | XYZ-25 | $R^{11}$-12 |
| 669. | Ar-1 | XYZ-25 | $R^{11}$-13 |
| 670. | Ar-1 | XYZ-25 | $R^{11}$-14 |
| 671. | Ar-1 | XYZ-25 | $R^{11}$-15 |
| 672. | Ar-1 | XYZ-25 | $R^{11}$-16 |
| 673. | Ar-1 | XYZ-25 | $R^{11}$-17 |
| 674. | Ar-1 | XYZ-25 | $R^{11}$-18 |
| 675. | Ar-1 | XYZ-25 | $R^{11}$-19 |
| 676. | Ar-1 | XYZ-25 | $R^{11}$-20 |
| 677. | Ar-1 | XYZ-25 | $R^{11}$-21 |
| 678. | Ar-1 | XYZ-25 | $R^{11}$-22 |
| 679. | Ar-1 | XYZ-25 | $R^{11}$-23 |
| 680. | Ar-1 | XYZ-25 | $R^{11}$-24 |
| 681. | Ar-1 | XYZ-25 | $R^{11}$-25 |
| 682. | Ar-1 | XYZ-25 | $R^{11}$-26 |
| 683. | Ar-1 | XYZ-25 | $R^{11}$-27 |
| 684. | Ar-1 | XYZ-25 | $R^{11}$-28 |
| 685. | Ar-1 | XYZ-25 | $R^{11}$-29 |
| 686. | Ar-1 | XYZ-26 | $R^{11}$-1 |
| 687. | Ar-1 | XYZ-26 | $R^{11}$-2 |
| 688. | Ar-1 | XYZ-26 | $R^{11}$-3 |
| 689. | Ar-1 | XYZ-26 | $R^{11}$-4 |
| 690. | Ar-1 | XYZ-26 | $R^{11}$-5 |
| 691. | Ar-1 | XYZ-26 | $R^{11}$-6 |
| 692. | Ar-1 | XYZ-26 | $R^{11}$-7 |
| 693. | Ar-1 | XYZ-26 | $R^{11}$-8 |
| 694. | Ar-1 | XYZ-26 | $R^{11}$-9 |
| 695. | Ar-1 | XYZ-26 | $R^{11}$-10 |
| 696. | Ar-1 | XYZ-26 | $R^{11}$-11 |
| 697. | Ar-1 | XYZ-26 | $R^{11}$-12 |
| 698. | Ar-1 | XYZ-26 | $R^{11}$-13 |
| 699. | Ar-1 | XYZ-26 | $R^{11}$-14 |
| 700. | Ar-1 | XYZ-26 | $R^{11}$-15 |
| 701. | Ar-1 | XYZ-26 | $R^{11}$-16 |
| 702. | Ar-1 | XYZ-26 | $R^{11}$-17 |
| 703. | Ar-1 | XYZ-26 | $R^{11}$-18 |
| 704. | Ar-1 | XYZ-26 | $R^{11}$-19 |
| 705. | Ar-1 | XYZ-26 | $R^{11}$-20 |
| 706. | Ar-1 | XYZ-26 | $R^{11}$-21 |
| 707. | Ar-1 | XYZ-26 | $R^{11}$-22 |
| 708. | Ar-1 | XYZ-26 | $R^{11}$-23 |
| 709. | Ar-1 | XYZ-26 | $R^{11}$-24 |
| 710. | Ar-1 | XYZ-26 | $R^{11}$-25 |
| 711. | Ar-1 | XYZ-26 | $R^{11}$-26 |
| 712. | Ar-1 | XYZ-26 | $R^{11}$-27 |
| 713. | Ar-1 | XYZ-26 | $R^{11}$-28 |
| 714. | Ar-1 | XYZ-27 | $R^{11}$-29 |
| 715. | Ar-1 | XYZ-27 | $R^{11}$-1 |
| 716. | Ar-1 | XYZ-27 | $R^{11}$-2 |
| 717. | Ar-1 | XYZ-27 | $R^{11}$-3 |
| 718. | Ar-1 | XYZ-27 | $R^{11}$-4 |
| 719. | Ar-1 | XYZ-27 | $R^{11}$-5 |
| 720. | Ar-1 | XYZ-27 | $R^{11}$-6 |
| 721. | Ar-1 | XYZ-27 | $R^{11}$-7 |
| 722. | Ar-1 | XYZ-27 | $R^{11}$-8 |
| 723. | Ar-1 | XYZ-27 | $R^{11}$-9 |
| 724. | Ar-1 | XYZ-27 | $R^{11}$-10 |
| 725. | Ar-1 | XYZ-27 | $R^{11}$-11 |
| 726. | Ar-1 | XYZ-27 | $R^{11}$-12 |
| 727. | Ar-1 | XYZ-27 | $R^{11}$-13 |
| 728. | Ar-1 | XYZ-27 | $R^{11}$-14 |
| 729. | Ar-1 | XYZ-27 | $R^{11}$-15 |
| 730. | Ar-1 | XYZ-27 | $R^{11}$-16 |
| 731. | Ar-1 | XYZ-27 | $R^{11}$-17 |
| 732. | Ar-1 | XYZ-27 | $R^{11}$-18 |
| 733. | Ar-1 | XYZ-27 | $R^{11}$-19 |
| 734. | Ar-1 | XYZ-27 | $R^{11}$-20 |
| 735. | Ar-1 | XYZ-27 | $R^{11}$-21 |
| 736. | Ar-1 | XYZ-27 | $R^{11}$-22 |
| 737. | Ar-1 | XYZ-27 | $R^{11}$-23 |
| 738. | Ar-1 | XYZ-27 | $R^{11}$-24 |
| 739. | Ar-1 | XYZ-27 | $R^{11}$-25 |
| 740. | Ar-1 | XYZ-27 | $R^{11}$-26 |
| 741. | Ar-1 | XYZ-27 | $R^{11}$-27 |
| 742. | Ar-1 | XYZ-27 | $R^{11}$-28 |
| 743. | Ar-1 | XYZ-27 | $R^{11}$-29 |
| 744. | Ar-1 | XYZ-28 | $R^{11}$-1 |
| 745. | Ar-1 | XYZ-28 | $R^{11}$-2 |
| 746. | Ar-1 | XYZ-28 | $R^{11}$-3 |
| 747. | Ar-1 | XYZ-28 | $R^{11}$-4 |
| 748. | Ar-1 | XYZ-28 | $R^{11}$-5 |
| 749. | Ar-1 | XYZ-28 | $R^{11}$-6 |
| 750. | Ar-1 | XYZ-28 | $R^{11}$-7 |
| 751. | Ar-1 | XYZ-28 | $R^{11}$-8 |
| 752. | Ar-1 | XYZ-28 | $R^{11}$-9 |
| 753. | Ar-1 | XYZ-28 | $R^{11}$-10 |
| 754. | Ar-1 | XYZ-28 | $R^{11}$-11 |
| 755. | Ar-1 | XYZ-28 | $R^{11}$-12 |
| 756. | Ar-1 | XYZ-28 | $R^{11}$-13 |
| 757. | Ar-1 | XYZ-28 | $R^{11}$-14 |
| 758. | Ar-1 | XYZ-28 | $R^{11}$-15 |
| 759. | Ar-1 | XYZ-28 | $R^{11}$-16 |
| 760. | Ar-1 | XYZ-28 | $R^{11}$-17 |
| 761. | Ar-1 | XYZ-28 | $R^{11}$-18 |
| 762. | Ar-1 | XYZ-28 | $R^{11}$-19 |
| 763. | Ar-1 | XYZ-28 | $R^{11}$-20 |
| 764. | Ar-1 | XYZ-28 | $R^{11}$-21 |
| 765. | Ar-1 | XYZ-28 | $R^{11}$-22 |
| 766. | Ar-1 | XYZ-28 | $R^{11}$-23 |
| 767. | Ar-1 | XYZ-28 | $R^{11}$-24 |
| 768. | Ar-1 | XYZ-28 | $R^{11}$-25 |
| 769. | Ar-1 | XYZ-28 | $R^{11}$-26 |
| 770. | Ar-1 | XYZ-28 | $R^{11}$-27 |
| 771. | Ar-1 | XYZ-28 | $R^{11}$-28 |
| 772. | Ar-1 | XYZ-28 | $R^{11}$-29 |
| 773. | Ar-1 | XYZ-29 | $R^{11}$-1 |
| 774. | Ar-1 | XYZ-29 | $R^{11}$-2 |
| 775. | Ar-1 | XYZ-29 | $R^{11}$-3 |
| 776. | Ar-1 | XYZ-29 | $R^{11}$-4 |
| 777. | Ar-1 | XYZ-29 | $R^{11}$-5 |
| 778. | Ar-1 | XYZ-29 | $R^{11}$-6 |
| 779. | Ar-1 | XYZ-29 | $R^{11}$-7 |
| 780. | Ar-1 | XYZ-29 | $R^{11}$-8 |
| 781. | Ar-1 | XYZ-29 | $R^{11}$-9 |
| 782. | Ar-1 | XYZ-29 | $R^{11}$-10 |
| 783. | Ar-1 | XYZ-29 | $R^{11}$-11 |
| 784. | Ar-1 | XYZ-29 | $R^{11}$-12 |
| 785. | Ar-1 | XYZ-29 | $R^{11}$-13 |
| 786. | Ar-1 | XYZ-29 | $R^{11}$-14 |
| 787. | Ar-1 | XYZ-29 | $R^{11}$-15 |
| 788. | Ar-1 | XYZ-29 | $R^{11}$-16 |
| 789. | Ar-1 | XYZ-29 | $R^{11}$-17 |

TABLE C-continued

| | Ar | -X-Y-Z- | $R^{11}/R^{12}$ |
|---|---|---|---|
| 790. | Ar-1 | XYZ-29 | $R^{11}$-18 |
| 791. | Ar-1 | XYZ-29 | $R^{11}$-19 |
| 792. | Ar-1 | XYZ-29 | $R^{11}$-20 |
| 793. | Ar-1 | XYZ-29 | $R^{11}$-21 |
| 794. | Ar-1 | XYZ-29 | $R^{11}$-22 |
| 795. | Ar-1 | XYZ-29 | $R^{11}$-23 |
| 796. | Ar-1 | XYZ-29 | $R^{11}$-24 |
| 797. | Ar-1 | XYZ-29 | $R^{11}$-25 |
| 798. | Ar-1 | XYZ-29 | $R^{11}$-26 |
| 799. | Ar-1 | XYZ-29 | $R^{11}$-27 |
| 800. | Ar-1 | XYZ-29 | $R^{11}$-28 |
| 801. | Ar-1 | XYZ-29 | $R^{11}$-29 |
| 802. | Ar-1 | XYZ-30 | $R^{11}$-1 |
| 803. | Ar-1 | XYZ-30 | $R^{11}$-2 |
| 804. | Ar-1 | XYZ-30 | $R^{11}$-3 |
| 805. | Ar-1 | XYZ-30 | $R^{11}$-4 |
| 806. | Ar-1 | XYZ-30 | $R^{11}$-5 |
| 807. | Ar-1 | XYZ-30 | $R^{11}$-6 |
| 808. | Ar-1 | XYZ-30 | $R^{11}$-7 |
| 809. | Ar-1 | XYZ-30 | $R^{11}$-8 |
| 810. | Ar-1 | XYZ-30 | $R^{11}$-9 |
| 811. | Ar-1 | XYZ-30 | $R^{11}$-10 |
| 812. | Ar-1 | XYZ-30 | $R^{11}$-11 |
| 813. | Ar-1 | XYZ-30 | $R^{11}$-12 |
| 814. | Ar-1 | XYZ-30 | $R^{11}$-13 |
| 815. | Ar-1 | XYZ-30 | $R^{11}$-14 |
| 816. | Ar-1 | XYZ-30 | $R^{11}$-15 |
| 817. | Ar-1 | XYZ-30 | $R^{11}$-16 |
| 818. | Ar-1 | XYZ-30 | $R^{11}$-17 |
| 819. | Ar-1 | XYZ-30 | $R^{11}$-18 |
| 820. | Ar-1 | XYZ-30 | $R^{11}$-19 |
| 821. | Ar-1 | XYZ-30 | $R^{11}$-20 |
| 822. | Ar-1 | XYZ-30 | $R^{11}$-21 |
| 823. | Ar-1 | XYZ-30 | $R^{11}$-22 |
| 824. | Ar-1 | XYZ-30 | $R^{11}$-23 |
| 825. | Ar-1 | XYZ-30 | $R^{11}$-24 |
| 826. | Ar-1 | XYZ-30 | $R^{11}$-25 |
| 827. | Ar-1 | XYZ-30 | $R^{11}$-26 |
| 828. | Ar-1 | XYZ-30 | $R^{11}$-27 |
| 829. | Ar-1 | XYZ-30 | $R^{11}$-28 |
| 830. | Ar-1 | XYZ-30 | $R^{11}$-29 |
| 831. | Ar-1 | XYZ-31 | $R^{11}$-1 |
| 832. | Ar-1 | XYZ-31 | $R^{11}$-2 |
| 833. | Ar-1 | XYZ-31 | $R^{11}$-3 |
| 834. | Ar-1 | XYZ-31 | $R^{11}$-4 |
| 835. | Ar-1 | XYZ-31 | $R^{11}$-5 |
| 836. | Ar-1 | XYZ-31 | $R^{11}$-6 |
| 837. | Ar-1 | XYZ-31 | $R^{11}$-7 |
| 838. | Ar-1 | XYZ-31 | $R^{11}$-8 |
| 839. | Ar-1 | XYZ-31 | $R^{11}$-9 |
| 840. | Ar-1 | XYZ-31 | $R^{11}$-10 |
| 841. | Ar-1 | XYZ-31 | $R^{11}$-11 |
| 842. | Ar-1 | XYZ-31 | $R^{11}$-12 |
| 843. | Ar-1 | XYZ-31 | $R^{11}$-13 |
| 844. | Ar-1 | XYZ-31 | $R^{11}$-14 |
| 845. | Ar-1 | XYZ-31 | $R^{11}$-15 |
| 846. | Ar-1 | XYZ-31 | $R^{11}$-16 |
| 847. | Ar-1 | XYZ-31 | $R^{11}$-17 |
| 848. | Ar-1 | XYZ-31 | $R^{11}$-18 |
| 849. | Ar-1 | XYZ-31 | $R^{11}$-19 |
| 850. | Ar-1 | XYZ-31 | $R^{11}$-20 |
| 851. | Ar-1 | XYZ-31 | $R^{11}$-21 |
| 852. | Ar-1 | XYZ-31 | $R^{11}$-22 |
| 853. | Ar-1 | XYZ-31 | $R^{11}$-23 |
| 854. | Ar-1 | XYZ-31 | $R^{11}$-24 |
| 855. | Ar-1 | XYZ-31 | $R^{11}$-25 |
| 856. | Ar-1 | XYZ-31 | $R^{11}$-26 |
| 857. | Ar-1 | XYZ-31 | $R^{11}$-27 |
| 858. | Ar-1 | XYZ-31 | $R^{11}$-28 |
| 859. | Ar-1 | XYZ-31 | $R^{11}$-29 |
| 860. | Ar-1 | XYZ-32 | $R^{11}$-1 |
| 861. | Ar-1 | XYZ-32 | $R^{11}$-2 |
| 862. | Ar-1 | XYZ-32 | $R^{11}$-3 |
| 863. | Ar-1 | XYZ-32 | $R^{11}$-4 |
| 864. | Ar-1 | XYZ-32 | $R^{11}$-5 |
| 865. | Ar-1 | XYZ-32 | $R^{11}$-6 |
| 866. | Ar-1 | XYZ-32 | $R^{11}$-7 |
| 867. | Ar-1 | XYZ-32 | $R^{11}$-8 |
| 868. | Ar-1 | XYZ-32 | $R^{11}$-9 |
| 869. | Ar-1 | XYZ-32 | $R^{11}$-10 |
| 870. | Ar-1 | XYZ-32 | $R^{11}$-11 |
| 871. | Ar-1 | XYZ-32 | $R^{11}$-12 |
| 872. | Ar-1 | XYZ-32 | $R^{11}$-13 |
| 873. | Ar-1 | XYZ-32 | $R^{11}$-14 |
| 874. | Ar-1 | XYZ-32 | $R^{11}$-15 |
| 875. | Ar-1 | XYZ-32 | $R^{11}$-16 |
| 876. | Ar-1 | XYZ-32 | $R^{11}$-17 |
| 877. | Ar-1 | XYZ-32 | $R^{11}$-18 |
| 878. | Ar-1 | XYZ-32 | $R^{11}$-19 |
| 879. | Ar-1 | XYZ-32 | $R^{11}$-20 |
| 880. | Ar-1 | XYZ-32 | $R^{11}$-21 |
| 881. | Ar-1 | XYZ-32 | $R^{11}$-22 |
| 882. | Ar-1 | XYZ-32 | $R^{11}$-23 |
| 883. | Ar-1 | XYZ-32 | $R^{11}$-24 |
| 884. | Ar-1 | XYZ-32 | $R^{11}$-25 |
| 885. | Ar-1 | XYZ-32 | $R^{11}$-26 |
| 886. | Ar-1 | XYZ-32 | $R^{11}$-27 |
| 887. | Ar-1 | XYZ-32 | $R^{11}$-28 |
| 888. | Ar-1 | XYZ-32 | $R^{11}$-29 |
| 889. | Ar-1 | XYZ-33 | $R^{11}$-1 |
| 890. | Ar-1 | XYZ-33 | $R^{11}$-2 |
| 891. | Ar-1 | XYZ-33 | $R^{11}$-3 |
| 892. | Ar-1 | XYZ-33 | $R^{11}$-4 |
| 893. | Ar-1 | XYZ-33 | $R^{11}$-5 |
| 894. | Ar-1 | XYZ-33 | $R^{11}$-6 |
| 895. | Ar-1 | XYZ-33 | $R^{11}$-7 |
| 896. | Ar-1 | XYZ-33 | $R^{11}$-8 |
| 897. | Ar-1 | XYZ-33 | $R^{11}$-9 |
| 898. | Ar-1 | XYZ-33 | $R^{11}$-10 |
| 899. | Ar-1 | XYZ-33 | $R^{11}$-11 |
| 900. | Ar-1 | XYZ-33 | $R^{11}$-12 |
| 901. | Ar-1 | XYZ-33 | $R^{11}$-13 |
| 902. | Ar-1 | XYZ-33 | $R^{11}$-14 |
| 903. | Ar-1 | XYZ-33 | $R^{11}$-15 |
| 904. | Ar-1 | XYZ-33 | $R^{11}$-16 |
| 905. | Ar-1 | XYZ-33 | $R^{11}$-17 |
| 906. | Ar-1 | XYZ-33 | $R^{11}$-18 |
| 907. | Ar-1 | XYZ-33 | $R^{11}$-19 |
| 908. | Ar-1 | XYZ-33 | $R^{11}$-20 |
| 909. | Ar-1 | XYZ-33 | $R^{11}$-21 |
| 910. | Ar-1 | XYZ-33 | $R^{11}$-22 |
| 911. | Ar-1 | XYZ-33 | $R^{11}$-23 |
| 912. | Ar-1 | XYZ-33 | $R^{11}$-24 |
| 913. | Ar-1 | XYZ-33 | $R^{11}$-25 |
| 914. | Ar-1 | XYZ-33 | $R^{11}$-26 |
| 915. | Ar-1 | XYZ-33 | $R^{11}$-27 |
| 916. | Ar-1 | XYZ-33 | $R^{11}$-28 |
| 917. | Ar-1 | XYZ-33 | $R^{11}$-29 |
| 918. | Ar-1 | XYZ-34 | $R^{11}$-1 |
| 919. | Ar-1 | XYZ-34 | $R^{11}$-2 |
| 920. | Ar-1 | XYZ-34 | $R^{11}$-3 |
| 921. | Ar-1 | XYZ-34 | $R^{11}$-4 |
| 922. | Ar-1 | XYZ-34 | $R^{11}$-5 |
| 923. | Ar-1 | XYZ-34 | $R^{11}$-6 |
| 924. | Ar-1 | XYZ-34 | $R^{11}$-7 |
| 925. | Ar-1 | XYZ-34 | $R^{11}$-8 |
| 926. | Ar-1 | XYZ-34 | $R^{11}$-9 |
| 927. | Ar-1 | XYZ-34 | $R^{11}$-10 |
| 928. | Ar-1 | XYZ-34 | $R^{11}$-11 |
| 929. | Ar-1 | XYZ-34 | $R^{11}$-12 |
| 930. | Ar-1 | XYZ-34 | $R^{11}$-13 |
| 931. | Ar-1 | XYZ-34 | $R^{11}$-14 |
| 932. | Ar-1 | XYZ-34 | $R^{11}$-15 |
| 933. | Ar-1 | XYZ-34 | $R^{11}$-16 |
| 934. | Ar-1 | XYZ-34 | $R^{11}$-17 |
| 935. | Ar-1 | XYZ-34 | $R^{11}$-18 |
| 936. | Ar-1 | XYZ-34 | $R^{11}$-19 |
| 937. | Ar-1 | XYZ-34 | $R^{11}$-20 |
| 938. | Ar-1 | XYZ-34 | $R^{11}$-21 |
| 939. | Ar-1 | XYZ-34 | $R^{11}$-22 |
| 940. | Ar-1 | XYZ-34 | $R^{11}$-23 |
| 941. | Ar-1 | XYZ-34 | $R^{11}$-24 |
| 942. | Ar-1 | XYZ-34 | $R^{11}$-25 |
| 943. | Ar-1 | XYZ-34 | $R^{11}$-26 |
| 944. | Ar-1 | XYZ-34 | $R^{11}$-27 |
| 945. | Ar-1 | XYZ-34 | $R^{11}$-28 |

TABLE C-continued

| | Ar | -X-Y-Z- | $R^{11}/R^{12}$ |
|---|---|---|---|
| 946. | Ar-1 | XYZ-34 | $R^{11}$-29 |
| 947. | Ar-1 | XYZ-35 | $R^{11}$-1 |
| 948. | Ar-1 | XYZ-35 | $R^{11}$-2 |
| 949. | Ar-1 | XYZ-35 | $R^{11}$-3 |
| 950. | Ar-1 | XYZ-35 | $R^{11}$-4 |
| 951. | Ar-1 | XYZ-35 | $R^{11}$-5 |
| 952. | Ar-1 | XYZ-35 | $R^{11}$-6 |
| 953. | Ar-1 | XYZ-35 | $R^{11}$-7 |
| 954. | Ar-1 | XYZ-35 | $R^{11}$-8 |
| 955. | Ar-1 | XYZ-35 | $R^{11}$-9 |
| 956. | Ar-1 | XYZ-35 | $R^{11}$-10 |
| 957. | Ar-1 | XYZ-35 | $R^{11}$-11 |
| 958. | Ar-1 | XYZ-35 | $R^{11}$-12 |
| 959. | Ar-1 | XYZ-35 | $R^{11}$-13 |
| 960. | Ar-1 | XYZ-35 | $R^{11}$-14 |
| 961. | Ar-1 | XYZ-35 | $R^{11}$-15 |
| 962. | Ar-1 | XYZ-35 | $R^{11}$-16 |
| 963. | Ar-1 | XYZ-35 | $R^{11}$-17 |
| 964. | Ar-1 | XYZ-35 | $R^{11}$-18 |
| 965. | Ar-1 | XYZ-35 | $R^{11}$-19 |
| 966. | Ar-1 | XYZ-35 | $R^{11}$-20 |
| 967. | Ar-1 | XYZ-35 | $R^{11}$-21 |
| 968. | Ar-1 | XYZ-35 | $R^{11}$-22 |
| 969. | Ar-1 | XYZ-35 | $R^{11}$-23 |
| 970. | Ar-1 | XYZ-35 | $R^{11}$-24 |
| 971. | Ar-1 | XYZ-35 | $R^{11}$-25 |
| 972. | Ar-1 | XYZ-35 | $R^{11}$-26 |
| 973. | Ar-1 | XYZ-35 | $R^{11}$-27 |
| 974. | Ar-1 | XYZ-35 | $R^{11}$-28 |
| 975. | Ar-1 | XYZ-35 | $R^{11}$-29 |
| 976. | Ar-1 | XYZ-36 | $R^{11}$-1 |
| 977. | Ar-1 | XYZ-36 | $R^{11}$-2 |
| 978. | Ar-1 | XYZ-36 | $R^{11}$-3 |
| 979. | Ar-1 | XYZ-36 | $R^{11}$-4 |
| 980. | Ar-1 | XYZ-36 | $R^{11}$-5 |
| 981. | Ar-1 | XYZ-36 | $R^{11}$-6 |
| 982. | Ar-1 | XYZ-36 | $R^{11}$-7 |
| 983. | Ar-1 | XYZ-36 | $R^{11}$-8 |
| 984. | Ar-1 | XYZ-36 | $R^{11}$-9 |
| 985. | Ar-1 | XYZ-36 | $R^{11}$-10 |
| 986. | Ar-1 | XYZ-36 | $R^{11}$-11 |
| 987. | Ar-1 | XYZ-36 | $R^{11}$-12 |
| 988. | Ar-1 | XYZ-36 | $R^{11}$-13 |
| 989. | Ar-1 | XYZ-36 | $R^{11}$-14 |
| 990. | Ar-1 | XYZ-36 | $R^{11}$-15 |
| 991. | Ar-1 | XYZ-36 | $R^{11}$-16 |
| 992. | Ar-1 | XYZ-36 | $R^{11}$-17 |
| 993. | Ar-1 | XYZ-36 | $R^{11}$-18 |
| 994. | Ar-1 | XYZ-36 | $R^{11}$-19 |
| 995. | Ar-1 | XYZ-36 | $R^{11}$-20 |
| 996. | Ar-1 | XYZ-36 | $R^{11}$-21 |
| 997. | Ar-1 | XYZ-36 | $R^{11}$-22 |
| 998. | Ar-1 | XYZ-36 | $R^{11}$-23 |
| 999. | Ar-1 | XYZ-36 | $R^{11}$-24 |
| 1000. | Ar-1 | XYZ-36 | $R^{11}$-25 |
| 1001. | Ar-1 | XYZ-36 | $R^{11}$-26 |
| 1002. | Ar-1 | XYZ-36 | $R^{11}$-27 |
| 1003. | Ar-1 | XYZ-36 | $R^{11}$-28 |
| 1004. | Ar-1 | XYZ-36 | $R^{11}$-29 |
| 1005. | Ar-1 | XYZ-37 | $R^{11}$-1 |
| 1006. | Ar-1 | XYZ-37 | $R^{11}$-2 |
| 1007. | Ar-1 | XYZ-37 | $R^{11}$-3 |
| 1008. | Ar-1 | XYZ-37 | $R^{11}$-4 |
| 1009. | Ar-1 | XYZ-37 | $R^{11}$-5 |
| 1010. | Ar-1 | XYZ-37 | $R^{11}$-6 |
| 1011. | Ar-1 | XYZ-37 | $R^{11}$-7 |
| 1012. | Ar-1 | XYZ-37 | $R^{11}$-8 |
| 1013. | Ar-1 | XYZ-37 | $R^{11}$-9 |
| 1014. | Ar-1 | XYZ-37 | $R^{11}$-10 |
| 1015. | Ar-1 | XYZ-37 | $R^{11}$-11 |
| 1016. | Ar-1 | XYZ-37 | $R^{11}$-12 |
| 1017. | Ar-1 | XYZ-37 | $R^{11}$-13 |
| 1018. | Ar-1 | XYZ-37 | $R^{11}$-14 |
| 1019. | Ar-1 | XYZ-37 | $R^{11}$-15 |
| 1020. | Ar-1 | XYZ-37 | $R^{11}$-16 |
| 1021. | Ar-1 | XYZ-37 | $R^{11}$-17 |
| 1022. | Ar-1 | XYZ-37 | $R^{11}$-18 |
| 1023. | Ar-1 | XYZ-37 | $R^{11}$-19 |
| 1024. | Ar-1 | XYZ-37 | $R^{11}$-20 |
| 1025. | Ar-1 | XYZ-37 | $R^{11}$-21 |
| 1026. | Ar-1 | XYZ-37 | $R^{11}$-22 |
| 1027. | Ar-1 | XYZ-37 | $R^{11}$-23 |
| 1028. | Ar-1 | XYZ-37 | $R^{11}$-24 |
| 1029. | Ar-1 | XYZ-37 | $R^{11}$-25 |
| 1030. | Ar-1 | XYZ-37 | $R^{11}$-26 |
| 1031. | Ar-1 | XYZ-37 | $R^{11}$-27 |
| 1032. | Ar-1 | XYZ-37 | $R^{11}$-28 |
| 1033. | Ar-1 | XYZ-37 | $R^{11}$-29 |
| 1034. | Ar-1 | XYZ-38 | $R^{11}$-1 |
| 1035. | Ar-1 | XYZ-38 | $R^{11}$-2 |
| 1036. | Ar-1 | XYZ-38 | $R^{11}$-3 |
| 1037. | Ar-1 | XYZ-38 | $R^{11}$-4 |
| 1038. | Ar-1 | XYZ-38 | $R^{11}$-5 |
| 1039. | Ar-1 | XYZ-38 | $R^{11}$-6 |
| 1040. | Ar-1 | XYZ-38 | $R^{11}$-7 |
| 1041. | Ar-1 | XYZ-38 | $R^{11}$-8 |
| 1042. | Ar-1 | XYZ-38 | $R^{11}$-9 |
| 1043. | Ar-1 | XYZ-38 | $R^{11}$-10 |
| 1044. | Ar-1 | XYZ-38 | $R^{11}$-11 |
| 1045. | Ar-1 | XYZ-38 | $R^{11}$-12 |
| 1046. | Ar-1 | XYZ-38 | $R^{11}$-13 |
| 1047. | Ar-1 | XYZ-38 | $R^{11}$-14 |
| 1048. | Ar-1 | XYZ-38 | $R^{11}$-15 |
| 1049. | Ar-1 | XYZ-38 | $R^{11}$-16 |
| 1050. | Ar-1 | XYZ-38 | $R^{11}$-17 |
| 1051. | Ar-1 | XYZ-38 | $R^{11}$-18 |
| 1052. | Ar-1 | XYZ-38 | $R^{11}$-19 |
| 1053. | Ar-1 | XYZ-38 | $R^{11}$-20 |
| 1054. | Ar-1 | XYZ-38 | $R^{11}$-21 |
| 1055. | Ar-1 | XYZ-38 | $R^{11}$-22 |
| 1056. | Ar-1 | XYZ-38 | $R^{11}$-23 |
| 1057. | Ar-1 | XYZ-38 | $R^{11}$-24 |
| 1058. | Ar-1 | XYZ-38 | $R^{11}$-25 |
| 1059. | Ar-1 | XYZ-38 | $R^{11}$-26 |
| 1060. | Ar-1 | XYZ-38 | $R^{11}$-27 |
| 1061. | Ar-1 | XYZ-38 | $R^{11}$-28 |
| 1062. | Ar-1 | XYZ-38 | $R^{11}$-29 |
| 1063. | Ar-1 | XYZ-39 | $R^{11}$-1 |
| 1064. | Ar-1 | XYZ-39 | $R^{11}$-2 |
| 1065. | Ar-1 | XYZ-39 | $R^{11}$-3 |
| 1066. | Ar-1 | XYZ-39 | $R^{11}$-4 |
| 1067. | Ar-1 | XYZ-39 | $R^{11}$-5 |
| 1068. | Ar-1 | XYZ-39 | $R^{11}$-6 |
| 1069. | Ar-1 | XYZ-39 | $R^{11}$-7 |
| 1070. | Ar-1 | XYZ-39 | $R^{11}$-8 |
| 1071. | Ar-1 | XYZ-39 | $R^{11}$-9 |
| 1072. | Ar-1 | XYZ-39 | $R^{11}$-10 |
| 1073. | Ar-1 | XYZ-39 | $R^{11}$-11 |
| 1074. | Ar-1 | XYZ-39 | $R^{11}$-12 |
| 1075. | Ar-1 | XYZ-39 | $R^{11}$-13 |
| 1076. | Ar-1 | XYZ-39 | $R^{11}$-14 |
| 1077. | Ar-1 | XYZ-39 | $R^{11}$-15 |
| 1078. | Ar-1 | XYZ-39 | $R^{11}$-16 |
| 1079. | Ar-1 | XYZ-39 | $R^{11}$-17 |
| 1080. | Ar-1 | XYZ-39 | $R^{11}$-18 |
| 1081. | Ar-1 | XYZ-39 | $R^{11}$-19 |
| 1082. | Ar-1 | XYZ-39 | $R^{11}$-20 |
| 1083. | Ar-1 | XYZ-39 | $R^{11}$-21 |
| 1084. | Ar-1 | XYZ-39 | $R^{11}$-22 |
| 1085. | Ar-1 | XYZ-39 | $R^{11}$-23 |
| 1086. | Ar-1 | XYZ-39 | $R^{11}$-24 |
| 1087. | Ar-1 | XYZ-39 | $R^{11}$-25 |
| 1088. | Ar-1 | XYZ-39 | $R^{11}$-26 |
| 1089. | Ar-1 | XYZ-39 | $R^{11}$-27 |
| 1090. | Ar-1 | XYZ-39 | $R^{11}$-28 |
| 1091. | Ar-1 | XYZ-39 | $R^{11}$-29 |
| 1092. | Ar-1 | XYZ-40 | $R^{11}$-1 |
| 1093. | Ar-1 | XYZ-40 | $R^{11}$-2 |
| 1094. | Ar-1 | XYZ-40 | $R^{11}$-3 |
| 1095. | Ar-1 | XYZ-40 | $R^{11}$-4 |
| 1096. | Ar-1 | XYZ-40 | $R^{11}$-5 |
| 1097. | Ar-1 | XYZ-40 | $R^{11}$-6 |
| 1098. | Ar-1 | XYZ-40 | $R^{11}$-7 |
| 1099. | Ar-1 | XYZ-40 | $R^{11}$-8 |
| 1100. | Ar-1 | XYZ-40 | $R^{11}$-9 |
| 1101. | Ar-1 | XYZ-40 | $R^{11}$-10 |

TABLE C-continued

| | Ar | -X-Y-Z- | $R^{11}/R^{12}$ |
|---|---|---|---|
| 1102. | Ar-1 | XYZ-40 | $R^{11}$-11 |
| 1103. | Ar-1 | XYZ-40 | $R^{11}$-12 |
| 1104. | Ar-1 | XYZ-40 | $R^{11}$-13 |
| 1105. | Ar-1 | XYZ-40 | $R^{11}$-14 |
| 1106. | Ar-1 | XYZ-40 | $R^{11}$-15 |
| 1107. | Ar-1 | XYZ-40 | $R^{11}$-16 |
| 1108. | Ar-1 | XYZ-40 | $R^{11}$-17 |
| 1109. | Ar-1 | XYZ-40 | $R^{11}$-18 |
| 1110. | Ar-1 | XYZ-40 | $R^{11}$-19 |
| 1111. | Ar-1 | XYZ-40 | $R^{11}$-20 |
| 1112. | Ar-1 | XYZ-40 | $R^{11}$-21 |
| 1113. | Ar-1 | XYZ-40 | $R^{11}$-22 |
| 1114. | Ar-1 | XYZ-40 | $R^{11}$-23 |
| 1115. | Ar-1 | XYZ-40 | $R^{11}$-24 |
| 1116. | Ar-1 | XYZ-40 | $R^{11}$-25 |
| 1117. | Ar-1 | XYZ-40 | $R^{11}$-26 |
| 1118. | Ar-1 | XYZ-40 | $R^{11}$-27 |
| 1119. | Ar-1 | XYZ-40 | $R^{11}$-28 |
| 1120. | Ar-1 | XYZ-40 | $R^{11}$-29 |
| 1121. | Ar-1 | XYZ-41 | $R^{11}$-1 |
| 1122. | Ar-1 | XYZ-41 | $R^{11}$-2 |
| 1123. | Ar-1 | XYZ-41 | $R^{11}$-3 |
| 1124. | Ar-1 | XYZ-41 | $R^{11}$-4 |
| 1125. | Ar-1 | XYZ-41 | $R^{11}$-5 |
| 1126. | Ar-1 | XYZ-41 | $R^{11}$-6 |
| 1127. | Ar-1 | XYZ-41 | $R^{11}$-7 |
| 1128. | Ar-1 | XYZ-41 | $R^{11}$-8 |
| 1129. | Ar-1 | XYZ-41 | $R^{11}$-9 |
| 1130. | Ar-1 | XYZ-41 | $R^{11}$-10 |
| 1131. | Ar-1 | XYZ-41 | $R^{11}$-11 |
| 1132. | Ar-1 | XYZ-41 | $R^{11}$-12 |
| 1133. | Ar-1 | XYZ-41 | $R^{11}$-13 |
| 1134. | Ar-1 | XYZ-41 | $R^{11}$-14 |
| 1135. | Ar-1 | XYZ-41 | $R^{11}$-15 |
| 1136. | Ar-1 | XYZ-41 | $R^{11}$-16 |
| 1137. | Ar-1 | XYZ-41 | $R^{11}$-17 |
| 1138. | Ar-1 | XYZ-41 | $R^{11}$-18 |
| 1139. | Ar-1 | XYZ-41 | $R^{11}$-19 |
| 1140. | Ar-1 | XYZ-41 | $R^{11}$-20 |
| 1141. | Ar-1 | XYZ-41 | $R^{11}$-21 |
| 1142. | Ar-1 | XYZ-41 | $R^{11}$-22 |
| 1143. | Ar-1 | XYZ-41 | $R^{11}$-23 |
| 1144. | Ar-1 | XYZ-41 | $R^{11}$-24 |
| 1145. | Ar-1 | XYZ-41 | $R^{11}$-25 |
| 1146. | Ar-1 | XYZ-41 | $R^{11}$-26 |
| 1147. | Ar-1 | XYZ-41 | $R^{11}$-27 |
| 1148. | Ar-1 | XYZ-41 | $R^{11}$-28 |
| 1149. | Ar-1 | XYZ-41 | $R^{11}$-29 |
| 1150. | Ar-1 | XYZ-42 | $R^{11}$-1 |
| 1151. | Ar-1 | XYZ-42 | $R^{11}$-2 |
| 1152. | Ar-1 | XYZ-42 | $R^{11}$-3 |
| 1153. | Ar-1 | XYZ-42 | $R^{11}$-4 |
| 1154. | Ar-1 | XYZ-42 | $R^{11}$-5 |
| 1155. | Ar-1 | XYZ-42 | $R^{11}$-6 |
| 1156. | Ar-1 | XYZ-42 | $R^{11}$-7 |
| 1157. | Ar-1 | XYZ-42 | $R^{11}$-8 |
| 1158. | Ar-1 | XYZ-42 | $R^{11}$-9 |
| 1159. | Ar-1 | XYZ-42 | $R^{11}$-10 |
| 1160. | Ar-1 | XYZ-42 | $R^{11}$-11 |
| 1161. | Ar-1 | XYZ-42 | $R^{11}$-12 |
| 1162. | Ar-1 | XYZ-42 | $R^{11}$-13 |
| 1163. | Ar-1 | XYZ-42 | $R^{11}$-14 |
| 1164. | Ar-1 | XYZ-42 | $R^{11}$-15 |
| 1165. | Ar-1 | XYZ-42 | $R^{11}$-16 |
| 1166. | Ar-1 | XYZ-42 | $R^{11}$-17 |
| 1167. | Ar-1 | XYZ-42 | $R^{11}$-18 |
| 1168. | Ar-1 | XYZ-42 | $R^{11}$-19 |
| 1169. | Ar-1 | XYZ-42 | $R^{11}$-20 |
| 1170. | Ar-1 | XYZ-42 | $R^{11}$-21 |
| 1171. | Ar-1 | XYZ-42 | $R^{11}$-22 |
| 1172. | Ar-1 | XYZ-42 | $R^{11}$-23 |
| 1173. | Ar-1 | XYZ-42 | $R^{11}$-24 |
| 1174. | Ar-1 | XYZ-42 | $R^{11}$-25 |
| 1175. | Ar-1 | XYZ-42 | $R^{11}$-26 |
| 1176. | Ar-1 | XYZ-42 | $R^{11}$-27 |
| 1177. | Ar-1 | XYZ-42 | $R^{11}$-28 |
| 1178. | Ar-1 | XYZ-42 | $R^{11}$-29 |
| 1179. | Ar-1 | XYZ-43 | $R^{11}$-1 |
| 1180. | Ar-1 | XYZ-43 | $R^{11}$-2 |
| 1181. | Ar-1 | XYZ-43 | $R^{11}$-3 |
| 1182. | Ar-1 | XYZ-43 | $R^{11}$-4 |
| 1183. | Ar-1 | XYZ-43 | $R^{11}$-5 |
| 1184. | Ar-1 | XYZ-43 | $R^{11}$-6 |
| 1185. | Ar-1 | XYZ-43 | $R^{11}$-7 |
| 1186. | Ar-1 | XYZ-43 | $R^{11}$-8 |
| 1187. | Ar-1 | XYZ-43 | $R^{11}$-9 |
| 1188. | Ar-1 | XYZ-43 | $R^{11}$-10 |
| 1189. | Ar-1 | XYZ-43 | $R^{11}$-11 |
| 1190. | Ar-1 | XYZ-43 | $R^{11}$-12 |
| 1191. | Ar-1 | XYZ-43 | $R^{11}$-13 |
| 1192. | Ar-1 | XYZ-43 | $R^{11}$-14 |
| 1193. | Ar-1 | XYZ-43 | $R^{11}$-15 |
| 1194. | Ar-1 | XYZ-43 | $R^{11}$-16 |
| 1195. | Ar-1 | XYZ-43 | $R^{11}$-17 |
| 1196. | Ar-1 | XYZ-43 | $R^{11}$-18 |
| 1197. | Ar-1 | XYZ-43 | $R^{11}$-19 |
| 1198. | Ar-1 | XYZ-43 | $R^{11}$-20 |
| 1199. | Ar-1 | XYZ-43 | $R^{11}$-21 |
| 1200. | Ar-1 | XYZ-43 | $R^{11}$-22 |
| 1201. | Ar-1 | XYZ-43 | $R^{11}$-23 |
| 1202. | Ar-1 | XYZ-43 | $R^{11}$-24 |
| 1203. | Ar-1 | XYZ-43 | $R^{11}$-25 |
| 1204. | Ar-1 | XYZ-43 | $R^{11}$-26 |
| 1205. | Ar-1 | XYZ-43 | $R^{11}$-27 |
| 1206. | Ar-1 | XYZ-43 | $R^{11}$-28 |
| 1207. | Ar-1 | XYZ-43 | $R^{11}$-29 |
| 1208. | Ar-1 | XYZ-44 | $R^{11}$-1 |
| 1209. | Ar-1 | XYZ-44 | $R^{11}$-2 |
| 1210. | Ar-1 | XYZ-44 | $R^{11}$-3 |
| 1211. | Ar-1 | XYZ-44 | $R^{11}$-4 |
| 1212. | Ar-1 | XYZ-44 | $R^{11}$-5 |
| 1213. | Ar-1 | XYZ-44 | $R^{11}$-6 |
| 1214. | Ar-1 | XYZ-44 | $R^{11}$-7 |
| 1215. | Ar-1 | XYZ-44 | $R^{11}$-8 |
| 1216. | Ar-1 | XYZ-44 | $R^{11}$-9 |
| 1217. | Ar-1 | XYZ-44 | $R^{11}$-10 |
| 1218. | Ar-1 | XYZ-44 | $R^{11}$-11 |
| 1219. | Ar-1 | XYZ-44 | $R^{11}$-12 |
| 1220. | Ar-1 | XYZ-44 | $R^{11}$-13 |
| 1221. | Ar-1 | XYZ-44 | $R^{11}$-14 |
| 1222. | Ar-1 | XYZ-44 | $R^{11}$-15 |
| 1223. | Ar-1 | XYZ-44 | $R^{11}$-16 |
| 1224. | Ar-1 | XYZ-44 | $R^{11}$-17 |
| 1225. | Ar-1 | XYZ-44 | $R^{11}$-18 |
| 1226. | Ar-1 | XYZ-44 | $R^{11}$-19 |
| 1227. | Ar-1 | XYZ-44 | $R^{11}$-20 |
| 1228. | Ar-1 | XYZ-44 | $R^{11}$-21 |
| 1229. | Ar-1 | XYZ-44 | $R^{11}$-22 |
| 1230. | Ar-1 | XYZ-44 | $R^{11}$-23 |
| 1231. | Ar-1 | XYZ-44 | $R^{11}$-24 |
| 1232. | Ar-1 | XYZ-44 | $R^{11}$-25 |
| 1233. | Ar-1 | XYZ-44 | $R^{11}$-26 |
| 1234. | Ar-1 | XYZ-44 | $R^{11}$-27 |
| 1235. | Ar-1 | XYZ-44 | $R^{11}$-28 |
| 1236. | Ar-1 | XYZ-44 | $R^{11}$-29 |
| 1237. | Ar-1 | XYZ-45 | $R^{11}$-1 |
| 1238. | Ar-1 | XYZ-45 | $R^{11}$-2 |
| 1239. | Ar-1 | XYZ-45 | $R^{11}$-3 |
| 1240. | Ar-1 | XYZ-45 | $R^{11}$-4 |
| 1241. | Ar-1 | XYZ-45 | $R^{11}$-5 |
| 1242. | Ar-1 | XYZ-45 | $R^{11}$-6 |
| 1243. | Ar-1 | XYZ-45 | $R^{11}$-7 |
| 1244. | Ar-1 | XYZ-45 | $R^{11}$-8 |
| 1245. | Ar-1 | XYZ-45 | $R^{11}$-9 |
| 1246. | Ar-1 | XYZ-45 | $R^{11}$-10 |
| 1247. | Ar-1 | XYZ-45 | $R^{11}$-11 |
| 1248. | Ar-1 | XYZ-45 | $R^{11}$-12 |
| 1249. | Ar-1 | XYZ-45 | $R^{11}$-13 |
| 1250. | Ar-1 | XYZ-45 | $R^{11}$-14 |
| 1251. | Ar-1 | XYZ-45 | $R^{11}$-15 |
| 1252. | Ar-1 | XYZ-45 | $R^{11}$-16 |
| 1253. | Ar-1 | XYZ-45 | $R^{11}$-17 |
| 1254. | Ar-1 | XYZ-45 | $R^{11}$-18 |
| 1255. | Ar-1 | XYZ-45 | $R^{11}$-19 |
| 1256. | Ar-1 | XYZ-45 | $R^{11}$-20 |
| 1257. | Ar-1 | XYZ-45 | $R^{11}$-21 |

TABLE C-continued

|  | Ar | -X-Y-Z- | $R^{11}/R^{12}$ |
|---|---|---|---|
| 1258. | Ar-1 | XYZ-45 | $R^{11}$-22 |
| 1259. | Ar-1 | XYZ-45 | $R^{11}$-23 |
| 1260. | Ar-1 | XYZ-45 | $R^{11}$-24 |
| 1261. | Ar-1 | XYZ-45 | $R^{11}$-25 |
| 1262. | Ar-1 | XYZ-45 | $R^{11}$-26 |
| 1263. | Ar-1 | XYZ-45 | $R^{11}$-27 |
| 1264. | Ar-1 | XYZ-45 | $R^{11}$-28 |
| 1265. | Ar-1 | XYZ-45 | $R^{11}$-29 |
| 1266. | Ar-1 | XYZ-46 | $R^{11}$-1 |
| 1267. | Ar-1 | XYZ-46 | $R^{11}$-2 |
| 1268. | Ar-1 | XYZ-46 | $R^{11}$-3 |
| 1269. | Ar-1 | XYZ-46 | $R^{11}$-4 |
| 1270. | Ar-1 | XYZ-46 | $R^{11}$-5 |
| 1271. | Ar-1 | XYZ-46 | $R^{11}$-6 |
| 1272. | Ar-1 | XYZ-46 | $R^{11}$-7 |
| 1273. | Ar-1 | XYZ-46 | $R^{11}$-8 |
| 1274. | Ar-1 | XYZ-46 | $R^{11}$-9 |
| 1275. | Ar-1 | XYZ-46 | $R^{11}$-10 |
| 1276. | Ar-1 | XYZ-46 | $R^{11}$-11 |
| 1277. | Ar-1 | XYZ-46 | $R^{11}$-12 |
| 1278. | Ar-1 | XYZ-46 | $R^{11}$-13 |
| 1279. | Ar-1 | XYZ-46 | $R^{11}$-14 |
| 1280. | Ar-1 | XYZ-46 | $R^{11}$-15 |
| 1281. | Ar-1 | XYZ-46 | $R^{11}$-16 |
| 1282. | Ar-1 | XYZ-46 | $R^{11}$-17 |
| 1283. | Ar-1 | XYZ-46 | $R^{11}$-18 |
| 1284. | Ar-1 | XYZ-46 | $R^{11}$-19 |
| 1285. | Ar-1 | XYZ-46 | $R^{11}$-20 |
| 1286. | Ar-1 | XYZ-46 | $R^{11}$-21 |
| 1287. | Ar-1 | XYZ-46 | $R^{11}$-22 |
| 1288. | Ar-1 | XYZ-46 | $R^{11}$-23 |
| 1289. | Ar-1 | XYZ-46 | $R^{11}$-24 |
| 1290. | Ar-1 | XYZ-46 | $R^{11}$-25 |
| 1291. | Ar-1 | XYZ-46 | $R^{11}$-26 |
| 1292. | Ar-1 | XYZ-46 | $R^{11}$-27 |
| 1293. | Ar-1 | XYZ-46 | $R^{11}$-28 |
| 1294. | Ar-1 | XYZ-46 | $R^{11}$-29 |
| 1295. | Ar-1 | XYZ-47 | $R^{11}$-1 |
| 1296. | Ar-1 | XYZ-47 | $R^{11}$-2 |
| 1297. | Ar-1 | XYZ-47 | $R^{11}$-3 |
| 1298. | Ar-1 | XYZ-47 | $R^{11}$-4 |
| 1299. | Ar-1 | XYZ-47 | $R^{11}$-5 |
| 1300. | Ar-1 | XYZ-47 | $R^{11}$-6 |
| 1301. | Ar-1 | XYZ-47 | $R^{11}$-7 |
| 1302. | Ar-1 | XYZ-47 | $R^{11}$-8 |
| 1303. | Ar-1 | XYZ-47 | $R^{11}$-9 |
| 1304. | Ar-1 | XYZ-47 | $R^{11}$-10 |
| 1305. | Ar-1 | XYZ-47 | $R^{11}$-11 |
| 1306. | Ar-1 | XYZ-47 | $R^{11}$-12 |
| 1307. | Ar-1 | XYZ-47 | $R^{11}$-13 |
| 1308. | Ar-1 | XYZ-47 | $R^{11}$-14 |
| 1309. | Ar-1 | XYZ-47 | $R^{11}$-15 |
| 1310. | Ar-1 | XYZ-47 | $R^{11}$-16 |
| 1311. | Ar-1 | XYZ-47 | $R^{11}$-17 |
| 1312. | Ar-1 | XYZ-47 | $R^{11}$-18 |
| 1313. | Ar-1 | XYZ-47 | $R^{11}$-19 |
| 1314. | Ar-1 | XYZ-47 | $R^{11}$-20 |
| 1315. | Ar-1 | XYZ-47 | $R^{11}$-21 |
| 1316. | Ar-1 | XYZ-47 | $R^{11}$-22 |
| 1317. | Ar-1 | XYZ-47 | $R^{11}$-23 |
| 1318. | Ar-1 | XYZ-47 | $R^{11}$-24 |
| 1319. | Ar-1 | XYZ-47 | $R^{11}$-25 |
| 1320. | Ar-1 | XYZ-47 | $R^{11}$-26 |
| 1321. | Ar-1 | XYZ-47 | $R^{11}$-27 |
| 1322. | Ar-1 | XYZ-47 | $R^{11}$-28 |
| 1323. | Ar-1 | XYZ-47 | $R^{11}$-29 |
| 1324. | Ar-1 | XYZ-48 | $R^{11}$-1 |
| 1325. | Ar-1 | XYZ-48 | $R^{11}$-2 |
| 1326. | Ar-1 | XYZ-48 | $R^{11}$-3 |
| 1327. | Ar-1 | XYZ-48 | $R^{11}$-4 |
| 1328. | Ar-1 | XYZ-48 | $R^{11}$-5 |
| 1329. | Ar-1 | XYZ-48 | $R^{11}$-6 |
| 1330. | Ar-1 | XYZ-48 | $R^{11}$-7 |
| 1331. | Ar-1 | XYZ-48 | $R^{11}$-8 |
| 1332. | Ar-1 | XYZ-48 | $R^{11}$-9 |
| 1333. | Ar-1 | XYZ-48 | $R^{11}$-10 |
| 1334. | Ar-1 | XYZ-48 | $R^{11}$-11 |
| 1335. | Ar-1 | XYZ-48 | $R^{11}$-12 |
| 1336. | Ar-1 | XYZ-48 | $R^{11}$-13 |
| 1337. | Ar-1 | XYZ-48 | $R^{11}$-14 |
| 1338. | Ar-1 | XYZ-48 | $R^{11}$-15 |
| 1339. | Ar-1 | XYZ-48 | $R^{11}$-16 |
| 1340. | Ar-1 | XYZ-48 | $R^{11}$-17 |
| 1341. | Ar-1 | XYZ-48 | $R^{11}$-18 |
| 1342. | Ar-1 | XYZ-48 | $R^{11}$-19 |
| 1343. | Ar-1 | XYZ-48 | $R^{11}$-20 |
| 1344. | Ar-1 | XYZ-48 | $R^{11}$-21 |
| 1345. | Ar-1 | XYZ-48 | $R^{11}$-22 |
| 1346. | Ar-1 | XYZ-48 | $R^{11}$-23 |
| 1347. | Ar-1 | XYZ-48 | $R^{11}$-24 |
| 1348. | Ar-1 | XYZ-48 | $R^{11}$-25 |
| 1349. | Ar-1 | XYZ-48 | $R^{11}$-26 |
| 1350. | Ar-1 | XYZ-48 | $R^{11}$-27 |
| 1351. | Ar-1 | XYZ-48 | $R^{11}$-28 |
| 1352. | Ar-1 | XYZ-48 | $R^{11}$-29 |
| 1353. | Ar-1 | XYZ-49 | $R^{11}$-1 |
| 1354. | Ar-1 | XYZ-49 | $R^{11}$-2 |
| 1355. | Ar-1 | XYZ-49 | $R^{11}$-3 |
| 1356. | Ar-1 | XYZ-49 | $R^{11}$-4 |
| 1357. | Ar-1 | XYZ-49 | $R^{11}$-5 |
| 1358. | Ar-1 | XYZ-49 | $R^{11}$-6 |
| 1359. | Ar-1 | XYZ-49 | $R^{11}$-7 |
| 1360. | Ar-1 | XYZ-49 | $R^{11}$-8 |
| 1361. | Ar-1 | XYZ-49 | $R^{11}$-9 |
| 1362. | Ar-1 | XYZ-49 | $R^{11}$-10 |
| 1363. | Ar-1 | XYZ-49 | $R^{11}$-11 |
| 1364. | Ar-1 | XYZ-49 | $R^{11}$-12 |
| 1365. | Ar-1 | XYZ-49 | $R^{11}$-13 |
| 1366. | Ar-1 | XYZ-49 | $R^{11}$-14 |
| 1367. | Ar-1 | XYZ-49 | $R^{11}$-15 |
| 1368. | Ar-1 | XYZ-49 | $R^{11}$-16 |
| 1369. | Ar-1 | XYZ-49 | $R^{11}$-17 |
| 1370. | Ar-1 | XYZ-49 | $R^{11}$-18 |
| 1371. | Ar-1 | XYZ-49 | $R^{11}$-19 |
| 1372. | Ar-1 | XYZ-49 | $R^{11}$-20 |
| 1373. | Ar-1 | XYZ-49 | $R^{11}$-21 |
| 1374. | Ar-1 | XYZ-49 | $R^{11}$-22 |
| 1375. | Ar-1 | XYZ-49 | $R^{11}$-23 |
| 1376. | Ar-1 | XYZ-49 | $R^{11}$-24 |
| 1377. | Ar-1 | XYZ-49 | $R^{11}$-25 |
| 1378. | Ar-1 | XYZ-49 | $R^{11}$-26 |
| 1379. | Ar-1 | XYZ-49 | $R^{11}$-27 |
| 1380. | Ar-1 | XYZ-49 | $R^{11}$-28 |
| 1381. | Ar-1 | XYZ-49 | $R^{11}$-29 |
| 1382. | Ar-1 | XYZ-50 | $R^{11}$-1 |
| 1383. | Ar-1 | XYZ-50 | $R^{11}$-2 |
| 1384. | Ar-1 | XYZ-50 | $R^{11}$-3 |
| 1385. | Ar-1 | XYZ-50 | $R^{11}$-4 |
| 1386. | Ar-1 | XYZ-50 | $R^{11}$-5 |
| 1387. | Ar-1 | XYZ-50 | $R^{11}$-6 |
| 1388. | Ar-1 | XYZ-50 | $R^{11}$-7 |
| 1389. | Ar-1 | XYZ-50 | $R^{11}$-8 |
| 1390. | Ar-1 | XYZ-50 | $R^{11}$-9 |
| 1391. | Ar-1 | XYZ-50 | $R^{11}$-10 |
| 1392. | Ar-1 | XYZ-50 | $R^{11}$-11 |
| 1393. | Ar-1 | XYZ-50 | $R^{11}$-12 |
| 1394. | Ar-1 | XYZ-50 | $R^{11}$-13 |
| 1395. | Ar-1 | XYZ-50 | $R^{11}$-14 |
| 1396. | Ar-1 | XYZ-50 | $R^{11}$-15 |
| 1397. | Ar-1 | XYZ-50 | $R^{11}$-16 |
| 1398. | Ar-1 | XYZ-50 | $R^{11}$-17 |
| 1399. | Ar-1 | XYZ-50 | $R^{11}$-18 |
| 1400. | Ar-1 | XYZ-50 | $R^{11}$-19 |
| 1401. | Ar-1 | XYZ-50 | $R^{11}$-20 |
| 1402. | Ar-1 | XYZ-50 | $R^{11}$-21 |
| 1403. | Ar-1 | XYZ-50 | $R^{11}$-22 |
| 1404. | Ar-1 | XYZ-50 | $R^{11}$-23 |
| 1405. | Ar-1 | XYZ-50 | $R^{11}$-24 |
| 1406. | Ar-1 | XYZ-50 | $R^{11}$-25 |
| 1407. | Ar-1 | XYZ-50 | $R^{11}$-26 |
| 1408. | Ar-1 | XYZ-50 | $R^{11}$-27 |
| 1409. | Ar-1 | XYZ-50 | $R^{11}$-28 |
| 1410. | Ar-1 | XYZ-50 | $R^{11}$-29 |
| 1411. | Ar-1 | XYZ-51 | $R^{11}$-1 |
| 1412. | Ar-1 | XYZ-51 | $R^{11}$-2 |
| 1413. | Ar-1 | XYZ-51 | $R^{11}$-3 |

TABLE C-continued

| | Ar | -X-Y-Z- | $R^{11}/R^{12}$ |
|---|---|---|---|
| 1414. | Ar-1 | XYZ-51 | $R^{11}$-4 |
| 1415. | Ar-1 | XYZ-51 | $R^{11}$-5 |
| 1416. | Ar-1 | XYZ-51 | $R^{11}$-6 |
| 1417. | Ar-1 | XYZ-51 | $R^{11}$-7 |
| 1418. | Ar-1 | XYZ-51 | $R^{11}$-8 |
| 1419. | Ar-1 | XYZ-51 | $R^{11}$-9 |
| 1420. | Ar-1 | XYZ-51 | $R^{11}$-10 |
| 1421. | Ar-1 | XYZ-51 | $R^{11}$-11 |
| 1422. | Ar-1 | XYZ-51 | $R^{11}$-12 |
| 1423. | Ar-1 | XYZ-51 | $R^{11}$-13 |
| 1424. | Ar-1 | XYZ-51 | $R^{11}$-14 |
| 1425. | Ar-1 | XYZ-51 | $R^{11}$-15 |
| 1426. | Ar-1 | XYZ-51 | $R^{11}$-16 |
| 1427. | Ar-1 | XYZ-51 | $R^{11}$-17 |
| 1428. | Ar-1 | XYZ-51 | $R^{11}$-18 |
| 1429. | Ar-1 | XYZ-51 | $R^{11}$-19 |
| 1430. | Ar-1 | XYZ-51 | $R^{11}$-20 |
| 1431. | Ar-1 | XYZ-51 | $R^{11}$-21 |
| 1432. | Ar-1 | XYZ-51 | $R^{11}$-22 |
| 1433. | Ar-1 | XYZ-51 | $R^{11}$-23 |
| 1434. | Ar-1 | XYZ-51 | $R^{11}$-24 |
| 1435. | Ar-1 | XYZ-51 | $R^{11}$-25 |
| 1436. | Ar-1 | XYZ-51 | $R^{11}$-26 |
| 1437. | Ar-1 | XYZ-51 | $R^{11}$-27 |
| 1438. | Ar-1 | XYZ-51 | $R^{11}$-28 |
| 1439. | Ar-1 | XYZ-51 | $R^{11}$-29 |
| 1440. | Ar-1 | XYZ-52 | $R^{11}$-1 |
| 1441. | Ar-1 | XYZ-52 | $R^{11}$-2 |
| 1442. | Ar-1 | XYZ-52 | $R^{11}$-3 |
| 1443. | Ar-1 | XYZ-52 | $R^{11}$-4 |
| 1444. | Ar-1 | XYZ-52 | $R^{11}$-5 |
| 1445. | Ar-1 | XYZ-52 | $R^{11}$-6 |
| 1446. | Ar-1 | XYZ-52 | $R^{11}$-7 |
| 1447. | Ar-1 | XYZ-52 | $R^{11}$-8 |
| 1448. | Ar-1 | XYZ-52 | $R^{11}$-9 |
| 1449. | Ar-1 | XYZ-52 | $R^{11}$-10 |
| 1450. | Ar-1 | XYZ-52 | $R^{11}$-11 |
| 1451. | Ar-1 | XYZ-52 | $R^{11}$-12 |
| 1452. | Ar-1 | XYZ-52 | $R^{11}$-13 |
| 1453. | Ar-1 | XYZ-52 | $R^{11}$-14 |
| 1454. | Ar-1 | XYZ-52 | $R^{11}$-15 |
| 1455. | Ar-1 | XYZ-52 | $R^{11}$-16 |
| 1456. | Ar-1 | XYZ-52 | $R^{11}$-17 |
| 1457. | Ar-1 | XYZ-52 | $R^{11}$-18 |
| 1458. | Ar-1 | XYZ-52 | $R^{11}$-19 |
| 1459. | Ar-1 | XYZ-52 | $R^{11}$-20 |
| 1460. | Ar-1 | XYZ-52 | $R^{11}$-21 |
| 1461. | Ar-1 | XYZ-52 | $R^{11}$-22 |
| 1462. | Ar-1 | XYZ-52 | $R^{11}$-23 |
| 1463. | Ar-1 | XYZ-52 | $R^{11}$-24 |
| 1464. | Ar-1 | XYZ-52 | $R^{11}$-25 |
| 1465. | Ar-1 | XYZ-52 | $R^{11}$-26 |
| 1466. | Ar-1 | XYZ-52 | $R^{11}$-27 |
| 1467. | Ar-1 | XYZ-52 | $R^{11}$-28 |
| 1468. | Ar-1 | XYZ-52 | $R^{11}$-29 |
| 1469. | Ar-1 | XYZ-53 | $R^{11}$-1 |
| 1470. | Ar-1 | XYZ-53 | $R^{11}$-2 |
| 1471. | Ar-1 | XYZ-53 | $R^{11}$-3 |
| 1472. | Ar-1 | XYZ-53 | $R^{11}$-4 |
| 1473. | Ar-1 | XYZ-53 | $R^{11}$-5 |
| 1474. | Ar-1 | XYZ-53 | $R^{11}$-6 |
| 1475. | Ar-1 | XYZ-53 | $R^{11}$-7 |
| 1476. | Ar-1 | XYZ-53 | $R^{11}$-8 |
| 1477. | Ar-1 | XYZ-53 | $R^{11}$-9 |
| 1478. | Ar-1 | XYZ-53 | $R^{11}$-10 |
| 1479. | Ar-1 | XYZ-53 | $R^{11}$-11 |
| 1480. | Ar-1 | XYZ-53 | $R^{11}$-12 |
| 1481. | Ar-1 | XYZ-53 | $R^{11}$-13 |
| 1482. | Ar-1 | XYZ-53 | $R^{11}$-14 |
| 1483. | Ar-1 | XYZ-53 | $R^{11}$-15 |
| 1484. | Ar-1 | XYZ-53 | $R^{11}$-16 |
| 1485. | Ar-1 | XYZ-53 | $R^{11}$-17 |
| 1486. | Ar-1 | XYZ-53 | $R^{11}$-18 |
| 1487. | Ar-1 | XYZ-53 | $R^{11}$-19 |
| 1488. | Ar-1 | XYZ-53 | $R^{11}$-20 |
| 1489. | Ar-1 | XYZ-53 | $R^{11}$-21 |
| 1490. | Ar-1 | XYZ-53 | $R^{11}$-22 |
| 1491. | Ar-1 | XYZ-53 | $R^{11}$-23 |
| 1492. | Ar-1 | XYZ-53 | $R^{11}$-24 |
| 1493. | Ar-1 | XYZ-53 | $R^{11}$-25 |
| 1494. | Ar-1 | XYZ-53 | $R^{11}$-26 |
| 1495. | Ar-1 | XYZ-53 | $R^{11}$-27 |
| 1496. | Ar-1 | XYZ-53 | $R^{11}$-28 |
| 1497. | Ar-1 | XYZ-53 | $R^{11}$-29 |
| 1498. | Ar-1 | XYZ-54 | $R^{11}$-1 |
| 1499. | Ar-1 | XYZ-54 | $R^{11}$-2 |
| 1500. | Ar-1 | XYZ-54 | $R^{11}$-3 |
| 1501. | Ar-1 | XYZ-54 | $R^{11}$-4 |
| 1502. | Ar-1 | XYZ-54 | $R^{11}$-5 |
| 1503. | Ar-1 | XYZ-54 | $R^{11}$-6 |
| 1504. | Ar-1 | XYZ-54 | $R^{11}$-7 |
| 1505. | Ar-1 | XYZ-54 | $R^{11}$-8 |
| 1506. | Ar-1 | XYZ-54 | $R^{11}$-9 |
| 1507. | Ar-1 | XYZ-54 | $R^{11}$-10 |
| 1508. | Ar-1 | XYZ-54 | $R^{11}$-11 |
| 1509. | Ar-1 | XYZ-54 | $R^{11}$-12 |
| 1510. | Ar-1 | XYZ-54 | $R^{11}$-13 |
| 1511. | Ar-1 | XYZ-54 | $R^{11}$-14 |
| 1512. | Ar-1 | XYZ-54 | $R^{11}$-15 |
| 1513. | Ar-1 | XYZ-54 | $R^{11}$-16 |
| 1514. | Ar-1 | XYZ-54 | $R^{11}$-17 |
| 1515. | Ar-1 | XYZ-54 | $R^{11}$-18 |
| 1516. | Ar-1 | XYZ-54 | $R^{11}$-19 |
| 1517. | Ar-1 | XYZ-54 | $R^{11}$-20 |
| 1518. | Ar-1 | XYZ-54 | $R^{11}$-21 |
| 1519. | Ar-1 | XYZ-54 | $R^{11}$-22 |
| 1520. | Ar-1 | XYZ-54 | $R^{11}$-23 |
| 1521. | Ar-1 | XYZ-54 | $R^{11}$-24 |
| 1522. | Ar-1 | XYZ-54 | $R^{11}$-25 |
| 1523. | Ar-1 | XYZ-54 | $R^{11}$-26 |
| 1524. | Ar-1 | XYZ-54 | $R^{11}$-27 |
| 1525. | Ar-1 | XYZ-54 | $R^{11}$-28 |
| 1526. | Ar-1 | XYZ-54 | $R^{11}$-29 |
| 1527. | Ar-1 | XYZ-55 | $R^{11}$-1 |
| 1528. | Ar-1 | XYZ-55 | $R^{11}$-2 |
| 1529. | Ar-1 | XYZ-55 | $R^{11}$-3 |
| 1530. | Ar-1 | XYZ-55 | $R^{11}$-4 |
| 1531. | Ar-1 | XYZ-55 | $R^{11}$-5 |
| 1532. | Ar-1 | XYZ-55 | $R^{11}$-6 |
| 1533. | Ar-1 | XYZ-55 | $R^{11}$-7 |
| 1534. | Ar-1 | XYZ-55 | $R^{11}$-8 |
| 1535. | Ar-1 | XYZ-55 | $R^{11}$-9 |
| 1536. | Ar-1 | XYZ-55 | $R^{11}$-10 |
| 1537. | Ar-1 | XYZ-55 | $R^{11}$-11 |
| 1538. | Ar-1 | XYZ-55 | $R^{11}$-12 |
| 1539. | Ar-1 | XYZ-55 | $R^{11}$-13 |
| 1540. | Ar-1 | XYZ-55 | $R^{11}$-14 |
| 1541. | Ar-1 | XYZ-55 | $R^{11}$-15 |
| 1542. | Ar-1 | XYZ-55 | $R^{11}$-16 |
| 1543. | Ar-1 | XYZ-55 | $R^{11}$-17 |
| 1544. | Ar-1 | XYZ-55 | $R^{11}$-18 |
| 1545. | Ar-1 | XYZ-55 | $R^{11}$-19 |
| 1546. | Ar-1 | XYZ-55 | $R^{11}$-20 |
| 1547. | Ar-1 | XYZ-55 | $R^{11}$-21 |
| 1548. | Ar-1 | XYZ-55 | $R^{11}$-22 |
| 1549. | Ar-1 | XYZ-55 | $R^{11}$-23 |
| 1550. | Ar-1 | XYZ-55 | $R^{11}$-24 |
| 1551. | Ar-1 | XYZ-55 | $R^{11}$-25 |
| 1552. | Ar-1 | XYZ-55 | $R^{11}$-26 |
| 1553. | Ar-1 | XYZ-55 | $R^{11}$-27 |
| 1554. | Ar-1 | XYZ-55 | $R^{11}$-28 |
| 1555. | Ar-1 | XYZ-55 | $R^{11}$-29 |
| 1556. | Ar-1 | XYZ-56 | $R^{11}$-1 |
| 1557. | Ar-1 | XYZ-56 | $R^{11}$-2 |
| 1558. | Ar-1 | XYZ-56 | $R^{11}$-3 |
| 1559. | Ar-1 | XYZ-56 | $R^{11}$-4 |
| 1560. | Ar-1 | XYZ-56 | $R^{11}$-5 |
| 1561. | Ar-1 | XYZ-56 | $R^{11}$-6 |
| 1562. | Ar-1 | XYZ-56 | $R^{11}$-7 |
| 1563. | Ar-1 | XYZ-56 | $R^{11}$-8 |
| 1564. | Ar-1 | XYZ-56 | $R^{11}$-9 |
| 1565. | Ar-1 | XYZ-56 | $R^{11}$-10 |
| 1566. | Ar-1 | XYZ-56 | $R^{11}$-11 |
| 1567. | Ar-1 | XYZ-56 | $R^{11}$-12 |
| 1568. | Ar-1 | XYZ-56 | $R^{11}$-13 |
| 1569. | Ar-1 | XYZ-56 | $R^{11}$-14 |

TABLE C-continued

| | Ar | -X-Y-Z- | $R^{11}/R^{12}$ |
|---|---|---|---|
| 1570. | Ar-1 | XYZ-56 | $R^{11}$-15 |
| 1571. | Ar-1 | XYZ-56 | $R^{11}$-16 |
| 1572. | Ar-1 | XYZ-56 | $R^{11}$-17 |
| 1573. | Ar-1 | XYZ-56 | $R^{11}$-18 |
| 1574. | Ar-1 | XYZ-56 | $R^{11}$-19 |
| 1575. | Ar-1 | XYZ-56 | $R^{11}$-20 |
| 1576. | Ar-1 | XYZ-56 | $R^{11}$-21 |
| 1577. | Ar-1 | XYZ-56 | $R^{11}$-22 |
| 1578. | Ar-1 | XYZ-56 | $R^{11}$-23 |
| 1579. | Ar-1 | XYZ-56 | $R^{11}$-24 |
| 1580. | Ar-1 | XYZ-56 | $R^{11}$-25 |
| 1581. | Ar-1 | XYZ-56 | $R^{11}$-26 |
| 1582. | Ar-1 | XYZ-56 | $R^{11}$-27 |
| 1583. | Ar-1 | XYZ-56 | $R^{11}$-28 |
| 1584. | Ar-1 | XYZ-56 | $R^{11}$-29 |
| 1585. | Ar-1 | XYZ-57 | $R^{11}$-1 |
| 1586. | Ar-1 | XYZ-57 | $R^{11}$-2 |
| 1587. | Ar-1 | XYZ-57 | $R^{11}$-3 |
| 1588. | Ar-1 | XYZ-57 | $R^{11}$-4 |
| 1589. | Ar-1 | XYZ-57 | $R^{11}$-5 |
| 1590. | Ar-1 | XYZ-57 | $R^{11}$-6 |
| 1591. | Ar-1 | XYZ-57 | $R^{11}$-7 |
| 1592. | Ar-1 | XYZ-57 | $R^{11}$-8 |
| 1593. | Ar-1 | XYZ-57 | $R^{11}$-9 |
| 1594. | Ar-1 | XYZ-57 | $R^{11}$-10 |
| 1595. | Ar-1 | XYZ-57 | $R^{11}$-11 |
| 1596. | Ar-1 | XYZ-57 | $R^{11}$-12 |
| 1597. | Ar-1 | XYZ-57 | $R^{11}$-13 |
| 1598. | Ar-1 | XYZ-57 | $R^{11}$-14 |
| 1599. | Ar-1 | XYZ-57 | $R^{11}$-15 |
| 1600. | Ar-1 | XYZ-57 | $R^{11}$-16 |
| 1601. | Ar-1 | XYZ-57 | $R^{11}$-17 |
| 1602. | Ar-1 | XYZ-57 | $R^{11}$-18 |
| 1603. | Ar-1 | XYZ-57 | $R^{11}$-19 |
| 1604. | Ar-1 | XYZ-57 | $R^{11}$-20 |
| 1605. | Ar-1 | XYZ-57 | $R^{11}$-21 |
| 1606. | Ar-1 | XYZ-57 | $R^{11}$-22 |
| 1607. | Ar-1 | XYZ-57 | $R^{11}$-23 |
| 1608. | Ar-1 | XYZ-57 | $R^{11}$-24 |
| 1609. | Ar-1 | XYZ-57 | $R^{11}$-25 |
| 1610. | Ar-1 | XYZ-57 | $R^{11}$-26 |
| 1611. | Ar-1 | XYZ-57 | $R^{11}$-27 |
| 1612. | Ar-1 | XYZ-57 | $R^{11}$-28 |
| 1613. | Ar-1 | XYZ-57 | $R^{11}$-29 |
| 1614. | Ar-1 | XYZ-58 | $R^{11}$-1 |
| 1615. | Ar-1 | XYZ-58 | $R^{11}$-2 |
| 1616. | Ar-1 | XYZ-58 | $R^{11}$-3 |
| 1617. | Ar-1 | XYZ-58 | $R^{11}$-4 |
| 1618. | Ar-1 | XYZ-58 | $R^{11}$-5 |
| 1619. | Ar-1 | XYZ-58 | $R^{11}$-6 |
| 1620. | Ar-1 | XYZ-58 | $R^{11}$-7 |
| 1621. | Ar-1 | XYZ-58 | $R^{11}$-8 |
| 1622. | Ar-1 | XYZ-58 | $R^{11}$-9 |
| 1623. | Ar-1 | XYZ-58 | $R^{11}$-10 |
| 1624. | Ar-1 | XYZ-58 | $R^{11}$-11 |
| 1625. | Ar-1 | XYZ-58 | $R^{11}$-12 |
| 1626. | Ar-1 | XYZ-58 | $R^{11}$-13 |
| 1627. | Ar-1 | XYZ-58 | $R^{11}$-14 |
| 1628. | Ar-1 | XYZ-58 | $R^{11}$-15 |
| 1629. | Ar-1 | XYZ-58 | $R^{11}$-16 |
| 1630. | Ar-1 | XYZ-58 | $R^{11}$-17 |
| 1631. | Ar-1 | XYZ-58 | $R^{11}$-18 |
| 1632. | Ar-1 | XYZ-58 | $R^{11}$-19 |
| 1633. | Ar-1 | XYZ-58 | $R^{11}$-20 |
| 1634. | Ar-1 | XYZ-58 | $R^{11}$-21 |
| 1635. | Ar-1 | XYZ-58 | $R^{11}$-22 |
| 1636. | Ar-1 | XYZ-58 | $R^{11}$-23 |
| 1637. | Ar-1 | XYZ-58 | $R^{11}$-24 |
| 1638. | Ar-1 | XYZ-58 | $R^{11}$-25 |
| 1639. | Ar-1 | XYZ-58 | $R^{11}$-26 |
| 1640. | Ar-1 | XYZ-58 | $R^{11}$-27 |
| 1641. | Ar-1 | XYZ-58 | $R^{11}$-28 |
| 1642. | Ar-1 | XYZ-58 | $R^{11}$-29 |
| 1643. | Ar-1 | XYZ-59 | $R^{11}$-1 |
| 1644. | Ar-1 | XYZ-59 | $R^{11}$-2 |
| 1645. | Ar-1 | XYZ-59 | $R^{11}$-3 |
| 1646. | Ar-1 | XYZ-59 | $R^{11}$-4 |
| 1647. | Ar-1 | XYZ-59 | $R^{11}$-5 |
| 1648. | Ar-1 | XYZ-59 | $R^{11}$-6 |
| 1649. | Ar-1 | XYZ-59 | $R^{11}$-7 |
| 1650. | Ar-1 | XYZ-59 | $R^{11}$-8 |
| 1651. | Ar-1 | XYZ-59 | $R^{11}$-9 |
| 1652. | Ar-1 | XYZ-59 | $R^{11}$-10 |
| 1653. | Ar-1 | XYZ-59 | $R^{11}$-11 |
| 1654. | Ar-1 | XYZ-59 | $R^{11}$-12 |
| 1655. | Ar-1 | XYZ-59 | $R^{11}$-13 |
| 1656. | Ar-1 | XYZ-59 | $R^{11}$-14 |
| 1657. | Ar-1 | XYZ-59 | $R^{11}$-15 |
| 1658. | Ar-1 | XYZ-59 | $R^{11}$-16 |
| 1659. | Ar-1 | XYZ-59 | $R^{11}$-17 |
| 1660. | Ar-1 | XYZ-59 | $R^{11}$-18 |
| 1661. | Ar-1 | XYZ-59 | $R^{11}$-19 |
| 1662. | Ar-1 | XYZ-59 | $R^{11}$-20 |
| 1663. | Ar-1 | XYZ-59 | $R^{11}$-21 |
| 1664. | Ar-1 | XYZ-59 | $R^{11}$-22 |
| 1665. | Ar-1 | XYZ-59 | $R^{11}$-23 |
| 1666. | Ar-1 | XYZ-59 | $R^{11}$-24 |
| 1667. | Ar-1 | XYZ-59 | $R^{11}$-25 |
| 1668. | Ar-1 | XYZ-59 | $R^{11}$-26 |
| 1669. | Ar-1 | XYZ-59 | $R^{11}$-27 |
| 1670. | Ar-1 | XYZ-59 | $R^{11}$-28 |
| 1671. | Ar-1 | XYZ-59 | $R^{11}$-29 |
| 1672. | Ar-1 | XYZ-60 | $R^{11}$-1 |
| 1673. | Ar-1 | XYZ-60 | $R^{11}$-2 |
| 1674. | Ar-1 | XYZ-60 | $R^{11}$-3 |
| 1675. | Ar-1 | XYZ-60 | $R^{11}$-4 |
| 1676. | Ar-1 | XYZ-60 | $R^{11}$-5 |
| 1677. | Ar-1 | XYZ-60 | $R^{11}$-6 |
| 1678. | Ar-1 | XYZ-60 | $R^{11}$-7 |
| 1679. | Ar-1 | XYZ-60 | $R^{11}$-8 |
| 1680. | Ar-1 | XYZ-60 | $R^{11}$-9 |
| 1681. | Ar-1 | XYZ-60 | $R^{11}$-10 |
| 1682. | Ar-1 | XYZ-60 | $R^{11}$-11 |
| 1683. | Ar-1 | XYZ-60 | $R^{11}$-12 |
| 1684. | Ar-1 | XYZ-60 | $R^{11}$-13 |
| 1685. | Ar-1 | XYZ-60 | $R^{11}$-14 |
| 1686. | Ar-1 | XYZ-60 | $R^{11}$-15 |
| 1687. | Ar-1 | XYZ-60 | $R^{11}$-16 |
| 1688. | Ar-1 | XYZ-60 | $R^{11}$-17 |
| 1689. | Ar-1 | XYZ-60 | $R^{11}$-18 |
| 1690. | Ar-1 | XYZ-60 | $R^{11}$-19 |
| 1691. | Ar-1 | XYZ-60 | $R^{11}$-20 |
| 1692. | Ar-1 | XYZ-60 | $R^{11}$-21 |
| 1693. | Ar-1 | XYZ-60 | $R^{11}$-22 |
| 1694. | Ar-1 | XYZ-60 | $R^{11}$-23 |
| 1695. | Ar-1 | XYZ-60 | $R^{11}$-24 |
| 1696. | Ar-1 | XYZ-60 | $R^{11}$-25 |
| 1697. | Ar-1 | XYZ-60 | $R^{11}$-26 |
| 1698. | Ar-1 | XYZ-60 | $R^{11}$-27 |
| 1699. | Ar-1 | XYZ-60 | $R^{11}$-28 |
| 1700. | Ar-1 | XYZ-60 | $R^{11}$-29 |
| 1701. | Ar-1 | XYZ-61 | $R^{11}$-1 |
| 1702. | Ar-1 | XYZ-61 | $R^{11}$-2 |
| 1703. | Ar-1 | XYZ-61 | $R^{11}$-3 |
| 1704. | Ar-1 | XYZ-61 | $R^{11}$-4 |
| 1705. | Ar-1 | XYZ-61 | $R^{11}$-5 |
| 1706. | Ar-1 | XYZ-61 | $R^{11}$-6 |
| 1707. | Ar-1 | XYZ-61 | $R^{11}$-7 |
| 1708. | Ar-1 | XYZ-61 | $R^{11}$-8 |
| 1709. | Ar-1 | XYZ-61 | $R^{11}$-9 |
| 1710. | Ar-1 | XYZ-61 | $R^{11}$-10 |
| 1711. | Ar-1 | XYZ-61 | $R^{11}$-11 |
| 1712. | Ar-1 | XYZ-61 | $R^{11}$-12 |
| 1713. | Ar-1 | XYZ-61 | $R^{11}$-13 |
| 1714. | Ar-1 | XYZ-61 | $R^{11}$-14 |
| 1715. | Ar-1 | XYZ-61 | $R^{11}$-15 |
| 1716. | Ar-1 | XYZ-61 | $R^{11}$-16 |
| 1717. | Ar-1 | XYZ-61 | $R^{11}$-17 |
| 1718. | Ar-1 | XYZ-61 | $R^{11}$-18 |
| 1719. | Ar-1 | XYZ-61 | $R^{11}$-19 |
| 1720. | Ar-1 | XYZ-61 | $R^{11}$-20 |
| 1721. | Ar-1 | XYZ-61 | $R^{11}$-21 |
| 1722. | Ar-1 | XYZ-61 | $R^{11}$-22 |
| 1723. | Ar-1 | XYZ-61 | $R^{11}$-23 |
| 1724. | Ar-1 | XYZ-61 | $R^{11}$-24 |
| 1725. | Ar-1 | XYZ-61 | $R^{11}$-25 |

TABLE C-continued

|  | Ar | -X-Y-Z- | $R^{11}/R^{12}$ |
|---|---|---|---|
| 1726. | Ar-1 | XYZ-61 | $R^{11}$-26 |
| 1727. | Ar-1 | XYZ-61 | $R^{11}$-27 |
| 1728. | Ar-1 | XYZ-61 | $R^{11}$-28 |
| 1729. | Ar-1 | XYZ-61 | $R^{11}$-29 |
| 1730. | Ar-1 | XYZ-62 | $R^{11}$-1 |
| 1731. | Ar-1 | XYZ-62 | $R^{11}$-2 |
| 1732. | Ar-1 | XYZ-62 | $R^{11}$-3 |
| 1733. | Ar-1 | XYZ-62 | $R^{11}$-4 |
| 1734. | Ar-1 | XYZ-62 | $R^{11}$-5 |
| 1735. | Ar-1 | XYZ-62 | $R^{11}$-6 |
| 1736. | Ar-1 | XYZ-62 | $R^{11}$-7 |
| 1737. | Ar-1 | XYZ-62 | $R^{11}$-8 |
| 1738. | Ar-1 | XYZ-62 | $R^{11}$-9 |
| 1739. | Ar-1 | XYZ-62 | $R^{11}$-10 |
| 1740. | Ar-1 | XYZ-62 | $R^{11}$-11 |
| 1741. | Ar-1 | XYZ-62 | $R^{11}$-12 |
| 1742. | Ar-1 | XYZ-62 | $R^{11}$-13 |
| 1743. | Ar-1 | XYZ-62 | $R^{11}$-14 |
| 1744. | Ar-1 | XYZ-62 | $R^{11}$-15 |
| 1745. | Ar-1 | XYZ-62 | $R^{11}$-16 |
| 1746. | Ar-1 | XYZ-62 | $R^{11}$-17 |
| 1747. | Ar-1 | XYZ-62 | $R^{11}$-18 |
| 1748. | Ar-1 | XYZ-62 | $R^{11}$-19 |
| 1749. | Ar-1 | XYZ-62 | $R^{11}$-20 |
| 1750. | Ar-1 | XYZ-62 | $R^{11}$-21 |
| 1751. | Ar-1 | XYZ-62 | $R^{11}$-22 |
| 1752. | Ar-1 | XYZ-62 | $R^{11}$-23 |
| 1753. | Ar-1 | XYZ-62 | $R^{11}$-24 |
| 1754. | Ar-1 | XYZ-62 | $R^{11}$-25 |
| 1755. | Ar-1 | XYZ-62 | $R^{11}$-26 |
| 1756. | Ar-1 | XYZ-62 | $R^{11}$-27 |
| 1757. | Ar-1 | XYZ-62 | $R^{11}$-28 |
| 1758. | Ar-1 | XYZ-62 | $R^{11}$-29 |
| 1759. | Ar-1 | XYZ-63 | $R^{11}$-1 |
| 1760. | Ar-1 | XYZ-63 | $R^{11}$-2 |
| 1761. | Ar-1 | XYZ-63 | $R^{11}$-3 |
| 1762. | Ar-1 | XYZ-63 | $R^{11}$-4 |
| 1763. | Ar-1 | XYZ-63 | $R^{11}$-5 |
| 1764. | Ar-1 | XYZ-63 | $R^{11}$-6 |
| 1765. | Ar-1 | XYZ-63 | $R^{11}$-7 |
| 1766. | Ar-1 | XYZ-63 | $R^{11}$-8 |
| 1767. | Ar-1 | XYZ-63 | $R^{11}$-9 |
| 1768. | Ar-1 | XYZ-63 | $R^{11}$-10 |
| 1769. | Ar-1 | XYZ-63 | $R^{11}$-11 |
| 1770. | Ar-1 | XYZ-63 | $R^{11}$-12 |
| 1771. | Ar-1 | XYZ-63 | $R^{11}$-13 |
| 1772. | Ar-1 | XYZ-63 | $R^{11}$-14 |
| 1773. | Ar-1 | XYZ-63 | $R^{11}$-15 |
| 1774. | Ar-1 | XYZ-63 | $R^{11}$-16 |
| 1775. | Ar-1 | XYZ-63 | $R^{11}$-17 |
| 1776. | Ar-1 | XYZ-63 | $R^{11}$-18 |
| 1777. | Ar-1 | XYZ-63 | $R^{11}$-19 |
| 1778. | Ar-1 | XYZ-63 | $R^{11}$-20 |
| 1779. | Ar-1 | XYZ-63 | $R^{11}$-21 |
| 1780. | Ar-1 | XYZ-63 | $R^{11}$-22 |
| 1781. | Ar-1 | XYZ-63 | $R^{11}$-23 |
| 1782. | Ar-1 | XYZ-63 | $R^{11}$-24 |
| 1783. | Ar-1 | XYZ-63 | $R^{11}$-25 |
| 1784. | Ar-1 | XYZ-63 | $R^{11}$-26 |
| 1785. | Ar-1 | XYZ-63 | $R^{11}$-27 |
| 1786. | Ar-1 | XYZ-63 | $R^{11}$-28 |
| 1787. | Ar-1 | XYZ-63 | $R^{11}$-29 |
| 1788. | Ar-1 | XYZ-64 | $R^{11}$-1 |
| 1789. | Ar-1 | XYZ-64 | $R^{11}$-2 |
| 1790. | Ar-1 | XYZ-64 | $R^{11}$-3 |
| 1791. | Ar-1 | XYZ-64 | $R^{11}$-4 |
| 1792. | Ar-1 | XYZ-64 | $R^{11}$-5 |
| 1793. | Ar-1 | XYZ-64 | $R^{11}$-6 |
| 1794. | Ar-1 | XYZ-64 | $R^{11}$-7 |
| 1795. | Ar-1 | XYZ-64 | $R^{11}$-8 |
| 1796. | Ar-1 | XYZ-64 | $R^{11}$-9 |
| 1797. | Ar-1 | XYZ-64 | $R^{11}$-10 |
| 1798. | Ar-1 | XYZ-64 | $R^{11}$-11 |
| 1799. | Ar-1 | XYZ-64 | $R^{11}$-12 |
| 1800. | Ar-1 | XYZ-64 | $R^{11}$-13 |
| 1801. | Ar-1 | XYZ-64 | $R^{11}$-14 |
| 1802. | Ar-1 | XYZ-64 | $R^{11}$-15 |
| 1803. | Ar-1 | XYZ-64 | $R^{11}$-16 |
| 1804. | Ar-1 | XYZ-64 | $R^{11}$-17 |
| 1805. | Ar-1 | XYZ-64 | $R^{11}$-18 |
| 1806. | Ar-1 | XYZ-64 | $R^{11}$-19 |
| 1807. | Ar-1 | XYZ-64 | $R^{11}$-20 |
| 1808. | Ar-1 | XYZ-64 | $R^{11}$-21 |
| 1809. | Ar-1 | XYZ-64 | $R^{11}$-22 |
| 1810. | Ar-1 | XYZ-64 | $R^{11}$-23 |
| 1811. | Ar-1 | XYZ-64 | $R^{11}$-24 |
| 1812. | Ar-1 | XYZ-64 | $R^{11}$-25 |
| 1813. | Ar-1 | XYZ-64 | $R^{11}$-26 |
| 1814. | Ar-1 | XYZ-64 | $R^{11}$-27 |
| 1815. | Ar-1 | XYZ-64 | $R^{11}$-28 |
| 1816. | Ar-1 | XYZ-64 | $R^{11}$-29 |
| 1817. | Ar-1 | XYZ-65 | $R^{11}$-1 |
| 1818. | Ar-1 | XYZ-65 | $R^{11}$-2 |
| 1819. | Ar-1 | XYZ-65 | $R^{11}$-3 |
| 1820. | Ar-1 | XYZ-65 | $R^{11}$-4 |
| 1821. | Ar-1 | XYZ-65 | $R^{11}$-5 |
| 1822. | Ar-1 | XYZ-65 | $R^{11}$-6 |
| 1823. | Ar-1 | XYZ-65 | $R^{11}$-7 |
| 1824. | Ar-1 | XYZ-65 | $R^{11}$-8 |
| 1825. | Ar-1 | XYZ-65 | $R^{11}$-9 |
| 1826. | Ar-1 | XYZ-65 | $R^{11}$-10 |
| 1827. | Ar-1 | XYZ-65 | $R^{11}$-11 |
| 1828. | Ar-1 | XYZ-65 | $R^{11}$-12 |
| 1829. | Ar-1 | XYZ-65 | $R^{11}$-13 |
| 1830. | Ar-1 | XYZ-65 | $R^{11}$-14 |
| 1831. | Ar-1 | XYZ-65 | $R^{11}$-15 |
| 1832. | Ar-1 | XYZ-65 | $R^{11}$-16 |
| 1833. | Ar-1 | XYZ-65 | $R^{11}$-17 |
| 1834. | Ar-1 | XYZ-65 | $R^{11}$-18 |
| 1835. | Ar-1 | XYZ-65 | $R^{11}$-19 |
| 1836. | Ar-1 | XYZ-65 | $R^{11}$-20 |
| 1837. | Ar-1 | XYZ-65 | $R^{11}$-21 |
| 1838. | Ar-1 | XYZ-65 | $R^{11}$-22 |
| 1839. | Ar-1 | XYZ-65 | $R^{11}$-23 |
| 1840. | Ar-1 | XYZ-65 | $R^{11}$-24 |
| 1841. | Ar-1 | XYZ-65 | $R^{11}$-25 |
| 1842. | Ar-1 | XYZ-65 | $R^{11}$-26 |
| 1843. | Ar-1 | XYZ-65 | $R^{11}$-27 |
| 1844. | Ar-1 | XYZ-65 | $R^{11}$-28 |
| 1845. | Ar-1 | XYZ-65 | $R^{11}$-29 |
| 1846. | Ar-1 | XYZ-66 | $R^{11}$-1 |
| 1847. | Ar-1 | XYZ-66 | $R^{11}$-2 |
| 1848. | Ar-1 | XYZ-66 | $R^{11}$-3 |
| 1849. | Ar-1 | XYZ-66 | $R^{11}$-4 |
| 1850. | Ar-1 | XYZ-66 | $R^{11}$-5 |
| 1851. | Ar-1 | XYZ-66 | $R^{11}$-6 |
| 1852. | Ar-1 | XYZ-66 | $R^{11}$-7 |
| 1853. | Ar-1 | XYZ-66 | $R^{11}$-8 |
| 1854. | Ar-1 | XYZ-66 | $R^{11}$-9 |
| 1855. | Ar-1 | XYZ-66 | $R^{11}$-10 |
| 1856. | Ar-1 | XYZ-66 | $R^{11}$-11 |
| 1857. | Ar-1 | XYZ-66 | $R^{11}$-12 |
| 1858. | Ar-1 | XYZ-66 | $R^{11}$-13 |
| 1859. | Ar-1 | XYZ-66 | $R^{11}$-14 |
| 1860. | Ar-1 | XYZ-66 | $R^{11}$-15 |
| 1861. | Ar-1 | XYZ-66 | $R^{11}$-16 |
| 1862. | Ar-1 | XYZ-66 | $R^{11}$-17 |
| 1863. | Ar-1 | XYZ-66 | $R^{11}$-18 |
| 1864. | Ar-1 | XYZ-66 | $R^{11}$-19 |
| 1865. | Ar-1 | XYZ-66 | $R^{11}$-20 |
| 1866. | Ar-1 | XYZ-66 | $R^{11}$-21 |
| 1867. | Ar-1 | XYZ-66 | $R^{11}$-22 |
| 1868. | Ar-1 | XYZ-66 | $R^{11}$-23 |
| 1869. | Ar-1 | XYZ-66 | $R^{11}$-24 |
| 1870. | Ar-1 | XYZ-66 | $R^{11}$-25 |
| 1871. | Ar-1 | XYZ-66 | $R^{11}$-26 |
| 1872. | Ar-1 | XYZ-66 | $R^{11}$-27 |
| 1873. | Ar-1 | XYZ-66 | $R^{11}$-28 |
| 1874. | Ar-1 | XYZ-66 | $R^{11}$-29 |
| 1875. | Ar-1 | XYZ-67 | $R^{11}$-1 |
| 1876. | Ar-1 | XYZ-67 | $R^{11}$-2 |
| 1877. | Ar-1 | XYZ-67 | $R^{11}$-3 |
| 1878. | Ar-1 | XYZ-67 | $R^{11}$-4 |
| 1879. | Ar-1 | XYZ-67 | $R^{11}$-5 |
| 1880. | Ar-1 | XYZ-67 | $R^{11}$-6 |
| 1881. | Ar-1 | XYZ-67 | $R^{11}$-7 |

TABLE C-continued

|      | Ar   | -X-Y-Z- | $R^{11}/R^{12}$ |
|------|------|---------|-----------------|
| 1882. | Ar-1 | XYZ-67 | $R^{11}$-8 |
| 1883. | Ar-1 | XYZ-67 | $R^{11}$-9 |
| 1884. | Ar-1 | XYZ-67 | $R^{11}$-10 |
| 1885. | Ar-1 | XYZ-67 | $R^{11}$-11 |
| 1886. | Ar-1 | XYZ-67 | $R^{11}$-12 |
| 1887. | Ar-1 | XYZ-67 | $R^{11}$-13 |
| 1888. | Ar-1 | XYZ-67 | $R^{11}$-14 |
| 1889. | Ar-1 | XYZ-67 | $R^{11}$-15 |
| 1890. | Ar-1 | XYZ-67 | $R^{11}$-16 |
| 1891. | Ar-1 | XYZ-67 | $R^{11}$-17 |
| 1892. | Ar-1 | XYZ-67 | $R^{11}$-18 |
| 1893. | Ar-1 | XYZ-67 | $R^{11}$-19 |
| 1894. | Ar-1 | XYZ-67 | $R^{11}$-20 |
| 1895. | Ar-1 | XYZ-67 | $R^{11}$-21 |
| 1896. | Ar-1 | XYZ-67 | $R^{11}$-22 |
| 1897. | Ar-1 | XYZ-67 | $R^{11}$-23 |
| 1898. | Ar-1 | XYZ-67 | $R^{11}$-24 |
| 1899. | Ar-1 | XYZ-67 | $R^{11}$-25 |
| 1900. | Ar-1 | XYZ-67 | $R^{11}$-26 |
| 1901. | Ar-1 | XYZ-67 | $R^{11}$-27 |
| 1902. | Ar-1 | XYZ-67 | $R^{11}$-28 |
| 1903. | Ar-1 | XYZ-67 | $R^{11}$-29 |
| 1904. | Ar-1 | XYZ-68 | $R^{11}$-1 |
| 1905. | Ar-1 | XYZ-68 | $R^{11}$-2 |
| 1906. | Ar-1 | XYZ-68 | $R^{11}$-3 |
| 1907. | Ar-1 | XYZ-68 | $R^{11}$-4 |
| 1908. | Ar-1 | XYZ-68 | $R^{11}$-5 |
| 1909. | Ar-1 | XYZ-68 | $R^{11}$-6 |
| 1910. | Ar-1 | XYZ-68 | $R^{11}$-7 |
| 1911. | Ar-1 | XYZ-68 | $R^{11}$-8 |
| 1912. | Ar-1 | XYZ-68 | $R^{11}$-9 |
| 1913. | Ar-1 | XYZ-68 | $R^{11}$-10 |
| 1914. | Ar-1 | XYZ-68 | $R^{11}$-11 |
| 1915. | Ar-1 | XYZ-68 | $R^{11}$-12 |
| 1916. | Ar-1 | XYZ-68 | $R^{11}$-13 |
| 1917. | Ar-1 | XYZ-68 | $R^{11}$-14 |
| 1918. | Ar-1 | XYZ-68 | $R^{11}$-15 |
| 1919. | Ar-1 | XYZ-68 | $R^{11}$-16 |
| 1920. | Ar-1 | XYZ-68 | $R^{11}$-17 |
| 1921. | Ar-1 | XYZ-68 | $R^{11}$-18 |
| 1922. | Ar-1 | XYZ-68 | $R^{11}$-19 |
| 1923. | Ar-1 | XYZ-68 | $R^{11}$-20 |
| 1924. | Ar-1 | XYZ-68 | $R^{11}$-21 |
| 1925. | Ar-1 | XYZ-68 | $R^{11}$-22 |
| 1926. | Ar-1 | XYZ-68 | $R^{11}$-23 |
| 1927. | Ar-1 | XYZ-68 | $R^{11}$-24 |
| 1928. | Ar-1 | XYZ-68 | $R^{11}$-25 |
| 1929. | Ar-1 | XYZ-68 | $R^{11}$-26 |
| 1930. | Ar-1 | XYZ-68 | $R^{11}$-27 |
| 1931. | Ar-1 | XYZ-68 | $R^{11}$-28 |
| 1932. | Ar-1 | XYZ-68 | $R^{11}$-29 |
| 1933. | Ar-1 | XYZ-69 | $R^{11}$-1 |
| 1934. | Ar-1 | XYZ-69 | $R^{11}$-2 |
| 1935. | Ar-1 | XYZ-69 | $R^{11}$-3 |
| 1936. | Ar-1 | XYZ-69 | $R^{11}$-4 |
| 1937. | Ar-1 | XYZ-69 | $R^{11}$-5 |
| 1938. | Ar-1 | XYZ-69 | $R^{11}$-6 |
| 1939. | Ar-1 | XYZ-69 | $R^{11}$-7 |
| 1940. | Ar-1 | XYZ-69 | $R^{11}$-8 |
| 1941. | Ar-1 | XYZ-69 | $R^{11}$-9 |
| 1942. | Ar-1 | XYZ-69 | $R^{11}$-10 |
| 1943. | Ar-1 | XYZ-69 | $R^{11}$-11 |
| 1944. | Ar-1 | XYZ-69 | $R^{11}$-12 |
| 1945. | Ar-1 | XYZ-69 | $R^{11}$-13 |
| 1946. | Ar-1 | XYZ-69 | $R^{11}$-14 |
| 1947. | Ar-1 | XYZ-69 | $R^{11}$-15 |
| 1948. | Ar-1 | XYZ-69 | $R^{11}$-16 |
| 1949. | Ar-1 | XYZ-69 | $R^{11}$-17 |
| 1950. | Ar-1 | XYZ-69 | $R^{11}$-18 |
| 1951. | Ar-1 | XYZ-69 | $R^{11}$-19 |
| 1952. | Ar-1 | XYZ-69 | $R^{11}$-20 |
| 1953. | Ar-1 | XYZ-69 | $R^{11}$-21 |
| 1954. | Ar-1 | XYZ-69 | $R^{11}$-22 |
| 1955. | Ar-1 | XYZ-69 | $R^{11}$-23 |
| 1956. | Ar-1 | XYZ-69 | $R^{11}$-24 |
| 1957. | Ar-1 | XYZ-69 | $R^{11}$-25 |
| 1958. | Ar-1 | XYZ-69 | $R^{11}$-26 |
| 1959. | Ar-1 | XYZ-69 | $R^{11}$-27 |
| 1960. | Ar-1 | XYZ-69 | $R^{11}$-28 |
| 1961. | Ar-1 | XYZ-69 | $R^{11}$-29 |
| 1962. | Ar-1 | XYZ-70 | $R^{11}$-1 |
| 1963. | Ar-1 | XYZ-70 | $R^{11}$-2 |
| 1964. | Ar-1 | XYZ-70 | $R^{11}$-3 |
| 1965. | Ar-1 | XYZ-70 | $R^{11}$-4 |
| 1966. | Ar-1 | XYZ-70 | $R^{11}$-5 |
| 1967. | Ar-1 | XYZ-70 | $R^{11}$-6 |
| 1968. | Ar-1 | XYZ-70 | $R^{11}$-7 |
| 1969. | Ar-1 | XYZ-70 | $R^{11}$-8 |
| 1970. | Ar-1 | XYZ-70 | $R^{11}$-9 |
| 1971. | Ar-1 | XYZ-70 | $R^{11}$-10 |
| 1972. | Ar-1 | XYZ-70 | $R^{11}$-11 |
| 1973. | Ar-1 | XYZ-70 | $R^{11}$-12 |
| 1974. | Ar-1 | XYZ-70 | $R^{11}$-13 |
| 1975. | Ar-1 | XYZ-70 | $R^{11}$-14 |
| 1976. | Ar-1 | XYZ-70 | $R^{11}$-15 |
| 1977. | Ar-1 | XYZ-70 | $R^{11}$-16 |
| 1978. | Ar-1 | XYZ-70 | $R^{11}$-17 |
| 1979. | Ar-1 | XYZ-70 | $R^{11}$-18 |
| 1980. | Ar-1 | XYZ-70 | $R^{11}$-19 |
| 1981. | Ar-1 | XYZ-70 | $R^{11}$-20 |
| 1982. | Ar-1 | XYZ-70 | $R^{11}$-21 |
| 1983. | Ar-1 | XYZ-70 | $R^{11}$-22 |
| 1984. | Ar-1 | XYZ-70 | $R^{11}$-23 |
| 1985. | Ar-1 | XYZ-70 | $R^{11}$-24 |
| 1986. | Ar-1 | XYZ-70 | $R^{11}$-25 |
| 1987. | Ar-1 | XYZ-70 | $R^{11}$-26 |
| 1988. | Ar-1 | XYZ-70 | $R^{11}$-27 |
| 1989. | Ar-1 | XYZ-70 | $R^{11}$-28 |
| 1990. | Ar-1 | XYZ-70 | $R^{11}$-29 |
| 1991. | Ar-1 | XYZ-71 | $R^{11}$-1 |
| 1992. | Ar-1 | XYZ-71 | $R^{11}$-2 |
| 1993. | Ar-1 | XYZ-71 | $R^{11}$-3 |
| 1994. | Ar-1 | XYZ-71 | $R^{11}$-4 |
| 1995. | Ar-1 | XYZ-71 | $R^{11}$-5 |
| 1996. | Ar-1 | XYZ-71 | $R^{11}$-6 |
| 1997. | Ar-1 | XYZ-71 | $R^{11}$-7 |
| 1998. | Ar-1 | XYZ-71 | $R^{11}$-8 |
| 1999. | Ar-1 | XYZ-71 | $R^{11}$-9 |
| 2000. | Ar-1 | XYZ-71 | $R^{11}$-10 |
| 2001. | Ar-1 | XYZ-71 | $R^{11}$-11 |
| 2002. | Ar-1 | XYZ-71 | $R^{11}$-12 |
| 2003. | Ar-1 | XYZ-71 | $R^{11}$-13 |
| 2004. | Ar-1 | XYZ-71 | $R^{11}$-14 |
| 2005. | Ar-1 | XYZ-71 | $R^{11}$-15 |
| 2006. | Ar-1 | XYZ-71 | $R^{11}$-16 |
| 2007. | Ar-1 | XYZ-71 | $R^{11}$-17 |
| 2008. | Ar-1 | XYZ-71 | $R^{11}$-18 |
| 2009. | Ar-1 | XYZ-71 | $R^{11}$-19 |
| 2010. | Ar-1 | XYZ-71 | $R^{11}$-20 |
| 2011. | Ar-1 | XYZ-71 | $R^{11}$-21 |
| 2012. | Ar-1 | XYZ-71 | $R^{11}$-22 |
| 2013. | Ar-1 | XYZ-71 | $R^{11}$-23 |
| 2014. | Ar-1 | XYZ-71 | $R^{11}$-24 |
| 2015. | Ar-1 | XYZ-71 | $R^{11}$-25 |
| 2016. | Ar-1 | XYZ-71 | $R^{11}$-26 |
| 2017. | Ar-1 | XYZ-71 | $R^{11}$-27 |
| 2018. | Ar-1 | XYZ-71 | $R^{11}$-28 |
| 2019. | Ar-1 | XYZ-71 | $R^{11}$-29 |
| 2020. | Ar-1 | XYZ-72 | $R^{11}$-1 |
| 2021. | Ar-1 | XYZ-72 | $R^{11}$-2 |
| 2022. | Ar-1 | XYZ-72 | $R^{11}$-3 |
| 2023. | Ar-1 | XYZ-72 | $R^{11}$-4 |
| 2024. | Ar-1 | XYZ-72 | $R^{11}$-5 |
| 2025. | Ar-1 | XYZ-72 | $R^{11}$-6 |
| 2026. | Ar-1 | XYZ-72 | $R^{11}$-7 |
| 2027. | Ar-1 | XYZ-72 | $R^{11}$-8 |
| 2028. | Ar-1 | XYZ-72 | $R^{11}$-9 |
| 2029. | Ar-1 | XYZ-72 | $R^{11}$-10 |
| 2030. | Ar-1 | XYZ-72 | $R^{11}$-11 |
| 2031. | Ar-1 | XYZ-72 | $R^{11}$-12 |
| 2032. | Ar-1 | XYZ-72 | $R^{11}$-13 |
| 2033. | Ar-1 | XYZ-72 | $R^{11}$-14 |
| 2034. | Ar-1 | XYZ-72 | $R^{11}$-15 |
| 2035. | Ar-1 | XYZ-72 | $R^{11}$-16 |
| 2036. | Ar-1 | XYZ-72 | $R^{11}$-17 |
| 2037. | Ar-1 | XYZ-72 | $R^{11}$-18 |

TABLE C-continued

| | Ar | -X-Y-Z- | $R^{11}/R^{12}$ |
|---|---|---|---|
| 2038. | Ar-1 | XYZ-72 | $R^{11}$-19 |
| 2039. | Ar-1 | XYZ-72 | $R^{11}$-20 |
| 2040. | Ar-1 | XYZ-72 | $R^{11}$-21 |
| 2041. | Ar-1 | XYZ-72 | $R^{11}$-22 |
| 2042. | Ar-1 | XYZ-72 | $R^{11}$-23 |
| 2043. | Ar-1 | XYZ-72 | $R^{11}$-24 |
| 2044. | Ar-1 | XYZ-72 | $R^{11}$-25 |
| 2045. | Ar-1 | XYZ-72 | $R^{11}$-26 |
| 2046. | Ar-1 | XYZ-72 | $R^{11}$-27 |
| 2047. | Ar-1 | XYZ-72 | $R^{11}$-28 |
| 2048. | Ar-1 | XYZ-72 | $R^{11}$-29 |
| 2049. | Ar-1 | XYZ-73 | $R^{11}$-1 |
| 2050. | Ar-1 | XYZ-73 | $R^{11}$-2 |
| 2051. | Ar-1 | XYZ-73 | $R^{11}$-3 |
| 2052. | Ar-1 | XYZ-73 | $R^{11}$-4 |
| 2053. | Ar-1 | XYZ-73 | $R^{11}$-5 |
| 2054. | Ar-1 | XYZ-73 | $R^{11}$-6 |
| 2055. | Ar-1 | XYZ-73 | $R^{11}$-7 |
| 2056. | Ar-1 | XYZ-73 | $R^{11}$-8 |
| 2057. | Ar-1 | XYZ-73 | $R^{11}$-9 |
| 2058. | Ar-1 | XYZ-73 | $R^{11}$-10 |
| 2059. | Ar-1 | XYZ-73 | $R^{11}$-11 |
| 2060. | Ar-1 | XYZ-73 | $R^{11}$-12 |
| 2061. | Ar-1 | XYZ-73 | $R^{11}$-13 |
| 2062. | Ar-1 | XYZ-73 | $R^{11}$-14 |
| 2063. | Ar-1 | XYZ-73 | $R^{11}$-15 |
| 2064. | Ar-1 | XYZ-73 | $R^{11}$-16 |
| 2065. | Ar-1 | XYZ-73 | $R^{11}$-17 |
| 2066. | Ar-1 | XYZ-73 | $R^{11}$-18 |
| 2067. | Ar-1 | XYZ-73 | $R^{11}$-19 |
| 2068. | Ar-1 | XYZ-73 | $R^{11}$-20 |
| 2069. | Ar-1 | XYZ-73 | $R^{11}$-21 |
| 2070. | Ar-1 | XYZ-73 | $R^{11}$-22 |
| 2071. | Ar-1 | XYZ-73 | $R^{11}$-23 |
| 2072. | Ar-1 | XYZ-73 | $R^{11}$-24 |
| 2073. | Ar-1 | XYZ-73 | $R^{11}$-25 |
| 2074. | Ar-1 | XYZ-73 | $R^{11}$-26 |
| 2075. | Ar-1 | XYZ-73 | $R^{11}$-27 |
| 2076. | Ar-1 | XYZ-73 | $R^{11}$-28 |
| 2077. | Ar-1 | XYZ-73 | $R^{11}$-29 |
| 2078. | Ar-1 | XYZ-74 | $R^{11}$-1 |
| 2079. | Ar-1 | XYZ-74 | $R^{11}$-2 |
| 2080. | Ar-1 | XYZ-74 | $R^{11}$-3 |
| 2081. | Ar-1 | XYZ-74 | $R^{11}$-4 |
| 2082. | Ar-1 | XYZ-74 | $R^{11}$-5 |
| 2083. | Ar-1 | XYZ-74 | $R^{11}$-6 |
| 2084. | Ar-1 | XYZ-74 | $R^{11}$-7 |
| 2085. | Ar-1 | XYZ-74 | $R^{11}$-8 |
| 2086. | Ar-1 | XYZ-74 | $R^{11}$-9 |
| 2087. | Ar-1 | XYZ-74 | $R^{11}$-10 |
| 2088. | Ar-1 | XYZ-74 | $R^{11}$-11 |
| 2089. | Ar-1 | XYZ-74 | $R^{11}$-12 |
| 2090. | Ar-1 | XYZ-74 | $R^{11}$-13 |
| 2091. | Ar-1 | XYZ-74 | $R^{11}$-14 |
| 2092. | Ar-1 | XYZ-74 | $R^{11}$-15 |
| 2093. | Ar-1 | XYZ-74 | $R^{11}$-16 |
| 2094. | Ar-1 | XYZ-74 | $R^{11}$-17 |
| 2095. | Ar-1 | XYZ-74 | $R^{11}$-18 |
| 2096. | Ar-1 | XYZ-74 | $R^{11}$-19 |
| 2097. | Ar-1 | XYZ-74 | $R^{11}$-20 |
| 2098. | Ar-1 | XYZ-74 | $R^{11}$-21 |
| 2099. | Ar-1 | XYZ-74 | $R^{11}$-22 |
| 2100. | Ar-1 | XYZ-74 | $R^{11}$-23 |
| 2101. | Ar-1 | XYZ-74 | $R^{11}$-24 |
| 2102. | Ar-1 | XYZ-74 | $R^{11}$-25 |
| 2103. | Ar-1 | XYZ-74 | $R^{11}$-26 |
| 2104. | Ar-1 | XYZ-74 | $R^{11}$-27 |
| 2105. | Ar-1 | XYZ-74 | $R^{11}$-28 |
| 2106. | Ar-1 | XYZ-74 | $R^{11}$-29 |
| 2107. | Ar-1 | XYZ-75 | $R^{11}$-1 |
| 2108. | Ar-1 | XYZ-75 | $R^{11}$-2 |
| 2109. | Ar-1 | XYZ-75 | $R^{11}$-3 |
| 2110. | Ar-1 | XYZ-75 | $R^{11}$-4 |
| 2111. | Ar-1 | XYZ-75 | $R^{11}$-5 |
| 2112. | Ar-1 | XYZ-75 | $R^{11}$-6 |
| 2113. | Ar-1 | XYZ-75 | $R^{11}$-7 |
| 2114. | Ar-1 | XYZ-75 | $R^{11}$-8 |
| 2115. | Ar-1 | XYZ-75 | $R^{11}$-9 |
| 2116. | Ar-1 | XYZ-75 | $R^{11}$-10 |
| 2117. | Ar-1 | XYZ-75 | $R^{11}$-11 |
| 2118. | Ar-1 | XYZ-75 | $R^{11}$-12 |
| 2119. | Ar-1 | XYZ-75 | $R^{11}$-13 |
| 2120. | Ar-1 | XYZ-75 | $R^{11}$-14 |
| 2121. | Ar-1 | XYZ-75 | $R^{11}$-15 |
| 2122. | Ar-1 | XYZ-75 | $R^{11}$-16 |
| 2123. | Ar-1 | XYZ-75 | $R^{11}$-17 |
| 2124. | Ar-1 | XYZ-75 | $R^{11}$-18 |
| 2125. | Ar-1 | XYZ-75 | $R^{11}$-19 |
| 2126. | Ar-1 | XYZ-75 | $R^{11}$-20 |
| 2127. | Ar-1 | XYZ-75 | $R^{11}$-21 |
| 2128. | Ar-1 | XYZ-75 | $R^{11}$-22 |
| 2129. | Ar-1 | XYZ-75 | $R^{11}$-23 |
| 2130. | Ar-1 | XYZ-75 | $R^{11}$-24 |
| 2131. | Ar-1 | XYZ-75 | $R^{11}$-25 |
| 2132. | Ar-1 | XYZ-75 | $R^{11}$-26 |
| 2133. | Ar-1 | XYZ-75 | $R^{11}$-27 |
| 2134. | Ar-1 | XYZ-75 | $R^{11}$-28 |
| 2135. | Ar-1 | XYZ-75 | $R^{11}$-29 |
| 2136. | Ar-1 | XYZ-76 | $R^{11}$-1 |
| 2137. | Ar-1 | XYZ-76 | $R^{11}$-2 |
| 2138. | Ar-1 | XYZ-76 | $R^{11}$-3 |
| 2139. | Ar-1 | XYZ-76 | $R^{11}$-4 |
| 2140. | Ar-1 | XYZ-76 | $R^{11}$-5 |
| 2141. | Ar-1 | XYZ-76 | $R^{11}$-6 |
| 2142. | Ar-1 | XYZ-76 | $R^{11}$-7 |
| 2143. | Ar-1 | XYZ-76 | $R^{11}$-8 |
| 2144. | Ar-1 | XYZ-76 | $R^{11}$-9 |
| 2145. | Ar-1 | XYZ-76 | $R^{11}$-10 |
| 2146. | Ar-1 | XYZ-76 | $R^{11}$-11 |
| 2147. | Ar-1 | XYZ-76 | $R^{11}$-12 |
| 2148. | Ar-1 | XYZ-76 | $R^{11}$-13 |
| 2149. | Ar-1 | XYZ-76 | $R^{11}$-14 |
| 2150. | Ar-1 | XYZ-76 | $R^{11}$-15 |
| 2151. | Ar-1 | XYZ-76 | $R^{11}$-16 |
| 2152. | Ar-1 | XYZ-76 | $R^{11}$-17 |
| 2153. | Ar-1 | XYZ-76 | $R^{11}$-18 |
| 2154. | Ar-1 | XYZ-76 | $R^{11}$-19 |
| 2155. | Ar-1 | XYZ-76 | $R^{11}$-20 |
| 2156. | Ar-1 | XYZ-76 | $R^{11}$-21 |
| 2157. | Ar-1 | XYZ-76 | $R^{11}$-22 |
| 2158. | Ar-1 | XYZ-76 | $R^{11}$-23 |
| 2159. | Ar-1 | XYZ-76 | $R^{11}$-24 |
| 2160. | Ar-1 | XYZ-76 | $R^{11}$-25 |
| 2161. | Ar-1 | XYZ-76 | $R^{11}$-26 |
| 2162. | Ar-1 | XYZ-76 | $R^{11}$-27 |
| 2163. | Ar-1 | XYZ-76 | $R^{11}$-28 |
| 2164. | Ar-1 | XYZ-76 | $R^{11}$-29 |
| 2165. | Ar-1 | XYZ-77 | $R^{11}$-1 |
| 2166. | Ar-1 | XYZ-77 | $R^{11}$-2 |
| 2167. | Ar-1 | XYZ-77 | $R^{11}$-3 |
| 2168. | Ar-1 | XYZ-77 | $R^{11}$-4 |
| 2169. | Ar-1 | XYZ-77 | $R^{11}$-5 |
| 2170. | Ar-1 | XYZ-77 | $R^{11}$-6 |
| 2171. | Ar-1 | XYZ-77 | $R^{11}$-7 |
| 2172. | Ar-1 | XYZ-77 | $R^{11}$-8 |
| 2173. | Ar-1 | XYZ-77 | $R^{11}$-9 |
| 2174. | Ar-1 | XYZ-77 | $R^{11}$-10 |
| 2175. | Ar-1 | XYZ-77 | $R^{11}$-11 |
| 2176. | Ar-1 | XYZ-77 | $R^{11}$-12 |
| 2177. | Ar-1 | XYZ-77 | $R^{11}$-13 |
| 2178. | Ar-1 | XYZ-77 | $R^{11}$-14 |
| 2179. | Ar-1 | XYZ-77 | $R^{11}$-15 |
| 2180. | Ar-1 | XYZ-77 | $R^{11}$-16 |
| 2181. | Ar-1 | XYZ-77 | $R^{11}$-17 |
| 2182. | Ar-1 | XYZ-77 | $R^{11}$-18 |
| 2183. | Ar-1 | XYZ-77 | $R^{11}$-19 |
| 2184. | Ar-1 | XYZ-77 | $R^{11}$-20 |
| 2185. | Ar-1 | XYZ-77 | $R^{11}$-21 |
| 2186. | Ar-1 | XYZ-77 | $R^{11}$-22 |
| 2187. | Ar-1 | XYZ-77 | $R^{11}$-23 |
| 2188. | Ar-1 | XYZ-77 | $R^{11}$-24 |
| 2189. | Ar-1 | XYZ-77 | $R^{11}$-25 |
| 2190. | Ar-1 | XYZ-77 | $R^{11}$-26 |
| 2191. | Ar-1 | XYZ-77 | $R^{11}$-27 |
| 2192. | Ar-1 | XYZ-77 | $R^{11}$-28 |
| 2193. | Ar-1 | XYZ-77 | $R^{11}$-29 |

TABLE C-continued

|  | Ar | -X-Y-Z- | $R^{11}/R^{12}$ |
|---|---|---|---|
| 2194. | Ar-1 | XYZ-78 | $R^{11}$-1 |
| 2195. | Ar-1 | XYZ-78 | $R^{11}$-2 |
| 2196. | Ar-1 | XYZ-78 | $R^{11}$-3 |
| 2197. | Ar-1 | XYZ-78 | $R^{11}$-4 |
| 2198. | Ar-1 | XYZ-78 | $R^{11}$-5 |
| 2199. | Ar-1 | XYZ-78 | $R^{11}$-6 |
| 2200. | Ar-1 | XYZ-78 | $R^{11}$-7 |
| 2201. | Ar-1 | XYZ-78 | $R^{11}$-8 |
| 2202. | Ar-1 | XYZ-78 | $R^{11}$-9 |
| 2203. | Ar-1 | XYZ-78 | $R^{11}$-10 |
| 2204. | Ar-1 | XYZ-78 | $R^{11}$-11 |
| 2205. | Ar-1 | XYZ-78 | $R^{11}$-12 |
| 2206. | Ar-1 | XYZ-78 | $R^{11}$-13 |
| 2207. | Ar-1 | XYZ-78 | $R^{11}$-14 |
| 2208. | Ar-1 | XYZ-78 | $R^{11}$-15 |
| 2209. | Ar-1 | XYZ-78 | $R^{11}$-16 |
| 2210. | Ar-1 | XYZ-78 | $R^{11}$-17 |
| 2211. | Ar-1 | XYZ-78 | $R^{11}$-18 |
| 2212. | Ar-1 | XYZ-78 | $R^{11}$-19 |
| 2213. | Ar-1 | XYZ-78 | $R^{11}$-20 |
| 2214. | Ar-1 | XYZ-78 | $R^{11}$-21 |
| 2215. | Ar-1 | XYZ-78 | $R^{11}$-22 |
| 2216. | Ar-1 | XYZ-78 | $R^{11}$-23 |
| 2217. | Ar-1 | XYZ-78 | $R^{11}$-24 |
| 2218. | Ar-1 | XYZ-78 | $R^{11}$-25 |
| 2219. | Ar-1 | XYZ-78 | $R^{11}$-26 |
| 2220. | Ar-1 | XYZ-78 | $R^{11}$-27 |
| 2221. | Ar-1 | XYZ-78 | $R^{11}$-28 |
| 2222. | Ar-1 | XYZ-78 | $R^{11}$-29 |
| 2223. | Ar-1 | XYZ-79 | $R^{11}$-1 |
| 2224. | Ar-1 | XYZ-79 | $R^{11}$-2 |
| 2225. | Ar-1 | XYZ-79 | $R^{11}$-3 |
| 2226. | Ar-1 | XYZ-79 | $R^{11}$-4 |
| 2227. | Ar-1 | XYZ-79 | $R^{11}$-5 |
| 2228. | Ar-1 | XYZ-79 | $R^{11}$-6 |
| 2229. | Ar-1 | XYZ-79 | $R^{11}$-7 |
| 2230. | Ar-1 | XYZ-79 | $R^{11}$-8 |
| 2231. | Ar-1 | XYZ-79 | $R^{11}$-9 |
| 2232. | Ar-1 | XYZ-79 | $R^{11}$-10 |
| 2233. | Ar-1 | XYZ-79 | $R^{11}$-11 |
| 2234. | Ar-1 | XYZ-79 | $R^{11}$-12 |
| 2235. | Ar-1 | XYZ-79 | $R^{11}$-13 |
| 2236. | Ar-1 | XYZ-79 | $R^{11}$-14 |
| 2237. | Ar-1 | XYZ-79 | $R^{11}$-15 |
| 2238. | Ar-1 | XYZ-79 | $R^{11}$-16 |
| 2239. | Ar-1 | XYZ-79 | $R^{11}$-17 |
| 2240. | Ar-1 | XYZ-79 | $R^{11}$-18 |
| 2241. | Ar-1 | XYZ-79 | $R^{11}$-19 |
| 2242. | Ar-1 | XYZ-79 | $R^{11}$-20 |
| 2243. | Ar-1 | XYZ-79 | $R^{11}$-21 |
| 2244. | Ar-1 | XYZ-79 | $R^{11}$-22 |
| 2245. | Ar-1 | XYZ-79 | $R^{11}$-23 |
| 2246. | Ar-1 | XYZ-79 | $R^{11}$-24 |
| 2247. | Ar-1 | XYZ-79 | $R^{11}$-25 |
| 2248. | Ar-1 | XYZ-79 | $R^{11}$-26 |
| 2249. | Ar-1 | XYZ-79 | $R^{11}$-27 |
| 2250. | Ar-1 | XYZ-79 | $R^{11}$-28 |
| 2251. | Ar-1 | XYZ-79 | $R^{11}$-29 |
| 2252. | Ar-1 | XYZ-80 | $R^{11}$-1 |
| 2253. | Ar-1 | XYZ-80 | $R^{11}$-2 |
| 2254. | Ar-1 | XYZ-80 | $R^{11}$-3 |
| 2255. | Ar-1 | XYZ-80 | $R^{11}$-4 |
| 2256. | Ar-1 | XYZ-80 | $R^{11}$-5 |
| 2257. | Ar-1 | XYZ-80 | $R^{11}$-6 |
| 2258. | Ar-1 | XYZ-80 | $R^{11}$-7 |
| 2259. | Ar-1 | XYZ-80 | $R^{11}$-8 |
| 2260. | Ar-1 | XYZ-80 | $R^{11}$-9 |
| 2261. | Ar-1 | XYZ-80 | $R^{11}$-10 |
| 2262. | Ar-1 | XYZ-80 | $R^{11}$-11 |
| 2263. | Ar-1 | XYZ-80 | $R^{11}$-12 |
| 2264. | Ar-1 | XYZ-80 | $R^{11}$-13 |
| 2265. | Ar-1 | XYZ-80 | $R^{11}$-14 |
| 2266. | Ar-1 | XYZ-80 | $R^{11}$-15 |
| 2267. | Ar-1 | XYZ-80 | $R^{11}$-16 |
| 2268. | Ar-1 | XYZ-80 | $R^{11}$-17 |
| 2269. | Ar-1 | XYZ-80 | $R^{11}$-18 |
| 2270. | Ar-1 | XYZ-80 | $R^{11}$-19 |
| 2271. | Ar-1 | XYZ-80 | $R^{11}$-20 |
| 2272. | Ar-1 | XYZ-80 | $R^{11}$-21 |
| 2273. | Ar-1 | XYZ-80 | $R^{11}$-22 |
| 2274. | Ar-1 | XYZ-80 | $R^{11}$-23 |
| 2275. | Ar-1 | XYZ-80 | $R^{11}$-24 |
| 2276. | Ar-1 | XYZ-80 | $R^{11}$-25 |
| 2277. | Ar-1 | XYZ-80 | $R^{11}$-26 |
| 2278. | Ar-1 | XYZ-80 | $R^{11}$-27 |
| 2279. | Ar-1 | XYZ-80 | $R^{11}$-28 |
| 2280. | Ar-1 | XYZ-80 | $R^{11}$-29 |
| 2281. | Ar-1 | XYZ-81 | $R^{11}$-1 |
| 2282. | Ar-1 | XYZ-81 | $R^{11}$-2 |
| 2283. | Ar-1 | XYZ-81 | $R^{11}$-3 |
| 2284. | Ar-1 | XYZ-81 | $R^{11}$-4 |
| 2285. | Ar-1 | XYZ-81 | $R^{11}$-5 |
| 2286. | Ar-1 | XYZ-81 | $R^{11}$-6 |
| 2287. | Ar-1 | XYZ-81 | $R^{11}$-7 |
| 2288. | Ar-1 | XYZ-81 | $R^{11}$-8 |
| 2289. | Ar-1 | XYZ-81 | $R^{11}$-9 |
| 2290. | Ar-1 | XYZ-81 | $R^{11}$-10 |
| 2291. | Ar-1 | XYZ-81 | $R^{11}$-11 |
| 2292. | Ar-1 | XYZ-81 | $R^{11}$-12 |
| 2293. | Ar-1 | XYZ-81 | $R^{11}$-13 |
| 2294. | Ar-1 | XYZ-81 | $R^{11}$-14 |
| 2295. | Ar-1 | XYZ-81 | $R^{11}$-15 |
| 2296. | Ar-1 | XYZ-81 | $R^{11}$-16 |
| 2297. | Ar-1 | XYZ-81 | $R^{11}$-17 |
| 2298. | Ar-1 | XYZ-81 | $R^{11}$-18 |
| 2299. | Ar-1 | XYZ-81 | $R^{11}$-19 |
| 2300. | Ar-1 | XYZ-81 | $R^{11}$-20 |
| 2301. | Ar-1 | XYZ-81 | $R^{11}$-21 |
| 2302. | Ar-1 | XYZ-81 | $R^{11}$-22 |
| 2303. | Ar-1 | XYZ-81 | $R^{11}$-23 |
| 2304. | Ar-1 | XYZ-81 | $R^{11}$-24 |
| 2305. | Ar-1 | XYZ-81 | $R^{11}$-25 |
| 2306. | Ar-1 | XYZ-81 | $R^{11}$-26 |
| 2307. | Ar-1 | XYZ-81 | $R^{11}$-27 |
| 2308. | Ar-1 | XYZ-81 | $R^{11}$-28 |
| 2309. | Ar-1 | XYZ-81 | $R^{11}$-29 |
| 2310. | Ar-1 | XYZ-82 | $R^{11}$-1 |
| 2311. | Ar-1 | XYZ-82 | $R^{11}$-2 |
| 2312. | Ar-1 | XYZ-82 | $R^{11}$-3 |
| 2313. | Ar-1 | XYZ-82 | $R^{11}$-4 |
| 2314. | Ar-1 | XYZ-82 | $R^{11}$-5 |
| 2315. | Ar-1 | XYZ-82 | $R^{11}$-6 |
| 2316. | Ar-1 | XYZ-82 | $R^{11}$-7 |
| 2317. | Ar-1 | XYZ-82 | $R^{11}$-8 |
| 2318. | Ar-1 | XYZ-82 | $R^{11}$-9 |
| 2319. | Ar-1 | XYZ-82 | $R^{11}$-10 |
| 2320. | Ar-1 | XYZ-82 | $R^{11}$-11 |
| 2321. | Ar-1 | XYZ-82 | $R^{11}$-12 |
| 2322. | Ar-1 | XYZ-82 | $R^{11}$-13 |
| 2323. | Ar-1 | XYZ-82 | $R^{11}$-14 |
| 2324. | Ar-1 | XYZ-82 | $R^{11}$-15 |
| 2325. | Ar-1 | XYZ-82 | $R^{11}$-16 |
| 2326. | Ar-1 | XYZ-82 | $R^{11}$-17 |
| 2327. | Ar-1 | XYZ-82 | $R^{11}$-18 |
| 2328. | Ar-1 | XYZ-82 | $R^{11}$-19 |
| 2329. | Ar-1 | XYZ-82 | $R^{11}$-20 |
| 2330. | Ar-1 | XYZ-82 | $R^{11}$-21 |
| 2331. | Ar-1 | XYZ-82 | $R^{11}$-22 |
| 2332. | Ar-1 | XYZ-82 | $R^{11}$-23 |
| 2333. | Ar-1 | XYZ-82 | $R^{11}$-24 |
| 2334. | Ar-1 | XYZ-82 | $R^{11}$-25 |
| 2335. | Ar-1 | XYZ-82 | $R^{11}$-26 |
| 2336. | Ar-1 | XYZ-82 | $R^{11}$-27 |
| 2337. | Ar-1 | XYZ-82 | $R^{11}$-28 |
| 2338. | Ar-1 | XYZ-82 | $R^{11}$-29 |
| 2339. | Ar-1 | XYZ-83 | $R^{11}$-1 |
| 2340. | Ar-1 | XYZ-83 | $R^{11}$-2 |
| 2341. | Ar-1 | XYZ-83 | $R^{11}$-3 |
| 2342. | Ar-1 | XYZ-83 | $R^{11}$-4 |
| 2343. | Ar-1 | XYZ-83 | $R^{11}$-5 |
| 2344. | Ar-1 | XYZ-83 | $R^{11}$-6 |
| 2345. | Ar-1 | XYZ-83 | $R^{11}$-7 |
| 2346. | Ar-1 | XYZ-83 | $R^{11}$-8 |
| 2347. | Ar-1 | XYZ-83 | $R^{11}$-9 |
| 2348. | Ar-1 | XYZ-83 | $R^{11}$-10 |
| 2349. | Ar-1 | XYZ-83 | $R^{11}$-11 |

TABLE C-continued

|  | Ar | -X-Y-Z- | $R^{11}/R^{12}$ |
|---|---|---|---|
| 2350. | Ar-1 | XYZ-83 | $R^{11}$-12 |
| 2351. | Ar-1 | XYZ-83 | $R^{11}$-13 |
| 2352. | Ar-1 | XYZ-83 | $R^{11}$-14 |
| 2353. | Ar-1 | XYZ-83 | $R^{11}$-15 |
| 2354. | Ar-1 | XYZ-83 | $R^{11}$-16 |
| 2355. | Ar-1 | XYZ-83 | $R^{11}$-17 |
| 2356. | Ar-1 | XYZ-83 | $R^{11}$-18 |
| 2357. | Ar-1 | XYZ-83 | $R^{11}$-19 |
| 2358. | Ar-1 | XYZ-83 | $R^{11}$-20 |
| 2359. | Ar-1 | XYZ-83 | $R^{11}$-21 |
| 2360. | Ar-1 | XYZ-83 | $R^{11}$-22 |
| 2361. | Ar-1 | XYZ-83 | $R^{11}$-23 |
| 2362. | Ar-1 | XYZ-83 | $R^{11}$-24 |
| 2363. | Ar-1 | XYZ-83 | $R^{11}$-25 |
| 2364. | Ar-1 | XYZ-83 | $R^{11}$-26 |
| 2365. | Ar-1 | XYZ-83 | $R^{11}$-27 |
| 2366. | Ar-1 | XYZ-83 | $R^{11}$-28 |
| 2367. | Ar-1 | XYZ-83 | $R^{11}$-29 |
| 2368. | Ar-1 | XYZ-84 | $R^{11}$-1 |
| 2369. | Ar-1 | XYZ-84 | $R^{11}$-2 |
| 2370. | Ar-1 | XYZ-84 | $R^{11}$-3 |
| 2371. | Ar-1 | XYZ-84 | $R^{11}$-4 |
| 2372. | Ar-1 | XYZ-84 | $R^{11}$-5 |
| 2373. | Ar-1 | XYZ-84 | $R^{11}$-6 |
| 2374. | Ar-1 | XYZ-84 | $R^{11}$-7 |
| 2375. | Ar-1 | XYZ-84 | $R^{11}$-8 |
| 2376. | Ar-1 | XYZ-84 | $R^{11}$-9 |
| 2377. | Ar-1 | XYZ-84 | $R^{11}$-10 |
| 2378. | Ar-1 | XYZ-84 | $R^{11}$-11 |
| 2379. | Ar-1 | XYZ-84 | $R^{11}$-12 |
| 2380. | Ar-1 | XYZ-84 | $R^{11}$-13 |
| 2381. | Ar-1 | XYZ-84 | $R^{11}$-14 |
| 2382. | Ar-1 | XYZ-84 | $R^{11}$-15 |
| 2383. | Ar-1 | XYZ-84 | $R^{11}$-16 |
| 2384. | Ar-1 | XYZ-84 | $R^{11}$-17 |
| 2385. | Ar-1 | XYZ-84 | $R^{11}$-18 |
| 2386. | Ar-1 | XYZ-84 | $R^{11}$-19 |
| 2387. | Ar-1 | XYZ-84 | $R^{11}$-20 |
| 2388. | Ar-1 | XYZ-84 | $R^{11}$-21 |
| 2389. | Ar-1 | XYZ-84 | $R^{11}$-22 |
| 2390. | Ar-1 | XYZ-84 | $R^{11}$-23 |
| 2391. | Ar-1 | XYZ-84 | $R^{11}$-24 |
| 2392. | Ar-1 | XYZ-84 | $R^{11}$-25 |
| 2393. | Ar-1 | XYZ-84 | $R^{11}$-26 |
| 2394. | Ar-1 | XYZ-84 | $R^{11}$-27 |
| 2395. | Ar-1 | XYZ-84 | $R^{11}$-28 |
| 2396. | Ar-1 | XYZ-84 | $R^{11}$-29 |
| 2397. | Ar-1 | XYZ-85 | $R^{11}$-1 |
| 2398. | Ar-1 | XYZ-85 | $R^{11}$-2 |
| 2399. | Ar-1 | XYZ-85 | $R^{11}$-3 |
| 2400. | Ar-1 | XYZ-85 | $R^{11}$-4 |
| 2401. | Ar-1 | XYZ-85 | $R^{11}$-5 |
| 2402. | Ar-1 | XYZ-85 | $R^{11}$-6 |
| 2403. | Ar-1 | XYZ-85 | $R^{11}$-7 |
| 2404. | Ar-1 | XYZ-85 | $R^{11}$-8 |
| 2405. | Ar-1 | XYZ-85 | $R^{11}$-9 |
| 2406. | Ar-1 | XYZ-85 | $R^{11}$-10 |
| 2407. | Ar-1 | XYZ-85 | $R^{11}$-11 |
| 2408. | Ar-1 | XYZ-85 | $R^{11}$-12 |
| 2409. | Ar-1 | XYZ-85 | $R^{11}$-13 |
| 2410. | Ar-1 | XYZ-85 | $R^{11}$-14 |
| 2411. | Ar-1 | XYZ-85 | $R^{11}$-15 |
| 2412. | Ar-1 | XYZ-85 | $R^{11}$-16 |
| 2413. | Ar-1 | XYZ-85 | $R^{11}$-17 |
| 2414. | Ar-1 | XYZ-85 | $R^{11}$-18 |
| 2415. | Ar-1 | XYZ-85 | $R^{11}$-19 |
| 2416. | Ar-1 | XYZ-85 | $R^{11}$-20 |
| 2417. | Ar-1 | XYZ-85 | $R^{11}$-21 |
| 2418. | Ar-1 | XYZ-85 | $R^{11}$-22 |
| 2419. | Ar-1 | XYZ-85 | $R^{11}$-23 |
| 2420. | Ar-1 | XYZ-85 | $R^{11}$-24 |
| 2421. | Ar-1 | XYZ-85 | $R^{11}$-25 |
| 2422. | Ar-1 | XYZ-85 | $R^{11}$-26 |
| 2423. | Ar-1 | XYZ-85 | $R^{11}$-27 |
| 2424. | Ar-1 | XYZ-85 | $R^{11}$-28 |
| 2425. | Ar-1 | XYZ-85 | $R^{11}$-29 |
| 2426. | Ar-1 | XYZ-86 | $R^{11}$-1 |
| 2427. | Ar-1 | XYZ-86 | $R^{11}$-2 |
| 2428. | Ar-1 | XYZ-86 | $R^{11}$-3 |
| 2429. | Ar-1 | XYZ-86 | $R^{11}$-4 |
| 2430. | Ar-1 | XYZ-86 | $R^{11}$-5 |
| 2431. | Ar-1 | XYZ-86 | $R^{11}$-6 |
| 2432. | Ar-1 | XYZ-86 | $R^{11}$-7 |
| 2433. | Ar-1 | XYZ-86 | $R^{11}$-8 |
| 2434. | Ar-1 | XYZ-86 | $R^{11}$-9 |
| 2435. | Ar-1 | XYZ-86 | $R^{11}$-10 |
| 2436. | Ar-1 | XYZ-86 | $R^{11}$-11 |
| 2437. | Ar-1 | XYZ-86 | $R^{11}$-12 |
| 2438. | Ar-1 | XYZ-86 | $R^{11}$-13 |
| 2439. | Ar-1 | XYZ-86 | $R^{11}$-14 |
| 2440. | Ar-1 | XYZ-86 | $R^{11}$-15 |
| 2441. | Ar-1 | XYZ-86 | $R^{11}$-16 |
| 2442. | Ar-1 | XYZ-86 | $R^{11}$-17 |
| 2443. | Ar-1 | XYZ-86 | $R^{11}$-18 |
| 2444. | Ar-1 | XYZ-86 | $R^{11}$-19 |
| 2445. | Ar-1 | XYZ-86 | $R^{11}$-20 |
| 2446. | Ar-1 | XYZ-86 | $R^{11}$-21 |
| 2447. | Ar-1 | XYZ-86 | $R^{11}$-22 |
| 2448. | Ar-1 | XYZ-86 | $R^{11}$-23 |
| 2449. | Ar-1 | XYZ-86 | $R^{11}$-24 |
| 2450. | Ar-1 | XYZ-86 | $R^{11}$-25 |
| 2451. | Ar-1 | XYZ-86 | $R^{11}$-26 |
| 2452. | Ar-1 | XYZ-86 | $R^{11}$-27 |
| 2453. | Ar-1 | XYZ-86 | $R^{11}$-28 |
| 2454. | Ar-1 | XYZ-86 | $R^{11}$-29 |
| 2455. | Ar-1 | XYZ-87 | $R^{11}$-1 |
| 2456. | Ar-1 | XYZ-87 | $R^{11}$-2 |
| 2457. | Ar-1 | XYZ-87 | $R^{11}$-3 |
| 2458. | Ar-1 | XYZ-87 | $R^{11}$-4 |
| 2459. | Ar-1 | XYZ-87 | $R^{11}$-5 |
| 2460. | Ar-1 | XYZ-87 | $R^{11}$-6 |
| 2461. | Ar-1 | XYZ-87 | $R^{11}$-7 |
| 2462. | Ar-1 | XYZ-87 | $R^{11}$-8 |
| 2463. | Ar-1 | XYZ-87 | $R^{11}$-9 |
| 2464. | Ar-1 | XYZ-87 | $R^{11}$-10 |
| 2465. | Ar-1 | XYZ-87 | $R^{11}$-11 |
| 2466. | Ar-1 | XYZ-87 | $R^{11}$-12 |
| 2467. | Ar-1 | XYZ-87 | $R^{11}$-13 |
| 2468. | Ar-1 | XYZ-87 | $R^{11}$-14 |
| 2469. | Ar-1 | XYZ-87 | $R^{11}$-15 |
| 2470. | Ar-1 | XYZ-87 | $R^{11}$-16 |
| 2471. | Ar-1 | XYZ-87 | $R^{11}$-17 |
| 2472. | Ar-1 | XYZ-87 | $R^{11}$-18 |
| 2473. | Ar-1 | XYZ-87 | $R^{11}$-19 |
| 2474. | Ar-1 | XYZ-87 | $R^{11}$-20 |
| 2475. | Ar-1 | XYZ-87 | $R^{11}$-21 |
| 2476. | Ar-1 | XYZ-87 | $R^{11}$-22 |
| 2477. | Ar-1 | XYZ-87 | $R^{11}$-23 |
| 2478. | Ar-1 | XYZ-87 | $R^{11}$-24 |
| 2479. | Ar-1 | XYZ-87 | $R^{11}$-25 |
| 2480. | Ar-1 | XYZ-87 | $R^{11}$-26 |
| 2481. | Ar-1 | XYZ-87 | $R^{11}$-27 |
| 2482. | Ar-1 | XYZ-87 | $R^{11}$-28 |
| 2483. | Ar-1 | XYZ-87 | $R^{11}$-29 |
| 2484. | Ar-1 | XYZ-88 | $R^{11}$-1 |
| 2485. | Ar-1 | XYZ-88 | $R^{11}$-2 |
| 2486. | Ar-1 | XYZ-88 | $R^{11}$-3 |
| 2487. | Ar-1 | XYZ-88 | $R^{11}$-4 |
| 2488. | Ar-1 | XYZ-88 | $R^{11}$-5 |
| 2489. | Ar-1 | XYZ-88 | $R^{11}$-6 |
| 2490. | Ar-1 | XYZ-88 | $R^{11}$-7 |
| 2491. | Ar-1 | XYZ-88 | $R^{11}$-8 |
| 2492. | Ar-1 | XYZ-88 | $R^{11}$-9 |
| 2493. | Ar-1 | XYZ-88 | $R^{11}$-10 |
| 2494. | Ar-1 | XYZ-88 | $R^{11}$-11 |
| 2495. | Ar-1 | XYZ-88 | $R^{11}$-12 |
| 2496. | Ar-1 | XYZ-88 | $R^{11}$-13 |
| 2497. | Ar-1 | XYZ-88 | $R^{11}$-14 |
| 2498. | Ar-1 | XYZ-88 | $R^{11}$-15 |
| 2499. | Ar-1 | XYZ-88 | $R^{11}$-16 |
| 2500. | Ar-1 | XYZ-88 | $R^{11}$-17 |
| 2501. | Ar-1 | XYZ-88 | $R^{11}$-18 |
| 2502. | Ar-1 | XYZ-88 | $R^{11}$-19 |
| 2503. | Ar-1 | XYZ-88 | $R^{11}$-20 |
| 2504. | Ar-1 | XYZ-88 | $R^{11}$-21 |
| 2505. | Ar-1 | XYZ-88 | $R^{11}$-22 |

TABLE C-continued

| | Ar | -X-Y-Z- | R11/R12 |
|---|---|---|---|
| 2506. | Ar-1 | XYZ-88 | $R^{11}$-23 |
| 2507. | Ar-1 | XYZ-88 | $R^{11}$-24 |
| 2508. | Ar-1 | XYZ-88 | $R^{11}$-25 |
| 2509. | Ar-1 | XYZ-88 | $R^{11}$-26 |
| 2510. | Ar-1 | XYZ-88 | $R^{11}$-27 |
| 2511. | Ar-1 | XYZ-88 | $R^{11}$-28 |
| 2512. | Ar-1 | XYZ-88 | $R^{11}$-29 |
| 2513. | Ar-1 | XYZ-89 | $R^{11}$-1 |
| 2514. | Ar-1 | XYZ-89 | $R^{11}$-2 |
| 2515. | Ar-1 | XYZ-89 | $R^{11}$-3 |
| 2516. | Ar-1 | XYZ-89 | $R^{11}$-4 |
| 2517. | Ar-1 | XYZ-89 | $R^{11}$-5 |
| 2518. | Ar-1 | XYZ-89 | $R^{11}$-6 |
| 2519. | Ar-1 | XYZ-89 | $R^{11}$-7 |
| 2520. | Ar-1 | XYZ-89 | $R^{11}$-8 |
| 2521. | Ar-1 | XYZ-89 | $R^{11}$-9 |
| 2522. | Ar-1 | XYZ-89 | $R^{11}$-10 |
| 2523. | Ar-1 | XYZ-89 | $R^{11}$-11 |
| 2524. | Ar-1 | XYZ-89 | $R^{11}$-12 |
| 2525. | Ar-1 | XYZ-89 | $R^{11}$-13 |
| 2526. | Ar-1 | XYZ-89 | $R^{11}$-14 |
| 2527. | Ar-1 | XYZ-89 | $R^{11}$-15 |
| 2528. | Ar-1 | XYZ-89 | $R^{11}$-16 |
| 2529. | Ar-1 | XYZ-89 | $R^{11}$-17 |
| 2530. | Ar-1 | XYZ-89 | $R^{11}$-18 |
| 2531. | Ar-1 | XYZ-89 | $R^{11}$-19 |
| 2532. | Ar-1 | XYZ-89 | $R^{11}$-20 |
| 2533. | Ar-1 | XYZ-89 | $R^{11}$-21 |
| 2534. | Ar-1 | XYZ-89 | $R^{11}$-22 |
| 2535. | Ar-1 | XYZ-89 | $R^{11}$-23 |
| 2536. | Ar-1 | XYZ-89 | $R^{11}$-24 |
| 2537. | Ar-1 | XYZ-89 | $R^{11}$-25 |
| 2538. | Ar-1 | XYZ-89 | $R^{11}$-26 |
| 2539. | Ar-1 | XYZ-89 | $R^{11}$-27 |
| 2540. | Ar-1 | XYZ-89 | $R^{11}$-28 |
| 2541. | Ar-1 | XYZ-89 | $R^{11}$-29 |
| 2542. | Ar-1 | XYZ-90 | $R^{11}$-1 |
| 2543. | Ar-1 | XYZ-90 | $R^{11}$-2 |
| 2544. | Ar-1 | XYZ-90 | $R^{11}$-3 |
| 2545. | Ar-1 | XYZ-90 | $R^{11}$-4 |
| 2546. | Ar-1 | XYZ-90 | $R^{11}$-5 |
| 2547. | Ar-1 | XYZ-90 | $R^{11}$-6 |
| 2548. | Ar-1 | XYZ-90 | $R^{11}$-7 |
| 2549. | Ar-1 | XYZ-90 | $R^{11}$-8 |
| 2550. | Ar-1 | XYZ-90 | $R^{11}$-9 |
| 2551. | Ar-1 | XYZ-90 | $R^{11}$-10 |
| 2552. | Ar-1 | XYZ-90 | $R^{11}$-11 |
| 2553. | Ar-1 | XYZ-90 | $R^{11}$-12 |
| 2554. | Ar-1 | XYZ-90 | $R^{11}$-13 |
| 2555. | Ar-1 | XYZ-90 | $R^{11}$-14 |
| 2556. | Ar-1 | XYZ-90 | $R^{11}$-15 |
| 2557. | Ar-1 | XYZ-90 | $R^{11}$-16 |
| 2558. | Ar-1 | XYZ-90 | $R^{11}$-17 |
| 2559. | Ar-1 | XYZ-90 | $R^{11}$-18 |
| 2560. | Ar-1 | XYZ-90 | $R^{11}$-19 |
| 2561. | Ar-1 | XYZ-90 | $R^{11}$-20 |
| 2562. | Ar-1 | XYZ-90 | $R^{11}$-21 |
| 2563. | Ar-1 | XYZ-90 | $R^{11}$-22 |
| 2564. | Ar-1 | XYZ-90 | $R^{11}$-23 |
| 2565. | Ar-1 | XYZ-90 | $R^{11}$-24 |
| 2566. | Ar-1 | XYZ-90 | $R^{11}$-25 |
| 2567. | Ar-1 | XYZ-90 | $R^{11}$-26 |
| 2568. | Ar-1 | XYZ-90 | $R^{11}$-27 |
| 2569. | Ar-1 | XYZ-90 | $R^{11}$-28 |
| 2570. | Ar-1 | XYZ-90 | $R^{11}$-29 |

Particular examples of compounds of the formula (I) are the following compounds and, the N-oxides, stereoisomers, tautomers and agriculturally or veterinarily acceptable salts thereof:

1-(2,6-dimethylphenyl)-3-[(E)-[3-[4-(trifluoromethoxy)phenyl]imidazo[4,5-f]quinolin-7-yl]methyleneamino]thiourea, (2Z)-3-(2,6-dimethylphenyl)-2-[(E)-[3-[4-(trifluoromethoxy)phenyl]imidazo[4,5-f]quinolin-7-yl]methylenehydrazono]thiazolidin-4-one, 1-(2-isopropylphenyl)-3-[(E)-[3-[4-(trifluoromethoxy)phenyl]imidazo[4,5-f]quinolin-7-yl]methyleneamino]thiourea, (2Z)-3-(2-isopropylphenyl)-2-[(E)-[3-[4-(trifluoromethoxy)phenyl]imidazo[4,5-f]quinolin-7-yl]methylenehydrazono]thiazolidin-4-one, 1-(2-isopropyl-5-methyl-phenyl)-3-[(E)-[3-[4-(trifluoromethoxy)phenyl]imidazo[4,5-f]quinolin-7-yl]methyleneamino]thiourea, (2Z)-3-(2-isopropyl-5-methyl-phenyl)-2-[(E)-[3-[4-(trifluoromethoxy)phenyl]imidazo[4,5-f]quinolin-7-yl]methylenehydrazono]thiazolidin-4-one, (2Z)-2-(2,6-dimethylphenyl)imino-3-[(E)-[3-[4-(trifluoromethoxy)phenyl]imidazo[4,5-f]quinolin-7-yl]methyleneamino]thiazolidin-4-one, (2Z)-2-(2-isopropylphenyl)imino-3-[(E)-[3-[4-(trifluoromethoxy)phenyl]imidazo[4,5-f]quinolin-7-yl]methyleneamino]thiazolidin-4-one, 1-(2,6-dimethylphenyl)-3-[(E)-[3-[6-(trifluoromethyl)pyridazin-3-yl]imidazo[4,5-f]quinolin-7-yl]methyleneamino]thiourea, (2Z)-3-(2,6-dimethylphenyl)-2-[(E)-[3-[6-(trifluoromethyl)pyridazin-3-yl]imidazo[4,5-f]quinolin-7-yl]methylenehydrazono]thiazolidin-4-one, 1-(2,6-dimethylphenyl)-3-[(E)-[3-[4-(trifluoromethoxy)phenyl]-4,5-dihydroimidazo[4,5-f]quinolin-7-yl]methyleneamino]thiourea, (2Z)-3-(2,6-dimethylphenyl)-2-[(E)-[3-[4-(trifluoromethoxy)phenyl]-4,5-dihydroimidazo[4,5-f]quinolin-7-yl]methylenehydrazono]thiazolidin-4-one, 1-(2,6-dimethylphenyl)-3-[(E)-[3-[4-(trifluoromethoxy)phenyl]-4,5-dihydroimidazo[4,5-f]quinazolin-7-yl]methyleneamino]thiourea, (2Z)-3-(2,6-dimethylphenyl)-2-[(E)-[3-[4-(trifluoromethoxy)phenyl]-4,5-dihydroimidazo[4,5-f]quinazolin-7-yl]methylenehydrazono]thiazolidin-4-one, 1-(2,6-dimethylphenyl)-3-[(E)-[3-[4-(trifluoromethoxy)phenyl]imidazo[4,5-f]quinazolin-7-yl]methyleneamino]thiourea, (2Z)-3-(2,6-dimethylphenyl)-2-[(E)-[3-[4-(trifluoromethoxy)phenyl]imidazo[4,5-f]quinazolin-7-yl]methylenehydrazono]thiazolidin-4-one, 1-(2,6-dimethylphenyl)-3-[(E)-[5,5-dioxo-3-[4-(trifluoromethoxy)phenyl]-4H-imidazo[2,3]thiopyrano[2,4-b]pyridin-7-yl]methyleneamino]thiourea, (2Z)-3-(2,6-dimethylphenyl)-2-[(E)-[5,5-dioxo-3-[4-(trifluoromethoxy)phenyl]-4H-imidazo[2,3]thiopyrano[2,4-b]pyridin-7-yl]methylenehydrazono]thiazolidin-4-one, 1-(2,6-dimethylphenyl)-3-[(E)-[5,5-dioxo-3-[4-(trifluoromethoxy)phenyl]-4H-imidazo[2,3]thiopyrano[2,4-d]pyrimidin-7-yl]methyleneamino]thiourea, (2Z)-3-(2,6-dimethylphenyl)-2-[(E)-[5,5-dioxo-3-[4-(trifluoromethoxy)phenyl]-4H-imidazo[2,3]thiopyrano[2,4-d]pyrimidin-7-yl]methylenehydrazono]thiazolidin-4-one, 1-(2,6-dimethylphenyl)-3-[(E)[3-[4-(trifluoromethoxy)phenyl]imidazo[4,5-f]quinoxalin-7-yl]methyleneamino]thiourea, (2Z)-3-(2,6-dimethylphenyl)-2-[(E)-[3-[4-(trifluoromethoxy)phenyl]imidazo[4,5-f]quinoxalin-7-yl]methylenehydrazono]thiazolidin-4-one, 1-(2,6-dimethylphenyl)-3-[(E)-[2-methyl-3-[4-(trifluoromethoxy)phenyl]-4,5-dihydropyrazolo[3,4-f]quinolin-7-yl]methyleneamino]thiourea, (2Z)-3-(2,6-dimethyl phenyl)-2-[(E)-[2-methyl-3-[4-(trifluoromethoxy)phenyl]-4,5-dihyd ropyrazolo[3,4-f]quinolin-7-yl]methylenehydrazono]thiazolidin-4-one, 1-(2,6-dimethylphenyl)-3-[(E)-[2-methyl-3-[4-(trifluoromethoxy)phenyl]-4,5-dihydropyrazolo[3,4-f]quinazolin-7-yl]methyleneamino]thiourea, (2Z)-3-(2,6-dimethylphenyl)-2-[(E)-[2-methyl-3-[4-(trifluoromethoxy)phenyl]-4,5-dihyd ropyrazolo[3,4-f]quinazolin-7-yl]methylenehydrazono]thiazolidin-4-one, 1-(2,6-dimethylphenyl)-3-[(E)-[3-[4-(trifluoromethoxy)phenyl]imidazo[4,5-f]quinoxalin-7-yl]methyleneamino]thiourea, (2Z)-3-(2,6-dimethyl phenyl)-2-[(E)-[3-[4-(trifluoromethoxy)phenyl]imidazo[4,5-f]quinoxalin-7-yl]methylenehydrazono]thiazolidin-4-one, 1-(2,6-dimethylphenyl)-3-[(E)-[2-methyl-3-[4-(trifluoromethoxy)phenyl]pyrazolo[3, 4-f]quinolin-7-yl]methyleneamino]thiourea, (2Z)-3-(2,6-dimethylphenyl)-2-[(E)-[2-methyl-3-[4-(trifluoromethoxy)phenyl]pyrazolo[3,4-f]quinolin-7-yl]methylenehydrazono]thiazolidin-4-one, 1-(2,6-dimethylphenyl)-3-[(E)-[2-methyl-3-[4-(trifluoromethoxy)phenyl]pyrazol[3,4-f]quinazolin-7-yl]methyleneamino]thiourea, (2Z)-3-(2,6-dimethylphenyl)-2-[(E)-[2-methyl-3-[4-(trifluoromethoxy)phenyl]pyrazolo[3,4-f]quinazolin-7-yl]methylenehydrazono]thiazolidin-4-one, 1-(2,6-dimethylphenyl)-3-[(E)-[3-[4-(trifluoromethoxy)phenyl]imidazo[4,5-h]isoquinolin-7-yl]methyleneamino]thiourea, (2Z)-3-(2,6-dimethylphenyl)-2-[(E)-[3-[4-(trifluoromethoxy)phenyl]imidazo[4,5-h]isoquinolin-7-yl]methylenehydrazono]thiazolidin-4-one, 1-(2,6-dimethylphenyl)-3-[(E)[2-methyl-5,5-dioxo-3-[4-(trifluoromethoxy)phenyl]-4H-pyrazolo[1,2]thiopyrano[3,4-b]pyridin-7-yl]methyleneamino]thiourea, (2Z)-3-(2,6-dimethylphenyl)-2-[(E)-[2-methyl-5,5-dioxo-3-[4-(trifluoromethoxy)phenyl]-4H-pyrazolo[1,2]thiopyrano[3,4-b]pyridin-7-yl]methylenehydrazono]thiazolidin-4-one, 1-(2,6-dimethylphenyl)-3-[(E)-[2-methyl-5,5-dioxo-3-[4-(trifluoromethoxy)phenyl]-4H-pyrazolo[1,2]thiopyrano[3,4-d]pyrimidin-7-yl]methyleneamino]thiourea, (2Z)-3-(2,6-dimethyl phenyl)-2-[(E)-[2-methyl-5,5-dioxo-3-[4-(trifluoromethoxy)phenyl]-4H-pyrazolo[1,2]thiopyrano[3,4-d]pyrimidin-7-yl]methylenehydrazono]thiazolidin-4-one, 1-(2,6-dimethylphenyl)-3-[(E)[3-[4-(trifluoromethoxy)phenyl]imidazo[4,5-h]quinolin-7-yl]methyleneamino]thiourea, (2Z)-3-(2,6-dimethylphenyl)-2-[(E)-[3-[4-(trifluoromethoxy)phenyl]imidazo[4,5-h]quinolin-7-yl]methylenehydrazono]thiazolidin-4-one, (2Z)-3-(2-isopropylphenyl)-4-methyl-2-[(E)-[3-[4-(trifluoromethoxy)phenyl]imidazo[4,5-f]quinolin-7-yl]methylenehydrazono]thiazolidin-4-ol, (2Z)-3-(2-isopropylphenyl)-2-[(E)-[3-[6-(trifluoromethyl)pyridazin-3-yl]imidazo[4,5-f]quinolin-7-yl]methylenehydrazono]thiazolidin-4-one, 1-(5-chloro-2-pyridyl)ethyl N-[3-[4-(trifluoromethoxy)phenyl]imidazo[4,5-f]quinolin-7-yl]carbamate, (2-isopropyl-5-methyl-cyclohexyl)N-[3-[4-(trifluoromethoxy)phenyl]imidazo[4,5-f]quinolin-7-yl]carbamate, 1-(2-isopropylphenyl)-3-[(E)-[3-[4-(trifluoromethoxy)phenyl]imidazo[4,5-h]quinolin-7-yl]methyleneamino]thiourea, (2Z)-2-(2-isopropylphenyl)imino-3-[(E)-[3-[4-(trifluoromethoxy)phenyl]imidazo[4,5-h]quinolin-7-yl]methyleneamino]thiazolidin-4-one, (2Z)-3-(2-isopropylphenyl)-2-[(E)-[3-[4-(trifluoromethoxy)phenyl]imidazo[4,5-h]quinolin-7-yl]methylenehydrazono]thiazolidin-4-one, (2Z)-2-(2,6-dimethyl phenyl)imino-3-[(E)-[3-[4-(trifluoromethoxy)phenyl]imidazo[4,5-h]quinolin-7-yl]methyleneamino]thiazolidin-4-one, 1-(2-isopropylphenyl)-3-[(E)-[2-methyl-3-[4-(trifluoromethoxy)phenyl]pyrazolo[3,4-f]quinolin-7-yl]methyleneamino]thiourea, (2Z)-3-(2-isopropylphenyl)-2-[(E)-[2-methyl-3-[4-(trifluoromethoxy)phenyl]pyrazolo[3,4-f]quinolin-7-yl]methylenehydrazono]thiazolidin-4-one, (E)-3-(2-isopropylphenyl)-N-[(E)-[3-[4-(trifluoromethoxy)phenyl]imidazo[4,5-f]quinolin-7-yl]methyleneamino]thiazolidin-2-imine, (E)-3-(2-isopropylphenyl)-N-[(E)-[3-[4-(trifluoromethoxy)phenyl]imidazo[4,5-f]quinolin-7-yl]methyleneamino]-1,3-thiazinan-2-imine, (E)-3-(2,6-dimethylphenyl)-N-[(E)-[3-[4-(trifluoromethoxy)phenyl]imidazo[4,5-f]quinolin-7-yl]methyleneamino]-1,3-thiazinan-2-imine, 1-(2-isopropylphenyl)-3-[(E)-[3-[4-(trifluoromethoxy)phenyl]imidazo[4,5-h]isoquinolin-7-yl]methyleneamino]thiourea, (2Z)-3-(2-isopropylphenyl)-2-[(E)-[3-[4-(trifluoromethoxy)phenyl]imidazo[4,5-h]isoquinolin-7-yl]methylenehydrazono]thiazolidin-4-one, (2Z)-2-(2-isopropylphenyl)imino-3-[(E)-[3-[4-(trifluoromethoxy)phenyl]imidazo[4,5-h]isoquinolin-7-yl]methyleneamino]thiazolidin-4-one, 2Z)-2-(2,6-dimethylphenyl)imino-3-[(E)-[3-[4-(trifluoromethoxy)phenyl]imidazo[4,5-h]isoquinolin-7-yl]methyleneamino]thiazolidin-4-one, (E)-3-(2,6-dimethylphenyl)-N-[(E)-[3-[4-(trifluoromethoxy)phenyl]imidazo[4,5-f]quinolin-7-yl]methyleneamino]thiazolidin-2-imine, 1-[(E)-[3-[4-(difluoromethoxy)phenyl]imidazo[4,5-f]quinolin-7-yl]methyleneamino]-3-(2-isopropylphenyl)thiourea, (2E)-2-[(E)-[3-[4-(difluoromethoxy)phenyl]imidazo[4,5-f]quinolin-7-yl]methylenehydrazono]-3-(2-isopropylphenyl)thiazolidin-4-one, (E)-1-[3-[4-(trifluoromethoxy)phenyl]imidazo[4,5-f]quinolin-7-yl]-N-[(2S,3R,4R,5S,6S)-3,4,5-trimethoxy-6-methyl-tetrahydropyran-2-yl]oxy-methanimine, (2Z)-3-(2-isopropylphenyl)-2-[(E)-[3-[4-(trifluoromethoxy)phenyl]imidazo[4,5-f]quinoxalin-7-yl]methylenehydrazono]thiazolidin-4-one, 1-(2-isopropylphenyl)-3-[(E)-[3-[4-(trifluoromethoxy)phenyl]imidazo[4,5-f]q uinoxalin-7-yl]methyleneamino]thiourea, and 1-(2-isopropylphenyl)-3-[(E)-[2-methyl-3-[4-(trifluoromethoxy)phenyl]pyrazolo[3,4-f]quinazolin-7-yl]methyleneamino]thiourea.

The compounds of the formula (I) can be prepared by the standard methods of organic chemistry, e.g. by the methods described hereinafter in schemes 1 to 27 and in the synthesis descriptions of the working examples. In schemes 1 to XX, the radicals Ar, $A^1$, $A^2$, $A^3$, $A^4$, $A^4$, $A^6$, $C^1$, $C^2$, Q, T, $X^1$, $X^2$, Y, $Z^1$, $Z^2$, R, $R^1$, $R^{11}$, $R^{Q3}$, $R^{Q3a}$, $R^{Q3b}$, $R^{Q4}$, $R^{Q4a}$, $R^{Q4b}$, $R^{x3}$, $R^{x3a}$, $R^{x1a}$, $R^{y1}$, $R^{y2}$, $R^z$ are as defined above for formula (I), if not otherwise specified. Suitable starting materials are the compounds of the formula INT as described above, in particular the compounds of formula (INT), wherein T is a single bond.

Compounds of formula (I) in which $X^1$ or $X^2$ are —C($R^{x3}$)=N— can be prepared by analogy to the methods described in WO 2011/017504, as depicted in scheme 1:

Scheme 1:

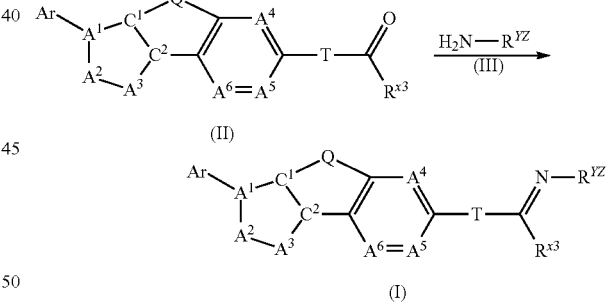

In Scheme 1, $R^{YZ}$ represents a radical Y—$Z^2$—$R^{12}$ or Y—$Z^1$—$R^{11}$, respectively, or a suitable precursor radical, e.g. OH, NH—$R^{y1}$, NH—$R^{y2}$ etc., which can be functionalized to generate the required moiety Y—$Z^2$—$R^{12}$ or Y—$Z^1$—$R^{11}$, respectively.

For this, an aldehyde or ketone compound of the formula (II) is reacted with a compound of the formula (III) in the presence or in the absence of a solvent. Suitable solvents are polar protic solvents. If the reaction is performed in the absence of a solvent, the compound of the formula (III) usually also act as solvent. Compounds of the formula (III) are commercially available or can be prepared according to standard procedures of the organic chemistry.

According to an embodiment of Scheme 1, an aldehyde or ketone compound of the formula (II) is first reacted with a hydrazine of the formula $R^{y1}NHNH_2$ or $R^{y2}NHNH_2$ followed by the reaction with an isocyanate of the formula $R^{11}$—NCO or with an isothiocyanate $R^{11}$—NCS to yield a compound of the formula (I), wherein Y—$Z^1$—$R^{11}$ is $N(R^{y1})$—C(O)—$NHR^{11}$ or $N(R^{y2})$—C(S)—$NHR^{11}$ or with an isocyanate of the formula $R^{12}$—NCO or with an isothiocyanate $R^{12}$—NCS to yield a compound of the formula (I), wherein Y—$Z^2$—$R^{12}$ is $N(R^{y1})$—C(O)—$NHR^{12}$ or $N(R^{y2})$—C(S)—$NHR^{12}$. Usually, the reaction is carried out in a polar aprotic solvent such as tetrahydrofuran.

According to another embodiment of Scheme 1, an aldehyde or ketone compound of the formula (II) is first reacted with a hydroxylamine followed by the reaction with a compound of formula $R^{11}$-L or $R^{12}$-L, where L is a suitable leaving group, such as halogen or activated OH. Thereby, a compound of the formula (I) will result, wherein Y is a single bond and $Z^1$ or $Z^2$, respectively, is O.

Compounds of the formula (I), wherein $X^1$, $X^2$ are a single bond and Y is —NH—C(=O)— (or wherein Y is a single bond and $X^1$, $X^2$ are —NH—C(=O)—) can be prepared as shown in the Scheme 2 below by analogy to the method described in Synthesis, 2010, 2990-2966.

Scheme 2:

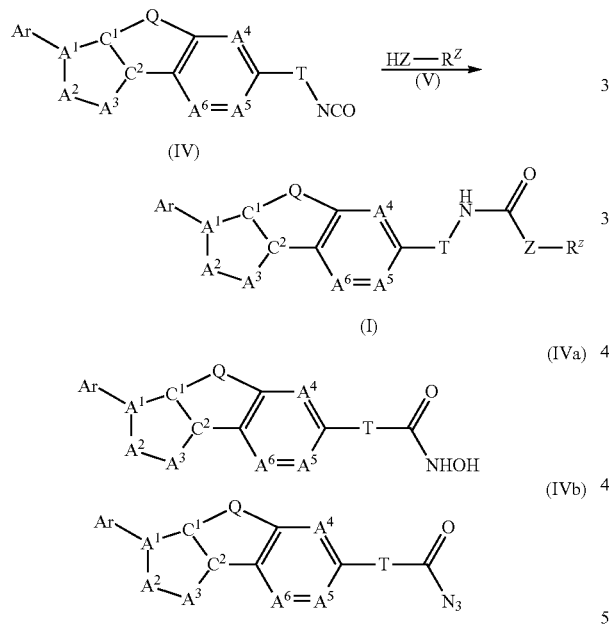

In scheme 2, Z is O or NH and $R^z$ corresponds to $R^{12}$ or Z—$R^z$ corresponds to Y—$Z^2$—$R^{12}$ or Y—$Z^1$—$R^{11}$, respectively. According to the method depicted in scheme 2, an isocyanate compound of the formula IV is reacted with the compound of formula (V) by standard methods of isocyanate chemistry. The isocyanate of the formula (IV) may be obtained e.g. via Lossen rearrangement of the corresponding hydroxamic acid (IVa). The isocyanate of the formula (IV) may also be obtained via Curtius rearrangement of the corresponding azide of the formula (IVb), e.g. by analogy to the method described in WO 2014/204622. To this end, the hydroxamic acid is reacted with 1-propanephosphonic acid cyclic anhydride (T3P) in the presence of a base. The base is preferably N-methylmorpholine.

For converting compounds of formula (I) in which $R^{x2}$ or $R^{y1}$ is H into compounds (I) in which $R^{x2}$ or $R^{y1}$ is not H, compounds of formula (I) in which $R^{x2}$ or $R^{y1}$ is H can be reacted with compounds of formulae $R^{x2}$-Lg or $R^{y1}$-Lg, wherein $R^{x2}$ or $R^{y1}$ is not H and Lg is a leaving group, such as a Br, Cl or I atom or a tosylate, mesylate or triflate, to yield compounds of formula (I), wherein $R^{x2}$ or $R^{y1}$ is different from H. The reaction is suitably carried out in the presence of a base such as sodium hydride or potassium hydride, suitably in a polar aprotic solvent such as N,N-dimethylformamide, tetrahydrofuran, dioxane, acetonitrile, dimethylsulfoxide or pyridine, or mixtures of these solvents, in a temperature range of from 0° C. and 100 C.

Carbamate compounds of the formula (I), in which Y is —$N(R^{y1})$—C(=O)—, and $Z^1$ or $Z^2$, respectively, is O can also be prepared as shown in Scheme 3 below and by analogy to the methods described in WO 2011/017513.

Scheme 3:

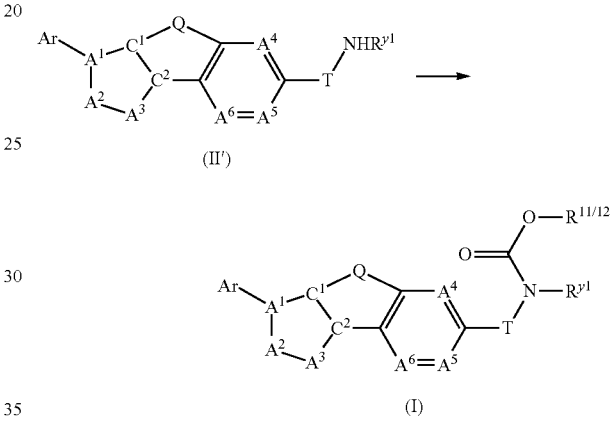

In scheme 3 $R^{11/12}$ corresponds to radicals $R^{11}$ or $R^{12}$, respectively. The reaction shown in scheme 3 can be performed by analogy to conventional methods of preparing carbamates. According to a first embodiment, the amine of the formula (II') is converted into either an isocyanate or p-nitrophenyl carbamate followed by treatment with an alcohol of the formula $R^{11}$—OH or $R^{12}$—OH, respectively, in the presence of an organic or inorganic base. According to another embodiment, the compound of the formula (II') is reacted with a chloroformate of the formula $R^{11/12}$—O—C(=O)—Cl. The chloroformate is prepared from the alcohols $R^{11/12}$OH by treatment with phosgene or triphosgene in the presence of a base, e.g. pyridine.

Compounds of formula (I), in which $X^1/X^2$ is —$N(R^{x2})$—C(=O)—, Y is —N=$C((S)_p$—$R^{y3})$ can be prepared by analogy to the methods described in WO 2013/009791, especially in schemes 1 to 11 described therein.

Compounds of formula (I), in which $X^1/X^2$ is —$N(R^{x2})$—C(=O)—, Y or Y" is —N=$C((O)_p$—$R^{y3})$ can be prepared by analogy to the methods described in WO 2013/009791, especially in schemes 1, 2 and 3 described therein, or by the methods described in in US 2012/0202687.

Compounds of the formula (II) and (II'), where T is a single bond can be prepared by analogy to the methods described in literature and in accordance with the methods described in the examples. Usually compounds of the formula (II) and (II') are prepared by the reactions shown in the following Scheme 4.

Scheme 4:

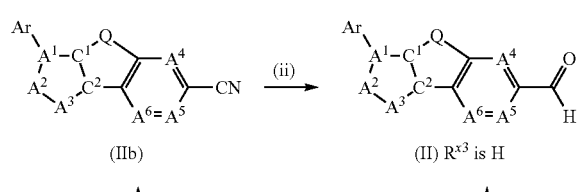

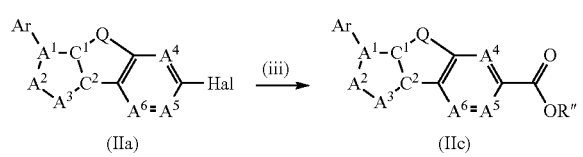

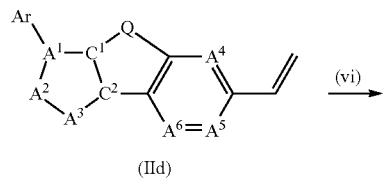

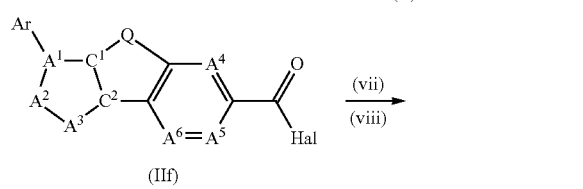

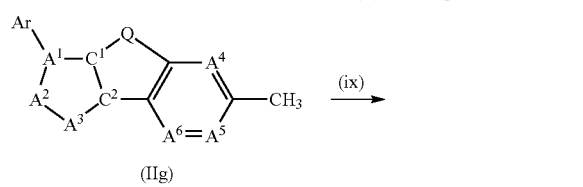

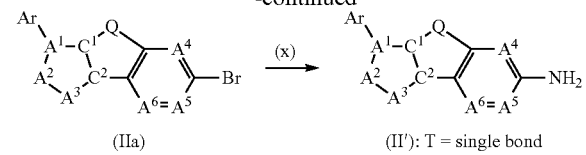

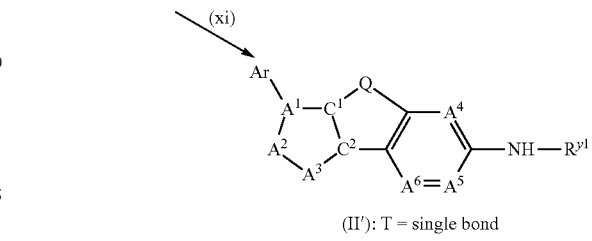

In scheme 4, R" is $C_1$-$C_6$-alkyl and Hal is halogen, preferably Cl or Br, in particular Br; $R^{y1}$ is as defined above but different from hydrogen.

Suitable reaction conditions for performing the preparation of the cyanide compound of the formula (IIb) (reaction step (i) of Scheme 4) by a Pd-catalyzed aromatic cyanation reaction of an aryl bromide of the formula (IIa) with an alkalimetal cyanide, preferably NaCN, can be taken from Journal of the American Chemical Society, 133 (28), 10999-11005; 2011. The reduction of a cyanide compound (IIb) to an aldehyde compound (II) shown in step (ii) of Scheme 4 can be performed with a metal alkoxyaluminum hydride. Suitable alkoxyaluminum hydrides are lithium alkoxyaluminum hydrides and sodium alkoxyaluminum hydrides, e.g. $Na[Al(OC_2H_5)_3H]$. Suitable reaction conditions for step (ii) of Scheme 4 can be taken from Organic Reactions (Hoboken, N.J., United States), pp 36, 1988. The conversion of the aryl bromide (IIa) into the ester compound (IIc) is shown in reaction step (iii) of Scheme 4. Suitable reaction conditions for the palladium-catalysed reaction can be taken from Journal of Medicinal Chemistry, 52 (22), 7258-7272; 2009. Suitable reaction conditions for performing the palladium catalyzed reaction step (iv) of Scheme 4 can be taken from Synlett, (6), 869-872; 2006. Suitable reaction conditions for performing the reaction step (v) of Scheme 4 can be taken from Journal of the American Chemical Society, 124(22), 6343-6348, 2002. Suitable reaction conditions for performing the reaction step (vi) of Scheme 4 can be taken from European Journal of Medicinal Chemistry, 49, 310-323; 2012.

Compounds of the formula (IIe) can be prepared by reacting $CH_3$ or ethyl carboxylic esters of the formula (IIc) with hydroxylamine. The reaction can be performed in analogy to the method described in J. Org. Chem., 2009, 74, 3540-3543.

Compounds of the formula (II) can also be prepared by reacting an acid halide of the formula (IIf) with N,O-dimethylhydroxyamide or N,O-dimethylhydroxyamide hydrochloride to give the corresponding Weinreb-amide, followed by treating the Weinreb-amide with an organometallic reagent, e.g. a Grignard reagent of the formula $R^{x3}MgBr$ or an organolithium reagent of the formula $R^{x3}Li$ as shown in step (viii) of Scheme 4. Reduction of the Weinreb amide with lithium aluminum hydride affords compounds of the formula (II), wherein $R^{x3}$ is hydrogen. The acid halide of the formula (IIf) can be prepared from the ester compound of the formula (IIc) according to standard methods.

Compounds of the formula (II), where $R^{x3}$ is H, can also be prepared by oxidation of a compound of the formula (IIg) as shown in step (ix) of scheme 4. Suitable oxidation agents are selenium(IV) oxide$_2$ or $MnO_2$.

Compounds of the formula (II'), wherein $R^{y1}$ is hydrogen, can be prepared by reacting a compound of the formula (IIa) with an alkali metal azide, preferably sodium azide in the presence of copper(I) as shown in reaction step (x) of Scheme 4. Compounds of the formula (II'), wherein $R^{y1}$ is different from hydrogen can be prepared by reacting a compound of the formula (IIa) with a primary amine of the formula $R^{y1}NH_2$ in the sense of a Buchwald-Hartwig amination as shown in reaction step (xi) of Scheme 4.

Compounds of the formula (II'), wherein T is different from a single bond, (i.e. T is $(CHR^{xa})_s$ with s being 1, 2, 3 or 4, cyclopropane-1,1-diyl or cyclopropane-1,2-diyl), and likewise the corresponding isocyanates (IV) can be prepared by applying conventional C—C-coupling reactions, starting from either the halogen compounds of formula (IIa), in particular from the corresponding Br or I compounds, or from the aldehydes of the formula (II). Suitable reaction sequences are depicted in scheme 5.

the formula (IIk) is subjected to a cyclopropanation reaction to yield the cyclopropanecarboxylic acid derivative of the formula (IIn). The cyclopropanation can be performed by analogy to the method described in US 2012/0202688. The thus obtained carboxylic acids of the formulae (IIm) and (IIn) can be converted in the corresponding amines or isocyanates (IIo), (IIp), (IIr or (IIs), respectively, using Hofman, Curtius, Schmidt or Lossen reaction sequences as described in US 2012/0202688.

The carboxylic acids of the formulae (IIm) and (IIn) may also be reduced to the corresponding amine or converted into the corresponding nitrile or aldehyde, which themselves may be reacted as depicted in schemes 1 to 4.

One may also start from the nitriles of formula (IIb) or the aldehydes of formula (II), which can converter to the corresponding hydroxymethyl compounds or aminomethyl compounds, which can be used for producing compounds of the formula (I), wherein $X^1$ or $X^2$, respectively, is $CH_2$.

Compounds of the formula (IIt), wherein $A^1$ is N, $A^2$ is CH, $A^3$ is N, Q is —CH=CH—, $A^4$, $A^5$ and $A^6$ are N or C—R and $R^{\#}$ is $CH_3$, $NH_2$ or halogen such as F, Cl, Br, I can Scheme 5:

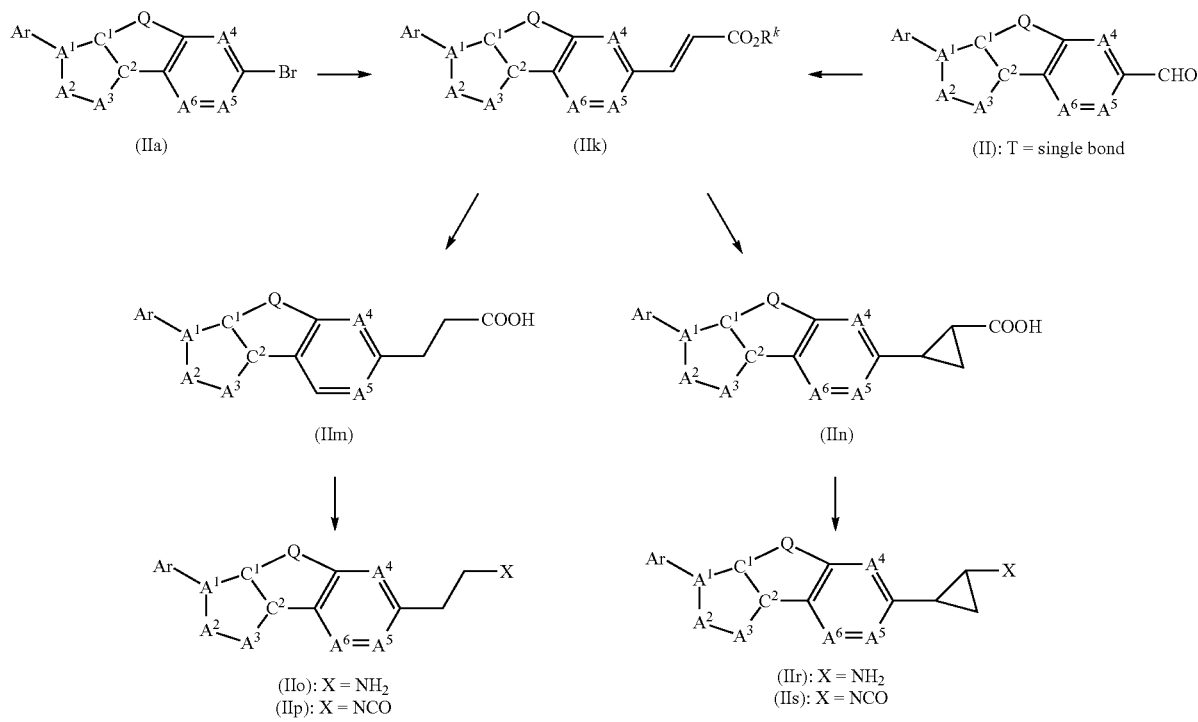

In scheme 5, $R^k$ is alkyl such as $CH_3$, $C_2H_5$, or tert.-butyl. For example, compounds of the formula (II'), where T is $CH_2CH_2$ and $R^{y1}$ is H can be prepared by reacting a compound of the formula (IIa) with a $C_1$-$C_4$-alkylacrylate in the presence of a transition metal catalyst, to yield a propenoic ester derivative of the formula (IIk). The propenoic ester derivative of the formula (IIk) may also be prepared starting from the aldehyde of the formula (II) using a Wittig or Wittig Horner reaction as described in US 2012/0202688. The propenoic ester derivative (IIk) is either hydrogenated followed by subsequent saponification to yield the corresponding propanoic acid derivative of the formula (IIm). In an alternative embodiment the propenoic acid derivative of be prepared by analogy to the methods described in literature and as shown in the following Scheme 6.

Scheme 6

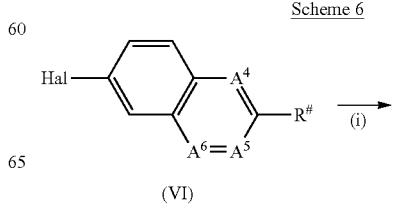

(VI)

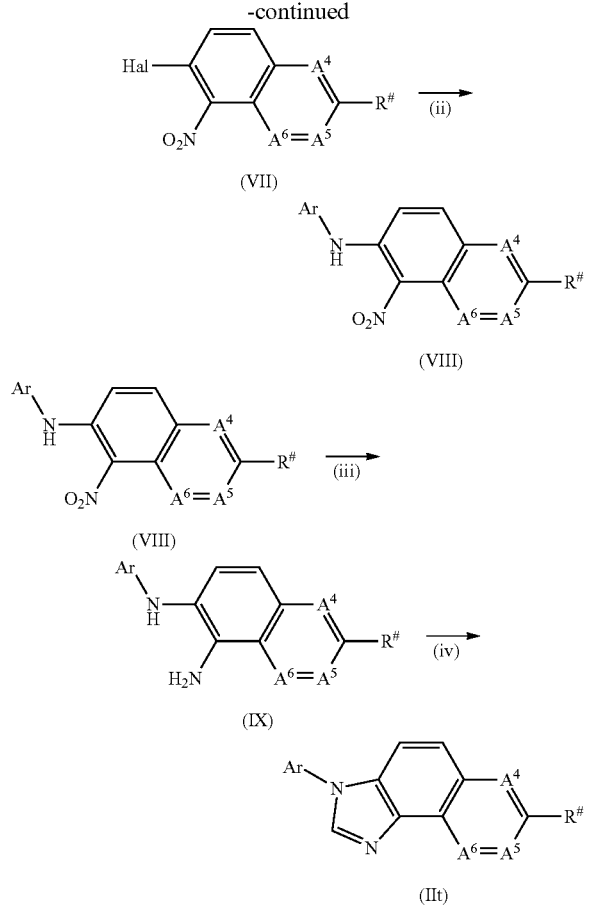

(VII)

(VIII)

(VIII)

(IX)

(IIt)

In Scheme 6, Hal is F, Cl, Br or I, preferably F. Compounds of the formula (IIt) can be prepared from compounds of the formula (VI) in analogy to the method shown in Journal of Heterocyclic Chemistry (1994), 31(1), 153-60. In step (i) of scheme 6, compound VI is subjected a nitration to yield the nitrocompound (VII). The nitration can be performed in analogy to the methods described in Journal of Heterocyclic Chemistry, 1994, vol. 31, #1, p. 153-160, U.S. Pat. No. 4,400,386 or U.S. Pat. No. 4,404,207. The nitrocompound (VII) is reacted in step (ii) of scheme 6 with an amine of the formula ArNH$_2$ to give a compound of formula (VIII). The reaction can be performed in analogy to the methods described in Journal of Heterocyclic Chemistry, 1994, vol. 31, #1, p. 153-160. Compound (VIII) is reduced to a diamine compound (IX) in step (iii) of scheme 6. A suitable reduction agent is for example stannous chloride. The reaction is effected in an alkanol, for example methanol. In step (iv) of scheme 6, the formation of compound (IIt) can be performed by treating the diamine compound (IX) with an acylating agent such as formic acid or an ester thereof.

Compounds of the formula (IIu), where A$^1$ is N, A$^2$ is CH, A$^3$ is N, Q is —CH=CH—, A$^4$ is N and A$^5$ is C—R, A$^6$ is C—R with R being OH, R$^\#$ is CH$_3$ can be prepared as shown in scheme 7 below. The condensation of a compound of formula X with a β-ketoester of formula XI in the presence of polyphosphoric acid to yield a compound of (IIu) can be performed in analogy to the methods given in Journal of the Chemical Society [Section] C: Organic, 1970, p. 829-833. In Scheme 7, R' is C$_1$-C$_6$-alkyl.

Scheme 7

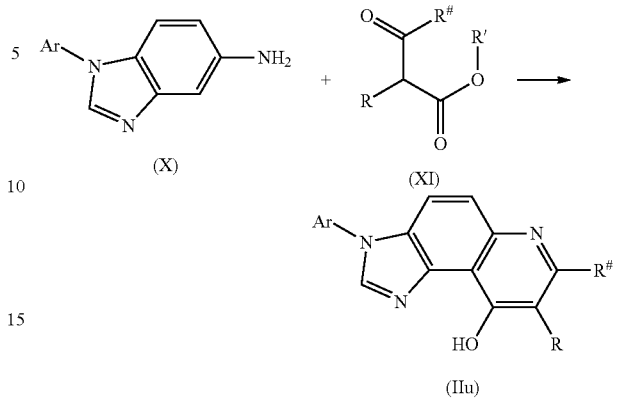

(X)

(XI)

(IIu)

Compounds of the formula (IIu), where A$^1$ is N, A$^2$ is CH, A$^3$ is N, Q is —CH=CH—, A$^4$ is N and A$^5$ is C—R, A$^6$ is C—R with R being OH, R$^\#$ is CH$_3$ can be prepared as shown in scheme 8. In a first step, the amine compound X is reacted with an aminoacrylic ester XII to yield a compound XIII which is then heated in a heat-transfer fluid such as Dowtherm from Sigma-Aldrich to give the compound of formula (IIu). The reaction sequence can be performed in analogy to the methods described in WO 2004/089950.

Scheme 8

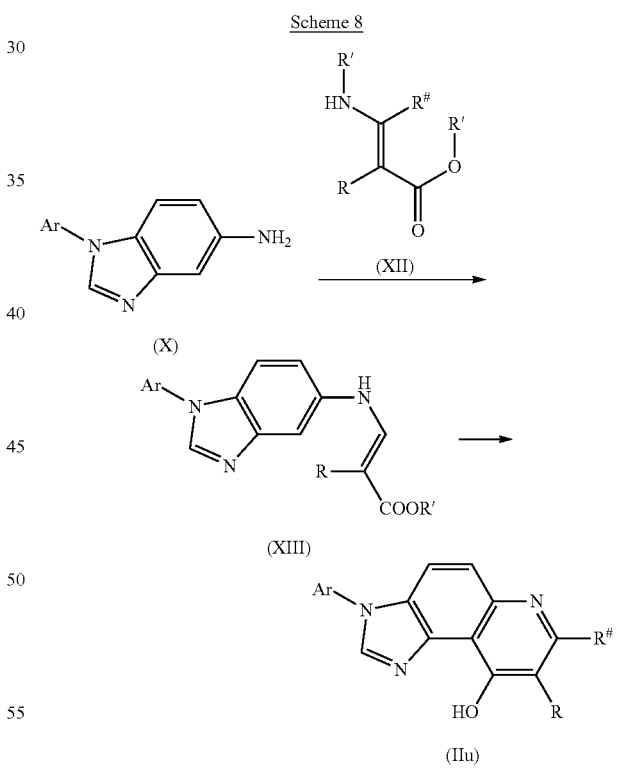

(X)

(XII)

(XIII)

(IIu)

Compounds of the formula (IIt), where A$^4$, A$^5$ and A$^6$ are as defined above, A$^1$ is N, A$^2$ is CH and A$^3$ is N can be prepared as shown in scheme 9. In step (i) of scheme 9, an imidazole-5-carboxylate of formula (XIV) is reacted with a compound (XV) in the presence of a base to give a ketone compound of formula (XVI) which is transformed into an ethene compound (XVII) in step (ii) of scheme 9. The photocyclization of the compound XVII using ultraviolet irradiation yields the compound of formula (IIt). The reaction sequence can be carried out in analogy to the methods described in Journal of Organic Chemistry, 57(5), 1390-405; 1992. In scheme 9, R' is $C_1$-$C_4$-alkyl, preferably methyl. $R^{\#}$ is methyl.

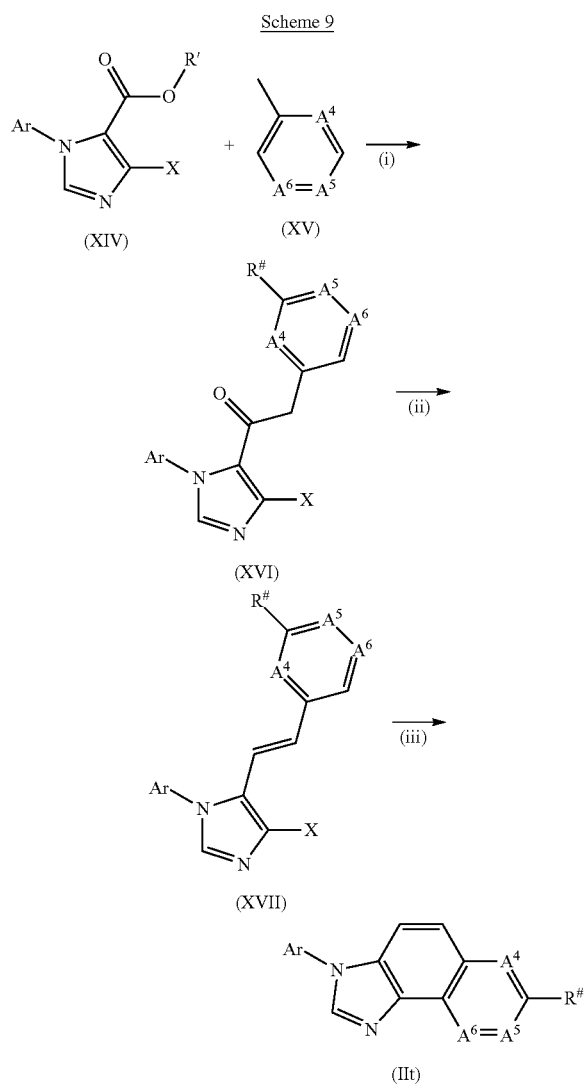

Compounds of the formula (IIa), wherein $A^1$ is N, $A^2$, $A^3$, $A^4$, $A^5$, $A^6$, $C^1$ and $C^2$ are as defined above can be prepared by analogy to the methods described in literature and in accordance with the methods described in the examples.

Usually compounds of the formula (IIa), where $A^1$ is N, $A^2$, $A^3$, $C^1$, $C^2$, $A^4$, $A^5$ and $A^6$ are as defined above, can be prepared as shown in the following Scheme 10.

Scheme 10

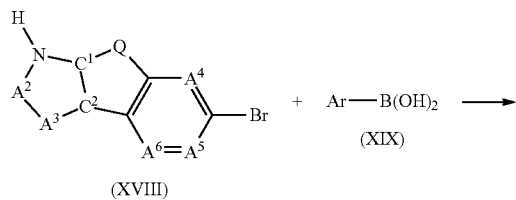

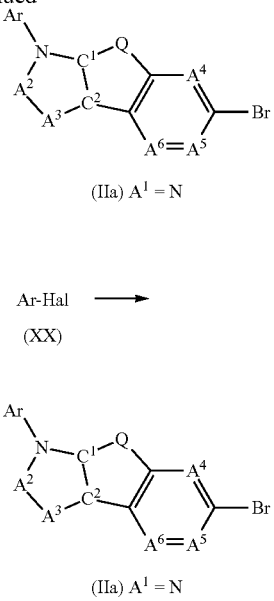

In Scheme 10, Hal is Br or I, preferably Br. Compounds of the formula (IIa), where $A^1$ is N can be prepared via copper-catalyzed coupling of a heteroarylbromide compound of the formula (XVIII) with a boronic acid of the formula (XIX) in the presence of a base in analogy to the method shown in ACS Medicinal Chemistry Letters, 4(2), 293-296; 2013. Alternatively, the compound of formula (IIa), where $A^1$ is N, can be prepared by reacting a compound of formula (XVIII) with an aryl halide of the formula (XX) in analogy to the method shown in Journal of Medicinal Chemistry, 56(5), 1865-1877, 2013. Compounds of the formula (XIX) and (XX) are known.

Compounds of the formula IIa, wherein $A^1$ is C, $A^2$ is O, $A^3$ is N, $C^1$ is C, $C^2$ is C, $A^4$, $A^5$, and $A^6$ are as defined above and Q is —C($R^{Q3a}R^{Q3b}$)—C($R^{Q4a}R^{Q4b}$)—, can be prepared by analogy to the methods described in literature and as shown in the following Scheme 11.

Scheme 11

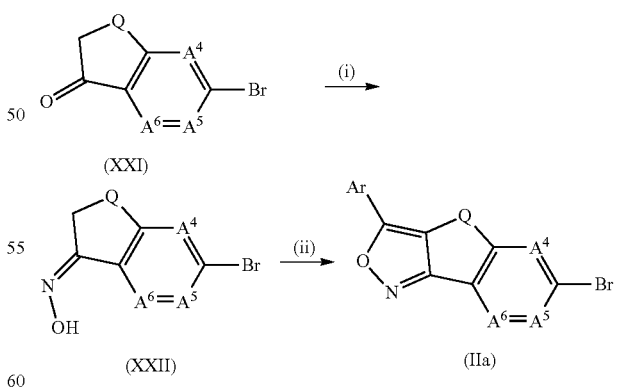

Suitable reaction conditions for performing the reaction step (i) of scheme 11, namely the reaction of the ketone compound of the formula (XXI) with hydroxylamine or hydroxylamine hydrochloride in the presence of a base to give the oxime compound of the formula (XXII) can be taken from Central European Journal of Chemistry 10(2), 360-367;

2012. Cyclisation with an ester of the formula Ar—C(=O)OR', where R' is $C_1$-$C_6$-alkyl, or an acid halide of the formula Ar—C(=O)Hal, where Hal is halogen, preferably Cl, in the presence of a base followed by dehydration using sulfuric acid or Burgees reagent yields the compound of formula (IIa) as outlined in step (ii) of scheme 11. Step (ii) of scheme 11 can be performed in analogy to the methods described in WO 2011/059784.

Compounds of the formula IIa, wherein $A^1$ is C, $A^2$ is NH, $A^3$ is N, $C^1$ is C, $C^2$ is C, $A^4$, $A^5$ and $A^6$ are as defined above and Q is —C($R^{Q3a}R^{Q3b}$)—C($R^{Q4a}R^{Q4b}$)—, can be prepared by analogy to the methods described in literature and as shown in the following Scheme 12.

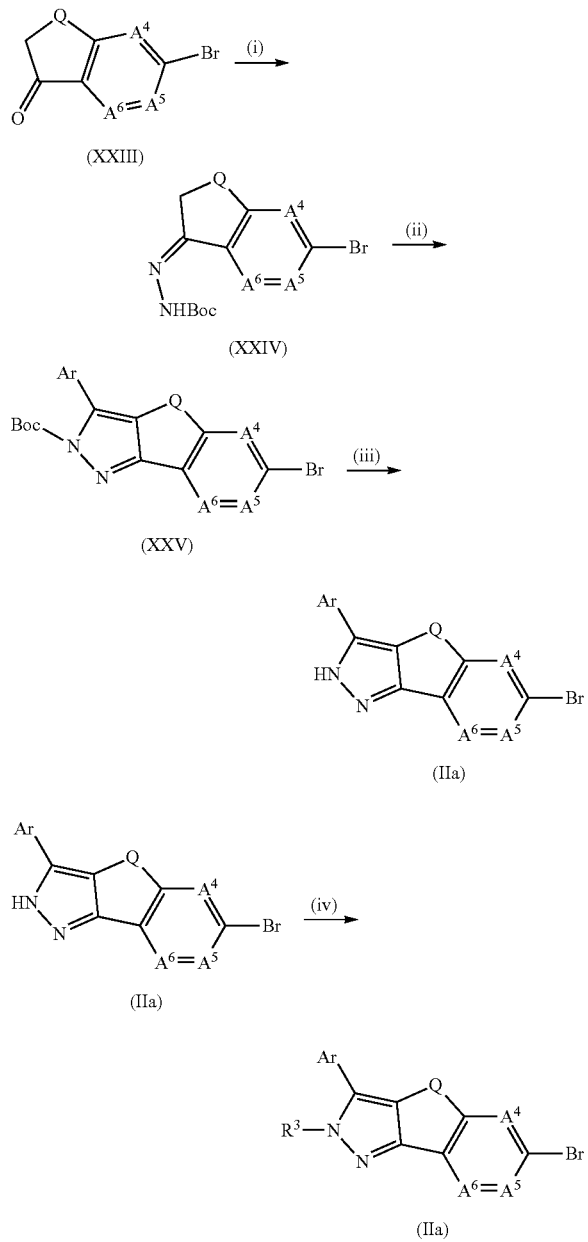

In Scheme 12, Boc means tert-butyloxycarbonyl. Step (i) of Scheme 12 can be performed by analogy to a conventional derivatization of ketones into their hydrazones by reacting a ketone compound (XXIII) with hydrazinecarboxylic acid 1,1-dimethylester to give a corresponding hydrazone compound (XXIV). A suitable method has been described in Synthetic Communications, 26(19), 3659-3669 (1996). In step (ii) of Scheme 12, the hyrazone compound (XXIV) is metalated with a strong base, e.g. a lithium amide base such as lithium diisopropylamide, and then reacted with the aromatic ester of the formula Ar—C(=O)OR, where R is $C_1$-$C_6$-alkyl followed by acid cyclization to give the Boc-protected pyrazole of the formula (XXV) in analogy to the method described in Synthetic Communications, 26(19), 3659-3669 (1996). Removal of the tert-butyloxycarbonyl group from the compound (XXV) to give the compound of formula (IIa) is shown in step (iii) of Scheme 12. The removal can be performed by analogy to conventional methods. For converting compounds of formula (IIa) in which $R^3$ is H into compounds (IIa) in which $R^3$ is not H, compounds of formula (IIa) in which $R^3$ is H can be reacted with compounds of formula $R^3$-Lg, wherein $R^3$ is not H and Lg is a leaving group, such as a Br, Cl or I atom or a tosylate, mesylate or triflate, to yield compounds of formula (I), wherein $R^{y1}$ is different from H, as shown in step (iv) of scheme 12.

Compounds of the formula IIa, wherein $A^1$ is N, $A^2$ is N, $A^3$ is C($R^7$) with $R^7$ is hydrogen, $C^1$ is C, $C^2$ is C, $A^4$, $A^5$ and $A^6$ are as defined above and Q is —C($R^{Q3a}R^{Q3b}$)—C($R^{Q4a}R^{Q4b}$)—, can be prepared by analogy to the methods described in literature and as shown in the following Scheme 13.

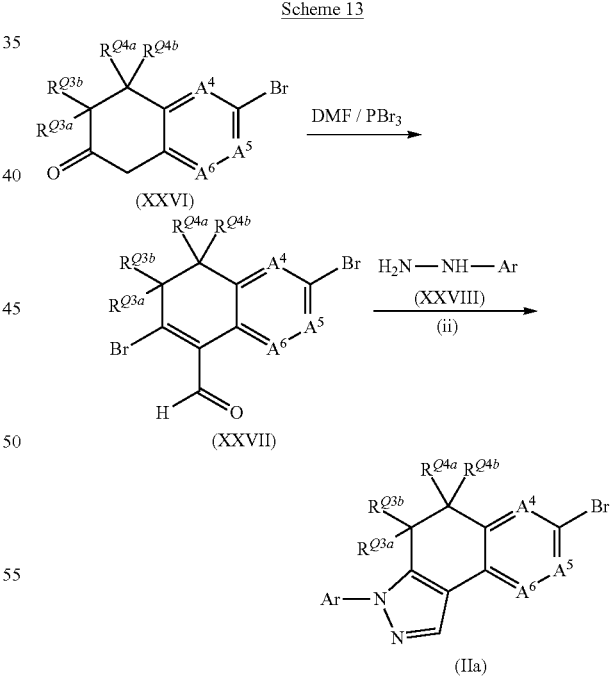

In Scheme 13, DMF means N,N-dimethylformamide. In step (i) of Scheme 13, the cyclohexanone compound of the formula (XXVI) is treated with dimethylformamide and phosphorus tribromide or phosphorus oxybromide in the sense of a Vilsmeier-Haack reaction to give the aldehyde compound (XXVII). The reaction is usually carried out in a chlorinated hydrocarbon such as dichloromethane or trichloroethylene. The reaction can be performed in analogy to the method described in Chemical Communications, 48(89), 10975-10977; 2012. In step (ii) of Scheme 13, the aldehyde compound (XXVII) is cyclized with an arylhydrazine of the formula (XXVIII) in the presence of a palladium catalyst and a phosphorus chelating ligand together with a base such as NaO-tert-butyl to give 1-aryl-1H-pyrazole compounds (IIa). The reaction can be performed in analogy to the method described in Tetrahedron, 62 (26), p. 6133-6442 (2006).

Compounds of the formula IIa, wherein $A^1$ is N, $A^2$ is N, $A^3$ is $C(R^7)$ and $R^7$ is hydrogen, $C^1$ is C, $C^2$ is C, $A^4$, $A^5$ and $A^6$ are as defined above and Q is —$C(R^{Q3a})$=$C(R^{Q4a})$—, can be prepared by analogy to the methods described in literature and as shown in the following Scheme 14.

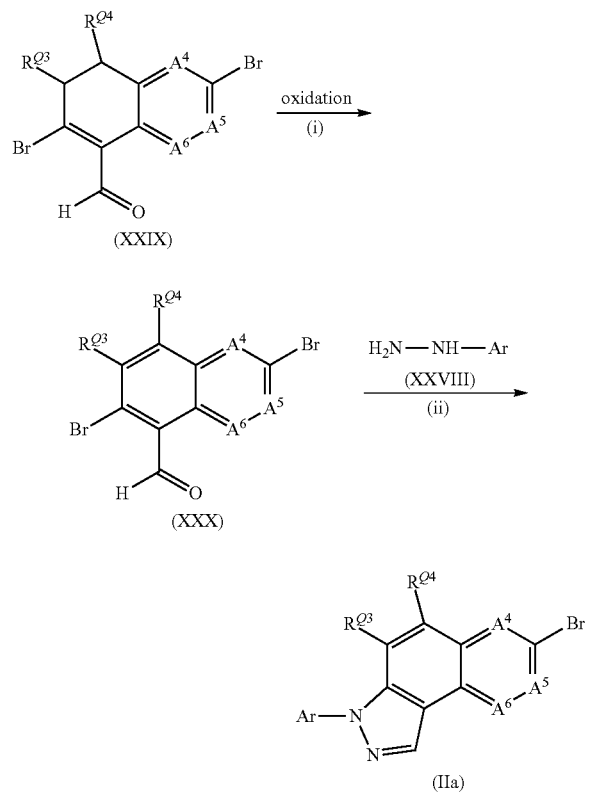

In step (i) of Scheme 14, compound (XXIX) is converted to an aromatic compound (XXX) by oxidation with an oxidation agent. A suitable oxidation agent is 2,3-dichloro-5,6-dicyanobenzoquinone. Suitable reaction conditions for performing step (i) of scheme 14 can be taken from Bioorganic & Medicinal Chemistry 11(4), 521-528, 2003. Step (ii) of Scheme 14 can be performed in analogy to step (ii) of Scheme 13. Compound (XXIX) can be obtained in analogy to the method described for the preparation of compounds of formula (XXVI), where $R^{Q3a}$ and $R^{Q4a}$ are each hydrogen.

Compounds of the formula IIa, wherein $A^1$ is N, $A^2$ is $CR^2$, $A^3$ is $CR^7$, $C^1$ is CH, $C^2$ is CH, $A^4$, $A^5$ and $A^6$ are as defined above and Q is —$C(R^{Q3a}R^{Q3b})$—$C(R^{Q4a}R^{Q4b})$—, can be prepared by analogy to the methods described in literature and as shown in the following Scheme 15.

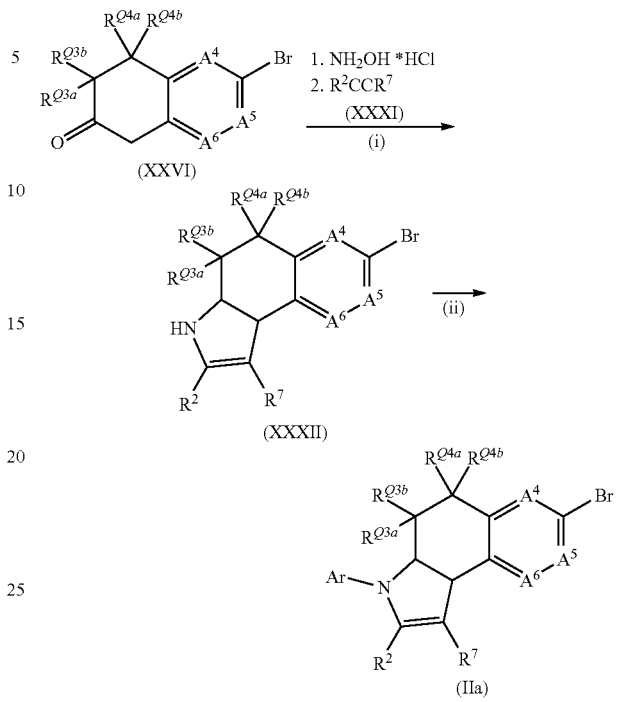

In step (i) of Scheme 15, the ketone compound (XXVI), hydroxylamine hydrochloride and an acetylene compound (XXXI) react in a one pot reaction to give the compound of the formula (XXXII). The reaction in step (i) of Scheme 15 can be performed in analogy to the method described in Tetrahedron 51(13), 1690-1692, 2010. Step (ii) of Scheme 15 can be performed in analogy to the methods described in Scheme 10.

Compounds of the formula IIa, wherein $A^1$ is N, $A^2$ is N, $A^3$ is N, $C^1$ is C, $C^2$ is C, $A^4$, $A^5$ and $A^6$ are as defined above and Q is —$C(R^{Q3a}R^{Q3b})$—$C(R^{Q4a}R^{Q4b})$—, can be prepared by analogy to the methods described in literature and as shown in the following Scheme 16.

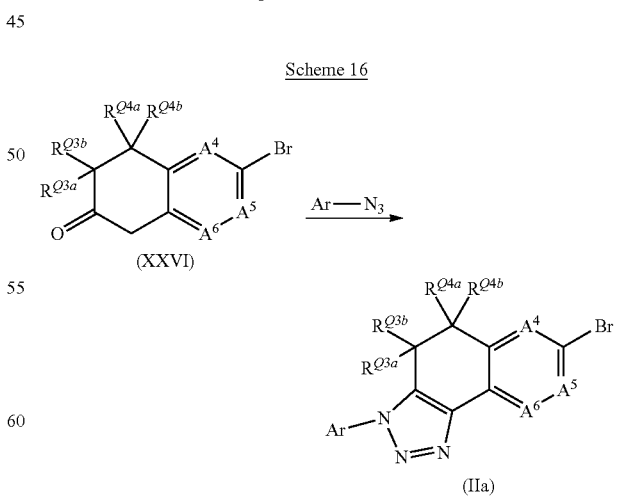

According to scheme 16, compounds of the formula (IIa) can be prepared by reacting a ketone compound of the formula (XXVI) with an arylazide in a sense of a Huisgen

[3+2] cycloaddition. This reaction can be performed by analogy to the method described in Chemistry—A European Journal, 18(19), 6088-6093, S6088/1-6088/47; 2012.

Compounds of the formula IIa, wherein $A^1$ is N, $A^2$ is N, $A^3$ is N, $C^1$ is C, $C^2$ is C, $A^4$, $A^5$ and $A^6$ are as defined above and Q is —C($R^{Q3}$)=C($R^{Q4}$)—, can be prepared by analogy to the methods described in literature and as shown in the following Scheme 17.

Scheme 17

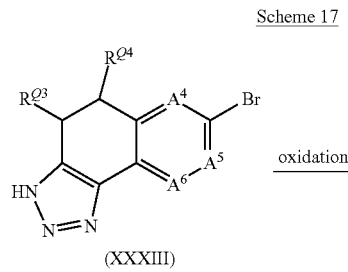

(XXXIII)

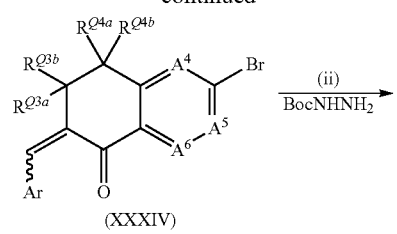

(XXXIV)

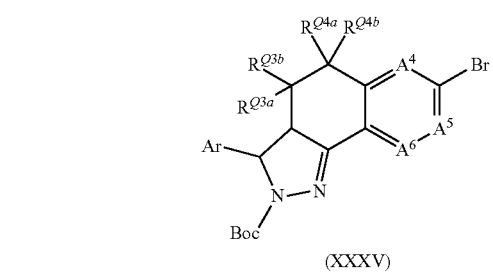

(XXXV)

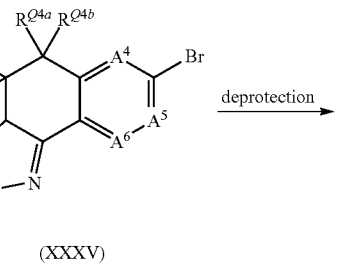

(XXXV)

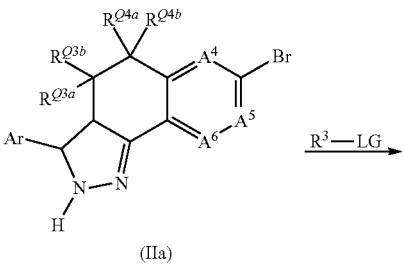

(IIa)

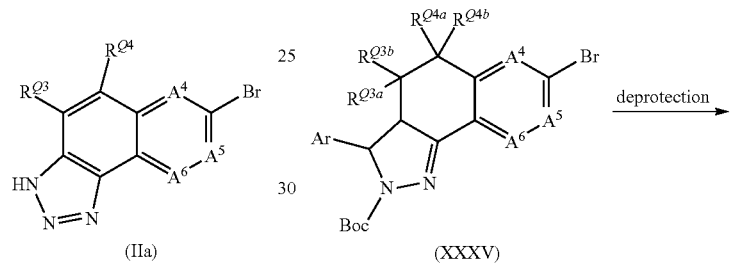

(IIa)

The oxidation in Scheme 17 can be performed in analogy to step (i) of Scheme 14. The compounds of the formula (XXXIII) can be prepared in analogy to the reaction shown in Scheme 16.

As a rule, compounds of the formula (IIa), where Q is —C($R^{Q3a}R^{Q3b}$)—C($R^{Q4a}R^{Q4b}$)— can be converted into compounds of the formula (IIa), where Q is —C($R^{Q3}$)=C($R^{Q4}$)— according to the method described in step (i) of Scheme 14.

Some of the reactions shown in the Schemes below may be performed in analogy to the reactions shown in the Schemes above.

Compounds of the formula IIa, wherein $A^1$ is C, $A^2$ is N($R^3$), $A^3$ is N, $C^1$ is CH, $C^2$ is C and Q is —C($R^{Q3a}R^{Q3b}$)—C($R^{Q4a}R^{Q4b}$)—, can be prepared by analogy to the methods described in literature and as shown in the following Scheme 18.

Scheme 18

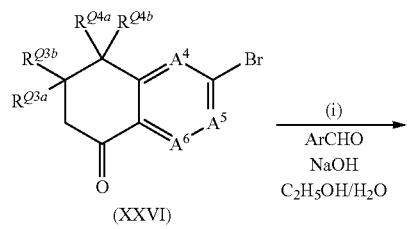

(XXVI)

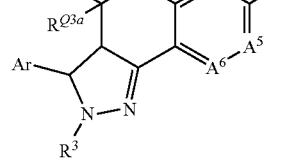

In Scheme 18, Boc means tert-butyloxycarbonyl and LG is a leaving group, such as a Br, Cl or I atom or a tosylate, mesylate or triflate.

Compounds of the formula IIa, wherein $A^1$ is C, $A^2$ is N($R^3$), $A^3$ is N, $C^1$ is C, $C^2$ is C, $A^4$, $A^5$ and $A^6$ are as defined above, and Q is —C($R^{Q3a}R^{Q3b}$)—C($R^{Q4a}R^{Q4b}$)—, can be prepared by analogy to the methods described in literature and as shown in the following Scheme 19. In Scheme 19, DDQ is 2,3-dichloro-5,6-dicyano-1,4-benzoquinone.

Scheme 19

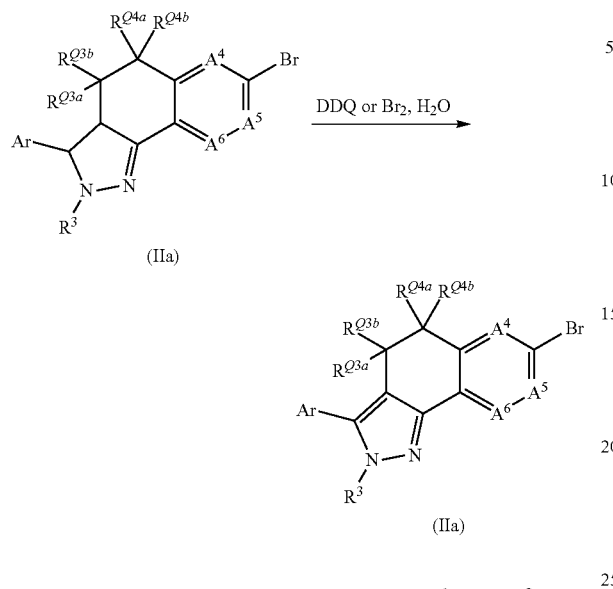

Compounds of the formula IIa, wherein $A^1$ is C, $A^2$ is O, $A^3$ is N, $C^1$ is C, $C^2$ is C, $A^4$, $A^5$ and $A^6$ are as defined above, and Q is —C($R^{Q3a}R^{Q3b}$)—C($R^{Q4a}R^{Q4b}$)—, can be prepared by analogy to the methods described in literature and as shown in the following Scheme 20. In Scheme 20, DDQ is 2,3-dichloro-5,6-dicyano-1,4-benzoquinone.

Scheme 20

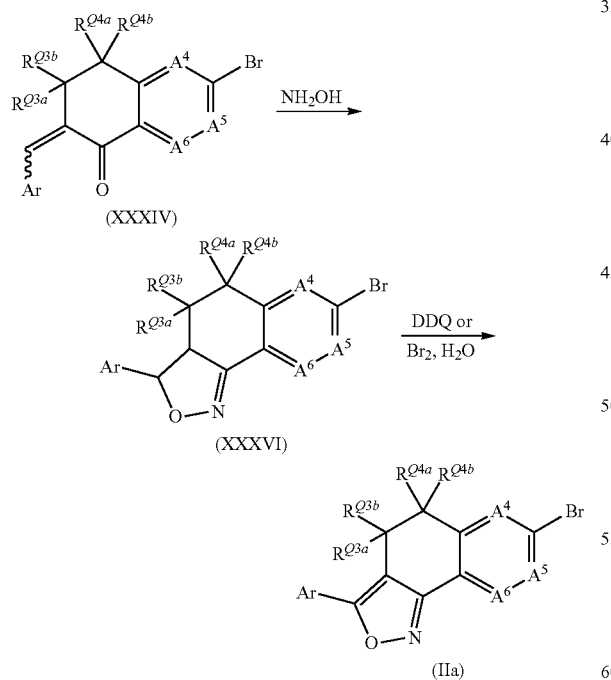

Compounds of the formula IIa, wherein $A^1$ is N, $A^2$ is CH, $A^3$ is N, $C^1$ is C, $C^2$ is C, $A^4$, $A^5$ and $A^6$ are as defined above and Q is —OC($R^{Q4a}R^{Q4b}$)—, can be prepared by analogy to the methods described in literature and as shown in the following Scheme 21.

Scheme 21

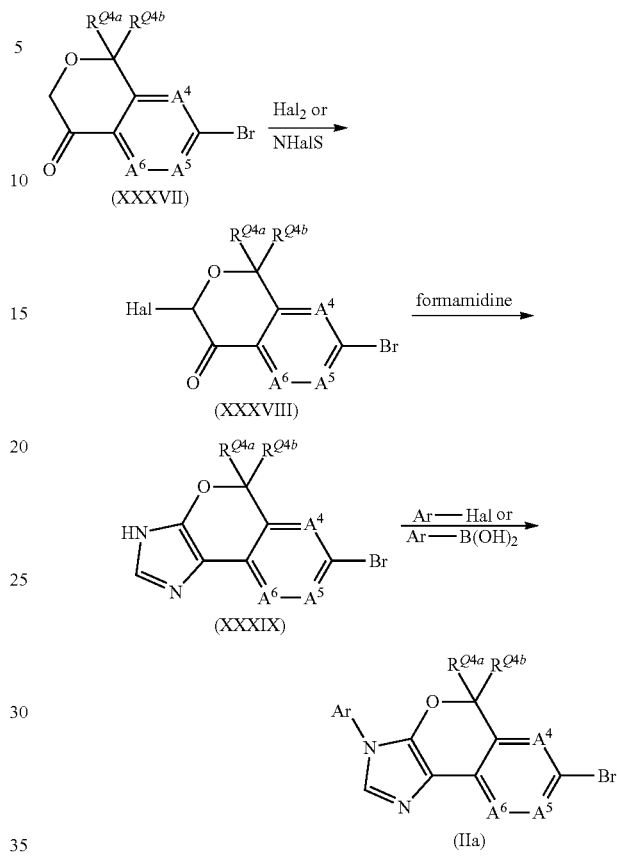

In Scheme 21, Hal is halogen, preferably Br, Cl or I and NHalS is N-halogenosuccinimide, preferably N-bromosuccinimide.

Compounds of the formula IIa, wherein $A^1$ is N, $A^2$ is CH, $A^3$ is N, $C^1$ is C, $C^2$ is C, $A^4$, $A^5$ and $A^6$ are as defined above and Q is —SC($R^{Q4a}R^{Q4b}$)—, can be prepared by analogy to the methods described in literature and as shown in the following Scheme 22.

Scheme 22

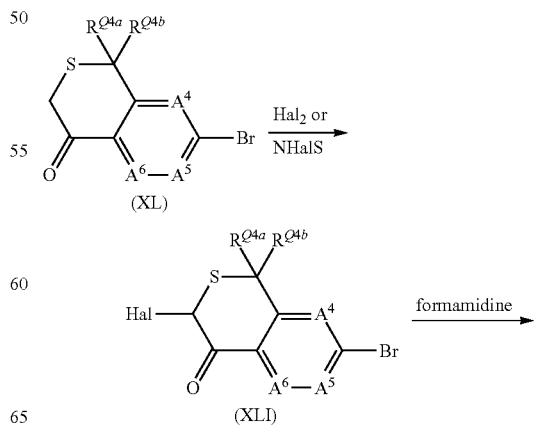

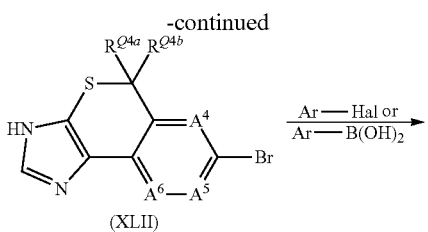

(XLII)

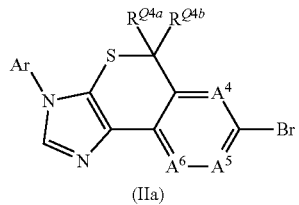

(IIa)

In Scheme 22, Hal is halogen, preferably Br, Cl or I and NHalS is N-halogenosuccinimide, preferably N-bromosuccinimide.

Compounds of the formula IIa, wherein $A^1$ is N, $A^2$ is CH, $A^3$ is N, $C^1$ is C, $C^2$ is C, $A^4$, $A^5$ and $A^6$ are as defined above and Q is —S(=O)C($R^{Q4a}R^{Q4b}$)— or —S(=O)$_2$C($R^{Q4a}R^{Q4b}$)—, can be prepared by treating a compound of the formula (IIa), where $A^1$ is N, $A^2$ is CH, $A^3$ is N, $C^1$ is C, $C^2$ is C, $A^4$, $A^5$ and $A^6$ are as defined above and Q is —SC($R^{Q4a}R^{Q4b}$)—, with an oxidazing agent such as 3-chloroperoxybenzoic acid or $RuCl_3$/$NaIO_4$.

Compounds of the formula IIa, wherein $A^1$ is N, $A^2$ is CH, $A^3$ is N, $C^1$ is C, $C^2$ is C, $A^4$, $A^5$ and $A^6$ are as defined above and and Q is —C($R^{Q4a}R^{Q4b}$)—O—, where $R^{Q4a}$ and $R^{Q4b}$ are both hydrogen, can be prepared by analogy to the methods described in literature and as shown in the following Scheme 23.

Scheme 23

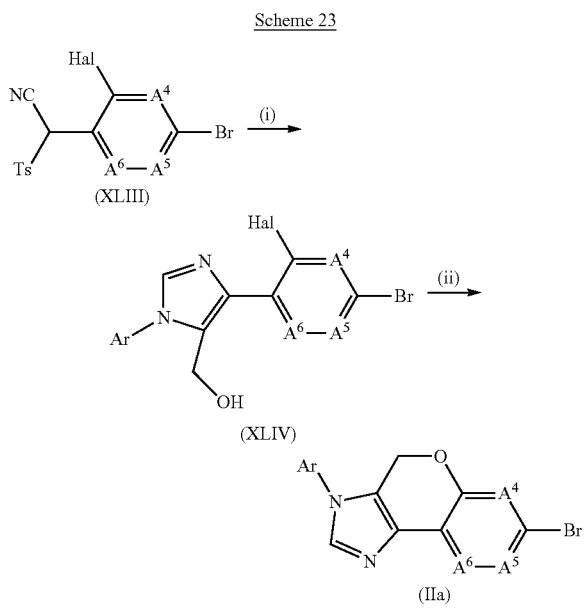

In Scheme 23, Ts is tosyl and Hal is halogen. In step (i) of Scheme 23, the cyano compound (XLIII) is treated with an amine of the formula Ar—$NH_2$ and glyoaldehyde, dimer to form the imidazolyl compound (XLIV). The reaction can be performed in analogy to the method described in WO 2004/013141. Step (ii) of Scheme 23 is performed under copper or palladium catalysis.

Compounds of the formula IIa, wherein $A^1$ is N, $A^2$ is CH, $A^3$ is N, $C^1$ is C, $C^2$ is C, $A^4$, $A^5$ and $A^6$ are as defined above and Q is —C($R^{Q4a}R^{Q4b}$)—S—, where $R^{Q4a}$ and $R^{Q4b}$ are both hydrogen, can be prepared by analogy to the methods described in literature and as shown in the following Scheme 24.

Scheme 24

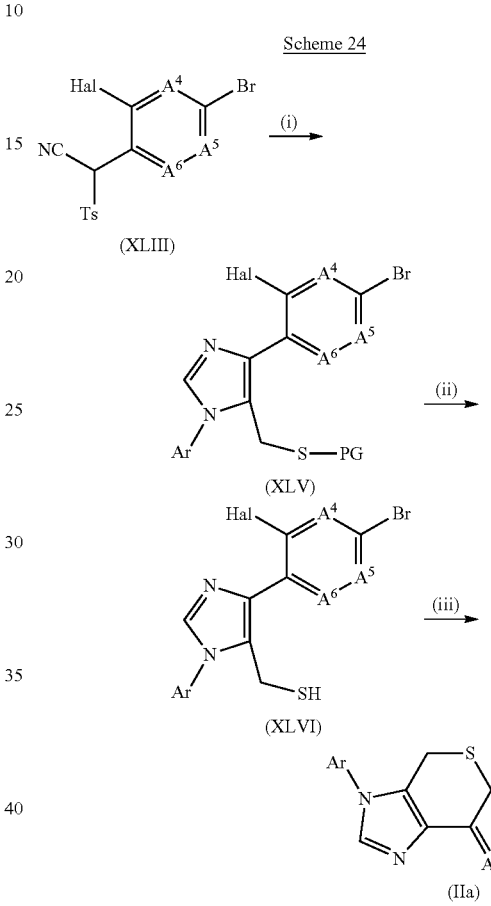

In Scheme 24, Ts is tosyl, Hal is halogen and PG is a sulfur protection group such as PMB (p-methoxybenzyl).

In step (i) of Scheme 24, the cyano compound (XLIII) is treated with an amine of the formula Ar—$NH_2$ and a protected sulfanylacetaldehyde of the formula PG-S—$CH_2$CHO to form an imidazolyl compound (XLVIVI). In step (ii) of Scheme 24, the sulfur is deprotected according to standard methods in the organic chemistry. Step (iii) of Scheme 24 is performed under copper or palladium catalysis to give the compound (IIa).

Compounds of the formula IIa, wherein $A^1$ is N, $A^2$ is CH, $A^3$ is N, $C^1$ is C, $C^2$ is C, $A^4$, $A^5$ and $A^6$ are as defined above and Q is —C($R^{Q4a}R^{Q4b}$)—S(O)— or C($R^{Q4a}R^{Q4b}$)—S(O)$_2$—, where $R^{Q4a}$ and $R^{Q4b}$ are both hydrogen can be prepared by treating a compound of the formula (IIa), where $A^1$ is N, $A^2$ is CH, $A^3$ is N, $C^1$ is C, $C^2$ is C, $A^4$, $A^5$ and $A^6$ are as defined above and Q is —SC($R^{Q4a}R^{Q4b}$)—, with an oxidazing agent such as 3-chloroperoxybenzoic acid or $RuCl_3$/$NaIO_4$.

Compounds of the formula (IIa), wherein $A^1$ is N, $A^2$ is CH, $A^3$ is N, $C^1$ is C, $C^2$ is C, $A^4$, $A^5$ and $A^6$ are as defined above and Q is —C($R^{Q4a}R^{Q4b}$)—N($R^{Q2}$)—, can be prepared by analogy to the methods described in literature and as shown in the following Scheme 25.

Scheme 25

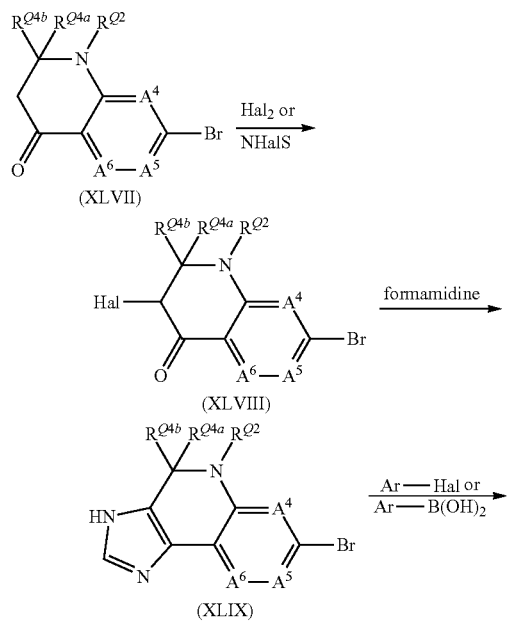

In Scheme 25, Hal is halogen, preferably Br, Cl or I and NHalS is N-halogenosuccinimide, preferably N-bromosuccinimide.

Compounds of the formula (IIa), wherein $A^1$ is N, $A^2$ is CH, $A^3$ is N, $C^1$ is C, $C^2$ is C, $A^4$, $A^5$ and $A^6$ are as defined above and and Q is —N($R^{Q2}$)—C($R^{Q4a}R^{Q4b}$), can be prepared by analogy to the methods described in literature and as shown in the following Scheme 26.

Scheme 26

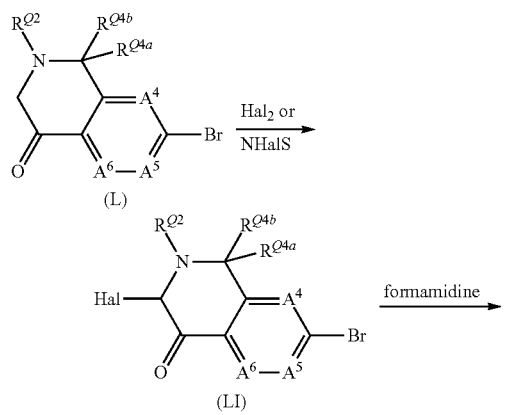

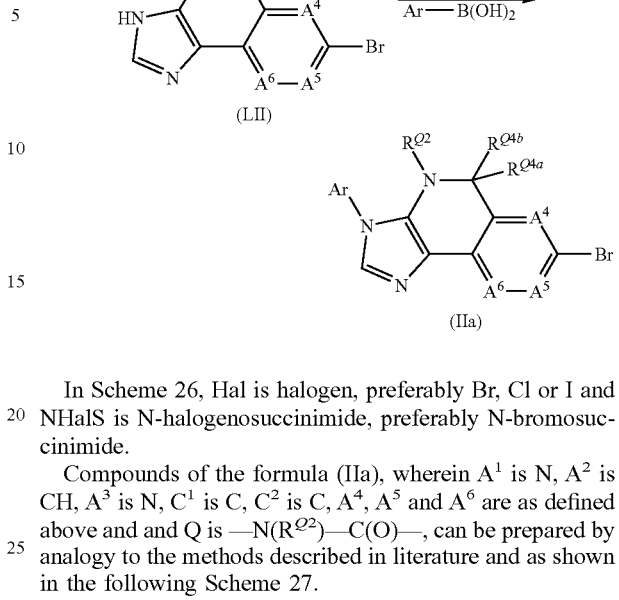

In Scheme 26, Hal is halogen, preferably Br, Cl or I and NHalS is N-halogenosuccinimide, preferably N-bromosuccinimide.

Compounds of the formula (IIa), wherein $A^1$ is N, $A^2$ is CH, $A^3$ is N, $C^1$ is C, $C^2$ is C, $A^4$, $A^5$ and $A^6$ are as defined above and and Q is —N($R^{Q2}$)—C(O)—, can be prepared by analogy to the methods described in literature and as shown in the following Scheme 27.

Scheme 27

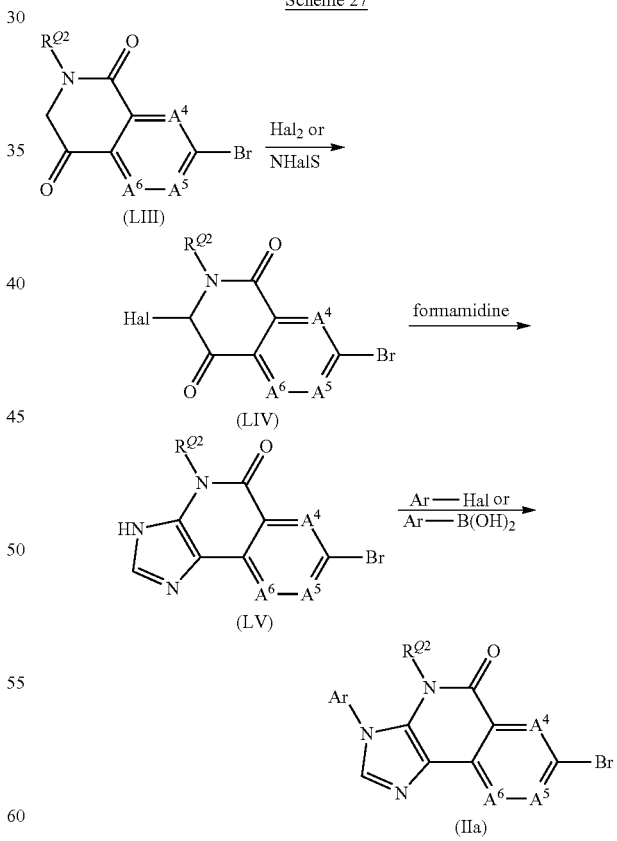

In Scheme 27, Hal is halogen, preferably Br, Cl or I and NHalS is N-halogenosuccinimide, preferably N-bromosuccinimide.

As a rule, the compounds of formula (I), especially (Ia), (Ib), (Ic) and (Id), including their stereoisomers, N-oxides and salts, as well as their precursors in the synthesis process, can be prepared by the methods described above or by customary modifications of the synthesis routes described. If individual compounds can not be prepared via the above-described routes, they can be prepared by derivatization of other compounds (I) or the respective precursor. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration with an appropriate solvent.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above. The invention also relates to the use of a compound of the invention, of a stereoisomer and/or of an agriculturally or veterinarily acceptable salt thereof for combating invertebrate pests.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

Alternatively preferably, the method of the invention serves for protecting plants from attack or infestation by invertebrate pests, which method comprises treating the plants with a pesticidally effective amount of at least one compound of the invention, a stereoisomer thereof and/or at least one agriculturally acceptable salt thereof.

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

The present invention also relates to a mixture of at least one compound of the present invention with at least one mixing partner as defined herein after. Preferred are binary mixtures of one compound of the present invention as component I with one mixing partner as defined herein after as component II. Preferred weight ratios for such binary mixtures are from 5000:1 to 1:5000, preferably from 1000:1 to 1:1000, more preferably from 100:1 to 1:100, particularly preferably from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

The following list M of pesticides, grouped and numbered according the Mode of Action Classification of the Insecticide Resistance Action Committee (IRAC), together with which the compounds of the present invention can be used and with which potential synergistic effects might be produced, is intended to illustrate the possible combinations, but not to impose any limitation:

M.1 Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-$CH_3$, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as: M.2A cyclodiene organoCl compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M.4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as M.7A juvenile hormone analogues as hydroprene, kinoprene and methoprene; or others as M.7B fenoxycarb or M.7C pyriproxyfen;

M.8 miscellaneous non-specific (multi-site) inhibitors, for example M.8A alkyl halides as methyl bromide and other alkyl halides, or M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fen-butatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example M.20A hydramethylnon, or M.20B acequinocyl, or M.20C fluacrypyrim;

M.21 Mitochondrial complex I electron transport inhibitors, for example M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (rynaxypyr®), cyantraniliprole (cyazypyr®), tetraniliprole, or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5d) and M.28.5h) to M.28.5l): M.28.5a)N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b)N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; M.28.5c)N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d)N-[4,6-dichloro-2-[(di-2-propyl-lambda-4-sulfanylidene)carbamoyl]-phenyl]-2-(3-c-chloro-2-pyridyl)-5-(trifluoromethyl)pyrazole-3-carboxamide; M.28.5h)N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i)N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l)N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or a compound selected from M.28.6: N(2-cyanopropan-2-yl)-N-(2,4-dimethylphenyl)-3-iodobenzene-1,2-dicarboxamide; or M.28.7: 3-Chloro-N-(2-cyanopropan-2-yl)-N-(2,4-dimethylphenyl)-benzene-1,2-dicarboxamide;

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl)sufinyl]phenyl]-3-(trifluoromethyl)-1H-1,2,4-triazole-5-amine, or actives on basis of *bacillus firmus* (Votivo, I-1582); or a compound selected from the group of M.29.6, wherein the compound is selected from M.29.6a) to M.29.6k):
M.29.6a) (E/Z)—N-[1-[(6-chloro-3-pyridyl)methyl]-2-pyridylidene]-2,2,2-trifluoro-acetamide; M.29.6b) (E/Z)—N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)—N-[1-[(6-bromo-3-pyridyl)methyl]-2-pyridylidene]-2,2,2-trifluoro-acetamide; M.29.6e) (E/Z)—N-[1-[1-(6-chloro-3-pyridyl)ethyl]-2-pyridylidene]-2,2,2-trifluoro-acetamide; M.29.6f) (E/Z)—N-[1-[(6-chloro-3-pyridyl)methyl]-2-pyridylidene]-2,2-difluoro-acetamide; M.29.6g) (E/Z)-2-chloro-N-[1-[(6-chloro-3-pyridyl)methyl]-2-pyridylidene]-2,2-difluoro-acetamide; M.29.6h) (E/Z)—N-[1-[(2-chloropyrimidin-5-yl)methyl]-2-pyridylidene]-2,2,2-trifluoro-acetamide; M.29.6i) (E/Z)—N-[1-[(6-chloro-3-pyridyl)methyl]-2-pyridylidene]-2,2,3,3,3-pentafluoro-propanamide); M.29.6j)N-[1-[(6-chloro-3-pyridyl)methyl]-2-pyridylidene]-2,2,2-trifluoro-thioacetamide; or M.29.6k)N-[1-[(6-chloro-3-pyridyl)methyl]-2-pyridylidene]-2,2,2-trifluoro-N'-isopropyl-acetamidine; or the compounds M.29.8: 8-chloro-N-[2-chloro-5-methoxyphenyl)sulfonyl]-6-trifluoromethyl)-imidazo[1,2-a]pyridine-2-carboxamide; or the compounds M.29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): 4-[5-(3,5-Dichlorophenyl)-5-trifluoromethyl-4,5-dihydroisoxazol-3-yl]-N-[(methoxyimino)methyl]-2-methylbenzamide; or M.29.10: 5-[3-[2,6-dichloro-4-(3,3-dichloroallyloxy)phenoxy]propoxy]-1H-pyrazole; or a compound selected from the group of M.29.11, wherein the compound is selected from M.29.11 b) to M.29.11p):
M.29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.29.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.29.11.d)N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide; M.29.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; M.29.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.29.11.k)N-[5-[[2-chloro-6-cyano-4-[1,2,2,3,3,3-hexafluoro-1-(trifluoromethyl) propyl]phenyl]carbamoyl]-2-cyano-phenyl]-4-cyano-2-methyl-benzamide; M.29.11.l)N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.29.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.29.11.p)N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or a compound selected from the group of M.29.12, wherein the compound is selected from M.29.12a) to M.29.12m):
M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-Methylsulfonyl-6-[2-(3-pyridyl)thiazol-5-yl]pyridine-2-carboxamide; M.29.12.e)N-Methylsulfonyl-6-[2-(3-pyridyl)thiazol-5-yl]pyridine-2-carboxamide; M.29.12.f)N-Ethyl-N-[4-methyl-2-(3-pyridyl)thiazol-5-yl]-3-methylthio-propanamide; M.29.12.g)N-Methyl-N-[4-methyl-2-(3-pyridyl)thiazol-5-yl]-3-methylthio-propanamide; M.29.12.h) N,2-Dimethyl-N-[4-methyl-2-(3-pyridyl)thiazol-5-yl]-3-methylthio-propanamide; M.29.12.i)N-Ethyl-2-methyl-N-[4-methyl-2-(3-pyridyl)thiazol-5-yl]-3-methylthio-propanamide; M.29.12.j)N-[4-Chloro-2-(3-pyridyl)thiazol-5-yl]-N-ethyl-2-methyl-3-methylthio-propanamide; M.29.12.k)N-[4-Chloro-2-(3-pyridyl)thiazol-5-yl]-N,2-dimethyl-3-methylthio-propanamide; M.29.12.l)N-[4-Chloro-2-(3-pyridyl)thiazol-5-yl]-N-methyl-3-methylthio-propanamide; M.29.12.m)N-[4-Chloro-2-(3-pyridyl)thiazol-5-yl]-N-ethyl-3-methylthio-propanamide; or the compounds M.29.14a) 1-[(6-Chloro-3-pyridinyl)methyl]-1,2,3,5,6,7-hexahydro-5-methoxy-7-methyl-8-nitroimidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e)N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropyl)ethyl]-N,5-dimethyl-N-pyridazin-4-yl-pyrazole-4-carboxamide; M.29.16h) N-methyl-1-(2-fluoro-1-methyl-propyl)-5-methyl-N-pyridazin-4-yl-pyrazole-4-carboxamide; M.29.16i) 1-(4,4-difluorocyclohexyl)-N-ethyl-5-methyl-N-pyridazin-4-yl-pyrazole-4-carboxamide;

or M.29.16j) 1-(4,4-difluorocyclohexyl)-N,5-dimethyl-N-pyridazin-4-yl-pyrazole-4-carboxamide.

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alan-wood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.22B.1 is described in CN10171577 and the analogue M.22B.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compounds M.28.6 and M.28.7 can be found in CN102613183. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *bacillus firmus* are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437.

The following list of fungicides, in conjunction with which the compounds of the present invention can be used, is intended to illustrate the possible combinations but does not limit them:

A) Respiration Inhibitors
  Inhibitors of complex III at $Q_o$ site (e.g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy.strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A. 1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methyl-pyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36), inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e.g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N(1,1,3-trimethylindan-4-yl)pyrazole-4-carboxamide (A.3.21), 3-(trifluoromethyl)-1-methyl-N(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e.g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[re-(2S,3R)-3-(2-chlorophenyl)-2-(2,4-difluorophenyl)-oxiranylmethyl]-5-thiocyanato-1H-[1,2,4]triazolo (B.1.31), 2-[rel-(2 S,3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B. 1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organoCl compounds (e.g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methylbenzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis (difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethylquinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or or structurally-similar and functionally identical to a naturally-occurring substance and extracts from biological sources that control pests or provide other crop protection uses as defined below, but have non-toxic mode of actions (such as growth or developmental regulation, attractants, repellents or defence activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclo-hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylhnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylme-thene-4,4'-diisocyanatae) are dispersed into an aqueous solution of a protective colloid (e.g. polyvinyl alcohol). The addition of a polyamine (e.g. hexamethylenediamine) results in the for-mation of a polyurea microcapsule. The monomers amount to 1-10 wt %. The wt % relate to the total CS composition.

xi) Dustable Powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e.g. components comprising compounds of the present invention and/or mixing partners as defined above, can be applied jointly (e.g. after tank mix) or consecutively.

The compounds of the present invention are suitable for use in protecting crops, plants, plant propagation materials, such as seeds, or soil or water, in which the plants are growing, from attack or infestation by invertebrate pests. Therefore, the present invention also relates to a plant protection method, which comprises contacting crops, plants, plant propagation materials, such as seeds, or soil or water, in which the plants are growing, to be protected from attack or infestation by invertebrate pests, with a pesticidally effective amount of a compound of the present invention.

The compounds of the present invention are also suitable for use in combating or controlling invertebrate pests. Therefore, the present invention also relates to a method of combating or controlling invertebrate pests, which comprises contacting the invertebrate pests, their habitat, breeding ground, or food supply, or the crops, plants, plant propagation materials, such as seeds, or soil, or the area, material or environment in which the invertebrate pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the invertebrate pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the invertebrate pest or plant).

The term "invertebrate pest" includes arthropods, gastropods, and nematodes. Preferred invertebrate pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called *Stevia*); natural rubber plants or ornamental and forestry plants, such as flowers (e.g. carnation, petunias, geranium/pelargoniums, pansies and *impatiens*), shrubs, broad-leaved trees (e.g. poplar) or evergreens, e.g. conifers; *eucalyptus*; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof.

Plants, which have been modified by mutagenesis or genetic engineering, and are of particular commercial importance, include alfalfa, rapeseed (e.g. oilseed rape), bean, carnation, chicory, cotton, eggplant, *eucalyptus*, flax, lentil, maize, melon, *papaya, petunia*, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus thuringiensis* (Bt), and code for the respective Bt toxins. Genetically modified plants with insect resistance are commercially available under trade names including Wide-Strike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agribiotech Applications (ISAAA)" (http://www.isaaa.org/gmapprovaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/I Surfactant, 0 to 200 g/I antifreezing agent, 0 to 400 g/l of binder, 0 to 200 g/l of a pigment and up to 1 liter of a solvent, preferably water.

Especially preferred FS formulations of the compounds of the present invention for seed treatment usually comprise from 0.1 to 80% by weight (1 to 800 g/I) of the active ingredient, from 0.1 to 20% by weight (1 to 200 g/I) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the present invention can be used as bait composition, gel, general insect spray, aerosol, as ultralow volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per m² treated material, desirably from 0.1 g to 50 g per m².

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds of the the present invention are especially suitable for efficiently combating invertebrate pests such as arthropods, gastropods and nematodes including but not limited to:

insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia (=Thermesia)* spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. Indicus, C. suppressalis, C. partellus; Choreutis pariana, Choristoneura* spp. such as *C. conflictana, C. fumiferana, C. longicellana, C. murinana, C. occidentalis, C. rosaceana; Chrysodeixis (=Pseudoplusia)* spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema (=Epinotia) aporema, Cydalima (=Diaphania) perspectalis, Cydia (=Carpocapsa)* spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu, Egira (=Xylomyges) curialis, Elasmopalpus lignosellus, Eldana saccharina, Endopiza viteana, Ennomos subsignaria, Eoreuma loftini, Ephestia* spp. such as *E. cautella, E. eutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera (=Heliothis armigera), H. zea (=Heliothis zea); Heliothis* spp. such as *H. assulta, H. subflexa, H. virescens; Hellula* spp. such as *H. undalis, H. rogatalis; Heliocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithocolletis blancardella, Lithophane antennata, Llattia octo (=Amyna axis), Lobesia botrana, Lophocampa* spp., *Loxagrotis albicosta, Loxostege* spp. such as *L. sticticalis, L. cererealis; Lymantria* spp. such as *L. dispar, L. monacha; Lyonetia clerkella, Lyonetia prunifoliella, Malacosoma* spp. such as *M. americanum, M. californicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge lanata, Melanchra picta, Melanitis leda, Mocis* spp. such as *M. lapites, M. repanda;*

*Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. such as *O. nubilalis, Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. such as *P. gossypiella, Peridroma saucia, Perileucoptera* spp., such as *P. coffeella, Phalera bucephala, Phryganidia californica, Phthorimaea* spp. such as *P. operculella; Phyllocnistis citrella, Phyllonorycter* spp. such as *P. blancardella, P. crataegella, P. issikii, P. ringoniella, Pieris* spp. such as *P. brassicae, P. rapae, P. napi; Pilocrocis tripunctata, Plathypena scabra, Platynota* spp. such as *P. flavedana, P. idaeusalis, P. stultana; Platyptilia carduidactyla, Plebejus argus, Plodia interpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga cerealella, Sparganothis pilleriana, Spilonota lechriaspis, S. ocellana, Spodoptera* (=*Lamphygma*) spp. such as *S. eridania, S. exigua, S. frugiperda, S. latifascia, S. littoralis, S. litura, S. ornithogalli; Stigmella* spp., *Stomopteryx subsecivella, Strymon bazochii, Sylepta derogata, Synanthedon* spp. such as *S. exitiosa, Tecia solanivora, Telehin licus, Thaumatopoea pityocampa, Thaumatotibia* (=*Cryptophlebia*) *leucotreta, Thaumetopoea pityocampa, Thecla* spp., *Theresimima ampelophaga, Thyrinteina* spp, *Tildenia inconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta* (=*Scrobipalpula*) *absoluta, Udea* spp. such as *U. rubigalis, U. rubigalis, Virachola* spp., *Yponomeuta padella,* and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabripennis; Anthonomus* spp. such as *A. eugenii, A. grandis, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilis, C. napi; Chaetocnema tibialis, Cleonus mendicus, Conoderus* spp. such as *C. vespertinus, Conotrachelus nenuphar, Cosmopolites* spp., *Costelytra zealandica, Crioceris asparagi Cryptolestes ferrugineus, Cryptorhynchus lapathi Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti* (*Diocalandra stigmaticollis*), *Enaphalodes rufulus, Epilachna* spp. such as *E. varivestis, E. vigintioctomaculata; Epitrix* spp. such as *E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophilus, Lixus* spp., *Luperodes* spp., *Lyctus* spp. such as *L. bruneus; Liogenys fuscus, Macrodactylus* spp. such as *M. subspinosus; Maladera matrida, Megaplatypus mutates, Megascelis* spp., *Melanotus communis, Meligethes* spp. such as *M. aeneus, Melolontha* spp. such as *M. hippocastani, M. melolontha; Metamasius hemipterus, Microtheca* spp., *Migdolus* spp. such as *M. fryanus, Monochamus* spp. such as *M. alternatus; Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochleariae; Phoracantha recurva, Phyllobius pyri, Phyllopertha horticola, Phyllophaga* spp. such as *P. helleri, Phyllotreta* spp. such as *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus; Saperda candida, Scolytus schevyrew Scyphophorus acupunctatus, Sitona lineatus, Sitophilus* spp. such as *S. granaria, S. oryzae, S. zeamais; Sphenophorus* spp. such as *S. levis; Stegobium paniceum, Sternechus* spp. such as *S. subsignatus; Strophomorphus ctenotus, Symphyletes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus;* and, *Zabrus* spp. such as *Z. tenebrioides;* insects from the order of Diptera for example *Aedes* spp. such as *A. aegypti A. albopictus, A. vexans; Anastrepha ludens, Anopheles* spp. such as *A. albimanus, A. crucians, A. freeborni A. gambiae, A. leucosphyrus, A. maculipennis, A. minimus, A. quadrimaculatus, A. sinensis; Bactrocera invadens, Bibio hortulanus, Calliphora erythrocephala, Calliphora vicina, Ceratitis capitata, Chrysomyia* spp. such as *C. bezziana, C. hominivorax, C. macellaria; Chrysops atlanticus, Chrysops discalis, Chrysops silacea, Cochliomyia* spp. such as *C. hominivorax; Contarinia* spp. such as *C. sorghicola; Cordylobia anthropophaga, Culex* spp. such as *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii, Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypo-* derma spp. such as *H. lineata; Hyppobosca* spp., *Hydrellia philippina, Leptoconops torrens, Liriomyza* spp. such as *L. sativae, L. trifolii; Lucilia* spp. such as *L. caprina, L. cuprina, L. sericata; Lycoria pectoralis, Mansonia titillanus, Mayetiola* spp. such as *M. destructor Musca* spp. such as *M. autumnalis, M. domestica; Muscina stabulans, Oestrus* spp. such as *O. ovis, Opomyza florum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa*, and *Wohlfahrtia* spp;

insects from the order of Thysanoptera for example, *Baliothrips biformis, Dichromothrips corbetti; Dichromothrips* ssp., *Echinothrips americanus, Enneothrips flavens, Frankliniella* spp. such as *F. fusca, F. occidentalis, F. tritici, Heliothrips* spp., *Hercinothrips femoralis, Kakothrips* spp., *Microcephalothrips abdominalis, Neohydatothrips samayunkar, Pezothrips kellyanus, Rhipiphorothrips cruentatus, Scirtothrips* spp. such as *S. citri, S. dorsalis, S. perseae; Stenchaetothrips* spp, *Taeniothrips cardamoni Taeniothrips inconsequens, Thrips* spp. such as *T. imagines, T. hawaiiensis, T. oryzae, T. palmi, T. parvispinus, T. tabaci;* insects from the order of Hemiptera for example, *Acizzia jamatonica, Acrosternum* spp. such as *A. hilare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *A. craccivora, A. fabae, A. forbes; A. gossypii, A. grossulariae, A. maidiradicis, A. pomi, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli (Paratrioza cockerelli), Bemisia* spp. such as *B. argentifolii, B. tabaci (Aleurodes tabac); Blissus* spp. such as *B. leucopterus; Brachycaudus* spp. such as *B. cardui, B. helichrysi, B. persicae, B. prunicola; Brachycolus* spp., *Brachycorynella asparagi, Brevicoryne brassicae, Cacopsylla* spp. such as *C. fulguralis, C. pyricola (Psylla piri), Calligypona marginata, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *C. hemipterus, C. lectularius; Coccomytilus halli, Coccus* spp. such as *C. hesperidum, C. pseudomagnoliarum; Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. such as *D. citrifolii; Dalbulus maidis, Diaphorina* spp. such as *D. citri, Diaspis* spp. such as *D. bromeliae, Dichelops furcatus, Diconocoris hewetti, Doralis spp., Dreyfusia nordmannianae, Dreyfusia piceae, Drosicha* spp., *Dysaphis* spp. such as *D. plantaginea, D. pyri, D. radicola; Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidiaspis leperii, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus; Fiorinia theae, Geococcus coffeae, Glycaspis brimblecombe Halyomorpha* spp. such as *H. halys; Heliopeltis* spp., *Homalodisca vitripennis (=H. coagulata), Horcias nobilellus, Hyalopterus pruni, Hyperomyzus lactucae, Icerya* spp. such as *I. purchase, Idiocerus* spp., *Idioscopus* spp., *Laodelphax striatellus, Lecanium* spp., *Lecanoideus floccissimus, Lepidosaphes* spp. such as *L. ulmi, Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) caryaefoliae, Metcafiella* spp., *Metopolophium dirhodum, Monellia costalis, Monelliopsis pecanis, Myzocallis coryi, Murgantia* spp., *Myzus* spp. such as *M. ascalonicus, M. ceras; M. nicotianae, M. persicae, M. varians; Nasonovia ribis-nigr Neotoxoptera formosana, Neomegalotomus* spp, *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagona, Pseudococcus* spp. such as *P. comstocki, Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus (=Stictocephala festina), Stephanitis nash Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis;* and *Viteus vitifolii,*

Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus*

*kuriphilus*, *Formica* spp., *Hoplocampa* spp. such as *H. minuta*, *H. testudinea*; *Iridomyrmex humilis*, *Lasius* spp. such as *L. niger*, *Linepithema humile*, *Liometopum* spp., *Leptocybe invasa*, *Monomorium* spp. such as *M. pharaonis*, *Monomorium*, *Nylandria fulva*, *Pachycondyla chinensis*, *Paratrechina longicornis*, *Paravespula* spp., such as *P. germanica*, *P. pennsylvanica*, *P. vulgaris*; *Pheidole* spp. such as *P. megacephala*; *Pogonomyrmex* spp. such as *P. barbatus*, *P. californicus*, *Polistes rubiginosa*, *Prenolepis impairs*, *Pseudomyrmex gracilis*, *Schelipron* spp., *Sirex cyaneus*, *Solenopsis* spp. such as *S. geminata*, *S.invicta*, *S. molesta*, *S. richteri*, *S. xyloni*, *Sphecius speciosus*, *Sphex* spp., *Tapinoma* spp. such as *T. melanocephalum*, *T. sessile*; *Tetramorium* spp. such as *T. caespitum*, *T. bicarinatum*, *Vespa* spp. such as *V. crabro*; *Vespula* spp. such as *V. squamosal*; *Wasmannia auropunctata*, *Xylocopa* sp;

Insects from the order Orthoptera for example *Acheta domesticus*, *Calliptamus italicus*, *Chortoicetes terminifera*, *Ceuthophilus* spp., *Diastrammena asynamora*, *Dociostaurus maroccanus*, *Gryllotalpa* spp. such as *G. africana*, *G. gryllotalpa*; *Gryllus* spp., *Hieroglyphus daganensis*, *Kraussaria angulifera*, *Locusta* spp. such as *L. migratoria*, *L. pardalina*; *Melanoplus* spp. such as *M. bivittatus*, *M. femurrubrum*, *M. mexicanus*, *M. sanguinipes*, *M. spretus*; *Nomadacris septemfasciata*, *Oedaleus senegalensis*, *Scapteriscus* spp., *Schistocerca* spp. such as *S. americana*, *S. gregaria*, *Stemopelmatus* spp., *Tachycines asynamorus*, and *Zonozerus variegatus*;

Pests from the Class Arachnida for example Acari, e.g. of the families Argasidae, Ixodidae and Sarcoptidae, such as *Amblyomma* spp. (e.g. *A. americanum*, *A. variegatum*, *A. maculatum*), *Argas* spp. such as *A. persicu*), *Boophilus* spp. such as *B. annulatus*, *B. decoloratus*, *B. microplus*, *Dermacentor* spp. such as *D. silvarum*, *D. andersoni*, *D. variabilis*, *Hyalomma* spp. such as *H. truncatum*, *Ixodes* spp. such as *I. ricinus*, *I. rubicundus*, *I. scapularis*, *I. holocyclus*, *I. pacificus*, *Rhipicephalus sanguineus*, *Ornithodorus* spp. such as *O. moubata*, *O. hermsi*, *O. turicata*, *Ornithonyssus bacoti*, *Otobius megnini*, *Dermanyssus gallinae*, *Psoroptes* spp. such as *P. ovis*, *Rhipicephalus* spp. such as *R. sanguineus*, *R. appendiculatus*, *Rhipicephalus evertsi*, *Rhizoglyphus* spp., *Sarcoptes* spp. such as *S. Scabiei*; and Family Eriophyidae including *Aceria* spp. such as *A. sheldoni*, *A. anthocoptes*, *Acallitus* spp., *Aculops* spp. such as *A. lycopersici*, *A. pelekassi*; *Aculus* spp. such as *A. schlechtendali*; *Colomerus vitis*, *Epitrimerus pyri*, *Phyllocoptruta oleivora*; *Eriophytes ribis* and *Eriophyes* spp. such as *Eriophyes sheldoni*; Family Tarsonemidae including *Hemitarsonemus* spp., *Phytonemus pallidus* and *Polyphagotarsonemus latus*, *Stenotarsonemus* spp. *Steneotarsonemus spinki*; Family Tenuipalpidae including *Brevipalpus* spp. such as *B. phoenicis*; Family Tetranychidae including *Eotetranychus* spp., *Eutetranychus* spp., *Oligonychus* spp., *Petrobia latens*, *Tetranychus* spp. such as *T. cinnabarinus*, *T. evansi*, *T. kanzawai*, *T. pacificus*, *T. phaseulus*, *T. telarius* and *T. urticae*, *Bryobia praetiosa*; *Panonychus* spp. such as *P. ulmi*, *P. citri*; *Metatetranychus* spp. and *Oligonychus* spp. such as *O. pratensis*, *O. perseae*, *Vasates lycopersici*; *Raoiella indica*, Family Carpoglyphidae including *Carpoglyphus* spp.; *Penthaleidae* spp. such as *Halotydeus destructor*, Family Demodicidae with species such as *Demodex* spp.; Family Trombicidea including *Trombicula* spp.; Family Macronyssidae including *Ornothonyssus* spp.; Family Pyemotidae including *Pyemotes tritici*; *Tyrophagus putrescentiae*; Family Acaridae including *Acarus siro*; Family Araneida including *Latrodectus mactans*, *Tegenaria agrestis*, *Chiracanthium* sp, *Lycosa* sp *Achaearanea tepidariorum* and *Loxosceles reclusa*;

Pests from the Phylum Nematoda, for example, plant parasitic nematodes such as root-knot nematodes, *Meloidogyne* spp. such as *M. hapla*, *M. incognita*, *M. javanica*; cyst-forming nematodes, *Globodera* spp. such as *G. rostochiensis*; *Heterodera* spp. such as *H. avenae*, *H. glycines*, *H. schachtii*, *H. trifolii*; Seed gall nematodes, *Anguina* spp.; Stem and foliar nematodes, *Aphelenchoides* spp. such as *A. besseyi*; Sting nematodes, *Belonolaimus* spp. such as *B. longicaudatus*; Pine nematodes, *Bursaphelenchus* spp. such as *B. lignicolus*, *B. xylophilus*; Ring nematodes, *Criconema* spp., *Criconemella* spp. such as *C. xenoplax* and *C. ornata*; and, *Criconemoides* spp. such as *Criconemoides informis*; *Mesocriconema* spp.; Stem and bulb nematodes, *Ditylenchus* spp. such as *D. destructor*, *D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus*, *P. neglectus*, *P. penetrans*, *P. curvitatus*, *P. goodeyi*; Burrowing nematodes, *Radopholus* spp. such as *R. similis*; *Rhadopholus* spp.; *Rhodopholus* spp.; Reniform nematodes, *Rotylenchus* spp. such as *R. robustus*, *R. reniformis*; *Scutellonema* spp.; Stubby-root nematode, *Trichodorus* spp. such as *T. obtusus*, *T. primitivus*; *Paratrichodorus* spp. such as *P. minor*; Stunt nematodes, *Tylenchorhynchus* spp. such as *T. claytoni*, *T. dubius*; Citrus nematodes, *Tylenchulus* spp. such as *T. semipenetrans*; Dagger nematodes, *Xiphinema* spp., and other plant parasitic nematode species;

Insects from the order Isoptera for example *Calotermes flavicollis*, *Coptotermes* spp. such as *C. formosanus*, *C. gestroi* *C. acinaciformis*; *Cornitermes cumulans*, *Cryptotermes* spp. such as *C. brevis*, *C. cavifrons*; *Globitermes sulfureus*, *Heterotermes* spp. such as *H. aureus*, *H. longiceps*, *H. tenuis*; *Leucotermes flavipes*, *Odontotermes* spp., *Incisitermes* spp. such as *I. minor*, *I. Snyder*, *Marginitermes hubbardi*, *Mastotermes* spp. such as *M. darwiniensis* *Neocapritermes* spp. such as *N. opacus*, *N. parvus*; *Neotermes* spp., *Procornitermes* spp., *Zootermopsis* spp. such as *Z. angusticollis*, *Z. nevadensis*, *Reticulitermes* spp. such as *R. hesperus*, *R. tibialis*, *R. speratus*, *R. flavipes*, *R. grassei* *R. lucifugus*, *R. santonensis*, *R. virginicus*; *Termes natalensis*, Insects from the order Blattaria for example *Blatta* spp. such as *B. orientalis*, *B. lateralis*; *Blattella* spp. such as *B. asahinae*, *B. germanica*; *Leucophaea maderae*, *Panchlora nivea*, *Periplaneta* spp. such as *P. americana*, *P. australasiae*, *P. brunnea*, *P. fuligginosa*, *P. japonica*; *Supella longipalpa*, *Parcoblatta pennsylvanica*, *Eurycotis floridana*, *Pycnoscelus surinamensis*, Insects from the order Siphonoptera for example *Cediopsylla simples*, *Ceratophyllus* spp., *Ctenocephalides* spp. such as *C. felis*, *C. canis*, *Xenopsylla cheopis*, *Pulex irritans*, *Trichodectes canis*, *Tunga penetrans*, and *Nosopsyllus fasciatus*, Insects from the order Thysanura for example *Lepisma saccharina*, *Ctenolepisma urbana*, and *Thermobia domestica*, Pests from the class Chilopoda for example *Geophilus* spp., *Scutigera* spp. such as *Scutigera coleoptrata*;

Pests from the class Diplopoda for example *Blaniulus guttulatus*, *Julus* spp., *Narceus* spp., Pests from the class Symphyla for example *Scutigerella immaculata*, Insects from the order Dermaptera, for example *Forficula auricularia*, Insects from the order Collembola, for example *Onychiurus* spp., such as *Onychiurus armatus*, Pests from the order Isopoda for example, *Armadillidium vulgare*, *Oniscus asellus*, *Porcellio scaber*, Insects from the order Phthiraptera, for example *Damalinia* spp., *Pediculus* spp. such as *Pediculus humanus capitis*, *Pediculus humanus corporis*, *Pediculus humanus humanus*, *Pthirus pubis*, *Haematopinus* spp. such as *Haematopinus eurysternus*, *Haematopinus suis*; *Linognathus* spp. such as *Linognathus vituli*; *Bovicola bovis*, *Menopon galllinae*, *Menacanthus stramineus* and *Solenopotes capillatus*, *Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata*, *Succinea* spp.; from the class of the helminths, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp. such as *Haemonchus contortus*; *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercora lis*, *Stronyloides* spp., *Taenia saginata*, *Taenia solium*, *Trichinella spiralis*, *Trichinella nativa*, *Trichinella britovi*, *Trichinella nelson*, *Trichinella pseudospiralis*, *Trichostrongulus* spp., *Trichuris trichiura*, *Wuchereria bancrofti*.

The compounds of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention.

The present invention also relates to the non-therapeutic use of compounds of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds of the present invention for controlling or combating parasites. Moreover, the present invention relates to a non-therapeutic method of combating or controlling parasites, which comprises applying to a locus a parasiticidally effective amount of a compound of the present invention.

The compounds of the present invention can be effective through both contact (via soil, glass, wall, bed net, carpet, blankets or animal parts) and ingestion (e.g. baits). Furthermore, the compounds of the present invention can be applied to any and all developmental stages.

The compounds of the present invention can be applied as such or in form of compositions comprising the compounds of the present invention.

The compounds of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the present invention and compositions comprising them can be applied orally, parenterally or topically, e.g. dermally. The compounds of the present invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention are especially useful for combating parasites of the following orders and species, respectively:

fleas (Siphonaptera), e.g. *Ctenocephalides felis*, *Ctenocephalides canis*, *Xenopsylla cheopis*, *Pulex irritans*, *Tunga penetrans*, and *Nosopsyllus fasciatus*; cockroaches (Blattaria-Blattodea), e.g. *Blattella germanica*, *Blattella asahinae*, *Periplaneta americana*, *Periplaneta japonica*, *Periplaneta brunnea*, *Periplaneta fuligginosa*, *Periplaneta australasiae*, and *Blatta orientalis*; flies, mosquitoes (Diptera), e.g. *Aedes aegypti*, *Aedes albopictus*, *Aedes vexans*, *Anastrepha ludens*, *Anopheles maculipennis*, *Anopheles crucians*, *Anopheles albimanus*, *Anopheles gambiae*, *Anopheles freeborni*, *Anopheles leucosphyrus*, *Anopheles minimus*, *Anopheles quadrimaculatus*, *Callliphora vicina*, *Chrysomya bezziana*, *Chrysomya hominivorax*, *Chrysomya macellaria*, *Chrysops discalis*, *Chrysops silacea*, *Chrysops atlanticus*, *Cochliomyia hominivorax*, *Cordylobia anthropophaga*, *Culicoides furens*, *Culex pipiens*, *Culex nigripalpus*, *Culex quinquefasciatus*, *Culex tarsalis*, *Culiseta inornata*, *Culiseta melanura*, *Dermatobia hominis*, *Fannia canicularis*, *Gas-* terophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola, and Tabanus similis; lice (Phthiraptera), e.g. Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus and Solenopotes capilllatus; ticks and parasitic mites (Parasitiformes): ticks (Ixodida), e.g. Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Omithodorus hermsi, Ornithodorus turicata and parasitic mites (Mesostigmata), e.g. Omithonyssus bacoti and Dermanyssus gallinae; Actinedida (Prostigmata) und Acaridida (Astigmata), e.g. Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., and Laminosioptes spp; Bugs (Heteropterida): Cimex lectularius, Cimex hemipterus, Reduvius senilis, Triatoma spp., Rhodnius ssp., Panstrongylus ssp., and Arilus critatus; Anoplurida, e.g. Haematopinus spp., Linognathus spp., Pediculus spp., Phtirus spp., and Solenopotes spp.; Mallophagida (suborders Arnblycerina and Ischnocerina), e.g. Trimenopon spp., Menopon spp., Trinoton spp., Bovicola spp., Werneckiella spp., Lepikentron spp., Trichodectes spp., and Felicola spp.; Roundworms Nematoda: Wipeworms and Trichinosis (Trichosyringida), e.g. Trichinellidae (Trichinella spp.), (Trichuridae) Trichuris spp., Capillaria spp.; Rhabditida, e.g. Rhabditis spp., Strongyloides spp., Helicephalobus spp.; Strongylida, e.g. Strongylus spp., Ancylostoma spp., Necator americanus, Bunostomum spp. (Hookworm), Trichostrongylus spp., Haemonchus contortus, Ostertagia spp., Cooperia spp., Nematodirus spp., Dictyocaulus spp., Cyathostoma spp., Oesophagostomum spp., Stephanurus dentatus, Ollulanus spp., Chabertia spp., Stephanurus dentatus, Syngamus trachea, Ancylostoma spp., Uncinaria spp., Globocephalus spp., Necator spp., Metastrongylus spp., Muellerius capillaris, Protostrongylus spp., Angiostrongylus spp., Parelaphostrongylus spp., Aleurostrongylus abstrusus, and Dioctophyma renale; Intestinal roundworms (Ascaridida), e.g. Ascaris lumbricoides, Ascaris suum, Ascaridia galli, Parascaris equorum, Enterobius vermicularis (Threadworm), Toxocara canis, Toxascaris leonine, Skrjabinema spp., and Oxyuris equi; Camallanida, e.g. Dracunculus medinensis (guinea worm); Spirurida, e.g. Thelazia spp., Wuchereria spp., Brugia spp., Onchocerca spp., Dirofilari spp.a, Dipetalonema spp., Setaria spp., Elaeophora spp., Spirocerca lupi, and Habronema spp.; Thorny headed worms (Acanthocephala), e.g. Acanthocephalus spp., Macracanthorhynchus hirudinaceus and Oncicola spp., Planarians (Plathelminthes): Flukes (Trematoda), e.g. Faciola spp., Fascioloides magna, Paragonimus spp., Dicrocoelium spp., Fasciolopsis buski, Clonorchis sinensis, Schistosoma spp., Trichobilharzia spp., Alaria alata, Paragonimus spp., and Nanocyetes spp.; Cercomeromorpha, in particular Cestoda (Tapeworms), e.g. Diphyllobothrium spp., Tenia spp., Echinococcus spp., Dipylidium caninum, Multiceps spp., Hymenolepis spp., Mesocestoides spp., Vampirolepis spp., Moniezia spp., Anoplocephala spp., Sirometra spp., Anoplocephala spp., and Hymenolepis spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the present invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

The present invention is now illustrated in further details by the following examples.

Compounds can be characterized e.g. by coupled High Performance Liquid Chromatography/mass spectrometry (HPLC/MS), by $^1$H-NMR and/or by their melting points.

Analytical HPLC:

Method 1: Phenomenex Kinetex 1.7 µm XB-C18 100A; 50×2.1 mm. Elution: acetonitrile+0.1% trifluoroacetic acid (TFA)/water+0.1% trifluoroacetic acid (TFA) in a ratio of from 5:95 to 95:5 in 1.5 minutes at 50° C.

Method 2: BEH C18 1.7 µm; 50×2.1 mm. Elution: acetonitrile+0.1% formic acid (FA)/water+0.1% 0.1% formic acid (FA) in a ratio of from 5:95 to 95:5 in 5 minutes at 40° C.

Method 3: Agilent Eclipse Plus C18, 50×4.6 mm, ID 5 µm; Elution: A=10 mM Amm. Formate (0.1% Formic Acid), B=Acetonitrile (0.1% Formic Acid), Flow=1.2 ml/min. at 30° C.; Gradient:=10% B to 100% B-3 min, hold for 1 min, 1 min-10% B. Run Time=5.01 min.

$^1$H-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: d for day(s), h for hour(s), min for minute(s), r.t./room temperature for 20-25° C., Rt for retention time; DMSO for dimethyl sulfoxide, OAc for acetate, EtOAc for ethyl acetate, THF for tetrahydrofuran, and t-BuOH for tert-butanol.

Synthesis Examples

Example 1: 3-(2,6-dimethylphenyl)-2-[(E)-[3-[4-(trifluoromethoxy)phenyl]imidazo[4,5-f]quinolin-7-yl]methylenehydrazono]thiazolidin-4-one (Compound C-2)

Step 1: 6-Fluoro-2-methyl-5-nitro-quinoline

To a solution of 6-fluoro 2-methylquinoline (5 g, 31 mmol) in concentrated sulfuric acid (30 mL) at 0° C. was added sodium nitrite (2.9 g, 34.12 mmol). The reaction mixture was stirred at room temperature for 12 h and subsequently poured into a mixture of ice and water. The mixture was basified with saturated sodium bicarbonate solution. The suspended solids were filtered and dried and purified by silica gel flash column chromatography eluting with 15% ethyl acetate in heptane to afford the title compound (3.5 g, 54% yield) as a yellow solid. LC/MS (method 3): $R_t$: 2.45 min; MS: m/z=207 (M)+; $^1$H NMR (300 MHz, DMSO-$d_6$): δ 8.34-8.29 (m, 2H), 7.96 (m, 1H), 7.71 (d, J=6 Hz, 1H), 2.70 (s, 3H).

Step 2: 2-Methyl-5-nitro-N-[4-(trifluoromethoxy)phenyl]quinolin-6-amine

A mixture of 6-fluoro-2-methyl-5-nitro-quinoline (2.2 g, 10.7 mmol) and 4-trifluoromethoxy aniline (3.78 g, 21.34 mmol) in acetonitrile was heated at 80° C. for 24 h. The reaction was allowed to cool to ambient temperature and was evaporated under vacuum. Water (100 mL) was added to the residue and the mixture was extracted with ethyl acetate (2×100 mL). The combined organic extracts were dried over anhydrous sodium sulfate and concentrated under vacuum to get a residue which was purified by silica gel flash column chromatography eluting with 12% ethyl acetate in heptane to afford the title product (3.5 g, 90% yield) as a yellow solid. LC/MS (method 3): $R_t$: 3.24 min; MS: m/z=364 (M+); $^1$H NMR (300 MHz, DMSO-$d_6$): δ 9.75 (s, 1H), 8.91 (d, J=9 Hz, 1H), 8.04 (s, 1H), 7.54-7.44 (m, 2H), 7.39 (m, 4H), 2.74 (s, 3H).

Step 3: 2-Methyl-N6-[4-(trifluoromethoxy)phenyl]quinoline-5,6-diamine

To a solution of 2-methyl-5-nitro-N-[4-(trifluoromethoxy)phenyl]quinolin-6-amine (3.5 g, 9.63 mmol) in methanol (50 mL) was added stannous chloride (6.5 g, 28.9 mmol) and maintained at 60° C. for 4 h. The reaction was cooled to ambient temperature and water (100 mL) was added and the mixture basified with saturated sodium bicarbonate solution. Ethyl acetate (200 mL) was added and the mixture was filtered through a celite bed. The organic part of the filtrate was separated and dried over anhydrous sodium sulfate and evaporated under reduced pressure. The residue obtained was triturated with pentane to get the title compound (3 g, 93% yield) as an off white solid. LC/MS (method 3): $R_t$: 2.05 min; MS: m/z=334 (M+); $^1$H NMR (300 MHz, DMSO-$d_6$): δ 8.47 (d, J=6 Hz, 1H), 7.58 (s, 1H), 7.37 (d, J=9 Hz, 1H), 7.28 (d, J=9 Hz, 1H), 7.19 (d, J=9 Hz, 1H), 7.12-7.17 (m, 2H), 6.47-6.67 (m, 2H), 5.54 (s, 2H), 2.59 (s, 3H).

Step 4: 7-Methyl-3-[4-(trifluoromethoxy)phenyl]imidazo[4,5-f]quinolone

2-Methyl-N6-[4-(trifluoromethoxy)phenyl]quinoline-5,6-diamine (3 g, 9 mmol) was taken up in formic acid (50 mL) and maintained at 50° C. for 5 h. The reaction was cooled to ambient temperature and the volatiles were evaporated under vacuum. The residue obtained was suspended in water (100 mL) and basified with saturated sodium bicarbonate solution. The mixture was extracted with ethyl acetate (2×100 mL). The combined ethyl acetate extracts were dried over anhydrous sodium sulfate and concentrated under vacuum to get the title product as a beige solid (2.8 g, 90% yield). LC/MS (method 3): $R_t$: 2.18 min; MS: m/z=344 (M+); $^1$H NMR (300 MHz, DMSO-$d_6$): δ 8.79 (d, J=9 Hz, 1H), 8.72 (s, 1H), 7.96-7.91 (m, 3H), 7.84 (d, J=9 Hz, 1H), 7.67-7.70 (m, 2H), 7.58 (d, J=9 Hz, 1H), 2.70 (s, 3H).

Step 5: 3-[4-(Trifluoromethoxy)phenyl]imidazo[4,5-f]quinoline-7-carbaldehyde

To a suspension of selenium dioxide (5.43 g, 48.94 mmol) in 1,4-dioxane (80 mL) at 60° C. 7-methyl-3-[4-(trifluoromethoxy)phenyl]imidazo[4,5-f]quinolone was added in one portion. The reaction mixture was heated at 80° C. for 12 h and subsequently cooled to ambient temperature. Water (100 mL) was added and the mixture was extracted with Ethyl acetate (2×100 mL). The combined organic extracts were passed through a celite bed and dried over anhydrous sodium sulphate and concentrated under vacuum. The residue obtained was purified by silica gel flash column chromatography eluting with 50% ethyl acetate in heptane to afford the title compound (2.6 g, 89% yield) as an off white solid. LC/MS (method 3): $R_t$: 2.86 min; MS: m/z=358 (M+); $^1$H NMR (300 MHz, DMSO-$d_6$): δ 10.17 (s, 1H), 9.11 (d, J=9 Hz, 1H), 8.85 (m, 1H), 8.17 (d, J=9 Hz, 1H), 8.143-8.146 (m, 2H), 7.95-7.98 (m, 2H), 7.72 (d, J=9 Hz, 2H).

Step 6: 1-(2,6-Dimethylphenyl)-3-[(E)-[3-[4-(trifluoromethoxy)phenyl]imidazo[4,5-f]quinolin-7-yl]methyleneamino]thiourea A mixture of 3-[4-(trifluoromethoxy)phenyl]imidazo[4,5-f]quinoline-7-carbaldehyde (400 mg, 1.12 mmol) and 1-amino-3-(2,6-dimethylphenyl)thiourea (220 mg, 1.12 mmol) in ethanol (30 mL) was heated at 80° C. for 5 h. The reaction mixture was allowed to cool to ambient temperature and the precipitated solid was collected by filtration and washed with cold ethanol and dried under vacuum to afford 500 mg (83% yield) of title compound as a beige solid. LC/MS (method 3): $R_t$: 3.10 min; MS: m/z=535 (M)+); $^1$H NMR (300 MHz, DMSO-$d_6$): δ 12.11 (s, 1H), 10.18 (s, 1H), 8.85-8.76 (m, 3H), 8.35 (s, 1H), 8.02-7.95 (m, 4H), 7.69-7.66 (m, 2H), 7.15-7.14 (m, 3H), 2.21 (s, 6H).

Step 7: 3-(2,6-dimethylphenyl)-2-[(E)-[3-[4-(trifluoromethoxy)phenyl]imidazo[4,5-f]quinolin-7-yl]methylenehydrazono]thiazolidin-4-one To a solution of 1-(2,6-dimethylphenyl)-3-[(E)-[3-[4-(trifluoromethoxy)phenyl]imidazo[4,5-f]quinolin-7-yl]methyleneamino]thiourea (200 mg, 0.37 mmol) and sodium acetate (90 mg, 1.12 mmol) in ethanol (20 mL) was added methyl bromoacetate (0.05 mL, 0.56 mmol) and reaction mixture was stirred at 65° C. for 48 h. The reaction mixture was evaporated under reduced pressure and water (50 mL) was added and extracted with ethyl acetate (2×50 mL). The combined organic extracts were dried over anhydrous sodium sulphate concentrated under vacuum and the residue was purified by silica gel flash column chromatography eluting with 30% ethyl acetate in n-heptane as an eluent to afford 150 mg (70% yield) of the title compound as a beige solid. LC/MS (method 3): $R_t$: 3.31 min; MS: m/z=575 (M$^+$). $^1$H NMR (300 MHz, DMSO-d$_6$): δ 9.00 (d, J=9 Hz, 1H), 8.79 (s, 1H), 8.34 (s, 1H), 8.29 (d, J=9 Hz, 1H), 8.03 (d, J=9 Hz, 1H), 7.96-7.92 (m, 3H), 7.71 (d, J=9 Hz, 2H), 7.34-7.29 (m, 1H), 7.25-7.23 (m, 2H), 4.34 (s, 2H), 2.14 (s, 6H).

Example 2: 3-(2-Isopropyl-5-methyl-phenyl)-2-[(E)-[3-[4-(trifluoromethoxy)phenyl]imidazo[4,5-f]quinolin-7-yl]methylenehydrazono]thiazolidin-4-one (Compound C-6)

Step 1: 1-(2-Isopropyl-5-methyl-phenyl)-3-[(E)-[3-[4-(trifluoromethoxy)phenyl]imidazo[4,5-f]quinolin-7-yl]methyleneamino]thiourea A mixture of 3-[4-(trifluoromethoxy)phenyl]imidazo[4,5-f]quinoline-7-carbaldehyde (200 mg, 0.56 mmol) and 1-amino-3-(2-isopropyl-5-methyl-phenyl)thiourea (140 mg, 0.62 mmol) in 30 mL of ethanol was heated at 80° C. for 2 h. The reaction mixture was allowed to cool to ambient temperature and the solid precipitated was filtered, washed with cold ethanol and dried to afford 210 mg (65% yield) of the title compound as a beige solid. LC/MS (method 3): $R_t$: 3.34 min; MS: m/z=563 (M$^+$); $^1$H NMR (300 MHz, DMSO-d$_6$): δ 12.11 (s, 1H), 10.25 (s, 1H), 8.87 (d, J=9 Hz, 1H), 8.78-8.75 (m, 2H), 8.37 (s, 1H), 8.03 (d, J=9.3 Hz, 1H), 7.93-7.97 (m, 3H), 7.71 (d, J=9 Hz, 2H), 7.28 (d, J=9 Hz, 1H), 7.15 (d, J=6 Hz, 1H), 7.02 (s, 1H), 3.17 (m, 1H), 2.31 (s, 3H), 1.22 (d, J=6 Hz, 6H).

Step 2: 3-(2-Isopropyl-5-methyl-phenyl)-2-[(E)-[3-[4-(trifluoromethoxy)phenyl]imidazo[4,5-f]quinolin-7-yl]methylenehydrazono]thiazolidin-4-one To a solution of 1-(2-isopropyl-5-methylphenyl)-3-[(E)-[3-[4-(trifluoromethoxy)phenyl]imidazo[4,5-f]quinolin-7-yl]methyleneamino]thiourea (160 mg, 0.28 mmol) and sodium acetate (70 mg, 0.85 mmol) in Ethanol (20 mL) was added Methyl bromoacetate (90 mg, 0.57 mmol) and the mixture was stirred at 45° C. for 24 h. The volatiles were evaporated under vacuum and water (50 mL) was added and the mixture extracted with ethylacetate (2×15 mL). The combined organic extracts were dried over anhydrous sodium sulfate and were concentrated under vacuum to get a residue which was purified by silica gel flash column chromatography eluting with 0.5% methanol in chloroform to afford 80 mg (47% yield) of the title compound as a beige solid. LC/MS (method 3): $R_t$: 3.56 min; MS: m/z=603 (M$^+$). $^1$H NMR (300 MHz, DMSO-d$_6$): δ 9.00 (d, J=9 Hz, 1H), 8.79 (s, 1H), 8.33 (s, 1H), 8.29 (d, J=14 Hz, 1H), 8.0 (d, J=15 Hz, 1H), 7.95-7.96 (m, 3H), 7.65-7.75 (m, 2H), 7.40 (d, J=9 Hz, 1H), 7.40 (d, J=9 Hz, 1H) 7.11 (s, 1H), 4.28 (m, 2H), 2.70-2.80 (m, 1H), 2.33 (s, 3H), 1.10-1.17 (m, 6H)

Example 3: 2-(2,6-Dimethylphenyl)imino-3-[(E)-[3-[4-(trifluoromethoxy)phenyl]imidazo[4,5-f]quinolin-7-yl]methyleneamino]thiazolidin-4-one (compound C-7)

Step 1: 3-Amino-2-(2,6-dimethylphenyl)imino-thiazolidin-4-one

To a solution of 1-amino-3-(2,6-dimethylphenyl)thiourea (200 mg, 1.02 mmol) and sodium acetate (170 mg, 2.05 mmol) in ethanol (20 mL) was added methyl bromoacetate (0.17 mL, 2.05 mmol) and the mixture stirred at 80° C. for 2 h. The reaction was evaporated under reduced pressure and water (20 mL) was added and the mixture was extracted with ethyl acetate (2×20 mL). The combined organic extract was dried over anhydrous sodium sulfate and concentrated under vacuum to yield the desired product as a white solid. LC/MS (method 3): $R_t$: 2.1 min; MS: m/z=236 (M$^+$). $^1$H NMR (300 MHz, DMSO-d$_6$): δ 7.05-7.02 (m, 2H), 6.88-6.93 (m, 1H), 5.33 (s, 2H), 3.96 (s, 2H), 2.05 (s, 6H).

Step 2: 2-(2,6-Dimethylphenyl)imino-3-[(E)-[3-[4-(trifluoromethoxy)phenyl]imidazo[4,5-f]quinolin-7-yl]methyleneamino]thiazolidin-4-one To a solution of 3-[4-(trifluoromethoxy)phenyl]benzo[e]benzimidazole-7-carbaldehyde (120 mg, 0.34 mmol) in acetic acid (10 mL) was added 3-amino-2-(2,6-dimethylphenyl)imino-thiazolidin-4-one (80 mg, 0.34 mmol) and the mixture stirred at ambient temperature for 1 h. The reaction was diluted with water (50 mL) and basified with saturated sodium bicarbonate solution and extracted with EtOAc (2×50 mL). The combined organic layer was dried over anhydrous sodium sulfate and concentrated under vacuum and the residue obtained was triturated with diethyl ether to afford 160 mg (83% yield) of title product as an off white solid. LC/MS (method 3): $R_t$: 3.40 min; MS: m/z=575 (M$^+$). $^1$H NMR (300 MHz, DMSO-d$_6$): δ 9.65 (s, 1H), 9.08 (d, J=6 Hz, 1H), 8.83 (s, 1H), 8.45 (d, J=9 Hz, 1H), 8.10-8.01 (m, 2H), 7.94-7.97 (m, 3H), 7.72 (d, J=9 Hz, 2H), 7.10 (d, J=6 Hz, 2H), 6.98 (m, 1H), 4.16 (s, 2H), 2.13 (s, 6H).

Example 4: 3-(2-isopropylphenyl)-2-[(E)-[3-[6-(trifluoromethyl)pyridazin-3-yl]imidazo[4,5-f]quinolin-7-yl]methylenehydrazono]thiazolidin-4-one (Compound C-10)

Step 1: 2-methyl-5-nitro-quinolin-6-amine 6-fluoro-2-methyl-5-nitro-quinoline (3.7 g, 16.9 mmol) was stirred in aqueous. Ammonia (200 ml, 27%) for 12 h. Water (100 mL) was added and the mixture Ethyl acetate (2×50 mL). The organic extracts were dried over anhydrous sodium sulphate and evaporated under vacuum to get the title compound as a yellow solid (3 g, 87%). LC/MS (method 3): $R_t$: 1.64 min MS: m/z=204 (M$^+$). $^1$H NMR (300 MHz, DMSO-d$_6$) 1H NMR (300 MHz, DMSO-d6) δ 8.84 (d, J=8.9 Hz, 1H), 8.15 (s, 2H), 7.86 (d, J=9.4 Hz, 1H), 7.46 (d, J=8.9 Hz, 1H), 7.37 (d, J=9.4 Hz, 1H), 2.56 (s, 3H).

Step 2: 2-methylquinoline-5,6-diamine

To a solution of 2-methyl-5-nitro-quinolin-6-amine (3 g, 14.76 mmol) in Methanol (50 mL) was added Stannous chloride dihydrate (11.1 g, 59 mmol) and the mixture heated at 60° C. for 12 h. The reaction was cooled to room temperature and diluted with water (20 mL).Saturated Sodium bicarbonate solution (50 mL) was added and the mixture extracted with Ethyl Acetate. The Ethyl acetate extracts were dried over anhydrous Sodium sulphate and evaporated under vacuum to get a residue which was purified by silica gel flash column chromatography using 5% MeOH in Dichloromethane as an eluent to afford the title compound (1.8 g, 70%); LC/MS (method 3): $R_t$: 0.56 min MS: m/z=174 (M$^+$); $^1$H NMR (300 MHz, DMSO-d$_6$) δ 8.21 (d, J=8.7 Hz, 1H), 7.16-7.00 (m, 3H), 4.95 (s, 2H), 4.72 (s, 2H), 2.50 (s, 3H).

Step 3: 7-methyl-3-[6-(trifluoromethyl)pyridazin-3-yl]imidazo[4,5-f]quinolone

A solution of 2-methylquinoline-5,6-diamine (2 g, 12 mmol) in Formic acid (20 mL) was stirred at r.t. for 12 h. The volatiles were evaporated under reduced pressure and the residue was taken up in water (100 mL) and was basified with saturated Sodium bicarbonate solution and extracted with EtOAc. The Ethyl acetate extracts were dried over anhydrous Sodium Sulphate and concentrated in vacuum and the residue obtained was purified by trituration with Diethyl ether to obtain the title compound (1.5 g, 71%). LC/MS (method 3): $R_t$: 0.62 min MS: m/z=184 ($M^+$); $^1H$ NMR (300 MHz, DMSO-$d_6$) δ 8.67 (d, J=8.4 Hz, 1H), 8.34 (s, 1H), 7.92 (d, J=9.0 Hz, 1H), 7.71 (d, J=9.0 Hz, 1H), 7.49 (d, J=8.4 Hz, 1H), 2.67 (s, 3H).

Step 4: 7-methyl-3-[6-(trifluoromethyl)pyridazin-3-yl]imidazo[4,5-f]quinoline

To a solution of 7-methyl-3H-imidazo[4,5-f]quinolone (0.2 g, 1.09 mmol) in N, N-Dimethyl formamide (1 mL), was added 3-chloro-6-(trifluoromethyl)pyridazine (0.2 g, 1.09 mmol), Cesium carbonate (0.89 g, 1.64 mmol), 8-Hydroxy quinolone (0.016 g, 0.11 mmol) and Copper Iodide (0.021 g, 0.11 mmol). The reaction mixture was heated at 90° C. for 2 h. The mixture was cooled to ambient temperature and water (50 mL) was added and extracted with Ethyl acetate (2×50 mL). The combined organic layer was dried over anhydrous Sodium sulphate and concentrated under vacuum and the residue was purified by silica gel flash column chromatography eluting with 2% Methanol in Dichloromethane to obtain the title compound (0.23 g, 64%). LC/MS (method 3): $R_t$: 1.83 min; MS: m/z=330.1 ($M^+$).

Step 5: 3-[6-(trifluoromethyl)pyridazin-3-yl]imidazo [4,5-f]quinoline-7-carbaldehyde To a pre-heated suspension of Selenium dioxide (0.34 g, 3.04 mmol) in 1,4-dioxane at 60° C., was added 7-methyl-3-[6-(trifluoromethyl)pyridazin-3-yl]imidazo[4,5-f]quinolone (0.25 g, 0.76 mmol). The temperature of the mixture was raised to 90° C. and stirred for 12 h. The reaction was cooled to ambient temperature and water (50 mL) was added and the mixture extracted with Ethyl acetate (50 mL×2). The combined organic layer was dried over anhydrous Sodium sulphate and concentrated under vacuum and the residue obtained was purified by silica gel flash column chromatography using 2% Methanol in Dichloromethane as the eluent to obtain the title compound (0.23 g, 64%). LC/MS (method 3): $R_t$: 2.47 min; MS: m/z=344 ($M^+$); $^1H$ NMR (300 MHz, DMSO-$d_6$) δ 9.35 (s, 1H), 9.00 (d, J=8.6 Hz, 1H), 8.85 (d, J=9.2 Hz, 1H), 8.79 (d, J=9.3 Hz, 1H), 8.72-8.61 (m, 2H), 7.61-7.48 (m, 2H).

Step 6: 1-(2-isopropylphenyl)-3-[(E)-[3-[6-(trifluoromethyl)pyridazin-3-yl]imidazo[4,5-f]quinolin-7-yl]methyleneamino]thiourea A solution of 3-[6-(trifluoromethyl)pyridazin-3-yl]imidazo[4,5-f]quinoline-7-carbaldehyde (0.1 g, 0.291 mmol) and 1-amino-3-(2-isopropylphenyl)thiourea (0.056 g, 0.269 mmol) in EtOH (10 mL) was heated at 80° C. for 12 h. The mixture was cooled to ambient temperature and the solid precipitated was collected by filtration and was washed with EtOH, dried under vacuum to get the desired product as an off white solid. (0.120 g, 77%). LC/MS (method 3): $R_t$: 2.94 min; MS: m/z=535 ($M^+$); $^1H$ NMR (300 MHz, DMSO-$d_6$) δ 12.15 (s, 1H), 10.32 (s, 1H), 9.34 (s, 1H), 8.93-8.74 (m, 4H), 8.65 (d, J=9.2 Hz, 1H), 8.39 (s, 1H), 8.09 (d, J=9.2 Hz, 1H), 7.44-7.28 (m, 2H), 7.32-7.17 (m, 2H), 3.17 (p, J=6.7 Hz, 1H), 1.22 (d, J=6.9 Hz, 6H).

Step 7: (2Z)-3-(2-isopropylphenyl)-2-[(E)-[3-[6-(trifluoromethyl)pyridazin-3-yl]imidazo[4,5-f]quinolin-7-yl]methylenehydrazono]thiazolidin-4-one To the solution of 1-(2-isopropylphenyl)-3-[(E)-[3-[6-(trifluoromethyl)pyridazin-3-yl]imidazo[4,5-f]quinolin-7-yl] methyleneamino]thiourea (0.1 g 0.187 mmol) in EtOH (10 mL) was added Sodium acetate (0.031 g, 0.374 mmol) and Methyl bromo acetate (0.057 g, 0.374 mmol) and the mixture was heated at 50° C. for 12 h. The mixture was cooled to ambient temperature and water (50 mL) was added and extracted with EtOAc (2×50 mL). The combined organic layer was dried over anhydrous Sodium sulphate and concentration under vacuum and the residue obtained was washed by trituration successively with Methanol and Diethyl ether to get the title compound as an off-white solid. (0.095 g, 88%) LC/MS (method 3): $R_t$: 3.16 min; MS: m/z=575 ($M^+$), $^1H$ NMR (300 MHz, DMSO-$d_6$) δ 9.35 (s, 1H), 9.02 (d, J=8.6 Hz, 1H), 8.81 (dd, J=11.8, 9.3 Hz, 2H), 8.65 (d, J=9.3 Hz, 1H), 8.37-8.25 (m, 2H), 8.08 (d, J=9.3 Hz, 1H), 7.60-7.44 (m, 2H), 7.43-7.26 (m, 2H), 4.33 (d, J=17.4 Hz, 1H), 4.20 (d, J=17.4 Hz, 1H), 2.81 (p, J=6.8 Hz, 1H), 1.17 (dd, J=14.4, 6.8 Hz, 6H).

Example 5: 1-(5-chloro-2-pyridyl)ethyl N-[3-[4-(trifluoromethoxy)phenyl]imidazo[4,5-f]quinolin-7-yl]carbamate (compound C-11)

Step 1: 3-[4-(trifluoromethoxy)phenyl]imidazo[4,5-f]quinoline-7-carboxylic acid

To a preheated suspension of Selenium dioxide (5.17 g, 46.61 mmol) in Pyridine (30 mL) at 60° C. was added 7-methyl-3-[4-(trifluoromethoxy)phenyl]imidazo[4,5-f]quinoline (4 g, 11.65 mmol) in one lot. The temperature was raised up to 100° C. and the mixture stirred for 3 h. The volatiles were evaporated under reduced pressure and water (150 mL) was added and the mixture was acidified with solid Potassium hydrogen sulphate and the mixture extracted with EtOAc (2×150 mL). The combined organic layer was passed through Celite bed and the bed washed with Tetrahydrofuran. The combined filtrate was dried over anhydrous Sodium sulphate and concentrated in vacuum to get a residue which was triturated with Diethyl ether to yield the title compound as a brown solid (4 g, 92%). LC/MS (method 3): $R_t$: 2.240 min; MS: m/z=374.1 ($M^+$); $^1H$ NMR (300 MHz, DMSO-$d_6$) δ 9.05 (d, J=8.5 Hz, 1H), 8.83 (s, 1H), 8.29 (d, J=8.5 Hz, 1H), 8.17-8.01 (m, 2H), 8.01-7.91 (m, 2H), 7.71 (d, J=8.4 Hz, 2H).

Step 2: 1-(5-chloro-2-pyridyl)ethyl N-[3-[4-(trifluoromethoxy)phenyl]imidazo[4,5-f]quinolin-7-yl]carbamate To a solution of 3-[4-(trifluoromethoxy)phenyl]imidazo [4,5-f]quinoline-7-carboxylic acid (0.2 g, 0.53 mmol) in Toluene (20 mL) was added a solution of Diphenylphosphorazidate (0.18 mL, 0.804 mmol) in toluene followed by Triethylamine (0.11 mL, 0.804 mmol) followed by 1-(5-chloro-2-pyridyl)ethanol (0.084 g, 0.536 mmol) and the mixture was heated at 100° C. for 1 h. The mixture was cooled to ambient temperature and saturated Sodium bicarbonate solution was added and the mixture extracted with Ethyl acetate (2×50 mL). The combined organic extracts were dried (anhydrous Sodium sulphate) and concentrated in vacuum to get a residue which was purified by silica gel flash column chromatography using 40% EtOAc in n-Heptane as the eluent to afford the title compound as an off-white solid (0.12 g, 42%). LC/MS (method 3): $R_t$: 3.13 min; MS: m/z=528.3 (M⁺); (300 MHz, DMSO-d₆) δ 10.66 (s, 1H), 8.84 (d, J=9.0 Hz, 1H), 8.70 (s, 1H), 8.62 (d, J=2.5 Hz, 1H), 8.15 (d, J=9.0 Hz, 1H), 8.00 (dd, J=8.4, 2.5 Hz, 1H), 7.92 (dd, J=9.0, 6.8 Hz, 3H), 7.69 (t, J=8.4 Hz, 3H), 7.61 (d, J=8.5 Hz, 1H), 5.84 (q, J=6.6 Hz, 1H), 1.58 (d, J=6.7 Hz, 3H).

Example 6: 1-(2-isopropylphenyl)-3-[(E)-[3-[4-(trifluoromethoxy)phenyl]imidazo[4,5-h]quinolin-7-yl]methyleneamino]thiourea (compound C-13)

Step 1: 3-[4-(trifluoromethoxy)phenyl]imidazo[4,5-h]quinoline-7-carbaldehyde

A mixture of 1-[4-(trifluoromethoxy)phenyl]benzimidazol-4-amine (1.5 g, 5.1 mmol) and 2-iminoethylvinamidinium tritetrafluoborate (5.46 g, 5.3 mmol) was taken up in 2-propanol (100 mL) and the mixture stirred under reflux for 16 h. The reaction mixture was allowed to cool to room temperature and 1M HCl (14 mL) was added. The mixture was stirred at 70° C. for a further 6 h. The mixture was allowed to cool to room temperature and left as such for 14 h. The precipitated solid was filtered, washed with cold 2-propanol and dried to afford 0.9 g (86%) of the title compound. LC/MS (method 3): $R_t$: 2.55 min; MS: m/z=358 (M⁺), ¹H NMR (300 MHz, DMSO-d₆) δ10.29 (s, 1H), 9.45 (d, J=2.0 Hz, 1H), 9.14 (d, J=2.0 Hz, 1H), 8.97 (s, 1H), 8.17 (d, J=8.9 Hz, 1H), 8.01 (d, J=8.8 Hz, 1H), 7.99-7.91 (m, 2H), 7.73 (d, J=8.4 Hz, 2H).

Step 2: 1-(2-isopropylphenyl)-3-[(E)-[3-[4-(trifluoromethoxy)phenyl]imidazo[4,5-h]quinolin-7-yl]methyleneamino]thiourea 3-[4-(trifluoromethoxy)phenyl]imidazo[4,5-h]quinoline-7-carbaldehyde (0.4 g, 1.12 mmol) and 1-amino-3-(2-isopropylphenyl)thiourea (0.23 g, 1.12 mmol) were taken up in Ethanol (12 mL) and the mixture heated to 60° C. for 4 h. The precipitated solid was filtered, washed sequentially with Ethanol and Pentane and dried to afford (0.418 g, 99%) of the title compound as a white solid. LC/MS (method 3): $R_t$: 3.15 min; MS: m/z=549 (M⁺), ¹H NMR (300 MHz, DMSO-d₆) δ 12.02 (s, 1H), 10.16 (s, 1H), 9.62 (d, J=2.0 Hz, 1H), 8.91 (d, J=2.1 Hz, 1H), 8.77 (s, 1H), 8.38 (s, 1H), 8.03-7.92 (m, 2H), 7.90 (s, 2H), 7.71 (d, J=8.4 Hz, 2H), 7.39 (d, J=7.6 Hz, 1H), 7.32 (ddd, J=12.4, 6.8, 3.8 Hz, 1H), 7.25 (q, J=4.1, 3.2 Hz, 2H), 3.18 (p, J=6.9 Hz, 1H), 1.22 (d, J=6.9 Hz, 6H).

Example 7: (2Z)-2-(2-isopropylphenyl)imino-3-[(E)-[3-[4-(trifluoromethoxy)phenyl]imidazo[4,5-h]quinolin-7-yl]methyleneamino]thiazolidin-4-one (compound C-16)

To a solution of 3-[4-(trifluoromethoxy)phenyl]imidazo[4,5-h]quinoline-7-carbaldehyde (0.15 g, 0.42 mmol) in Acetic acid (5 mL) was added 3-amino-2-(2,6-dimethylphenyl)imino-thiazolidin-4-one (0.1 g, 0.42 mmol) and the mixture stirred at ambient temperature for 5 h. The mixture was diluted with a mixture of Ethyl acetate and water and partitioned. The separated organic layer was washed successively with a saturated solution of Sodium bicarbonate, saturated brine, dried (anhydrous Sodium sulphate) and evaporated under reduced pressure. The residue was subjected to silica gel flash column chromatography to obtain the title compound (0.057 g, 22%). LC/MS (method 3): $R_t$:1.85; MS: m/z=589.6 (M⁺), ¹H NMR (300 MHz, DMSO-d₆) δ9.49 (d, J=2.0 Hz, 1H), 9.40 (s, 1H), 9.01 (d, J=2.1 Hz, 1H), 8.79 (s, 1H), 8.07 (d, J=8.9 Hz, 1H), 7.94 (d, J=8.5 Hz, 3H), 7.71 (d, J=8.4 Hz, 2H), 7.32 (d, J=7.4 Hz, 1H), 7.16 (m, 2H), 6.89 (d, J=7.5 Hz, 1H), 4.19 (s, 2H), 3.04 (p, J=7.0 Hz, 1H), 1.16 (d, J=6.9 Hz, 6H).

Example 8: (2Z)-3-(2-isopropylphenyl)-2-[(E)-[3-[4-(trifluoromethoxy)phenyl]imidazo[4,5-h]quinolin-7-yl]methylenehydrazono]thiazolidin-4-one (compound C-17)

To a solution of 1-(2-isopropylphenyl)-3-[(E)-[3-[4-(trifluoromethoxy)phenyl]imidazo[4,5-h]quinolin-7-yl]methyleneamino]thiourea (0.2 g, 0.365 mmol) in Ethanol (8 mL) was added Methyl bromoacetate (0.22 g, 1.46 mmol) and Sodium acetate (0.09 g, 1.09 mmol). The reaction mixture stirred for 5 h at 40° C. and subsequently cooled and partitioned with Ethyl acetate and water. The organic layer was separated dried (anhydrous Sodium sulphate) and evaporated under reduced pressure. The residue was purified by silica gel flash column chromatography to afford the title compound (0.12 g, 96%). LC/MS (method 3): $R_t$: 3.27 min; MS: m/z=589 (M⁺), ¹H NMR (300 MHz, DMSO-d₆) δ9.38 (d, J=2.0 Hz, 1H), 8.76 (s, 1H), 8.72 (d, J=2.1 Hz, 1H), 8.58 (s, 1H), 8.01-7.84 (m, 4H), 7.70 (d, J=8.4 Hz, 2H), 7.51 (q, J=8.1, 7.7 Hz, 2H), 7.41-7.33 (m, 1H), 7.30 (d, J=8.0 Hz, 1H), 4.40-4.10 (m, 2H), 2.91-2.76 (m, 1H), 1.17 (dd, J=11.2, 6.8 Hz, 6H).

Example 9: 1-(2-isopropylphenyl)-3-[(E)-[3-[4-(trifluoromethoxy)phenyl]imidazo[4,5-h]isoquinolin-7-yl]methyleneamino]thiourea (compound C-24)

Step 1: N-[(3-bromophenyl)methyl]-1,1-dimethoxy-propan-2-amine

To a solution of 3-bromo benzyl amine (4 g, 21.62 mmol) in Dichloroethane (60 mL) was added Pyruvic aldehyde dimethyl acetal (2.6 g, 21.62 mmol) and Sodium triacetoxyborohydride (6.4 g, 30.19 mmol). The mixture was stirred at ambient temperature for 16 h. A solution of Sodium hydroxide (2N) was added and the mixture partitioned. The aqueous layer was extracted with Dichloromethane (2×80 mL). The combined organic extracts were washed with brine (40 mL), dried (anhydrous Sodium sulphate) and concentrated under reduced pressure to afford 9.5 g (Quantitative) of the title compound as an oil. LCMS (method 3): $R_t$: 1.56 min; MS: m/z=288.1 (M⁺). ¹H NMR (300 MHz, DMSO-d₆) 1H NMR (300 MHz, DMSO-d6) δ 7.54 (t, J=1.7 Hz, 1H), 7.40 (m, 1H), 7.37-7.20 (m, 2H), 4.09 (d, J=5.8 Hz, 1H), 3.84-3.57 (m, 2H), 3.29 (s, 3H), 3.25 (s, 3H), 2.63 (p, J=6.3 Hz, 1H), 1.89 (d, J=37.5 Hz, 1H), 0.94 (d, J=6.4 Hz, 3H).

Step 2: 7-bromo-3-methyl-isoquinoline

Chlorosulfonic acid (38.6 g, 346 mmol) was cooled to 0° C. and N-[(3-bromophenyl)methyl]-1,1-dimethoxy-propan-2-amine (9.5 g, 33.10 mmol) was added drop wise and the mixture heated to 100° C. for 1 h. The mixture was subsequently cooled to ambient temperature, poured into a mixture of ice and water and extracted the Methyl t-butyl ether (2×60 mL). The aqueous layer was cooled to ~5° C. and basified with Sodium hydroxide solution. Then basified solution was then extracted with Dichloromethane (2×100 mL). The combined Dichloromethane extracts were dried (anhydrous Sodium sulphate) and concentrated under reduced pressure and the residue purified by silica gel flash chromatography (eluent 12-15% Ethyl acetate in heptane) to afford 4.2 g (57%) of the title compound as a yellow solid. LC/MS (method 3): $R_t$: 2.30 min; MS: m/z=222.1 ($M^+$). $^1$H NMR (300 MHz, CDCl$_3$) δ 9.11 (s, 1H), 8.10 (d, J=1.9 Hz, 1H), 7.72 (dd, J=8.8, 1.9 Hz, 1H), 7.62 (d, J=8.8 Hz, 1H), 7.48 (s, 1H), 2.70 (s, 3H).

Step 3: 7-bromo-3-methyl-8-nitro-isoquinoline

To a solution of 7-bromo-3-methyl-isoquinoline (4.2 g, 19 mmol) in concentrated Sulphuric acid (24 mL) was added Potassium nitrate (1.93 g, 19 mmol) portion wise at 0° C. The mixture was allowed to warm to ambient temperature and stirred for 4 h. The mixture was subsequently poured into ice and neutralized using aqueous Ammonia solution. The precipitated solid was filtered and the filter cake washed with water (10 mL) and Diethyl ether (10 mL). The solid was purified by silica gel flash chromatography (eluent 15-18% Ethyl acetate in heptane) to afford 3.2 g (63%) of the title compound. LC/MS (method 3): $R_t$: 2.7 min; MS: m/z=267 ($M^+$). $^1$H NMR (300 MHz, CDCl$_3$) δ 9.06 (s, 1H), 7.81 (d, J=8.9 Hz, 1H), 7.74 (d, J=8.9 Hz, 1H), 7.55 (s, 1H), 2.73 (s, 3H).

Step 4: 3-methyl-8-nitro-N-[4-(trifluoromethoxy) phenyl]isoquinolin-7-amine

To a suspension of NaH (0.43 g, 18.mmol) in Tetrahydrofuran (35 mL) at 0° C. was added 4-trifluromethoxy aniline (2.4 g, 13.5 mmol) and heated at 60° C. for 30 min. 7-bromo-3-methyl-8-nitro-isoquinoline (3.2 g, 12.03 mmol) was added and the mixture was maintained at 60° C. for 12 h. The mixture was cooled to ambient temperature, diluted with water (25 mL), extracted with Ethyl acetate (2×40 mL). The combined organic extracts were dried (anhydrous Sodium sulphate) and concentrated under reduced pressure. The residue was triturated with Diethyl ether (10 mL) to afford 2.9 g (67%) of the title compound. LC/MS (method 3): $R_t$: 2.9 min; MS: m/z=364.1 ($M^+$). $^1$H NMR (300 MHz, DMSO-d$_6$) δ 9.54 (s, 1H), 9.36 (s, 1H), 7.97 (d, J=9.3 Hz, 1H), 7.68 (s, 1H), 7.59 (d, J=9.2 Hz, 1H), 7.38 (s, 4H), 2.60 (s, 3H).

Step 5: 3-methyl-N7-[4-(trifluoromethoxy)phenyl] isoquinoline-7,8-diamine

To a solution of 3-methyl-8-nitro-N-[4-(trifluoromethoxy)phenyl]isoquinolin-7-amine (8.8 gm, 24.2 mmol) in methanol (160 mL) was added Stannous chloride dehydrate (27.34 g, 121.17 mmol) and the mixture heated at 85° C. for 12 h. The volatiles were removed under reduced pressure and the residue diluted with water (100 mL), Ethyl acetate (200 ml) and saturated Sodium bicarbonate solution (100 mL). The mixture was filtered through Celite. The filtrate was partitioned and the organic layer was dried (anhydrous Sodium sulphate) and evaporated under reduced pressure. The residue was purified by silica gel flash chromatography (eluent 18-20% ethyl acetate in heptane) to afford 7 g (87%) of the title compound. LC/MS (method 3): $R_t$: 2.16 min; MS: m/z=334.2 ($M^{+1}$). $^1$H NMR (300 MHz, DMSO-d$_6$) δ 9.43 (s, 1H), 7.58 (s, 1H), 7.42 (s, 1H), 7.36 (d, J=8.5 Hz, 1H), 7.10 (d, J=8.5 Hz, 2H), 7.01 (d, J=8.5 Hz, 1H), 6.70-6.57 (m, 2H), 5.83 (s, 2H), 2.55 (s, 3H).

Step 6: 7-methyl-3-[4-(trifluoromethoxy)phenyl] imidazo[4,5-h]isoquinoline

A solution of 3-methyl-N7-[4-(trifluoromethoxy)phenyl] isoquinoline-7,8-diamine (7.0 g, 21 mmol) in formic acid (40 mL) was stirred at ambient temperature for 12 h. The mixture was evaporated under reduced pressure and the residue diluted with water (50 mL) and neutralized using Sodium bicarbonate solution. The mixture was extracted with Ethyl acetate (2×100 mL) and the organic extracts separated and drived (anhydrous Sodium sulphate) and concentrated under reduced pressure. The residue was purified by silica gel flash chromatography (eluent 20-22% Ethyl acetate in Heptane) to afford 4.2 g (58%) of title compound. LC/MS (method 3): $R_t$: 2.22 min; MS: m/z=344.2 ($M^{+1}$). $^1$H NMR (300 MHz, DMSO-d$_6$) δ 9.77 (s, 1H), 8.75 (s, 1H), 7.98 (d, J=8.9 Hz, 1H), 7.95-7.88 (m, 2H), 7.80 (s, 1H), 7.77 (d, J=9.1 Hz, 1H), 7.69 (d, J=8.5 Hz, 2H), 2.66 (s, 3H).

Step 7: 7-methyl-3-[4-(trifluoromethoxy)phenyl] imidazo[4,5-h]isoquinolin N-oxide To a solution of 7-methyl-3-[4-(trifluoromethoxy)phenyl] imidazo[4,5-h]isoquinoline (2.5 g, 7.28 mmol) in Dichloromethane (25 mL) was added m-chloroperbenzoic acid (1.89 g, 10.95 mmol) and stirred for 12 h. The mixture was subsequently diluted with water (50 mL), basified with saturated Sodium bicarbonate solution (25 mL) and extracted with Ethyl acetate (2×80 mL). The combined organic extracts were dried (anhydrous Sodium sulphate) and concentrated and the residue triturated with pentane to afford 2.5 g (96%) of the title compound. LC/MS (method 3): $R_t$: 1.38 min; MS: m/z=360.3 ($M^+$). $^1$H NMR (300 MHz, CDCl$_3$) δ 10.21 (s, 1H), 8.40 (s, 1H), 8.06 (s, 1H), 8.00 (d, J=8.9 Hz, 1H), 7.81 (d, J=9.0 Hz, 1H), 7.64 (d, J=8.7 Hz, 2H), 7.53 (d, J=8.4 Hz, 2H), 2.96 (s, 3H).

Step 8: [3-[4-(trifluoromethoxy)phenyl]imidazo[4,5-h]isoquinolin-7-yl]methyl acetate A solution of 7-methyl-3-[4-(trifluoromethoxy)phenyl] imidazo[4,5-h]isoquinolin N-oxide (2.5 g, 6.96 mmol) in Acetic anhydride (25 mL) was heated at 140° C. for 12 h. The mixture was cooled to ambient temperature and the volatiles were removed invacuo. The residue was purified by silica gel flash chromatography (eluent 5-8% Methanol in Dichloromethane) to afford 2.6 g (93%) of the title compound. LC/MS (method 3): $R_t$: 1.55 min; MS: m/z=402.4 ($M^+$). $^1$H NMR (300 MHz, DMSO-d$_6$) 1H NMR (300 MHz, DMSO-d6) δ 9.85 (s, 1H), 8.81 (s, 1H), 8.80 (s, 1H), 8.12-8.00 (m, 2H), 7.94 (m, 2H), 7.70 (m, 2H), 5.34 (s, 2H), 2.16 (s, 3H).

Step 9: [3-[4-(trifluoromethoxy)phenyl]imidazo[4,5-h]isoquinolin-7-yl]methanol

To a solution of [3-[4-(trifluoromethoxy)phenyl]imidazo [4,5-h]isoquinolin-7-yl]methyl acetate (2.6 g, 6.48 mmol) in Tetrahydrofuran (15 mL) and water (10 mL) was added a solution of Lithium hydroxide monohydrate (0.409 g, 9.74 mmol) in water (1 mL). The mixture was stirred for 4 h and subsequently diluted with water (30 mL), acidified with 1N HCl and extracted with Ethyl acetate (2×50 mL). The combined organic extracts were dried (anhydrous Sodium sulphate) and concentrated under reduced pressure. The residue was purified by silica gel flash chromatography (eluent 25-30% Ethyl acetate in Heptane) to afford 1.0 g (43.1%) of title compound. LC/MS (method 3): R$_t$: 1.29 min; MS: m/z=360 (M$^+$). $^1$H NMR (300 MHz, DMSO-d$_6$) δ 9.80 (s, 1H), 8.77 (s, 1H), 8.06-7.98 (m, 2H), 7.97-7.91 (m, 2H), 7.89 (d, J=9.1 Hz, 1H), 7.69 (d, J=8.5 Hz, 2H), 5.52 (t, J=5.8 Hz, 1H), 4.79 (d, J=5.6 Hz, 2H).

Step 10: 3-[4-(trifluoromethoxy)phenyl]imidazo[4,5-h]isoquinoline-7-carbaldehyde To a solution of [3-[4-(trifluoromethoxy)phenyl]imidazo[4,5-h]isoquinolin-7-yl]methanol (1.0 g, 2.78 mmol) in Dichloromethane (15.0 mL) was added Dess-Martin periodinane (3.54 g, 8.34 mmol) and the mixture stirred at ambient temperature for 12 h. Sodium thiosulphate solution (20 mL) was subsequently added and the mixture extracted with Dichloromethane (2×30 mL). The combined organic extracts were dried (anhydrous Sodium sulphate) concentrated under reduced pressure and the residue purified by silica gel flash column chromatography (eluent 24-25% Ethyl acetate in Heptane) to afford 0.8 g (80%) of the title compound. LC/MS (method 3): R$_t$: 1.53 min; MS: m/z=358 (M$^+$).1H NMR (300 MHz, DMSO-d$_6$) δ 10.21 (s, 1H), 10.03 (s, 1H), 8.91 (s, 1H), 8.69 (s, 1H), 8.17 (s, 2H), 7.97 (m, 2H), 7.71 (m, 2H).

Step 11: 1-(2-isopropylphenyl)-3-[(E)-[3-[4-(trifluoromethoxy)phenyl]imidazo[4,5-h]isoquinolin-7-yl]methyleneamino]thiourea (C-24)

To a solution of 3-[4-(trifluoromethoxy)phenyl]imidazo[4,5-h]isoquinoline-7-carbaldehyde (0.2 g, 0.56 mmol) in Ethanol (3 mL) was added 1-amino-3-(2-isopropylphenyl)thiourea (0.117 g, 0.56 mmol) and the mixture heated at 85° C. for 2 h. The mixture was cooled and the precipitated solids were filtered, washed with cold Ethanol (2 mL) and triturated with n-pentane (5 mL) and dried to afford the title compound 0.180 g (59%). LC/MS (method 3): R$_t$: 1.78 min; MS: m/z=549 (M$^{+1}$). $^1$H NMR (300 MHz, DMSO-d$_6$) δ 12.04 (s, 1H), 10.10 (s, 1H), 9.86 (s, 1H), 9.00 (s, 1H), 8.82 (s, 1H), 8.43 (s, 1H), 8.07 (d, J=8.9 Hz, 1H), 8.01 (s, 2H), 7.81 (d, J=9.0 Hz, 1H), 7.69 (d, J=8.5 Hz, 2H), 7.39 (d, J=7.6 Hz, 1H), 7.37-7.28 (m, 1H), 7.25 (d, J=4.1 Hz, 2H), 3.17 (p, J=6.9 Hz, 1H), 1.21 (d, J=6.9 Hz, 6H).

Example 10: (2Z)-3-(2-isopropylphenyl)-2-[(E)-[3-[4-(trifluoromethoxy)phenyl]imidazo[4,5-h]isoquinolin-7-yl]methylenehydrazono]thiazolidin-4-one (compound C-26)

To a solution of 1-(2-isopropylphenyl)-3-[(E)-[3-[4-(trifluoromethoxy)phenyl]imidazo[4,5-h]isoquinolin-7-yl]methyleneamino]thiourea (0.130 g, 0.237 mmol) in Ethanol (5 mL), Sodium acetate (0.058 g, 0.71 mmol) and Methyl bromo acetate (0.073 g, 0.477 mmol) were added. and the mixture stirred at 40° C. for 12 h. The mixture was subsequently cooled to ambient temperature, diluted with water (15 mL) and extracted with Ethyl acetate (2×15 mL). The combined extracts were dried (anhydrous Sodium sulphate), evaporated and the residue purified by silica gel column chromatography (eluent 35-40% Ethyl acetate in Heptane) to afford 0.078 g (56%) of the title compound. LC/MS (method 1): R$_t$: 1.88 min; MS: m/z=589.6 (M$^+$). $^1$H NMR (300 MHz, DMSO-d$_6$) 1H NMR 6 9.90 (s, 1H), 8.84 (s, 1H), 8.53 (s, 1H), 8.41 (s, 1H), 8.06 (m, 2H), 8.00-7.86 (m, 2H), 7.70 (d, J=8.4 Hz, 2H), 7.52 (m, 2H), 7.36 (m, H), 7.30 (dd, J=7.9, 1.5 Hz, 1H), 4.43-4.09 (m, 2H), 2.81 (p, J=6.9 Hz, 1H), 1.16 (dd, J=12.5, 6.8 Hz, 6H).

Example 11: (2Z)-2-(2-isopropylphenyl)imino-3-[(E)-[3-[4-(trifluoromethoxy)phenyl]imidazo[4,5-h]isoquinolin-7-yl]methyleneamino]thiazolidin-4-one (compound C-28)

To a solution of 3-[4-(trifluoromethoxy)phenyl]imidazo[4,5-h]isoquinoline-7-carbaldehyde (0.2 g, 0.56 mmol) in acetic acid (3.0 mL) was added 3-amino-2-(2,6-dimethylphenyl)imino-thiazolidin-4-one (0.139 g, 0.56 mmol) and stirred at room temperature for 12 h. The mixture was diluted with water (10 mL) and neutralized with saturated Sodium bicarbonate solution and extracted with Ethyl acetate (2×25 mL). The combined organic extracts were dried (anhydrous Sodium sulphate) and concentrated under reduced pressure. The residue was purified by silica gel chromatography (eluent 70-75% Ethyl acetate in heptane) to afford 0.040 g (12%) of the title compound LC/MS (method 1): R$_t$: 1.83 min; MS: m/z=589.6 (M$^+$). $^1$H NMR (300 MHz, DMSO-d$_6$) δ 9.90 (s, 1H), 8.84 (s, 1H), 8.53 (s, 1H), 8.40 (s, 1H), 8.09 (d, J=9.0 Hz, 1H), 8.03 (d, J=9.1 Hz, 1H), 7.94 (d, J=8.9 Hz, 2H), 7.70 (d, J=8.5 Hz, 2H), 7.59-7.45 (m, 2H), 7.42-7.33 (m, 1H), 7.29 (d, J=7.7 Hz, 1H), 4.39-4.09 (m, 2H), 2.90-2.76 (m, 1H), 1.16 (dd, J=12.4, 6.8 Hz, 6H).

Example 12: 1-[3-[4-(trifluoromethoxy)phenyl]imidazo[4,5-f]quinolin-7-yl]-N-[(2S,3R,4R,5S,6S)-3,4,5-trimethoxy-6-methyl-tetrahydropyran-2-yl]oxy-methanimine (compound C-33)

A mixture of 3-[4-(trifluoromethoxy)phenyl]imidazo[4,5-f]quinoline-7-carbaldehyde (0.15 g, 0.42 mmol) and O-[(2S,3R,4R,5S,6S)-3,4,5-trimethoxy-6-methyl-tetrahydropyran-2-yl]hydroxylamine (0.093 g, 0.42 mmol) in EtOH (10 mL) was heated at 60° C. for 12 h. The mixture was cooled to ambient temperature and the solid precipitated was collected by filtration and washed with EtOH, dried under vacuum to get the title compound as an off-white solid. (0.120 g, 77%) LC/MS (method 1): R$_t$: 1.196 min; MS: m/z=561.2 (M$^+$). $^1$H NMR (400 MHz, DMSO-d$_6$) δ 8.9 (m, 1H), 8.8 (s, 1H), 8.53 (s, 1H), 8.15 (m, 1H), 8.05 (m, 1H), 7.95 (m, 4H), 7.75 (m, 1H), 5.6 (m, 1H), 3.85 (m, 1H), 3.3 (m, 4H), 3.55 (m, 7H), 3.05 (m, 1H), 1.1 (m, 3H).

Example 13: 1-(2-isopropylphenyl)-3-[(E)-[3-[4-(trifluoromethoxy)phenyl]imidazo[4,5-f]quinoxalin-7-yl]methyleneamino]thiourea (compound C-35)

Step 1: Ethyl N-(3-chloro-2-nitro-phenyl)carbamate

A solution of 3-chloro-2-nitro aniline (0.52 g, 3.01 mmol) in Ethyl chloroformate (4 mL) was heated at 110° C. for 2 h. The volatiles were distilled out and the residue diluted with water and extracted with Ethyl acetate (2×20 mL), the combined organic layer washed with Sodium bicarbonate solution, water and brine solution. The organic layer were dried over Sodium sulfate and concentrated under reduced pressure and the residue washed with n-heptane to get the pure product (0.42 g, Yield: 57%) as a pale orange solid. $^1$H NMR (300 MHz, CDCl$_3$) δ 8.12 (dd, J=8.5, 1.1 Hz, 1H), 7.50 (s, 1H), 7.42 (t, J=8.3 Hz, 1H), 7.22 (dd, J=8.1, 1.2 Hz, 1H), 4.24 (q, J=7.1 Hz, 2H), 1.32 (t, J=7.1 Hz, 3H).

Step 2: Ethyl N-[2-nitro-3-[4-(trifluoromethoxy)anilino]phenyl]carbamate

A solution of Ethyl N-(3-chloro-2-nitro-phenyl)carbamate (0.2 g, 0.81 mmol) in Toluene (4 mL) was degassed with nitrogen gas for 20 min, BINAP (0.05 g, 0.08 mmol), Pd(OAc)$_2$ (0.03 g, 0.13 mmol) and Cesium carbonate (0.4 g, 1.23 mmol) were added. The mixture was degassed for 10 minutes, and 4-trifluoromethoxy aniline (0.150 g, 0.85 mmol) was added and again degassing was done for 10 minutes. The mixture was heated at 110° C. for 1 h, cooled to ambient temperature and filtered through Celite, the filtrate diluted with water (15 mL) and extracted with ethyl acetate (2×15 mL). The organic layers were separated and dried over sodium sulfate and concentrated under reduced pressure and the residue purified by silica gel column chromatography (eluent ethyl acetate (2%) and heptane (98%) to get the title compound (0.140 g, Yield: 44%). LC/MS: R$_t$: 3.39 min; MS: m/z=384.1 (M$^-$), $^1$H NMR (300 MHz, CDCl$_3$) δ 9.52 (s, 1H), 8.98 (s, 1H), 7.80 (dd, J=8.3, 1.2 Hz, 1H), 7.33 (d, J=8.4 Hz, 1H), 7.26-7.29 (m, 4H), 6.85 (dd, J=8.6, 1.2 Hz, 1H), 4.27 (q, J=7.1 Hz, 2H), 1.36 (t, J=7.1 Hz, 3H).

Step 3: Ethyl N-[2-amino-3-[4-(trifluoromethoxy)anilino]phenyl]carbamate

To a stirred solution of Ethyl N-[2-nitro-3-[4-(trifluoromethoxy)anilino]phenyl]carbamate (0.140 g, 0.36 mmol) in Ethyl acetate (5 mL) was added tin chloride dihydrate (0.246 g, 1.09 mmol) at ambient temperature and heated at 80° C. for 4 h. The reaction cooled to rt and Sodium bicarbonate solution (15 mL) was added. The mixture was filtered through celite, the filtrate was diluted with Ethyl acetate and partitioned. The organic layers were washed with water, brine solution, dried (anhydrous Sodium sulphate) and concentrated under reduced pressure. The residue was triturated with n-Pentane to get the title compound (0.095 g, 73%) as a pale brown solid. LC/MS: R$_t$: 2.89 min; MS: m/z=356.2 (M$^+$), $^1$H NMR (300 MHz, DMSO-d$_6$) δ 8.64 (s, 1H), 7.48 (s, 1H), 7.10 (d, J=8.8 Hz, 3H), 6.85 (dd, J=7.8, 1.4 Hz, 1H), 6.75-6.63 (m, 2H), 6.54-6.59 (m, 1H), 4.58 (s, 2H), 4.10 (q, J=7.1 Hz, 2H), 1.33-1.17 (m, 3H).

Step 4: Ethyl N-[1-[4-(trifluoromethoxy)phenyl]benzimidazol-4-yl]carbamate

A solution of Ethyl N-[2-amino-3-[4-(trifluoromethoxy)anilino]phenyl]carbamate (0.120 g, 0.34 mmol) in Formic acid (4 mL) was heated at 80° C. for 4 h. The volatiles were evaporated under vacuum and Sodium bicarbonate solution (15 mL) was added and the mixture extracted with Ethyl acetate (2×15 mL). The combined organic extracts were dried over Sodium sulfate and concentrated under reduced pressure to get a residue which was purified by silica gel column chromatography (eluent 12%:Ethyl acetate in Heptane) to get the title compound (0.08 g, Yield: 64.8%). LC/MS: R$_t$: 3.10 min; MS: m/z=366.2 (M$^+$), $^1$H NMR (300 MHz, DMSO-d$_6$) δ 9.04 (s, 1H), 8.57 (s, 1H), 7.91-7.79 (m, 2H), 7.70 (dd, J=6.8, 2.0 Hz, 1H), 7.64 (d, J=8.5 Hz, 2H), 7.37-7.21 (m, 2H), 4.18 (q, J=7.1 Hz, 2H), 1.26 (t, J=7.1 Hz, 3H).

Step 5: Ethyl N-[5-nitro-1-[4-(trifluoromethoxy)phenyl]benzimidazol-4-yl]carbamate To a stirred solution of Ethyl N-[1-[4-(trifluoromethoxy)phenyl]benzimidazol-4-yl]carbamate (0.05 g, 0.14 mmol) in con.sulfuric acid (2 mL) was added Potassium nitrate (0.02 g, 0.16 mmol) at rt and stirred for 2 h. The reaction mixture was neutralized with sodium bicarbonate solution and extracted with Ethyl acetate. The organic layers were dried over sodium sulfate and concentrated under reduced pressure and the residue purified by silica gel column chromatography (eluent Ethyl acetate (22%) in Heptane) to obtain the title compound (0.02 g, Yield: 36%). LC/MS: R$_t$: 2.84 min; MS: m/z=411 (M$^+$), $^1$H NMR (300 MHz, DMSO-6) δ 10.10 (s, 1H), 8.81 (s, 1H), 8.08-7.84 (m, 3H), 7.68 (d, J=8.4 Hz, 2H), 7.55 (d, J=9.0 Hz, 1H), 4.11 (q, J=7.1 Hz, 2H), 1.22 (t, J=7.1 Hz, 3H).

Step 6: 5-nitro-1-[4-(trifluoromethoxy)phenyl]benzimidazol-4-amine

To a solution of Ethyl N-[5-nitro-1-[4-(trifluoromethoxy)phenyl]benzimidazol-4-yl]carbamate (0.05 g, 0.12 mmol) in Ethanol (3 mL) was added a solution of Potassium hydroxide (0.120 g, 2.139 mmol) in water (1.5 mL) at rt and the mixture heated at 100° C. for 4 h. The mixture was cooled to ambient temperature, diluted with water and neutralized with Hydrochloric acid solution (1N) and subsequently extracted with Ethyl acetate (2×5 mL). The combined organic layer was dried over sodium sulfate and concentrated under reduced pressure to get a residue which was purified by neutral alumina column chromatography to obtain the title compound (0.030 g, 72%). LC/MS: R$_t$: 2.899 min; MS: m/z=339 (M$^+$), $^1$H NMR (300 MHz, DMSO-d$_6$) δ 8.60 (s, 1H), 7.97 (d, J=9.4 Hz, 1H), 7.95-7.78 (m, 4H), 7.67 (d, J=8.4 Hz, 2H), 6.85 (d, J=9.4 Hz, 1H).

Step 7: 1-[4-(trifluoromethoxy)phenyl]benzimidazole-4,5-diamine

To a stirred solution of 5-nitro-1-[4-(trifluoromethoxy)phenyl]benzimidazol-4-amine (0.1 g, 0.3 mmol) in Ethyl acetate (5 mL) was added tin chloride dihydrate (0.270 g, 1.18 mmol) at RT and heated at 80° C. for 2 h. The mixture was cooled to ambient temperature and a solution of sodium bicarbonate solution was added and the, then filtered through celite. The filtrate was extracted with Ethyl acetate and the Ethyl acetate extracts washed successively with water, brine and dried over anhydrous Sodium sulphate and evaporated invacuo to obtain the title compound as a brown solid (0.09 g, Yield: 95%). LC/MS: R$_t$: 1.184 min; MS: m/z=309.2 (M$^+$), $^1$H NMR (300 MHz, DMSO-d$_6$) δ 8.27 (s, 1H), 7.84-7.71 (m, 2H), 7.58 (d, J=8.5 Hz, 2H), 6.77-6.59 (m, 2H), 4.71 (s, 4H).

Step 8: Ethyl 3-[4-(trifluoromethoxy)phenyl]imidazo[4,5-f]quinoxaline-7-carboxylate To a stirred solution of 1-[4-(trifluoromethoxy)phenyl]benzimidazole-4,5-diamine (2.4 g, 7.79 mmol) in N-Methyl pyrrolidone (20 mL) was added Ethyl bromo pyruvate (1.5 g, 7.7 mmol) at RT and the mixture was stirred at rt for 12 h. The reaction mixture was diluted with water and extracted with Ethyl acetate and the extracts dried over anhydrous Sodium sulphate and concentrated under reduced pressure The resulting residue was purified by silica gel column chromatography (eluent 45% Ethyl acetate in Heptane) to get the title compound (0.875 g, 28%), LC/MS: R$_t$: 2.836 min; MS: m/z=403 (M$^+$), $^1$H NMR (300 MHz, DMSO-d$_6$) δ 9.49 (s, 1H), 8.91 (s, 1H), 8.24 (d, J=9.1 Hz, 1H), 8.06 (d, J=9.1 Hz, 1H), 8.03-7.91 (m, 2H), 7.72 (d, J=8.4 Hz, 2H), 4.52 (q, J=7.1 Hz, 2H), 1.45 (t, J=7.1 Hz, 3H).

Step 9: [3-[4-(trifluoromethoxy)phenyl]imidazo[4,5-f]quinoxalin-7-yl]methanol

To a stirred solution of Ethyl 3-[4-(trifluoromethoxy)phenyl]imidazo[4,5-f]quinoxaline-7-carboxylate (0.05 g, 0.12 mmol) in Dichloromethane (3 mL) and Methanol (3 mL) mixture was added Sodium borohydride (0.056 g, 1.49 mmol) at rt and stirred for 1 h. The reaction mixture was diluted with water and extracted with Ethyl acetate and the extracts washed with brine, dried over sodium sulfate and concentrated under reduced pressure. The resulting residue was triturated with Diethyl ether to get the desired product as an off-white solid (0.04 g, Yield: 89%). LC/MS: $R_t$: 2.226 min; MS: m/z=361 (M$^+$), $^1$H NMR (300 MHz, CDCl$_3$) δ 8.96 (s, 1H), 8.38 (s, 1H), 8.06 (d, J=9.1 Hz, 1H), 7.87 (d, J=9.1 Hz, 1H), 7.71-7.62 (m, 2H), 7.52 (d, J=8.5 Hz, 2H), 5.1 (s, 2H), 3.4 (s, 1H).

Step 10: 3-[4-(trifluoromethoxy)phenyl]imidazo[4,5-f]quinoxaline-7-carbaldehyde

To a stirred solution of [3-[4-(trifluoromethoxy)phenyl]imidazo[4,5-f]quinoxalin-7-yl]methanol (0.04 g, 0.1 mmol) in Dichloromethane (3 mL) was added Dess-Martin Periodinone (0.081 g, 0.191 mmol) at 0° C. and stirred for 3 h. Sodium thiosulphate solution and water were added and the mixture extracted with Ethyl acetate. The organic extracts were dried over anhydrous Sodium sulphate and evaporated and the resulting residue was purified by washing with diethyl ether and n-heptane, to afford the desired product (0.03 g, 86%) as white solid. LC/MS: $R_t$: 1.499 min; MS: m/z=359.4 (M$^+$), $^1$H NMR (300 MHz, DMSO-d$_6$) 1H NMR (300 MHz, DMSO-d6) δ 10.33 (s, 1H), 9.40 (s, 1H), 8.94 (s, 1H), 8.28 (d, J=9.1 Hz, 1H), 8.09 (d, J=9.1 Hz, 1H), 8.04-7.91 (m, 2H), 7.73 (d, J=8.4 Hz, 2H).

Step 11: 1-(2-isopropylphenyl)-3-[(E)-[3-[4-(trifluoromethoxy)phenyl]imidazo[4,5-f]quinoxalin-7-yl]methyleneamino]thiourea To a stirred solution of 3-[4-(trifluoromethoxy)phenyl]imidazo[4,5-f]quinoxaline-7-carbaldehyde (0.25 g, 0.7 mmol) in Ethanol (6 mL) was added 1-amino-3-(2-isopropylphenyl)thiourea (0.145 g, 0.7 mmol) at rt and the mixture heated at 80° C. for 2 h. The reaction mixture was cooled to 0° C. and stirred for 20 min to precipitate out a solid which was filtered, washed with cold Ethanol and dried to afford the desired product (0.2 g, 52%) as a pale yellow solid. LC/MS: $R_t$: 1.803 min; MS: m/z=550.6 (M$^+$), $^1$H NMR (300 MHz, DMSO-d$_6$) δ 12.32 (s, 1H), 10.41 (s, 1H), 10.01 (s, 1H), 8.85 (s, 1H), 8.48 (s, 1H), 8.06 (d, J=9.1 Hz, 1H), 8.03-7.89 (m, 4H), 7.71 (d, J=8.4 Hz, 2H), 7.44-7.17 (m, 3H), 3.16 (p, J=6.9 Hz, 1H), 1.21 (d, J=6.9 Hz, 6H).

Example 14: 3-(2-isopropylphenyl)-2-[[3-[4-(trifluoromethoxy)phenyl]imidazo[4,5-f]quinoxalin-7-yl]methylenehydrazono]thiazolidin-4-one (compound C-34)

To a stirred solution of 1-(2-isopropylphenyl)-3-[[3-[4-(trifluoromethoxy)phenyl]imidazo[4,5-f]quinoxalin-7-yl]methyleneamino]thiourea (0.170 g, 0.31 mmol) in Ethanol (5 mL) were added Methyl bromoacetate (0.24 g, 1.56 mmol) and Sodium acetate (0.076 g, 0.92 mmol) and stirred at rt for 24 h. The mixture was diluted with water and extracted with Dichloromethane, the organic layers partitioned and dried (anhydrous Sodium sulphate) and evaporated under reduced pressure to get a residue which was purified by silica gel column chromatography (eluent: 3% Methanol in Dichloromethane) to obtain the title compound (0.130 g, 68%). LC/MS: $R_t$: 3.314 min; MS: m/z=590 (M$^+$), $^1$H NMR (300 MHz, DMSO-d$_6$) δ 9.48 (s, 1H), 8.84 (s, 1H), 8.47 (s, 1H), 8.12 (d, J=8.9 Hz, 1H), 8.01 (d, J=9.0 Hz, 1H), 7.99-7.88 (m, 2H), 7.71 (d, J=8.3 Hz, 2H), 7.62-7.46 (m, 2H), 7.44-7.27 (m, 2H), 4.43-4.17 (m, 2H), 2.82 (p, J=6.9 Hz, 1H), 1.18 (dd, J=17.5, 6.8 Hz, 6H).

Example 15: 1-(2-isopropylphenyl)-3-[(E)-[2-methyl-3-[4-(trifluoromethoxy)phenyl]pyrazolo[3,4-f]quinazolin-7-yl]methyleneamino]thiourea (compound C-36)

Step 1: 2-methyl-7,8-dihydro-6H-quinazolin-5-one 2-(dimethylaminomethylene)cyclohexane-1,3-dione (11.8 g, 70.62 mmol) and Acetamidine hydrochloride (7.35 g, 77.74 mmol) was taken up in EtOH (100 mL) and heated to reflux. Diisopropyl ethyl amine (10.95 g, 84.71 mmol) was added drop wise in 20 min and the mixture was refluxed for a further 3 h. The mixture was cooled to ambient temperature, poured into ice water (100 mL) and acidified with acetic acid. The resulting suspension was stirred for 30 min and extracted with Ethyl acetate (2×100 mL). The combined organic extracts were partitioned and dried over anhydrous Sodium sulphate and concentrated under reduced pressure. The residue was purified by silica gel flash chromatography (eluent 2-4% MeOH in Dichloromethane) to afford 6 g (52% yield) of the title compound as a yellowish solid. LC/MS (method 3): $R_t$: 0.87 min; MS: m/z=163 (M$^{+1}$); $^1$H NMR (300 MHz, DMSO-d$_6$); δ 8.79 (s, 1H), 2.84 (t, J=6.2 Hz, 2H), 2.50 (s, 3H), 2.36 (p, J=1.9 Hz, 1H), 1.95 (p, J=6.4 Hz, 2H), 1.76 (s, 1H).

Step 2: 2-methyl-6-[4-(trifluoromethoxy)benzoyl]-7,8-dihydro-6H-quinazolin-5-one To a solution of 2-methyl-7,8-dihydro-6H-quinazolin-5-one (1.5 g, 9.25 mmol) in Toluene (10 mL) at ambient temperature was added Lithium Hexamethyldisilazide (2.32 g, 13.87 mmol) and stirred for 10 min This mixture was subsequently added to a solution of 4-trifluromethoxy benzoyl chloride (2.079 g, 9.25 mmol) in toluene drop wise and stirred for a further 30 min. Subsequently, water (25 mL) was added and the mixture extracted with Ethyl acetate (2×50 mL). The combined organic extracts were dried (anhydrous Sodium sulphate), concentrated under reduced pressure and the residue purified by flash chromatography (Eluent 40-45% Ethyl acetate in heptane) to afford 1.5 g (46%) of the title compound. LC/MS (method 3): $R_t$: 1.52 min; MS: m/z=351 (M$^{+1}$).

Step 3: 2,7-dimethyl-3-[4-(trifluoromethoxy)phenyl]-4,5-dihydropyrazolo[3,4-f]quinazoline To a solution of 2-methyl-6-[4-(trifluoromethoxy)benzoyl]-7,8-dihydro-6H-quinazolin-5-one (1.5 g, 4.28 mmol) in EtOH (15 mL) was added Methyl hydrazine sulfate (0.93 g, 6.42 mmol) and triethylamine (0.65 g, 6.43 mmol) and was heated to reflux for 2 h. The mixture was subsequently cooled to ambient temperature, diluted with water (25 mL) and extracted with Ethyl acetate (2×40 mL). The combined organic extracts were dried (anhydrous Sodium sulphate), evaporated invacuo and the residue purified by silica gel flash column chromatography (eluent 1-2% Methanol in Dichloromethane) to afford 0.28 g (18%) of the title compound. LC/MS (method 3): $R_t$: 1.597 min; MS: m/z=361 (M$_{+1}$); $^1$H NMR (300 MHz, CDCl$_3$); δ 9.01 (s, 1H), 7.40 (t, J=7.5 Hz, 4H), 3.89 (s, 3H), 3.12 (t, J=7.4 Hz, 2H), 2.85 (t, J=7.5 Hz, 2H), 2.78 (s, 3H).

Step 4: 2,7-dimethyl-3-[4-(trifluoromethoxy)phenyl] pyrazolo[3,4-f]quinazoline To a solution of 2,7-dimethyl-3-[4-(trifluoromethoxy) phenyl]-4,5-dihydropyrazolo[3,4-f]quinazoline (0.25 g, 0.694 mmol) in Dichloromethane (6 mL) at 0° C. was added 2,3-Dichloro-5,6-dicyano-1,4-benzoquinone (0.24 g, 1.03 mmol) and stirred at ambient temperature for 12 h. The mixture was subsequently evaporated and the residue triturated with n-Pentane to afford 0.230 g (92%) of the title compound. LC/MS (method 1): $R_t$: 1.61 min; MS: m/z=359 ($M^{+1}$). $^1$H NMR (300 MHz, CDCl$_3$); δ 9.99 (s, 1H), 7.97 (d, J=9.0 Hz, 1H), 7.71 (d, J=9.3 Hz, 1H), 7.66-7.55 (m, 2H), 7.48 (d, J=8.3 Hz, 2H), 4.24 (s, 3H), 3.05 (s, 3H).

Step 5: 2-methyl-3-[4-(trifluoromethoxy)phenyl] pyrazolo[3,4-f]quinazoline-7-carbaldehyde 2,7-dimethyl-3-[4-(trifluoromethoxy)phenyl]pyrazolo[3,4-f]quinazoline (0.23 g, 0.64 mmol) was dissolved in 1,4-dioxane (4 mL) and Selenium Dioxide (0.107 g, 0.96 mmol) was added and the mixture heated at 110° C. for 12 h. The reaction was cooled to ambient temperature and Water (20 mL) was added and the mixture extracted with Ethyl acetate (2×25 mL). The combined organic extracts were dried (anhydrous Sodium sulphate) and concentrated under reduced pressure. The residue was purified by silica gel flash column chromatography (eluent 2% Methanol in Dichloromethane) to afford 0.170 g (70%) of the title compound as a solid. LC/MS (method 3): $R_t$: 1.59 min; MS: m/z=373 ($M^+$).

Step 6: 1-(2-isopropylphenyl)-3-[(E)-[2-methyl-3-[4-(trifluoromethoxy)phenyl]pyrazolo[3,4-f]quinazolin-7-yl]methyleneamino]thiourea 2-methyl-3-[4-(trifluoromethoxy)phenyl]pyrazolo[3,4-f]quinazoline-7-carbaldehyde (0.170 g, 0.45 mmol) was dissolved in EtOH (3 mL) and 1-amino-3-(2-isopropylphenyl) thiourea (0.095 g, 0.96 mmol) was added and the mixture heated at 85° C. for 2 h. The mixture was cooled to ambient temperature and the precipitated solids were filtered, washed with cold Ethanol (2 mL) and triturated with n-Pentane (5 mL) and dired to afford 0.042 g (16%) of the title compound. LC/MS (method 3): $R_t$: 1.84 min; MS: m/z=564 ($M^{+1}$). $^1$H NMR (300 MHz, DMSO-d) δ 12.29 (s, 1H), 10.12 (s, 1H), 9.94 (s, 1H), 8.42 (s, 1H), 8.06 (d, J=9.1 Hz, 1H), 7.91 (d, J=8.6 Hz, 2H), 7.66 (d, J=8.3 Hz, 2H), 7.54 (d, J=9.2 Hz, 1H), 7.44-7.13 (m, 4H), 4.24 (s, 3H), 3.14 (q, J=6.8 Hz, 1H), 1.21 (d, J=6.9 Hz, 6H).

The compounds summarized in the following table were prepared by analogy to the methods given in Examples 1 to 15:

| Compound | IUPAC-Name: | m/z | Rt [min] |
| --- | --- | --- | --- |
| C-1 | 1-(2,6-dimethylphenyl)-3-[(E)-[3-[4-(trifluoromethoxy)phenyl]imidazo[4,5-f]quinolin-7-yl]methyleneamino]thiourea | 535 | 3.103 |
| C-2 | (2Z)-3-(2,6-dimethylphenyl)-2-[(E)-[3-[4-(trifluoromethoxy)phenyl]imidazo[4,5-f]quinolin-7-yl]methylenehydrazono]thiazolidin-4-one | 575 | 3.317 |
| C-3 | 1-(2-isopropylphenyl)-3-[(E)-[3-[4-(trifluoromethoxy)phenyl]imidazo[4,5-f]quinolin-7-yl]methyleneamino]thiourea | 549 | 3.263 |
| C-4 | (2Z)-3-(2-isopropylphenyl)-2-[(E)-[3-[4-(trifluoromethoxy)phenyl]imidazo[4,5-f]quinolin-7-yl]methylenehydrazono]thiazolidin-4-one | 589 | 3.427 |
| C-5 | 1-(2-isopropyl-5-methyl-phenyl)-3-[(E)-[3-[4-(trifluoromethoxy)phenyl]imidazo[4,5-f]quinolin-7-yl]methyleneamino]thiourea | 563 | 3.34 |
| C-6 | (2Z)-3-(2-isopropyl-5-methyl-phenyl)-2-[(E)-[3-[4-(trifluoromethoxy)phenyl]imidazo[4,5-f]quinolin-7-yl]methylenehydrazono]thiazolidin-4-one | 603 | 3.558 |
| C-7 | (2Z)-2-(2,6-dimethylphenyl)imino-3-[(E)-[3-[4-(trifluoromethoxy)phenyl]imidazo[4,5-f]quinolin-7-yl]methyleneamino]thiazolidin-4-one | 575 | 3.407 |
| C-8 | (2Z)-2-(2-isopropylphenyl)imino-3-[(E)-[3-[4-(trifluoromethoxy)phenyl]imidazo[4,5-f]quinolin-7-yl]methyleneamino]thiazolidin-4-one | 589 | 3.555 |
| C-9 | (2Z)-3-(2-isopropylphenyl)-4-methyl-2-[(E)-[3-[4-(trifluoromethoxy)phenyl]imidazo[4,5-f]quinolin-7-yl]methylenehydrazono]thiazolidin-4-ol | 605 | 3.326 |
| C-10 | (2Z)-3-(2-isopropylphenyl)-2-[(E)-[3-[6-(trifluoromethyl)pyridazin-3-yl]imidazo[4,5-f]quinolin-7-yl]methylenehydrazono]thiazolidin-4-one | 575.2 | 3.164 |
| C-11 | 1-(5-chloro-2-pyridyl)ethyl N-[3-[4-(trifluoromethoxy)phenyl]imidazo[4,5-f]quinolin-7-yl]carbamate | 528.3 | 3.13 |
| C-12 | (2-isopropyl-5-methyl-cyclohexyl) N-[3-[4-(trifluoromethoxy)phenyl]imidazo[4,5-f]quinolin-7-yl]carbamate | 527.4 | 4.105 |
| C-13 | 1-(2-isopropylphenyl)-3-[(E)-[3-[4-(trifluoromethoxy)phenyl]imidazo[4,5-h]quinolin-7-yl]methyleneamino]thiourea | 549 | 3.15 |
| C-14 | 1-(2,6-dimethylphenyl)-3-[(E)-[3-[4-(trifluoromethoxy)phenyl]imidazo[4,5-h]quinolin-7-yl]methyleneamino]thiourea | 535 | 3.0 |
| C-15 | (2Z)-3-(2,6-dimethylphenyl)-2-[(E)-[3-[4-(trifluoromethoxy)phenyl]imidazo[4,5-h]quinolin-7-yl]methylenehydrazono]thiazolidin-4-one | 575 | 3.2 |
| C-16 | (2Z)-2-(2-isopropylphenyl)imino-3-[(E)-[3-[4-(trifluoromethoxy)phenyl]imidazo[4,5-h]quinolin-7-yl]methyleneamino]thiazolidin-4-one | 589 | 1.84 |
| C-17 | (2Z)-3-(2-isopropylphenyl)-2-[(E)-[3-[4-(trifluoromethoxy)phenyl]imidazo[4,5-h]quinolin-7-yl]methylenehydrazono]thiazolidin-4-one | 589 | 3.3 |
| C-18 | (2Z)-2-(2,6-dimethylphenyl)imino-3-[(E)-[3-[4-(trifluoromethoxy)phenyl]imidazo[4,5-h]quinolin-7-yl]methyleneamino]thiazolidin-4-one | 574 | 3.19 |
| C-19 | 1-(2-isopropylphenyl)-3-[(E)-[2-methyl-3-[4-(trifluoromethoxy)phenyl]pyrazolo[3,4-f]quinolin-7-yl]methyleneamino]thiourea | 563.1 | 1.298 |
| C-20 | (2Z)-3-(2-isopropylphenyl)-2-[(E)-[2-methyl-3-[4-(trifluoromethoxy)phenyl]pyrazolo[3,4-f]quinolin-7-yl]methylenehydrazono]thiazolidin-4-one | 603.1 | 1.401 |
| C-21 | (E)-3-(2-isopropylphenyl)-N-[(E)-[3-[4-(trifluoromethoxy)phenyl]imidazo[4,5-f]quinolin-7-yl]methyleneamino]thiazolidin-2-imine | 575 | 3.581 |

-continued

| Compound | IUPAC-Name: | m/z | Rt [min] |
|---|---|---|---|
| C-22 | (E)-3-(2-isopropylphenyl)-N-[(E)-[3-[4-(trifluoromethoxy)phenyl]imidazo[4,5-f]quinolin-7-yl]methyleneamino]-1,3-thiazinan-2-imine | 589 | 3.563 |
| C-23 | (E)-3-(2,6-dimethylphenyl)-N-[(E)-[3-[4-(trifluoromethoxy)phenyl]imidazo[4,5-f]quinolin-7-yl]methyleneamino]-1,3-thiazinan-2-imine | 575 | 1.86 |
| C-24 | 1-(2-isopropylphenyl)-3-[(E)-[3-[4-(trifluoromethoxy)phenyl]imidazo[4,5-h]isoquinolin-7-yl]methyleneamino]thiourea | 549 | 1.779 |
| C-25 | 1-(2,6-dimethylphenyl)-3-[(E)-[3-[4-(trifluoromethoxy)phenyl]imidazo[4,5-h]isoquinolin-7-yl]methyleneamino]thiourea | 535 | 1.707 |
| C-26 | (2Z)-3-(2-isopropylphenyl)-2-[(E)-[3-[4-(trifluoromethoxy)phenyl]imidazo[4,5-h]isoquinolin-7-yl]methylenehydrazono]thiazolidin-4-one | 589.6 | 1.833 |
| C-27 | (2Z)-3-(2,6-dimethylphenyl)-2-[(E)-[3-[4-(trifluoromethoxy)phenyl]imidazo[4,5-h]isoquinolin-7-yl]methylenehydrazono]thiazolidin-4-one | 575.6 | 1.783 |
| C-28 | (2Z)-2-(2-isopropylphenyl)imino-3-[(E)-[3-[4-(trifluoromethoxy)phenyl]imidazo[4,5-h]isoquinolin-7-yl]methyleneamino]thiazolidin-4-one | 589.6 | 1.825 |
| C-29 | (2Z)-2-(2,6-dimethylphenyl)imino-3-[(E)-[3-[4-(trifluoromethoxy)phenyl]imidazo[4,5-h]isoquinolin-7-yl]methyleneamino]thiazolidin-4-one | 575 | 1.791 |
| C-30 | (E)-3-(2,6-dimethylphenyl)-N-[(E)-[3-[4-(trifluoromethoxy)phenyl]imidazo[4,5-f]quinolin-7-yl]methyleneamino]thiazolidin-2-imine | 561.6 | 1.865 |
| C-31 | 1-[(E)-[3-[4-(difluoromethoxy)phenyl]imidazo[4,5-f]quinolin-7-yl]methyleneamino]-3-(2-isopropylphenyl)thiourea | 531.5 | 1.693 |
| C-32 | (2E)-2-[(E)-[3-[4-(difluoromethoxy)phenyl]imidazo[4,5-f]quinolin-7-yl]methylenehydrazono]-3-(2-isopropylphenyl)thiazolidin-4-one | 571 | 1.78 |
| C-33 | (E)-1-[3-[4-(trifluoromethoxy)phenyl]imidazo[4,5-f]quinolin-7-yl]-N-[(2S,3R,4R,5S,6S)-3,4,5-trimethoxy-6-methyl-tetrahydropyran-2-yl]oxy-methanimine | 561.2 | 1.196 |
| C-34 | (2Z)-3-(2-isopropylphenyl)-2-[(E)-[3-[4-(trifluoromethoxy)phenyl]imidazo[4,5-f]quinoxalin-7-yl]methylenehydrazono]thiazolidin-4-one | 590 | 3.314 |
| C-35 | 1-(2-isopropylphenyl)-3-[(E)-[3-[4-(trifluoromethoxy)phenyl]imidazo[4,5-f]quinoxalin-7-yl]methyleneamino]thiourea | 550.6 | 1.803 |
| C-36 | 1-(2-isopropylphenyl)-3-[(E)-[2-methyl-3-[4-(trifluoromethoxy)phenyl]pyrazolo[3,4-f]quinazolin-7-yl]methyleneamino]thiourea | 564 | 1.84 |

Biology:

Example B1: Action on Yellow Fever Mosquito (*Aedes aegypti*)

For evaluating control of yellow fever mosquito (*Aedes aegypti*) the test unit consisted of 96-well-microtiter plates containing 200 µl of tap water per well and 5-15 freshly hatched *A. aegypti* larvae.

The active compounds were formulated using a solution containing 75% (v/v) water and 25% (v/v) DMSO. Different concentrations of formulated compounds or mixtures were sprayed onto the insect diet at 2.5 µl, using a custom built micro atomizer, at two replications.

After application, microtiter plates were incubated at 28+1° C., 80+5% RH for 2 days. Larval mortality was then visually assessed.

In this test, compounds C-1, C-2, C-4, C-5, C-6, C-7, C-8, C-9, C-11, C-14, C-15, C-16, C-17, C-19, C-20, C-21, C-22, C-23, C-26, C-27, C-28, C-29 at 800 ppm showed at least 75% mortality in comparison with untreated controls.

Example B2: Action on Orchid *Thrips* (*Dichromothrips Corbetti*)

*Dichromothrips* corbettiadults used for bioassay were obtained from a colony maintained continuously under laboratory conditions. For testing purposes, the test compound is diluted in a 1:1 mixture of acetone:water (vol:vol), plus Kinetic® HV at a rate of 0.01% v/v.

*Thrips* potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult *thrips*. All test arenas were held under continuous light and a temperature of about 28° C. for duration of the assay. After 3 days, the numbers of live *thrips* were counted on each petal. The percent mortality was recorded 72 hours after treatment.

In this test, compounds C-2, C-4, C-5, C-6, C-7, C-8, C-9, C-10, C-14, C-15, C-16, C-17, C-21, C-22, C-23, C-26, C-27, C-31, C-32 at 500 ppm showed at least 75% mortality in comparison with untreated controls.

Example B3: Action on Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 25±1° C. and about 75±5% relative humidity for 5 days. Egg and larval mortality was then visually assessed.

In this test, compounds C-1, C-2, C-3, C-4, C-5, C-6, C-7, C-8, C-9, C-10, C-11, C-12, C-13, C14, C-15, C-16, C-17, C-19, C-20, C-21, C-22, C-23, C-24, C-25, C-26, C-27, C-28, C-29, C-30 at 800 ppm showed at least 75% mortality in comparison with untreated controls.

Example B4: Action on Silverleaf Whitefly (*Bemisia argentifolii*) (Adults)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds C-3, C-4, C-6, C-8, C-9, C-10, C-16, C-17, C-19, C-20, C-21, C-23, C29 at 500 ppm showed at least 75% mortality in comparison with untreated controls.

Example B5: Action on Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28+10C and about 80+5% relative humidity for 5 days. Egg and larval mortality was then visually assessed.

In this test, compounds C-1, C-2, C-4, C-5, C-6, C-7, C-8, C-9, C-10, C-13, C-14, C-15, C-16, C-17, C-19, C-20, C-21, C-22, C-23, C-24, C-25, C-26, C-27, C-28, C-29 at 800 ppm showed at least 75% mortality in comparison with untreated controls.

Example B6: Action on Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, compounds C-1, C-2, C-3, C-4, C-5, C-6, C-7, C-8, C-9, C-10, C-13, C-14, C-15, C16, C-17, C-19, C-20, C-21, C-22, C-23, C-24, C-25, C-26, C-27, C-28, C-29, C-30 at 800 ppm showed at least 75% mortality in comparison with untreated controls.

Example B7: Action on Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compounds C-6, C-10, C-21, C-28 at 800 ppm showed at least 75% mortality in comparison with untreated controls.

Example B8: Action on Green Peach Aphid (*Myzus persicae*) (Mixed Life Stages)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds C-5, C-6, C-9, C-11, C-30 at 800 ppm showed at least 75% mortality in comparison with untreated controls.

Example B9: Action on Diamond Back Moth (*Plutella xylostella*)

The active compound is dissolved at the desired concentration in a mixture of 1:1 (vol:vol) distilled water:acetone. Surfactant (Kinetic® HV) is added at a rate of 0.01% (vol/vol). The test solution is prepared at the day of use.

Leaves of cabbage were dipped in test solution and air-dried. Treated leaves were placed in petri dishes lined with moist filter paper and inoculated with ten $3^{rd}$ instar larvae. Mortality was recorded 72 hours after treatment. Feeding damages were also recorded using a scale of 0-100%.

In this test, compounds C-2, C-3, C-4, C-5, C-6, C-7, C-8, C-9, C-10, C-13, C-14, C-15, C-16, C-17, C-20, C-21, C-22, C-23, C-24, C-25, C-26, C-27, C-28, C-29, C-30, C-31, C-32 at 500 ppm showed at least 75% mortality in comparison with untreated controls.

Example B10: Action on Southern Armyworm (*Spodoptera eridania*), 2nd Instar Larvae The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compounds C-2, C-3, C-4, C-5, C-6, C-7, C-8, C-9, C-10, C-13, C-15, C-16, C-19, C-20, C-21, C-23, C-24, C-26, C-27, C-28, C-29 at 500 ppm showed at least 75% mortality in comparison with untreated controls.

The invention claimed is:
1. Compounds of formula I;

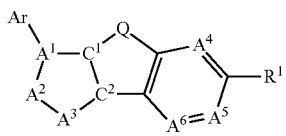

wherein
$C^1$ is C or CH;
$C^2$ is C or CH;
$A^1$ is N or C;
$A^2$ is N, $C(R^2)$, $N(R^3)$, O, S or $C(R^4,R^5)$;
$A^3$ is N, O, S, $N(R^6)$, $C(R^7)$ or $C(R^8,R^9)$;
$A^4$ is N or C(R);
$A^5$ is N or C(R);
$A^6$ is N or C(R);
wherein one or two non-adjacent bonds in the 5-membered ring formed by $C^1$, $C^2$, $A^1$, $A^2$ and $A^3$ are double bonds, while the others are single bonds, provided that the bond between $A^1$ and $A^2$ or the bond between $A^1$ and $C^1$ or the bond between $A^2$ and $A^3$ or the bond between $C^1$ and $C^2$ or the bond between $A^3$ and $C^2$ is a double bond further provided that at least one of $A^1$, $A^2$ and $A^3$ is N, $N(R^3)$ or $N(R^6)$,
provided that 1 or 2 of $A^4$, $A^5$ and $A^6$ is N;

and wherein
$R^2$, $R^7$ independently of each other, are selected from the group consisting of hydrogen, halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 6 mentioned radicals are unsubstituted or partially or completely halogenated, $C(O)$—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, $C(O)$—$NR^bR^c$, $C(O)$—$R^d$, $SO_2NR^bR^c$ and $S(=O)_mR^e$;
$R^3$, $R^6$ independently of each other, are selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 6 mentioned radicals are unsubstituted or partially or completely halogenated, $C(O)$—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, $C(O)$—$NR^bR^c$, $C(O)$—$R^d$, $SO_2NR^bR^c$, $S(=O)_mR^e$, phenyl and benzyl, wherein the phenyl ring in the last 2 radicals is unsubstituted or carry 1, 2, 3, 4 or 5 radicals $R^f$;
$R^4$, $R^5$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or $C(R^4,R^5)$ is a carbonyl group or thiocarbonyl group;
$R^8$, $R^9$ independently of each other, are selected from the group consisting of hydrogen, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio or $C(R^8,R^9)$ is a carbonyl group or thiocarbonyl group;
Ar is phenyl or 5- or 6-membered hetaryl, which are unsubstituted or carry 1, 2, 3 or 4 radicals $R^{Ar}$, which are identical or different, wherein
$R^{Ar}$ independently of each other, are selected from the group consisting of halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 6 mentioned radicals are unsubstituted or partially or completely halogenated, $C(O)$—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, $C(O)$—$NR^bR^c$, $C(O)$—$R^d$, $SO_2NR^bR^c$ and $S(=O)_mR^e$, one radical may also be phenyl, phenoxy, phenylcarbonyl, phenylthio or benzyl, wherein the phenyl ring in the last 5 radicals is unsubstituted or carry 1, 2, 3, 4 or 5 radicals $R^f$;
Q is —O—, —S—, —S(=O)—, —S(=O)$_2$—, —C($R^{Q2a}R^{Q2b}$)—, —N($R^{Q1}$)—, —N($R^{Q2}$)—C (=O)—, —N(R$^{Q2}$)—C(=S)—, —O—C(=O)—, —C(R$^{Q3}$)=C(R$^{Q4}$)—, —C(R$^{Q3a}$R$^{Q3b}$)—C (R$^{Q4a}$R$^{Q4b}$)—, —C(R$^{Q3a}$R$^{Q3b}$)—C(=O)—, —O—C (R$^{Q4a}$R$^{Q4b}$)—, —S(=O)$_n$—C(R$^{Q4a}$R$^{Q4b}$)—, —N=C (R$^{Q3c}$), —S(O)$_2$—N(R$^{Q2}$)— or —N(R$^{Q2}$)—C (R$^{Q4a}$R$^{Q4b}$)—, wherein n is 0, 1 or 2;

R$^{Q1}$, R$^{Q2}$ independently of each other are selected from the group consisting of hydrogen, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, wherein the alkyl, cycloalkyl, cycloalkoxy and alkoxy parts of the last 6 mentioned radicals are unsubstituted or partially or completely halogenated, C(O)—OR$^a$, NR$^b$R$^c$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, wherein the phenyl ring in the last 2 radicals is unsubstituted or carry 1, 2, 3, 4 or 5 radicals R$^f$;

R$^{Q3}$, R$^{Q4}$ independently of each other, are selected from the group consisting of hydrogen, halogen, OH, CN, C$_1$-C$_4$-alkyl, C$_1$-C$_4$-haloalkyl, C$_1$-C$_4$-alkoxy, C$_1$-C$_4$-haloalkoxy, C(O)—OR$^a$, NR$^b$R$^c$, C$_1$-C$_6$-alkylen-NR$^b$R$^c$, O—C$_1$-C$_6$-alkylen-NR$^b$R$^c$, C$_1$-C$_6$-alkylen-CN, NH—C$_1$-C$_6$-alkylen-NR$^b$R$^c$, C(O)—NR$^b$R$^c$, C(O)—R$^d$, SO$_2$NR$^b$R$^c$ and S(=O)$_m$R$^e$;

R$^{Q2a}$, R$^{Q2b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio or —C(R$^{Q2a}$R$^{Q2b}$)— is C=O or C=S;

R$^{Q3a}$, R$^{Q3b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^{Q3c}$ is selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^{Q4a}$, R$^{Q4b}$ independently of each other, are selected from the group consisting of hydrogen, halogen, CN, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio;

R$^1$ is a moiety of the formula -T-X$^1$—Y—Z$^1$—R$^{11}$ or a moiety -T-X$^2$—Y—Z$^2$—R$^{12}$, wherein R$^{11}$ is selected from the group consisting of C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, wherein the alkyl, cycloalkyl, cycloalkoxy and alkoxy parts of the last four mentioned radicals are unsubstituted or partially or completely halogenated, C$_1$-C$_6$-alkylen-NR$^b$R$^c$, C$_1$-C$_6$-alkylen-CN, C(O)—NR$^b$R$^c$, C(O)—R$^d$, aryl, arylcarbonyl, aryl-C$_1$-C$_4$-alkyl, aryloxy-C$_1$-C$_4$-alkyl, hetaryl, hetarylcarbonyl, hetaryl-C$_1$-C$_4$-alkyl and hetaryloxy-C$_1$-C$_4$-alkyl, wherein the aryl and hetaryl rings in the last 8 radicals are unsubstituted or carry 1, 2, 3, 4 or 5 radicals R$^g$ and wherein hetaryl is a 5- or 6-membered monocyclic hetaryl or a 8-, 9- or 10-membered bicyclic hetaryl;

R$^{12}$ is a radical of the formula A;

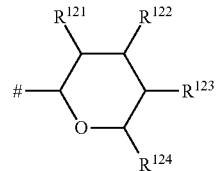

(A)

wherein # indicates the point of attachment to Z$^2$;

R$^{121}$, R$^{122}$, R$^{123}$ independently of each other are selected from the group consisting of hydrogen, halogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_1$-C$_6$-alkoxy, C$_1$-C$_6$-haloalkoxy, C$_2$-C$_6$-alkenyloxy, C$_2$-C$_6$-alkynyloxy, C$_1$-C$_6$-alkoxy-C$_1$-C$_4$-alkoxy, C$_1$-C$_6$-alkylcarbonlyoxy, C$_1$-C$_6$-haloalkylcarbonlyoxy, C$_1$-C$_6$-alkenylcarbonlyoxy, C$_3$-C$_6$-cycloalkylcarbonlyoxy and NR$^b$R$^c$, or one of R$^{121}$, R$^{122}$, R$^{123}$ also is oxo;

R$^{124}$ is selected from the group consisting of hydrogen, C$_1$-C$_6$-alkyl, C$_1$-C$_6$-haloalkyl, C$_1$-C$_6$-alkoxy-C$_1$-C$_4$-alkyl, C$_1$-C$_6$-alkoxy, C$_1$-C$_6$-haloalkoxy and C$_2$-C$_6$-alkenyloxy;

T is selected from a single bond, (CHR$^{xa}$)$_s$ with s being 1, 2, 3 or 4, cyclopropane-1,1-diyl or cyclopropane-1,2-diyl, X$^1$, X$^2$ independently of each other, are selected from NR$^{x1}$, a bivalent group —N(R$^{x2}$)—C(=O)—, wherein C=(O) is bound to Y, a bivalent group —N(R$^{x2}$)—C(=S)—, wherein C=(S) is bound to Y, and a bivalent group —C(R$^{x3}$)=N—, wherein the nitrogen is bound to Y, Y is a single bond, or one of the bivalent groups —N(R$^{y1}$)—C(=O)—, —N(R$^{y2}$)—C(=S)—, —N=C((O)$_p$—R$^{y3}$)— or —N=C((S)$_p$—R$^{y3}$)—, wherein the left hand nitrogen atom in the four groups is bound to X$^1$ or X$^2$, respectively, and wherein p is 0 or 1, provided that Y is not a single bond, if X$^1$ or X$^2$ are a single bond;

Z$^1$ is O, S, N—R$^{z1}$, C(R$^{z3}$)=C((S)$_q$—R$^{z4}$)—N(R$^{z5}$), wherein R$^{11}$ is bound to the nitrogen atom and q is 0 or 1, or C(S—R$^{z6}$)=N, wherein R$^{11}$ is bound to the nitrogen atom; or Y—Z$^1$ is selected from the following bivalent radicals N(R$^{y4}$)—C(S—R$^{z6}$)=N, O—N(R$^{y4}$)—C(S—R$^{z6}$)=N and N(R$^{y44}$)—N(R$^{y4}$)—C(S—R$^{z6}$)=N, wherein in these bivalent radicals R$^{11}$ is bound to the nitrogen atom, Z$^2$ is O, S or N—R$^{z2}$; and wherein R$^{x1}$, R$^{x2}$ independently of each other, are selected from the group consisting of hydrogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, wherein the alkyl, cycloalkyl, cycloalkoxy and alkoxy parts of the last four mentioned radicals are unsubstituted or partially or completely halogenated, C(O)—OR$^a$, C$_1$-C$_6$-alkylen-NR$^b$R$^c$, C$_1$-C$_6$-alkylen-CN, C(O)—NR$^b$R$^c$, C(O)—R$^d$, SO$_2$NR$^b$R$^c$, S(=O)$_m$R$^e$, phenyl and benzyl, wherein the phenyl ring in the last 2 radicals is unsubstituted or carry 1, 2, 3, 4 or 5 radicals R$^f$;

R$^{x3}$ is selected from the group consisting of hydrogen, halogen, CN, C$_1$-C$_6$-alkyl, C$_1$-C$_6$-haloalkyl, C$_1$-C$_6$- alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, wherein the alkyl, cycloalkyl, cycloalkoxy and alkoxy parts of the last 6 mentioned radicals are unsubstituted or partially or completely halogenated, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, phenyl, phenoxy, phenylcarbonyl, phenylthio and benzyl, wherein the phenyl ring in the last 5 radicals is unsubstituted or carry 1, 2, 3, 4 or 5 radicals $R^f$;

$R^{xa}$ is selected from the group consisting of hydrogen, halogen and $C_1$-$C_6$-alkyl, it being possible for s=2, 3 or 4 that $R^{xa}$ is identical or different;

p is 0 or 1;

$R^{y1}$, $R^{y2}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, $S(=O)_mR^e$, phenyl and benzyl, wherein the phenyl ring in the last 2 radicals is unsubstituted or carry 1, 2, 3, 4 or 5 radicals $R^f$;

$R^{y3}$ is selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkoxy-$C_1$-$C_4$-alkyl, $C_3$-$C_6$-cycloalkyl-$C_1$-$C_4$-alkyl, wherein the alkyl, cycloalkyl and alkoxy parts of the last four mentioned radicals are unsubstituted or partially or completely halogenated, $C_1$-$C_6$-alkylen-$NR^bR^c$, $C_1$-$C_6$-alkylen-CN, C(O)—$NR^bR^c$, C(O)—$R^d$, phenyl, phenylcarbonyl and benzyl, wherein the phenyl ring in the last 3 radicals is unsubstituted or carry 1, 2, 3, 4 or 5 radicals $R^f$;

$R^{y4}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, $S(=O)_mR^e$, phenyl and benzyl, wherein the phenyl ring in the last 2 radicals is unsubstituted or carry 1, 2, 3, 4 or 5 radicals $R^f$;

$R^{y44}$ is selected from the group consisting of hydrogen, $C_1$-$C_6$-alkyl, $C_1$-$C_6$-haloalkyl, C(O)—$NR^bR^c$, C(O)—$R^d$, phenyl, phenylcarbonyl and benzyl, wherein the phenyl ring in the last 3 radicals is unsubstituted or carries 1, 2, 3, 4 or 5 radicals $R^f$;

$R^{z1}$, $R^{z2}$ independently of each other are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, C(O)—$OR^a$, $C_1$-$C_6$-alkylen-$NR^bR^c$, $C_1$-$C_6$-alkylen-CN, C(O)—$NR^bR^c$, C(O)—$R^d$, $SO_2NR^bR^c$, $S(=O)_mR^e$, phenyl and benzyl, wherein the phenyl ring in the last 2 radicals is unsubstituted or carry 1, 2, 3, 4 or 5 radicals $R^f$, or wherein $R^{z1}$ together with $R^{y3}$, if present, form a linear $C_1$-$C_6$-alkylene group or a linear $C_2$-$C_6$-alkenylene group, wherein, in the linear $C_1$-$C_6$-alkylene group and the linear $C_2$-$C_6$-alkenylene group, a $CH_2$ moiety is retained or is replaced by a carbonyl group or a group C=N—R', 1 or 2 $CH_2$ moieties are retained or replaced by O or S, the linear $C_1$-$C_6$-alkylene group and the linear $C_2$-$C_6$-alkenylene group is unsubstituted or substituted by 1, 2, 3, 4, 5 or 6 radicals $R^{hh}$, and any combination thereof;

$R^{z3}$, $R^{z6}$ independently of each other, are selected from the group consisting of hydrogen, CN, halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last four mentioned radicals are unsubstituted or partially or completely halogenated, phenyl and benzyl, wherein the phenyl ring in the last 2 radicals is unsubstituted or carries 1, 2, 3, 4 or 5 radicals $R^f$, or wherein $R^{y4}$ together with $R^{z6}$, if present, form a linear $C_1$-$C_6$-alkylene group or a linear $C_2$-$C_6$-alkenylene group, wherein in the linear $C_1$-$C_6$-alkylene group and the linear $C_2$-$C_6$-alkenylene group, a $CH_2$ moiety is be replaced by a carbonyl group or a group C=N—R', 1 or 2 $CH_2$ moieties are replaced by O or S, the linear $C_1$-$C_6$-alkylene group and the linear $C_1$-$C_6$-alkenylene group are unsubstituted or substituted by 1, 2, 3, 4, 5 or 6 radicals $R^{hh}$, and any combination thereof;

$R^{z4}$, $R^{z5}$ independently of each other, are selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last four mentioned radicals are unsubstituted or partially or completely halogenated, phenyl and benzyl, wherein the phenyl ring in the last 2 radicals is unsubstituted or carries 1, 2, 3, 4 or 5 radicals $R^f$ or wherein $R^{z4}$ together with $R^{z5}$, if present, form a linear $C_1$-$C_6$-alkylene group or a linear $C_2$-$C_6$-alkenylene group, wherein in the linear $C_1$-$C_6$-alkylene group and the linear $C_2$-$C_6$-alkenylene group, a $CH_2$ moiety is replaced by a carbonyl group or a group C=N—R', 1 or 2 $CH_2$ moieties are replaced by O or S, the linear $C_1$-$C_6$-alkylene group and the linear $C_2$-$C_6$-alkenylene group are unsubstituted or substituted by 1, 2, 3, 4, 5 or 6 radicals $R^{hh}$, and any combination thereof;

R is selected from the group consisting of hydrogen, halogen, $N_3$, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, wherein the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$, one radical is also phenyl, phenoxy, phenylcarbonyl, phenylthio or benzyl, wherein the phenyl ring in the last 5 radicals is unsubstituted or carries 1, 2, 3, 4 or 5 radicals R$^f$, and any combination thereof;

R' is selected from the group consisting of hydrogen, halogen, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkoxy-$C_1$-$C_4$-alkyl, $C_3$-$C_6$-cycloalkyl-$C_1$-$C_4$-alkyl, wherein the alkyl, cycloalkyl, cycloalkoxy and alkoxy parts of the last 6 mentioned radicals are unsubstituted or partially or completely halogenated, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, phenyl, phenoxy, phenylcarbonyl, phenylthio and benzyl, wherein the phenyl ring in the last 5 radicals is unsubstituted or carry 1, 2, 3, 4 or 5 radicals R$^f$; and wherein each m is independently 0, 1 or 2;

each R$^a$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, $C_1$-$C_6$-alkylen-NR$^b$R$^c$, $C_1$-$C_6$-alkylen-CN, phenyl and benzyl, wherein the phenyl ring in the last 2 radicals is unsubstituted or carry 1, 2, 3, 4 or 5 radicals R$^f$;

each R$^b$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, $C_1$-$C_6$-alkylen-CN, phenyl and benzyl, wherein the phenyl ring in the last 2 radicals is unsubstituted or carry 1, 2, 3, 4 or 5 radicals R$^f$;

each R$^c$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, $C_1$-$C_6$-alkylen-CN, phenyl and benzyl, wherein the phenyl ring in the last 2 radicals is unsubstituted or carry 1, 2, 3, 4 or 5 radicals R$^f$; each moiety NR$^b$R$^c$ forms an N-bound, saturated 5- to 8-membered heterocycle, which in addition to the nitrogen atom has 1 or 2 further heteroatoms or heteroatom moieties selected from O, S(=O)$_m$ and N—R', wherein R' is hydrogen or $C_1$-$C_6$-alkyl and wherein the N-bound heterocycle is unsubstituted or carries 1, 2, 3, 4, 5 or 6 radicals selected from halogen, $C_1$-$C_4$-alkyl, $C_1$-$C_4$-haloalkyl, $C_1$-$C_4$-alkoxy and $C_1$-$C_4$-haloalkoxy, and any combination thereof;

each R$^d$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkoxy-$C_1$-$C_4$-alkyl, wherein the alkyl, cycloalkyl, cycloalkoxy and alkoxy parts of the last 4 mentioned radicals are unsubstituted or partially or completely halogenated, phenyl and benzyl, wherein the phenyl ring in the last 2 radicals is unsubstituted or carry 1, 2, 3, 4 or 5 radicals R$^f$;

each R$^e$ is selected from the group consisting of $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, wherein the alkyl and cycloalkyl parts of the last 2 mentioned radicals are unsubstituted or partially or completely halogenated, phenyl and benzyl, wherein the phenyl ring in the last 2 radicals is unsubstituted or carry 1, 2, 3, 4 or 5 radicals R$^f$;

each R$^f$ is selected from the group consisting of halogen, N$_3$, OH, CN, NO$_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, wherein the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$;

each R$^g$ is selected from the group consisting of halogen, N$_3$, OH, CN, NO$_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, cycloalkyl, cycloalkoxy and alkoxy parts of the last 6 mentioned radicals are unsubstituted or partially or completely halogenated, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$;

each R$^{hh}$ is selected from halogen, OH, $C_1$-$C_6$-alkyl, $C_3$-$C_6$-cycloalkyl, and CN;

and the N-oxides, stereoisomers, tautomers and agriculturally or veterinarily acceptable salts thereof.

2. The compounds of claim 1, wherein the compound of formula I is a compound of the formulae Ia, Ib, Ic or Id, an N-oxide, stereoisomer, tautomer or agriculturally or veterinarily acceptable salt thereof:

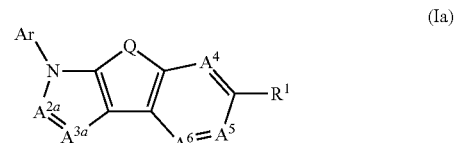

(Ia)

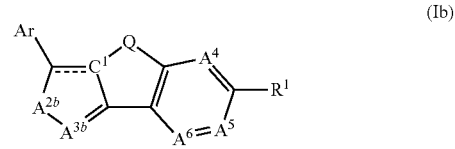

(Ib)

223

-continued (Ic)

(Id)

wherein in formula Ia
$A^{2a}$ is N or $C(R^2)$; and
$A^{3a}$ is N or $C(R^7)$;
wherein in formula Ib
$C^1$ is CH or C, provided that ---- indicates a single bond, if $C^1$ is CH or a double bond, if $C^1$ is C,
$A^{2b}$ is $N(R^3)$, O or S; and
$A^{3b}$ is N or $C(R^7)$;
provided that one or both of $A^{2b}$ and $A^{3b}$ are N or $N(R^3)$, respectively;
wherein in formula Ic
$C^1$ and $C^2$ are both CH or both C provided that ---- indicates a single bond, if $C^1$ and $C^2$ are CH or a double bond, if $C^1$ and $C^2$ are C,
$A^{2c}$ is N or $C(R^2)$; and
$A^{3c}$ is O, S, $N(R^6)$ or $C(R^8,R^9)$;
wherein in formula Id
$A^{2d}$ is $N(R^3)$, O, S or $C(R^4,R^5)$; and
$A^{3d}$ is O, S, $N(R^6)$ or $C(R^8,R^9)$;
provided that at least one of $A^{2d}$ and $A^{3d}$ is different from O and S and further provided that the bond between $A^{2d}$ and $A^{3d}$ is a single bond;
wherein k is 0 or 1;
and wherein $A^4$, $A^5$, $A^6$, Ar, $R^1$, $R^2$, $R^3$, $R^4$, $R^5$, $R^6$, $R^7$, $R^8$ and $R^9$ are as defined in claim 1.

3. The compound of claim 2, selected from compounds of the formulae (I), (Ia), (Ib), (Ic) and (Id), wherein
$A^4$ is N, while $A^5$ is CH and $A^6$ is CH; or
$A^5$ is N, while $A^4$ is CH and $A^6$ is CH; or
$A^6$ is N, while $A^4$ is CH and $A^5$ is CH; or
$A^4$ is N, $A^5$ is N and $A^6$ is CH; or
$A^4$ is N, $A^6$ is N and $A^5$ is CH; or
$A^5$ is N, $A^6$ is N and $A^4$ is CH.

4. The compound of claim 1, wherein Q is selected from the group consisting of O, S, —$CH_2$—, —$N(R^{Q1})$—, —CH=CH—, —$CH_2CH_2$—, —N=CH—, O—$CH_2$, —S—$CH_2$, —S(=O)—$CH_2$—, —S(=O)$_2$—$CH_2$—, —$N(R^{Q2})$—C(=O)—, —$N(R^{Q2})$—C(=S)—, —$N(R^{Q2})$—S(=O)$_2$—, and —$N(R^{Q2})$—$CH_2$—, wherein $R^{Q1}$ and $R^{Q2}$ are as defined in claim 1.

5. The compound of claim 1, wherein Ar is phenyl, pyridyl, pyrimidinyl or pyridazinyl, which are unsubstituted or carry 1, 2 or 3 radicals $R^{Ar}$.

6. The compound of claim 1, wherein $R^{Ar}$ is selected from the group consisting of halogen, $C_1$-$C_6$-alkyl, $C_1$-$C_6$-haloalkyl, $C_1$-$C_6$-alkoxy, $C_1$-$C_6$-haloalkoxy and S—$R^e$, wherein $R^e$ is $C_1$-$C_6$-alkyl or $C_1$-$C_6$-haloalkyl.

7. The compound of claim 1, wherein $R^1$ is a moiety -T-$X^1$—Y—$Z^1$—$R^{11}$.

8. The compound of claim 1, wherein $R^H$ is aryl, aryl-$C_1$-$C_4$-alkyl, hetaryl, or hetaryl-$C_1$-$C_4$-alkyl, wherein the aryl and hetaryl rings in the last 4 radicals are unsubstituted

224 or carry 1, 2, 3, 4 or 5 radicals $R^g$ and wherein hetaryl is a 5- or 6-membered monocyclic hetaryl.

9. The compound of claim 1, wherein $R^1$ is a moiety -T-$X^2$—Y—$Z^2$—$R^{12}$, wherein
T is a single bond, $CH_2$, $CH_2CH_2$ or cyclopropan-1,2-diyl;
$X^2$ is CH=N or NHC(O);
Y is a single bond;
$Z^2$ is O; and
$R^{12}$ is a radical of the formula A, wherein
$R^{121}$ is $C_1$-$C_4$-alkoxy;
$R^{122}$ is $C_1$-$C_4$-alkoxy or $C_3$-$C_4$-alkenyloxy;
$R^{123}$ is OH, $C_1$-$C_4$-alkoxy or $C_3$-$C_4$-alkenyloxy; and
$R^{124}$ is $C_1$-$C_4$-alkyl or $C_1$-$C_4$-alkoxy-$C_1$-$C_4$-alkyl.

10. The compound of claim 1, which is selected from the group consisting of compounds: 1-(2,6-dimethylphenyl)-3-[(E)-[3-[4-(trifluoromethoxy)phenyl]imidazo[4,5-f]quinolin-7-yl]methyleneamino]thiourea, (2Z)-3-(2,6-dimethylphenyl)-2-[(E)-[3-[4-(trifluoromethoxy)phenyl]imidazo[4,5-f]quinolin-7-yl]methylenehydrazono]thiazolidin-4-one, 1-(2-isopropylphenyl)-3-[(E)-[3-[4-(trifluoromethoxy)phenyl]imidazo[4,5-f]quinolin-7-yl]methyleneamino]thiourea, (2Z)-3-(2-isopropylphenyl)-2-[(E)-[3-[4-(trifluoromethoxy)phenyl]imidazo[4,5-f]quinolin-7-yl]methylenehydrazono]thiazolidin-4-one, 1-(2-isopropyl-5-methyl-phenyl)-3-[(E)-[3-[4-(trifluoromethoxy)phenyl]imidazo[4,5-f]quinolin-7-yl]methyleneamino]thiourea, (2Z)-3-(2-isopropyl-5-methyl-phenyl)-2-[(E)-[3-[4-(trifluoromethoxy)phenyl]imidazo[4,5-f]quinolin-7-yl]methylenehydrazono]thiazolidin-4-one, (2Z)-2-(2,6-dimethylphenyl)imino-3-[(E)-[3-[4-(trifluoromethoxy)phenyl]imidazo[4,5-f]quinolin-7-yl]methyleneamino]thiazolidin-4-one, (2Z)-2-(2-isopropylphenyl)imino-3-[(E)-[3-[4-(trifluoromethoxy)phenyl]imidazo[4,5-f]quinolin-7-yl]methyleneamino]thiazolidin-4-one, 1-(2,6-dimethylphenyl)-3-[(E)-[3-[6-(trifluoromethyl)pyridazin-3-yl]imidazo[4,5-f]quinolin-7-yl]methyleneamino]thiourea, (2Z)-3-(2,6-dimethylphenyl)-2-[(E)-[4-[6-(trifluoromethyl)pyridazin-3-yl]imidazo[4,5-f]quinolin-7-yl]methylenehydrazono]thiazolidin-4-one, 1-(2,6-dimethylphenyl)-3-[(E)-[4-[4-(trifluoromethoxy)phenyl]-4,5-dihydroimidazo[4,5-f]quinolin-7-yl]methyleneamino]thiourea, (2Z)-3-(2,6-dimethylphenyl)-2-[(E)-[3-[4-(trifluoromethoxy)phenyl]-4,5-dihydroimidazo[4,5-f]quinolin-7-yl]methylenehydrazono]thiazolidin-4-one, 1-(2,6-dimethylphenyl)-3-[(E)-[4-[4-(trifluoromethoxy)phenyl]-4,5-dihydroimidazo[4,5-f]quinazolin-7-yl]methyleneamino]thiourea, (2Z)-3-(2,6-dimethylphenyl)-2-[(E)-[3-[4-(trifluoromethoxy)phenyl]-4,5-dihydroimidazo[4,5-f]quinazolin-7-yl]methylenehydrazono]thiazolidin-4-one, 1-(2,6-dimethylphenyl)-3-[(E)-[3-[4-(trifluoromethoxy)phenyl]imidazo[4,5-f]quinazolin-7-yl]methyleneamino]thiourea, (2Z)-3-(2,6-dimethylphenyl)-2-[(E)-[3-[4-(trifluoromethoxy)phenyl]imidazo[4,5-f]quinazolin-7-yl]methylenehydrazono]thiazolidin-4-one, 1-(2,6-dimethylphenyl)-3-[(E)-[5,5-dioxo-3-[4-(trifluoromethoxy)phenyl]-4H-imidazo[2,3]thiopyrano[2,4-b]pyridin-7-yl]methyleneamino]thiourea, (2Z)-3-(2,6-dimethylphenyl)-2-[(E)-[5,5-dioxo-3-[4-(trifluoromethoxy)phenyl]-4H-imidazo[2,3]thiopyrano[2,4-b]pyridin-7-yl]methylenehydrazono]thiazolidin-4-one, 1-(2,6-dimethylphenyl)-3-[(E)-[5,5-dioxo-3-[4-(trifluoromethoxy)phenyl]-4H-imidazo[2,3]thiopyrano[2,4-d]pyrimidin-7-yl]methyleneamino]thiourea, (2Z)-3-(2,6-dimethylphenyl)-2-[(E)-[5,5-dioxo-3-[4-(trifluoromethoxy)phenyl]-4H-imidazo[2,3]thiopyrano[2,4-d]pyrimidin-7-yl]methylenehydrazono]thiazolidin-4-one, 1-(2,6-dimethylphenyl)-3-[(E)-[3-[4-(trifluoromethoxy)phenyl]imidazo[4,5-f]quinoxalin-7-yl]methyleneamino]thiourea, (2Z)-3-(2,6-dimethylphenyl)-2-[(E)-[3-[4-(trifluoromethoxy)phenyl]imidazo[4,5-f]quinoxalin-7-yl]methylenehydrazono]thiazolidin-4-one, 1-(2,6-dimethylphenyl)-3-[(E)-[2-methyl-3-[4-(trifluoromethoxy)phenyl]-4,5-dihydropyrazolo[3,4-f]quinolin-7-yl]methyleneamino]thiourea, (2Z)-3-(2,6-dimethylphenyl)-2-[(E)-[2-methyl-3-[4-(trifluoromethoxy)phenyl]-4,5-dihydropyrazolo[3,4-f]quinolin-7-yl]methylenehydrazono]thiazolidin-4-one, 1-(2,6-dimethylphenyl)-3-[(E)-[2-methyl-3-[4-(trifluoromethoxy)phenyl]-4,5-dihydropyrazolo[3,4-f]quinazolin-7-yl]methyleneamino]thiourea, (2Z)-3-(2,6-dimethylphenyl)-2-[(E)-[2-methyl-3-[4-(trifluoromethoxy)phenyl]-4,5-dihydropyrazolo[3,4-f]quinazolin-7-yl]methylenehydrazono]thiazolidin-4-one, 1-(2,6-dimethylphenyl)-3-[(E)-[3-[4-(trifluoromethoxy)phenyl]imidazo[4,5-f] quinoxalin-7-yl]methyleneamino]thiourea, (2Z)-3-(2,6-dimethylphenyl)-2-[(E)-[3-[4-(trifluoromethoxy)phenyl]imidazo[4,5-f]quinoxalin-7-yl]methylenehydrazono]thiazolidin-4-one, 1-(2,6-dimethylphenyl)-3-[(E)-[2-methyl-3-[4-(trifluoromethoxy)phenyl]pyrazolo[3,4-f] quinolin-7-yl]methyleneamino]thiourea, (2Z)-3-(2,6-dimethylphenyl)-2-[(E)-[2-methyl-3-[4-(trifluoromethoxy)phenyl]pyrazolo[3,4-f]quinolin-7-yl]methylenehydrazono]thiazolidin-4-one, 1-(2,6-dimethylphenyl)-3-[(E)-[2-methyl-3-[4-(trifluoromethoxy)phenyl]pyrazolo[3,4-f]quinazolin-7-yl]methyleneamino]thiourea, (2Z)-3-(2,6-dimethylphenyl)-2-[(E)-[2-methyl-3-[4-(trifluoromethoxy)phenyl]pyrazolo[3,4-f]quinazolin-7-yl]methylenehydrazono]thiazolidin-4-one, 1-(2,6-dimethylphenyl)-3-[(E)-[3-[4-(trifluoromethoxy)phenyl]imidazo[4,5-h]isoquinolin-7-yl]methyleneamino]thiourea, (2Z)-3-(2,6-dimethylphenyl)-2-[(E)-[3-[4-(trifluoromethoxy)phenyl]imidazo[4,5-f]isoquinolin-7-yl]methylenehydrazono]thiazolidin-4-one, 1-(2,6-dimethylphenyl)-3-[(E)-[2-methyl-5,5-dioxo-3-[4-(trifluoromethoxy)phenyl]-4H-pyrazolo[1,2]thiopyrano[3,4-b]pyridin-7-yl]methyleneamino]thiourea, (2Z)-3-(2,6-dimethylphenyl)-2-[(E)-[2-methyl-5,5-dioxo-3-[4-(trifluoromethoxy)phenyl]-4H-pyrazolo[1,2]thiopyrano[3,4-b]pyridin-7-yl]methylenehydrazono]thiazolidin-4-one, 1-(2,6-dimethylphenyl)-3-[(E)-[2-methyl-5,5-dioxo-3-[4-(trifluoromethoxy)phenyl]-4H-pyrazolo[1,2]thiopyrano[3,4-d]pyrimidin-7-yl]methyleneamino]thiourea, (2Z)-3-(2,6-dimethylphenyl)-2-[(E)-[2-methyl-5,5-dioxo-3-[4-(trifluoromethoxy)phenyl]-4H-pyrazolo[1,2]thiopyrano[3,4-d]pyrimidin-7-yl]methylenehydrazono]thiazolidin-4-one, 1-(2,6-dimethylphenyl)-3-[(E)-[3-[4-(trifluoromethoxy)phenyl]imidazo[4,5-h] quinolin-7-yl]methyleneamino]thiourea, (2Z)-3-(2,6-dimethylphenyl)-2-[(E)-[3-[4-(trifluoromethoxy)phenyl]imidazo[4,5-h]quinolin-7-yl]methylenehydrazono]thiazolidin-4-one, (2Z)-3-(2-isopropylphenyl)-4-methyl-2-[(E)-[3-[4-(trifluoromethoxy)phenyl]imidazo[4,5-f] quinolin-7-yl]methylenehydrazono]thiazolidin-4-ol, (2Z)-3-(2-isopropylphenyl)-2-[(E)-[3 [6-(trifluoromethyl)pyridazin-3-yl]imidazo[4,5-f]quinolin-7-yl]methylenehydrazono]thiazolidin-4-one, 1-(5-chloro-2-pyridyl)ethyl N-[3-[4-(trifluoromethoxy)phenyl]imidazo[4,5-f] quinolin-7-yl] carbamate, (2-isopropyl-5-methyl-cyclohexyl) N-[3-[4-(trifluoromethoxy)phenyl]imidazo[4,5-f]quinolin-7-yl]carbamate, 1-(2-isopropylphenyl)-3-[(E)-[3-[4-(trifluoromethoxy)phenyl]imidazo[4,5-h]quinolin-7-yl]methyleneamino]thiourea, (2Z)-2-(2-isopropylphenyl)imino-3-[(E)-[3-[4-(trifluoromethoxy)phenyl]imidazo[4,5-h] quinolin-7-yl]methyleneamino]thiazolidin-4-one, (2Z)-3-(2-isopropylphenyl)-2-[(E)-[3-[4-(trifluoromethoxy)phenyl]imidazo[4,5-h]quinolin-7-yl]methylenehydrazono]thiazolidin-4-one, (2Z)-2-(2,6-dimethylphenyl)imino-3-[(E)-[3-[4-(trifluoromethoxy)phenyl]imidazo[4,5-h]quinolin-7-yl]methyleneamino]thiazolidin-4-one, 1-(2-isopropylphenyl)-3-[(E)-[2-methyl-3-[4-(trifluoromethoxy)phenyl]pyrazolo[3,4-f]quinolin-7-yl]methyleneamino] thiourea, (2Z)-3-(2-isopropylphenyl)-2-[(E)-[2-methyl-3-[4-(trifluoromethoxy)phenyl]pyrazolo[3,4-f]quinolin-7-yl]methylenehydrazono]thiazolidin-4-one, (E)-3-(2-isopropylphenyl)-N-[(E)-[3-[4-(trifluoromethoxy)phenyl]imidazo[4,5-f]quinolin-7-yl]methyleneamino]thiazolidin-2-imine, (E)-3-(2-isopropylphenyl)-N-[(E)-[3-[4-(trifluoromethoxy)phenyl]imidazo[4,5-f]quinolin-7-yl]methyleneamino]-1,3-thiazinan-2-imine, (E)-3-(2,6-dimethylphenyl)-N-[(E)-[3-[4-(trifluoromethoxy)phenyl]imidazo[4,5-f]quinolin-7-yl]methyleneamino]-1,3-thiazinan-2-imine, 1-(2-isopropylphenyl)-3-[(E)-[3-[4-(trifluoromethoxy)phenyl]imidazo[4,5-f]isoquinolin-7-yl]methyleneamino]thiourea, (2Z)-3-(2-isopropylphenyl)-2-[(E)-[3-[4-(trifluoromethoxy)phenyl]imidazo[4,5-h]isoquinolin-7-yl]methylenehydrazono]thiazolidin-4-one, (2Z)-2-(2-isopropylphenyl)imino-3-[(E)-[3-[4-(trifluoromethoxy)phenyl]imidazo[4,5-h]isoquinolin-7-yl]methyleneamino]thiazolidin-4-one, 2Z)-2-(2,6-dimethylphenyl)imino-3-[(E)-[3-[4-(trifluoromethoxy)phenyl]imidazo[4,5-f]isoquinolin-7-yl]methyleneamino]thiazolidin-4-one, (E)-3-(2,6-dimethylphenyl)-N-[(E)-[3-[4-(trifluoromethoxy)phenyl]imidazo[4,5-f]quinolin-7-yl]methyleneamino]thiazolidin-2-imine, 1-[(E)-[3-[4-(difluoromethoxy)phenyl]imidazo[4,5-f]quinolin-7-yl]methyleneamino]-3-(2-isopropylphenyl)thiourea, (2E)-2-[(E)-[3-[4-(difluoromethoxy)phenyl]imidazo[4,5-f]quinolin-7-yl]methylenehydrazono]-3-(2-isopropylphenyl)thiazolidin-4-one, (E)-1-[3-[4-(trifluoromethoxy)phenyl]imidazo[4,5-f]quinolin-7-yl]-N-[(2S,3R,4R,5 S,6S)-3,4,5-trimethoxy-6-methyl-tetrahydropyran-2-yl]oxy-methanimine, (2Z)-3-(2-isopropylphenyl)-2-[(E)-[3-[4-(trifluoromethoxy)phenyl]imidazo[4,5-f]quinoxalin-7-yl]methylenehydrazono]thiazolidin-4-one, 1-(2-isopropylphenyl)-3-[(E)-[3-[4-(trifluoromethoxy)phenyl]imidazo[4,5-f]quinoxalin-7-yl]methyleneamino]thiourea, 1-(2-isopropylphenyl)-3-[(E)-[2-methyl-3-[4-(trifluoromethoxy)phenyl]pyrazolo[3,4-f]quinazolin-7-yl]methyleneamino]thiourea, and the N-oxides, stereoisomers, tautomers and agriculturally or veterinarily acceptable salts thereof.

11. A composition comprising at least one compound of the formula I, as defined in claim 1, any stereoisomer thereof or any agriculturally or veterinarily acceptable salt thereof, and at least one agriculturally or veterinarily acceptable carrier selected from the group consisting of an inert liquid, and a solid.

12. A method for controlling invertebrate pests, the method comprising treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one imine compound of the formula I as defined in claim 1, a stereoisomer thereof or an agriculturally acceptable salt thereof.

13. A method for treating or protecting an animal from infestation or infection by invertebrate pests, the method-comprising bringing the animal in contact with a pesticidally effective amount of at least one compound of the formula I as defined in claim 1, a stereoisomer thereof or at least one veterinarily acceptable salt thereof.

* * * * *